US008815587B2

(12) United States Patent
Harris et al.

(10) Patent No.: US 8,815,587 B2
(45) Date of Patent: Aug. 26, 2014

(54) POSTPARTUM CELLS DERIVED FROM UMBILICAL TISSUE AND METHODS OF MAKING AND USING THE SAME

(75) Inventors: Ian R. Harris, Radnor, PA (US); Darin J. Messina, Downingtown, PA (US); Anthony J. Kihm, Princeton, NJ (US); Agnieszka Seyda, Edison, NJ (US); David C. Colter, Hamilton, NJ (US)

(73) Assignee: DePuy Synthes Products, LLC, Raynham, MA (US)

( * ) Notice: Subject to any disclaimer, the term of this patent is extended or adjusted under 35 U.S.C. 154(b) by 954 days.

(21) Appl. No.: 12/946,609

(22) Filed: Nov. 15, 2010

(65) Prior Publication Data

US 2012/0315251 A1    Dec. 13, 2012

Related U.S. Application Data

(60) Division of application No. 11/315,897, filed on Dec. 22, 2005, now abandoned, which is a continuation-in-part of application No. 10/877,012, filed on Jun. 25, 2004, now Pat. No. 7,510,873.

(60) Provisional application No. 60/483,264, filed on Jun. 27, 2003, provisional application No. 60/639,088, filed on Dec. 23, 2004.

(51) Int. Cl.
*C12N 5/073* (2010.01)

(52) U.S. Cl.
USPC ............................ 435/375; 435/366; 424/583

(58) Field of Classification Search
CPC .. C12N 5/0605; C12N 5/0618; C12N 5/0619; C12N 5/0621; C12N 5/0653; C12N 5/0655; C12N 5/067; C12N 5/0676; C12N 5/0657
See application file for complete search history.

(56) References Cited

U.S. PATENT DOCUMENTS

| | | |
|---|---|---|
| 3,665,061 A | 5/1972 | Eberly, Jr. |
| 3,930,954 A | 1/1976 | Irie et al. |
| 4,290,962 A | 9/1981 | Tachi et al. |
| 4,352,883 A | 10/1982 | Lim |
| 4,487,865 A | 12/1984 | Balazs et al. |
| 4,882,162 A | 11/1989 | Ikada et al. |
| 4,925,667 A | 5/1990 | Fellows et al. |
| 4,963,489 A | 10/1990 | Naughton et al. |
| 5,004,681 A | 4/1991 | Boyse et al. |
| 5,192,553 A | 3/1993 | Boyse et al. |
| 5,248,608 A | 9/1993 | Van Dooren et al. |
| 5,284,766 A | 2/1994 | Okano et al. |
| 5,286,632 A | 2/1994 | Jones |
| 5,320,962 A | 6/1994 | Stiles et al. |
| 5,342,761 A | 8/1994 | MacLeod |
| 5,437,994 A | 8/1995 | Emerson et al. |
| 5,443,950 A | 8/1995 | Naughton et al. |
| 5,456,835 A | 10/1995 | Castino et al. |
| 5,466,233 A | 11/1995 | Weiner et al. |
| 5,474,987 A | 12/1995 | Cohen et al. |
| 5,486,359 A | 1/1996 | Caplan et al. |
| 5,506,134 A | 4/1996 | Soule et al. |
| 5,580,777 A | 12/1996 | Bernard et al. |
| 5,589,376 A | 12/1996 | Anderson et al. |
| 5,670,483 A | 9/1997 | Zhang et al. |
| 5,677,181 A | 10/1997 | Parish |
| 5,693,332 A | 12/1997 | Hansbrough |
| 5,698,518 A | 12/1997 | Carson et al. |
| 5,707,643 A | 1/1998 | Ogura et al. |
| 5,718,922 A | 2/1998 | Herrero-Vanrell et al. |
| 5,736,516 A | 4/1998 | Louis |
| 5,811,094 A | 9/1998 | Caplan et al. |
| 5,827,735 A | 10/1998 | Young et al. |
| 5,834,308 A | 11/1998 | Peck et al. |
| 5,840,580 A | 11/1998 | Terstappen et al. |
| 5,842,477 A | 12/1998 | Naughton et al. |
| 5,843,780 A | 12/1998 | Thomson |
| 5,843,781 A | 12/1998 | Ballermann |
| 5,855,619 A | 1/1999 | Caplan et al. |
| 5,869,079 A | 2/1999 | Wong et al. |
| 5,902,598 A | 5/1999 | Chen et al. |
| 5,902,741 A | 5/1999 | Purchio et al. |
| 5,906,934 A | 5/1999 | Grande et al. |
| 5,919,702 A | 7/1999 | Purchio et al. |
| 5,942,225 A | 8/1999 | Bruder et al. |
| 5,955,343 A | 9/1999 | Holmes et al. |
| 5,962,325 A | 10/1999 | Naughton et al. |
| 5,994,094 A | 11/1999 | Hötten et al. |
| 6,001,647 A | 12/1999 | Peck et al. |
| 6,022,743 A | 2/2000 | Naughton et al. |
| 6,059,968 A | 5/2000 | Wolf |

(Continued)

FOREIGN PATENT DOCUMENTS

| | | |
|---|---|---|
| CN | 1407088 | 2/2003 |
| EP | 0 333 328 | 9/1989 |

(Continued)

OTHER PUBLICATIONS

In the U.S. Patent and Trademark Office, Non-Final Office Action in re: U.S. Appl. No. 10/877,012, dated Sep. 24, 2007, 18 pages.
In the U.S. Patent and Trademark Office, Final Office Action in re: U.S. Appl. No. 10/877,012, dated Mar. 15, 2007, 13 pages.
In the U.S. Patent and Trademark Office, Non-Final Office Action in re: U.S. Appl. No. 10/877,012, dated Jul. 18, 2006, 26 pages.
In the U.S. Patent and Trademark Office, Non-Final Office Action in re: U.S. Appl. No. 11/315,897, dated Jun. 13, 2008, 12 pages.
In the U.S. Patent and Trademark Office, Non-Final Office Action in re: U.S. Appl. No. 10/877,446, dated Feb. 28, 2008, 19 pages.
In the U.S. Patent and Trademark Office, Final Office Action in re: U.S. Appl. No. 10/877,446, dated Jun. 27, 2007, 24 pages.
In the U.S. Patent and Trademark Office, Non-Final Office Action in re: U.S. Appl. No. 10/877,446, dated Nov. 20, 2006, 24 pages.

(Continued)

*Primary Examiner* — Allison Ford
(74) *Attorney, Agent, or Firm* — Bernard F. Plantz; Johnson & Johnson

(57) ABSTRACT

Cells derived from human umbilical cords are disclosed along with methods for their therapeutic use. Isolation techniques, culture methods and detailed characterization of the cells with respect to their cell surface markers, gene expression, and their secretion of trophic factors are described.

6 Claims, 1 Drawing Sheet

(56) References Cited

U.S. PATENT DOCUMENTS

| | | |
|---|---|---|
| 6,140,039 A | 10/2000 | Naughton et al. |
| 6,153,591 A | 11/2000 | Cai et al. |
| 6,171,610 B1 | 1/2001 | Vacanti et al. |
| 6,179,872 B1 | 1/2001 | Bell et al. |
| 6,200,606 B1 | 3/2001 | Peterson et al. |
| 6,200,806 B1 | 3/2001 | Thomson |
| 6,214,369 B1 | 4/2001 | Grande et al. |
| 6,221,904 B1 | 4/2001 | Agus et al. |
| 6,251,090 B1 | 6/2001 | Avery et al. |
| 6,291,240 B1 | 9/2001 | Mansbridge et al. |
| 6,326,201 B1 | 12/2001 | Fung et al. |
| 6,331,313 B1 | 12/2001 | Wong et al. |
| 6,333,029 B1 | 12/2001 | Vyakarnam et al. |
| 6,355,239 B1 | 3/2002 | Bruder et al. |
| 6,355,699 B1 | 3/2002 | Vyakarnam et al. |
| 6,358,737 B1 | 3/2002 | Bonewald et al. |
| 6,372,494 B1 | 4/2002 | Naughton et al. |
| 6,375,972 B1 | 4/2002 | Guo et al. |
| 6,387,367 B1 | 5/2002 | Davis-Sproul et al. |
| 6,391,297 B1 | 5/2002 | Halvorsen |
| 6,429,013 B1 | 8/2002 | Halvorsen et al. |
| 6,436,704 B1 | 8/2002 | Roberts et al. |
| 6,495,645 B1 | 12/2002 | Okano et al. |
| 6,497,875 B1 | 12/2002 | Sorrell et al. |
| 6,511,511 B1 | 1/2003 | Slivka et al. |
| 6,528,245 B2 | 3/2003 | Sanchez-Ramos et al. |
| 6,534,084 B1 | 3/2003 | Vyakarnam et al. |
| 6,555,374 B1 | 4/2003 | Gimble et al. |
| 6,592,623 B1 | 7/2003 | Bowlin et al. |
| 6,599,323 B2 | 7/2003 | Melican et al. |
| 6,610,535 B1 | 8/2003 | Lu et al. |
| 6,638,765 B1 | 10/2003 | Rosenberg |
| 6,673,606 B1 | 1/2004 | Tennekoon et al. |
| 6,680,198 B1 | 1/2004 | Snyder et al. |
| 6,686,198 B1 | 2/2004 | Melton et al. |
| 6,703,017 B1 | 3/2004 | Peck et al. |
| 6,916,655 B2 | 7/2005 | Yasumoto et al. |
| 7,413,734 B2 | 8/2008 | Mistry et al. |
| 7,510,873 B2 | 3/2009 | Mistry et al. |
| 7,524,489 B2 | 4/2009 | Messina et al. |
| 7,560,276 B2 | 7/2009 | Harmon et al. |
| 7,875,272 B2 | 1/2011 | Messina et al. |
| 7,875,273 B2 | 1/2011 | Messina et al. |
| 8,039,258 B2 | 10/2011 | Harris et al. |
| 8,658,152 B2 | 2/2014 | Messina et al. |
| 2001/0024824 A1 | 9/2001 | Moss et al. |
| 2001/0031256 A1 | 10/2001 | Edge |
| 2001/0046489 A1 | 11/2001 | Habener et al. |
| 2002/0022676 A1 | 2/2002 | He et al. |
| 2002/0028510 A1 | 3/2002 | Sanberg et al. |
| 2002/0062151 A1 | 5/2002 | Altman et al. |
| 2002/0081725 A1 | 6/2002 | Tsang et al. |
| 2002/0098584 A1 | 7/2002 | Palmer et al. |
| 2002/0119565 A1 | 8/2002 | Clarke et al. |
| 2002/0123141 A1 | 9/2002 | Hariri |
| 2002/0150986 A1 | 10/2002 | Lau |
| 2002/0151056 A1 | 10/2002 | Sasai et al. |
| 2002/0160471 A1 | 10/2002 | Kisiday et al. |
| 2002/0160510 A1 | 10/2002 | Hariri |
| 2002/0164307 A1 | 11/2002 | Habener et al. |
| 2002/0164791 A1 | 11/2002 | Van Der Kooy et al. |
| 2002/0168763 A1 | 11/2002 | Yan et al. |
| 2002/0182241 A1 | 12/2002 | Borenstein et al. |
| 2002/0182728 A1 | 12/2002 | Ramiya et al. |
| 2002/0187550 A1 | 12/2002 | Dinsmore et al. |
| 2002/0192816 A1 | 12/2002 | Roberts et al. |
| 2003/0003574 A1 | 1/2003 | Toma et al. |
| 2003/0007954 A1 | 1/2003 | Naughton et al. |
| 2003/0031657 A1 | 2/2003 | Habener et al. |
| 2003/0032178 A1 | 2/2003 | Williams et al. |
| 2003/0032179 A1 | 2/2003 | Hariri |
| 2003/0032183 A1 | 2/2003 | Sheridan |
| 2003/0049837 A1 | 3/2003 | Weiss et al. |
| 2003/0059939 A1 | 3/2003 | Page et al. |
| 2003/0082155 A1 | 5/2003 | Habener et al. |
| 2003/0082160 A1 | 5/2003 | Yu et al. |
| 2003/0096409 A1 | 5/2003 | Yasumoto et al. |
| 2003/0104997 A1 | 6/2003 | Black et al. |
| 2003/0109036 A1 | 6/2003 | Wu |
| 2003/0113910 A1 | 6/2003 | Levanduski |
| 2003/0118566 A1 | 6/2003 | Neuman et al. |
| 2003/0124721 A1 | 7/2003 | Cheatham et al. |
| 2003/0138948 A1 | 7/2003 | Fisk et al. |
| 2003/0138950 A1 | 7/2003 | McAlister et al. |
| 2003/0138951 A1 | 7/2003 | Yin |
| 2003/0148513 A1 | 8/2003 | Sugaya et al. |
| 2003/0161818 A1 | 8/2003 | Weiss et al. |
| 2003/0162290 A1 | 8/2003 | Inoue et al. |
| 2003/0170215 A1 | 9/2003 | Tsang et al. |
| 2003/0175963 A1 | 9/2003 | Rosenberg |
| 2003/0180269 A1 | 9/2003 | Hariri |
| 2003/0186439 A1 | 10/2003 | Nakauchi et al. |
| 2003/0199447 A1 | 10/2003 | Goldman et al. |
| 2003/0203483 A1 | 10/2003 | Seshi |
| 2003/0203484 A1 | 10/2003 | Black et al. |
| 2003/0207450 A1 | 11/2003 | Young et al. |
| 2003/0211087 A1 | 11/2003 | Goldman |
| 2003/0211603 A1 | 11/2003 | Earp et al. |
| 2003/0211605 A1 | 11/2003 | Lee et al. |
| 2003/0212024 A1 | 11/2003 | Keating et al. |
| 2003/0219894 A1 | 11/2003 | Seino et al. |
| 2003/0228295 A1 | 12/2003 | Svendsen |
| 2003/0228693 A1 | 12/2003 | Tsuzuki et al. |
| 2003/0235563 A1 | 12/2003 | Strom et al. |
| 2003/0235909 A1 | 12/2003 | Hariri et al. |
| 2004/0005704 A1 | 1/2004 | Csete et al. |
| 2004/0009566 A1 | 1/2004 | Okano et al. |
| 2004/0009593 A1 | 1/2004 | Keirstead et al. |
| 2004/0014206 A1 | 1/2004 | Robl et al. |
| 2004/0014210 A1 | 1/2004 | Jessell et al. |
| 2004/0014211 A1 | 1/2004 | Ogle et al. |
| 2004/0014662 A1 | 1/2004 | Lindquist et al. |
| 2004/0028657 A1 | 2/2004 | Okano |
| 2004/0028660 A1 | 2/2004 | Hariri et al. |
| 2004/0029269 A1 | 2/2004 | Goldman et al. |
| 2004/0033597 A1 | 2/2004 | Toma et al. |
| 2004/0037818 A1 | 2/2004 | Brand et al. |
| 2004/0048372 A1 | 3/2004 | Hariri |
| 2004/0058412 A1 | 3/2004 | Ho et al. |
| 2004/0063202 A1 | 4/2004 | Petersen et al. |
| 2004/0072344 A1 | 4/2004 | Inoue et al. |
| 2004/0136967 A1 | 7/2004 | Weiss et al. |
| 2004/0137619 A1 | 7/2004 | Tsuzuki et al. |
| 2005/0019865 A1 | 1/2005 | Kihm et al. |
| 2005/0032209 A1 | 2/2005 | Messina et al. |
| 2005/0037491 A1 | 2/2005 | Mistry et al. |
| 2005/0054098 A1 | 3/2005 | Mistry et al. |
| 2005/0058629 A1 | 3/2005 | Harmon et al. |
| 2005/0058630 A1 | 3/2005 | Harris et al. |
| 2005/0058631 A1 | 3/2005 | Kihm et al. |
| 2005/0074435 A1 | 4/2005 | Casper et al. |
| 2005/0089513 A1 | 4/2005 | Sakuragawa et al. |
| 2005/0148074 A1 | 7/2005 | Davies et al. |
| 2005/0249731 A1 | 11/2005 | Aslan et al. |
| 2006/0153815 A1 | 7/2006 | Seyda et al. |
| 2006/0153816 A1 | 7/2006 | Brown et al. |
| 2006/0153817 A1 | 7/2006 | Kihm et al. |
| 2006/0153818 A1 | 7/2006 | Dhanaraj et al. |
| 2006/0154366 A1 | 7/2006 | Brown et al. |
| 2006/0154367 A1 | 7/2006 | Kihm et al. |
| 2006/0166361 A1 | 7/2006 | Seyda et al. |
| 2006/0171930 A1 | 8/2006 | Seyda et al. |
| 2006/0188983 A1 | 8/2006 | Harris et al. |
| 2006/0233765 A1 | 10/2006 | Messina et al. |
| 2006/0233766 A1 | 10/2006 | Messina et al. |
| 2006/0234376 A1 | 10/2006 | Mistry et al. |
| 2007/0009494 A1 | 1/2007 | Mistry et al. |
| 2007/0014771 A1 | 1/2007 | Mistry et al. |
| 2007/0036767 A1 | 2/2007 | Mistry et al. |
| 2007/0141700 A1 | 6/2007 | Harmon |
| 2007/0160588 A1 | 7/2007 | Kihm |
| 2007/0178073 A1 | 8/2007 | Chang et al. |
| 2007/0218549 A1 | 9/2007 | Mansbridge |
| 2007/0264269 A1 | 11/2007 | Harmon et al. |

(56) References Cited

U.S. PATENT DOCUMENTS

| | | |
|---|---|---|
| 2007/0264713 A1 | 11/2007 | Terstegge et al. |
| 2007/0275362 A1 | 11/2007 | Edinger et al. |
| 2008/0112939 A1 | 5/2008 | Colter et al. |
| 2008/0145934 A1 | 6/2008 | Harris et al. |
| 2008/0166328 A1 | 7/2008 | Harmon et al. |
| 2008/0226595 A1 | 9/2008 | Edinger et al. |
| 2010/0210013 A1 | 8/2010 | Mistry et al. |
| 2010/0215714 A1 | 8/2010 | Messina et al. |
| 2010/0260843 A1 | 10/2010 | Messina et al. |
| 2010/0272803 A1 | 10/2010 | Mistry et al. |
| 2013/0022585 A1 | 1/2013 | Messina et al. |
| 2014/0045263 A1 | 2/2014 | Mistry et al. |

FOREIGN PATENT DOCUMENTS

| | | |
|---|---|---|
| EP | 0 382 214 | 2/1990 |
| EP | 0 529 751 | 3/1993 |
| EP | 0 552 380 | 7/1993 |
| EP | 1 216 718 | 6/2002 |
| EP | 1 264 877 | 12/2002 |
| EP | 1 302 535 | 4/2003 |
| EP | 1 312 669 | 5/2003 |
| EP | 1 316 322 | 6/2003 |
| EP | 1 405 649 | 4/2004 |
| JP | 2003-235549 | 8/2003 |
| JP | 2004-254682 | 9/2004 |
| WO | WO 90/11354 | 10/1990 |
| WO | WO 92/03917 | 3/1992 |
| WO | WO 93/04169 | 3/1993 |
| WO | WO 94/25584 | 11/1994 |
| WO | WO 95/17911 | 7/1995 |
| WO | WO 95/23216 | 8/1995 |
| WO | WO 96/01316 | 1/1996 |
| WO | WO 96/05309 | 2/1996 |
| WO | WO 98/17791 | 4/1998 |
| WO | WO 98/51317 | 11/1998 |
| WO | WO 99/03973 | 1/1999 |
| WO | WO 99/28444 | 6/1999 |
| WO | WO 99/47163 | 9/1999 |
| WO | WO 00/09666 | 2/2000 |
| WO | WO 00/38762 | 7/2000 |
| WO | WO 00/43355 | 7/2000 |
| WO | WO 00/46351 | 8/2000 |
| WO | WO 00/53795 A1 | 9/2000 |
| WO | WO 00/73421 | 12/2000 |
| WO | WO 01/11011 | 2/2001 |
| WO | WO 01/19379 | 3/2001 |
| WO | WO 01/34775 | 5/2001 |
| WO | WO 02/36751 | 5/2002 |
| WO | WO 02/46373 | 6/2002 |
| WO | WO 02/059278 | 8/2002 |
| WO | WO 02/061053 | 8/2002 |
| WO | WO 02/062969 | 8/2002 |
| WO | WO 02/063962 | 8/2002 |
| WO | WO 02/064748 | 8/2002 |
| WO | WO 02/064755 | 8/2002 |
| WO | WO 02/086107 | 10/2002 |
| WO | WO 03/023020 | 3/2003 |
| WO | WO 03/025149 | 3/2003 |
| WO | WO 03/029443 | 4/2003 |
| WO | WO 03/029445 | 4/2003 |
| WO | WO 03/039489 | 5/2003 |
| WO | WO 03/042405 | 5/2003 |
| WO | WO 03/048336 | 6/2003 |
| WO | WO 03/055992 | 7/2003 |
| WO | WO 03/064601 | 8/2003 |
| WO | WO 03/066832 | 8/2003 |
| WO | WO 03/068937 | 8/2003 |
| WO | WO 03/070922 | 8/2003 |
| WO | WO 03/072728 | 9/2003 |
| WO | WO 03/080822 | 10/2003 |
| WO | WO 03/087333 | 10/2003 |
| WO | WO 03/087392 | 10/2003 |
| WO | WO 03/089619 | 10/2003 |
| WO | WO 03/100038 | 12/2003 |
| WO | WO 03/102134 | 12/2003 |
| WO | WO 03/102151 | 12/2003 |
| WO | WO 03/104442 | 12/2003 |
| WO | WO 2004/011012 | 2/2004 |
| WO | WO 2004/011621 | 2/2004 |
| WO | WO 2004/016747 | 2/2004 |
| WO | WO 2004/023100 | 3/2004 |
| WO | WO 2004/072273 | 8/2004 |
| WO | WO 2005/001076 | 1/2005 |
| WO | WO 2005/001077 | 1/2005 |
| WO | WO 2005/001078 | 1/2005 |
| WO | WO 2005/001079 | 1/2005 |
| WO | WO 2005/001080 | 1/2005 |
| WO | WO 2005/003334 | 1/2005 |
| WO | WO 2005/021738 | 3/2005 |
| WO | WO 2005/003334 A3 | 4/2005 |
| WO | WO 2005/038012 | 4/2005 |
| WO | WO 2005/042703 | 5/2005 |
| WO | WO 2005/085421 | 9/2005 |
| WO | WO 2005/003334 R | 12/2005 |
| WO | WO 2006/027229 | 3/2006 |
| WO | WO 2006/036826 | 4/2006 |
| WO | WO 2006/071773 | 7/2006 |
| WO | WO 2006/071777 | 7/2006 |
| WO | WO 2006/071778 | 7/2006 |
| WO | WO 2006/071794 | 7/2006 |
| WO | WO 2006/071802 | 7/2006 |
| WO | WO 2006/083394 | 8/2006 |
| WO | WO 2006/105152 | 10/2006 |
| WO | WO 2006/071794 A3 | 1/2007 |
| WO | WO 2006/071794 R | 6/2007 |
| WO | WO 2007/073552 | 6/2007 |
| WO | WO 2007/108003 | 9/2007 |
| WO | WO 2008/045498 | 4/2008 |
| WO | WO 2008/060541 | 5/2008 |

OTHER PUBLICATIONS

In the U.S. Patent and Trademark Office, Non-Final Office Action in re: U.S. Appl. No. 10/877,269, dated Jan. 17, 2008, 10 pages.
In the U.S. Patent and Trademark Office, Final Office Action in re: U.S. Appl. No. 10/877,269, dated Aug. 14, 2007, 6 pages.
In the U.S. Patent and Trademark Office, Non-Final Office Action in re: U.S. Appl. No. 10/877,269, dated May 3, 2007, 12 pages.
In the U.S. Patent and Trademark Office, Non-Final Office Action in re: U.S. Appl. No. 11/315,898, dated Feb. 13, 2008, 12 pages.
In the U.S. Patent and Trademark Office, Final Office Action in re: U.S. Appl. No. 11/315,943, dated Aug. 20, 2008, 7 pages.
In the U.S. Patent and Trademark Office, Non-Final Office Action in re: U.S. Appl. No. 11/315,943, dated Feb. 12, 2008, 11 pages.
In the U.S. Patent and Trademark Office, Non-Final Office Action in re: U.S. Appl. No. 10/877,445, dated Jul. 11, 2008, 12 pages.
In the U.S. Patent and Trademark Office, Non-Final Office Action in re: U.S. Appl. No. 10/877,445, dated Mar. 19, 2008, 12 pages.
In the U.S. Patent and Trademark Office, Final Office Action in re: U.S. Appl. No. 10/877,445, dated Nov. 5, 2007, 17 pages.
In the U.S. Patent and Trademark Office, Non-Final Office Action in re: U.S. Appl. No. 10/877,445, dated May 17, 2007, 20 pages.
In the U.S. Patent and Trademark Office, Final Office Action in re: U.S. Appl. No. 10/877,445, dated Sep. 11, 2006, 30 pages.
In the U.S. Patent and Trademark Office, Non-Final Office Action in re: U.S. Appl. No. 10/877,445, dated Nov. 21, 2005, 17 pages.
In the U. S. Patent and Trademark Office, Non-Final Office Action in re: U.S. Appl. No. 11/322,372 dated Sep. 3, 2008, 13 pages.
In the U.S. Patent and Trademark Office, Non-Final Office Action in re: U.S. Appl. No. 10/877,541, dated Jul. 25, 2007, 13 pages.
In the U.S. Patent and Trademark Office, Advisory Office Action in re: U.S. Appl. No. 10/877,541, dated Apr. 18, 2007, 4 pages.
In the U.S. Patent and Trademark Office, Final Office Action in re: U.S. Appl. No. 10/877,541, dated Jan. 10, 2007, 19 pages.
In the U.S. Patent and Trademark Office, Non-Final Office Action in re: U.S. Appl. No. 10/877,541, dated Feb. 22, 2006, 13 pages.
In the U.S. Patent and Trademark Office, Advisory Office Action in re: U.S. Appl. No. 11/317,574, dated Jun. 4, 2008, 3 pages.
In the U.S. Patent and Trademark Office, Final Office Action in re: U.S. Appl. No. 11/317,574, dated Mar. 5, 2008, 10 pages.

(56) References Cited

OTHER PUBLICATIONS

In the U.S. Patent and Trademark Office, Final Office Action in re: U.S. Appl. No. 11/317,574, dated Aug. 10, 2007, 14 pages.
In the U.S. Patent and Trademark Office, Non-Final Office Action in re: U.S. Appl. No. 10/877,009 dated Jan. 9, 2008, 12 pages.
In the U.S. Patent and Trademark Office, Final Office Action in re: U.S. Appl. No. 10/877,009, dated Jul. 25, 2007, 17 pages.
In the U.S. Patent and Trademark Office, Non-Final Office Action in re: U.S. Appl. No. 10/877,009, dated Nov. 21, 2006, 15 pages.
In the U.S. Patent and Trademark Office, Non-Final Office Action in re: U.S. Appl. No. 10/876,998, dated Jun. 25, 2008, 9 pages.
In the U.S. Patent and Trademark Office, Final Office Action in re: U.S. Appl. No. 10/876,998, dated Feb. 27, 2008, 18 pages.
In the U.S. Patent and Trademark Office, Non-Final Office Action in re: U.S. Appl. No. 10/876,998, dated Jul. 13, 2007, 30 pages.
In the U.S. Patent and Trademark Office, Final Office Action in re: U.S. Appl. No. 10/876,998, dated Oct. 18, 2006, 29 pages.
In the U.S. Patent and Trademark Office, Non-Final Office Action in re: U.S. Appl. No. 10/876,998, dated Mar. 30, 2006, 24 pages.
In the U.S. Patent and Trademark Office, Non-Final Office Action in re: U.S. Appl. No. 11/321,863, dated Aug. 19, 2008, 15 pages.
In the U.S. Patent and Trademark Office, Non-Final Office Action in re: U.S. Appl. No. 11/322,003, dated Jun. 2, 2008, 14 pages.
In the U.S. Patent and Trademark Office, Non-Final Office Action in re: U.S. Appl. No. 11/321,864, dated Apr. 21, 2008, 7 pages.
In the U.S. Patent and Trademark Office, Final Office Action in re: U.S. Appl. No. 11/315,969, dated May 19, 2008, 9 pages.
In the U.S. Patent and Trademark Office, Non-Final Office Action in re: U.S. Appl. No. 11/315,969, dated Nov. 1, 2007, 12 pages.
In the U.S. Patent and Trademark Office, Final Office Action in re: U.S. Appl. No. 11/304,091, dated Apr. 11, 2008, 11 pages.
In the U.S. Patent and Trademark Office, Non-Final Office Action in re: U.S. Appl. No. 11/304,091, dated Feb. 23, 2007, 9 pages.
In the U. S. Patent and Trademark Office, Final Office Action in re: U.S. Appl. No. 11/315,898, dated Sep. 16, 2008, 8 pages.
In the U. S. Patent and Trademark Office, Non-Final Office Action in re: U.S. Appl. No. 11/317,574, dated Sep. 30, 2008, 23 pages.
In the U. S. Patent and Trademark Office, Final Office Action in re: U.S. Appl. No. 11/315,969, dated Dec. 23, 2008, 11 pages.
In the U. S. Patent and Trademark Office, Final Office Action in re: U.S. Appl. No. 11/321,864, dated Jan. 8, 2009, 10 pages.
In the U. S. Patent and Trademark Office, Final Office Action in re: U.S. Appl. No. 11/321,863, dated Feb. 12, 2009, 15 pages.
In the U. S. Patent and Trademark Office, Non-Final Office Action in re: U.S. Appl. No. 11/315,943, dated Feb. 20, 2009, 9 pages.
In the U. S. Patent and Trademark Office, Final Office Action in re: U.S. Appl. No. 10/877,445, dated Mar. 19, 2009, 15 pages.
In the U. S. Patent and Trademark Office, Non-Final Office Action in re: U.S. Appl. No. 11/481,481, dated Mar. 20, 2009, 12 pages.
In the U. S. Patent and Trademark Office, Final Office Action in re: U.S. Appl. No. 11/315,897, dated Mar. 20, 2009, 13 pages.
In the U. S. Patent and Trademark Office, Non-Final Office Action in re: U.S. Appl. No. 11/481,480, dated Mar. 20, 2009, 13 pages.
In the U. S. Patent and Trademark Office, Final Office Action in re: U.S. Appl. No. 11/322,003 dated Feb. 13, 2009, 17 pages.
In the U. S. Patent and Trademark Office, Final Office Action in re: U.S. Appl. No. 10/876,998 dated Feb. 13, 2009, 10 pages.
In the U. S. Patent and Trademark Office, Final Office Action in re: U.S. Appl. No. 11/322,372 dated Feb. 13, 2009, 14 pages.
In the U. S. Patent and Trademark Office, Non-Final Office Action in re: U.S. Appl. No. 11/315,898 dated Feb. 18, 2009, 10 pages.
In the U. S. Patent and Trademark Office, Non-Final Office Action in re: U.S. Appl. No. 11/481,456 dated Apr. 16, 2009, 14 pages.
In the U. S. Patent and Trademark Office, Final Office Action in re: U.S. Appl. No. 11/317,574 dated Apr. 29, 2009, 21 pages.
In the U. S. Patent and Trademark Office, Advisory Action in re: U.S. Appl. No. 11/315,969 dated Sep. 29, 2009, 9 pages.
In the U. S. Patent and Trademark Office, Advisory Action in re: U.S. Appl. No. 11/322,372 dated May 12, 2009, 10 pages.
In the U. S. Patent and Trademark Office, Non-Final Office Action in re: U.S. Appl. No. 10/877,446 dated Jun. 12, 2009, 16 pages.
In the U. S. Patent and Trademark Office, Final Office Action in re: U.S. Appl. No. 11/322,372 dated Aug. 6, 2009, 12 pages.
In the U. S. Patent and Trademark Office, Final Office Action in re: U.S. Appl. No. 11/481,456 dated Oct. 9, 2009, 11 pages.
In the U. S. Patent and Trademark Office, Final Office Action in re: U.S. Appl. No. 10/877,445 dated Aug. 25, 2009, 18 pages.
In the U. S. Patent and Trademark Office, Final Office Action in re: U.S. Appl. No. 11/321,863 dated Aug. 7, 2009, 11 pages.
In the U. S. Patent and Trademark Office, Final Office Action in re: U.S. Appl. No. 11/321,864 dated Aug. 17, 2009, 13 pages.
In the U. S. Patent and Trademark Office, Final Office Action in re: U.S. Appl. No. 11/315,969 dated May 13, 2009, 11 pages.
In the U. S. Patent and Trademark Office, Non-Final Office Action in re: U.S. Appl. No. 11/317,574 dated Dec. 28, 2009, 26 pages.
In the U. S. Patent and Trademark Office, Non-Final Office Action in re: U.S. Appl. No. 11/321,863 dated Jan. 7, 2010, 13 pages.
In the U. S. Patent and Trademark Office, Non-Final Office Action in re: U.S. Appl. No. 11/321,864 dated Jan. 27, 2010, 12 pages.
In the U. S. Patent and Trademark Office, Non-Final Office Action in re: U.S. Appl. No. 11/315,969 dated Jan. 27, 2010, 12 pages.
In the U. S. Patent and Trademark Office, Non-Final Office Action in re: U.S. Appl. No. 11/315,943 dated Feb. 19, 2010, 13 pages.
In the U. S. Patent and Trademark Office, Final Office Action in re: U.S. Appl. No. 11/316,104 dated Mar. 24, 2010, 12 pages.
In the U. S. Patent and Trademark Office, Non-Final Office Action in re: U.S. Appl. No. 11/481,456 dated May 14, 2010, 9 pages.
In the U. S. Patent and Trademark Office, Non-Final Office Action in re: U.S. Appl. No. 11/481,481 dated May 13, 2010, 9 pages.
In the U. S. Patent and Trademark Office, Final Office Action in re: U.S. Appl. No. 11/315,897 dated May 14, 2010, 13 pages.
In the U. S. Patent and Trademark Office, Non-Final Office Action in re: U.S. Appl. No. 11/481,480 dated May 17, 2010, 10 pages.
In the U. S. Patent and Trademark Office, Final Office Action in re: U.S. Appl. No. 10/877,445 dated Jul. 8, 2010, 20 pages.
In the U. S. Patent and Trademark Office, Non-Final Office Action in re: U.S. Appl. No. 10/876,998 dated Aug. 3, 2010, 14 pages.
In the U. S. Patent and Trademark Office, Final Office Action in re: U.S. Appl. No. 11/321,863 dated Aug. 17, 2010, 15 pages.
In the U. S. Patent and Trademark Office, Final Office Action in re: U.S. Appl. No. 11/321,864 dated Aug. 31, 2010, 7 pages.
In the U. S. Patent and Trademark Office, Final Office Action in re: U.S. Appl. No. 11/315,969 dated Aug. 31, 2010, 6 pages.
In the U. S. Patent and Trademark Office, Final Office Action in re: U.S. Appl. No. 11/322,372 dated Aug. 31, 2010, 11 pages.
In the U. S. Patent and Trademark Office, Non-Final Office Action in re: U.S. Appl. No. 11/316,104 dated Sep. 21, 2010, 13 pages.
In the U. S. Patent and Trademark Office, Final Office Action in re: U.S. Appl. No. 11/317,574 dated Oct. 6, 2010, 16 pages.
In the U. S. Patent and Trademark Office, Non-Final Office Action in re: U.S. Appl. No. 12/054,718 dated Sep. 29, 2010, 18 pages.
In the U. S. Patent and Trademark Office, Non-Final Office Action in re: U.S. Appl. No. 11/322,372 dated Jan. 21, 2010, 10 pages.
In the U. S. Patent and Trademark Office, Final Office Action in re: U.S. Appl. No. 11/481,481 dated Sep. 18, 2009, 11 pages.
In the U. S. Patent and Trademark Office, Advisory Action in re: U.S. Appl. No. 11/315,897 dated Jun. 30, 2009, 3 pages.
In the U. S. Patent and Trademark Office, Non-Final Action in re: U.S. Appl. No. 11/315,897 dated Sep. 2, 2009, 12 pages.
In the U. S. Patent and Trademark Office, Final Action in re: U.S. Appl. No. 11/481,480 dated Sep. 17, 2009, 12 pages.
In the U. S. Patent and Trademark Office, Final Action in re: U.S. Appl. No. 10/877,446 dated Jun. 4, 2010, 17 pages.
In the U. S. Patent and Trademark Office, Non-Final Action in re: U.S. Appl. No. 11/316,104 dated Oct. 31, 2008, 15 pages.
In the U. S. Patent and Trademark Office, Final Action in re: U.S. Appl. No. 10/876,998 dated May 27, 2009, 14 pages.
In the U. S. Patent and Trademark Office, Non-Final Action in re: U.S. Appl. No. 10/876,998 dated Nov. 24, 2009, 7 pages.
In the U. S. Patent and Trademark Office, Final Action in re: U.S. Appl. No. 11/322,003 dated Feb. 13, 2009, 17 pages.

(56) References Cited

OTHER PUBLICATIONS

In the U. S. Patent and Trademark Office, Non-Final Action in re: U.S. Appl. No. 10/876,998 dated Feb. 1, 2011, 11 pages.
In the U. S. Patent and Trademark Office, Non-Final Action in re: U.S. Appl. No. 11/481,456 dated Feb. 3, 2011, 10 pages.
In the U. S. Patent and Trademark Office, Non-Final Action in re: U.S. Appl. No. 11/481,481 dated Feb. 3, 2011, 10 pages.
In the U. S. Patent and Trademark Office, Non-Final Action in re: U.S. Appl. No. 12/389,305 dated Feb. 8, 2011, 14 pages.
In the U. S. Patent and Trademark Office, Non-Final Action in re: U.S. Appl. No. 11/481,480 dated Feb. 3, 2011, 10 pages.
In the U.S. Patent and Trademark Office, Final Office Action in re: U.S. Appl. No. 10/877,446 dated Nov. 2, 2011, 12 pages.
In the U.S. Patent and Trademark Office, Final Office Action in re: U.S. Appl. No. 12/389,305 dated Oct. 12, 2011, 12 pages.
In the U.S. Patent and Trademark Office, Final Office Action in re: U.S. Appl. No. 12/429,849 dated Mar. 20, 2012, 9 pages.
In the U. S. Patent and Trademark Office, Final Action in re: U.S. Appl. No. 11/481,456 dated Oct. 11, 2011, 6 pages.
In the U. S. Patent and Trademark Office, Final Action in re: U.S. Appl. No. 11/481,446 dated Nov. 2, 2011, 12 pages.
International Search Report for PCT/US2004/020931, dated Feb. 4, 2005, 5 pages (WO 2005/003334).
Written Opinion for PCT/US2004/020931, dated Feb. 4, 2005, 8 pages (WO 2005/003334).
International Search Report for PCT/US2005/046851, dated Nov. 21, 2006, 8 pages (WO 2006/071794).
Written Opinion for PCT/US2005/046851, dated Nov. 21, 2006, 12 pages (WO 2006/071794).
"Cell Isolation Theory", in Tissue Dissociation Guide, Worthington Biochemical, accessible at http://www.tissuedissociation.com, accessed Aug. 8, 2007.
"Cell Lysis, p. 2" http://www.piercenet.com/objects/view.cfm?type=Page&ID=1904ED25-8FA4-475C-8068-C2EB13D5F4E7; accessed Aug. 7, 2008.
"Unigene Entry for Hs.522632, Homo sapiens TMP Metallopeptidase Inhibitor 1 (TIMP1)," printed from http://www.ncbi.nlm.nih.gov/UniGene on Oct. 12, 2006.
Abbas, A.K. et al., Cellular and Molecular Immunology, 5th Ed. (2003) Saunders, Philadelphia, p. 171.
Aboody, K.S. et al., "Neural Stem Cells Display Extensive Tropism for Pathology in Adult Brain: Evidence From Intracranial Gliomase," *PNAS*, 2000; 97(23):12846-12851.
Agbulut, O. et al., "Comparison of Human Skeletal Myoblasts and Bone Marrow-Derived CD133+ Progenitors for the Repair of Infarcted Myocardium," *Journal of the American College of Cardiology*, 2004; 44(2):458-463.
Age-Related Eye Disease Study Research Group, "A Randomized, Placebo-Controlled, Clinical Trial of High-Dose Supplementation With Vitamins C and E, Beta Carotene, and Zinc for Age-Related Macular Degeneration and Vision Loss," AREDS Report No. 8, *Arch Ophthalmol.*, 2001; 119(10): 1417-1436.
Aggarwal et al., "Human Mesenchymal Stem Cells Modulate Allogeneic Immune Cell Responses," *Blood*, 2005; 105(4):1815-1822.
Aldskogius, H. et al., "Strategies for Repair of the Deafferented Spinal Cord," *Brain Res. Rev.*, 2002; 40:301-308.
Allcock, H.R. et al., "Synthesis of Poly[(Amino Acid Alkyl Ester)Phosphazenes]1-3," *Macromolecules*, 1977; 10(4):824-830.
Altman, G.H. et al., "Advanced Bioreactor With Controlled Application of Multi-Dimensional Strain for Tissue Engineering," *J. Biomech. Eng.*, 2002; 124:742-749.
Altman, R.D. et al., "Radiographic Assessment of Progression in Osteoarthritis," *Arthritis & Rheum.*, 1987; 30(11):1214-1225.
Anseth, K.S. et al., "In Situ Forming Degradable Networks and Their Application in Tissue Engineering and Drug Delivery," *J. of Controlled Release*, 2002; 78:199-209.
Armulik, A. et al., "Endothelial/Pericyte Interactions," *Circ. Res.*, 2005; 97:512-523.

Aston, J. E., et al., "Repair of Articular Surfaces by Allografts of Articular and Growth-Plate Cartilage," *Journal of Bone and Joint Surgery*, 1986; 68-B(1):29-35.
Auda-Boucher, G. et al., "Staging of the Commitment of Murine Cardiac Cell Progenitors," *Dev. Bio.*, 2000; 225(1):214-225.
Avital, I. et al., "Isolation, Characterization, and Transplantation of Bone Marrow-Derived Hepatocyte Stem Cells," *Biochem. & Biophys. Res. Comm.*, 2001; 288:156-164.
Azizi, S.A. et al., "Engraftment and Migration of Human Bone Marrow Stromal Cells Implanted in the Brains of Albino Rats—Similarities to Astrocyte Grafts," *Proc. Natl. Acad. Sci. USA*, 1998; 95:3908-3913.
Bai, M., et al, "Dimerization of the Extracellular Calcium-sensing Receptor (CaR) on the Cell Surface of CaR-Transfected HEK293 Cells," *J. Biol Chem.*, 1998; 273(36): 23605-23610.
Baker, K.A. et al., "Intrastriatal and Intranigral Grafting of hNT Neurons in the 6-OHDA Rat Model of Parkinson's Disease," *Exper. Neurol.*, 2000; 162:350-360.
Bakhshi, et al. "Mesenchymal stem cells from the Wharton's jelly of umbilical cord segments provide stromal support for the maintenance of cord blood hematopoietic stem cells during long-term ex vivo culture", Transfusion, 2008; 48: 2638-2644.
Balis, F. et al., "Central Nervous System Pharmacology of Antileukemic Drugs," *Am. J. of Pediatric Hematol. Oncol.*, 1989; 11(1):74-86.
Balkema, G.W. et al., "Impaired Visual Thresholds in Hypopigmented Animals," Visual Neuroscience, 1991; 6:577-585.
Bao, Z.Z. et al., "Regulation of Chamber-Specific Gene Expression in the Developing Heart by IrX 4," *Science*, 1999; 283(5405):1161-1164 (Abstract 1 page).
Barberi, T. et al., "Neural Subtype Specification of Fertilization and Nuclear Transfer Embryonic Stem Cells and Application in Parkinsonian Mice," *Nature Biotechnology*, 2003; 21(10):1200-1207.
Beck, R.W. et al., "A Clinical Comparison of Visual Field Testing With a New Automated Perimeter, The Humphrey Field Analyzer, and the Goldmann Perimeter," *Ophthalmology*, 1985; 92(1):77-82.
Bergers, G. et al., "The Role of Pericytes in Blood-Vessel Formation and Maintenance," Neuro-Oncology, 2005; 7:452-464.
Bhindi, R. et al., "Rat Models of Myocardial Infarction," *Thromb Haemost*, 2006; 96:602-610.
Björklund, L.M. et al., "Embryonic Stem Cells Develop Into Functional Dopaminergic Neurons After Transplantation in a Parkinson Rat Model," PNAS, 2002; 99(4):2344-2349.
Blakemore et al., "Modelling Large Areas of Demyelination in the Rat Reveals the Potential and Possible Limitations of Transplanted Glial Cells for Remyelination in the CNS," *GLIA*, 2002; 38:155-168.
Bradley, B.A., "The Role of HLA Matching in Transplantation," *Immunol. Lett.*, 1991; 29:55-59.
Brodsky, S.V., "Coagulation, Fibrinolysis and Angiogenesis: New Insights From Knockout Mice," *Exp. Nephrol.*, 2002; 10:299-306.
Brooks, P., "Inflammation as an Important Feature of Osteoarthritis," *Bull. World Health Org.*, 2003; 81(9):689-690.
Brown, J.A. et al., "Blockade of Programmed Death-1 Ligands on Dendritic Cells Enhances T Cell Activation and Cytokine Production," *J. Immunology*, 2003; 170:1257-1266.
Bruder et al., "Mesenchymal Stem Cell Surface Antigen SB-10 Corresponds to Activated Leukocyte Cell Adhesion Molecule and Is Involved in Osteogenic Differentiation," Journal of Bone and Mineral Research, 1998; 13(4):655-663.
Burnstein, R.M. et al., "Differentiation and Migration of Long Term Expanded Human Neural Progenitors in a Partial Lesion Model of Parkinson's Disease," *Intern. J. of Biochem. & Cell Biology*, 2004; 36:702-713.
Bussolati et al., "Isolation of Renal Progenitor Cells from Adult Human Kidney," *American Journal of Pathology*, 2005; 166(2):545-555.
Caballero, S. et al., "The Many Possible Roles of Stem Cells in Age-Related Macular Degeneration," *Graefe's Arch. Clin. Exp. Ophthalmol.*, 2004; 242:85-90.
Campbell, I.K. et al., "Human Articular Cartilage and Chondrocytes Produce Hemopoietic Colony-Stimulating Factors in Culture in Response to IL-1," *J. of Immun.*, 1991; 147(4):1238-1246.

(56) References Cited

OTHER PUBLICATIONS

Can et al., "Concise Review: Human Umbilical Cord Stroma with Regard to the Source of Fetus-Derived Stem Cells," Stem Cells, 2007; 25:2886-2895.
Cao, Q. et al., "Stem Cell Repair of Central Nervous System Injury," *J. of Neuroscience Res.*, 2002; 68:501-510.
Caplan, A.I. et al., "Mesenchymal Stem Cells: Building Blocks for Molecular Medicine in the 21st Century," Trends in Molecular Med., 2001; 7(6):259-264.
Carter, D. et al., "Characterization of MSC Potential to Treat GVHD Using Molecular Markers Linked to MSC-Mediated Immunosuppression in Vitro," *Blood*, 2005; 106(11) part 2, Abstract No. 4322, 160B.
Chader et al., "Animal Models in Research on Retinal Degenerations: Past Progress and Future Hope," Vision Research, 2002; 42:393-399.
Chagraoui, J. et al., "Fetal Liver Stroma Consists of Cells in Epithelial-To-Mesenchymal Transition," *Blood*, 2003; 101(8):2973-2982.
Chen, D. et al. "Differential Roles for Bone Morphogenic Protein (BMP) Receptor Type IB and IA in Differentiation and Specification of Mesenchymal Precursor Cells to Osteoblast and Adipocyte Lineages," *J. Cell Biol.*, 1998; 142(1):295-305.
Chen, J. et al., "Therapeutic Benefit of Intravenous Administration of Bone Marrow Stromal Cells after Cerebral Ischemia in Rats," *Stroke*, 2001; 32(4):1005-1011.
Cheng, A. et al. "Nitric Oxide Acts in a Positive Feedback Loop With BDNF to Regulate Neural Progenitor Cell Proliferation and Differentiation in the Mammalian Brain," Dev. Biol., 2003; 258:319-333.
Constantini, S. et al., "The Effects of Methylprednisolone and the Ganglioside GM1 on Acute Spinal Cord Injury in Rats," *J. Neurosurg.*, 1994; 80(1):97-111.
Coumans, B. et al., "Lymphoid Cell Apoptosis Induced by Trophoblastic Cells: A Model of Active Foeto-Placental Tolerance," *J. of Immunological Methods*, 1999; 224:185-196.
D'Cruz, P.M. et al., "Mutation of the Receptor Tyrosine Kinase Gene Mertk in the Retinal Dystrophic RCS Rat," *Hum. Mol. Genet.*, 2000; 9(4):645-651.
Daley, G.Q. et al., "Realistic Prospects for Stem Cell Therapeutics," *Hematol.*, 2003; 398-418.
Danon, D. et al., "Macrophage Treatment of Pressure Sores in Paraplegia," *J. Wound Care*, 1998; 7(6):281-283.
Danon, D. et al., "Treatment of Human Ulcers by Application of Macrophages Prepared From a Blood Unit," *Exp. Gerontol.*, 1997; 32(6):633-641.
Davies, S.M. et al., "Engraftment and Survival After Unrelated-Donor Bone Marrow Transplantation: A Report From the National Marrow Donor Program," Blood, 2000; 96(13):4096-4102.
Dawson, T.M. et al., "Neuroprotective and Neurorestorative Strategies for Parkinson's Disease," *Nat. Neurosci.*, 2002; 5 Suppl.:1058-1061.
del Monte, F. et al., "Improvement in Survival and Cardiac Metabolism After Gene Transfer of Sarcoplasmic Reticulum Ca$^{2+}$-ATPase in a Rat Model of Heart Failure," *Circulation*, 2001;104:1424-1429.
Diao et al, "Human Umbilical Cord Mesenchymal Stem Cells: Osteogenesis In Vivo as Seed Cells for Bone Tissue Engineering," J. BioMed Mater Res., 2009; 91A:123-131.
Dickinson, A.M. et al., "Non-HLA Immunogenetics in Hematopoietic Stem Cell Transplantation," *Curr. Opin. Immunol.*, 2005; 17(5):517-525.
Dimri, G.P. et al., "A Biomarker That Identifies Senescent Human Cells in Culture and in Aging Skin In Vivo," *Proc. Natl. Acad. Sci. USA*, 1995; 92:9363-9367.
Domb, A. et al., "Degradable Polymers for Site-Specific Drug Delivery," *Polymers for Advanced Technologies*, 1992; 3:279-292.
Doshi, S.N. et al., "Evolving Role of Tissue Factor and Its Pathway Inhibitor," *Critical Care Med.*, 2002; 30(5):S241-S250.
Doyle, J., "Spiraling Complexity, Robustness, and Fragility in Biology," http://www.cds.caltech.edu/~doyle/CmplxNets/Bio1.pdf, available online Feb. 28, 2004.

Draper et al., "Surface Antigens of Human Embryonic Stem Cells: Changes Upon Differentiation in Culture," J. Anat., 2002; 200:249-258.
Du, Y. et al., "Functional Reconstruction of Rabbit Corneal Epithelium by Human Limbal Cells Cultured on Amniotic Membrane," *Molecular Vision*, 2003; 9:635-643.
Dykens, J. et al., "Photoreceptor Preservation in the S334ter Model of Retinitis Pigmentosa by a Novel Estradiol Analog", *Biochemical Pharmacology*, 2004; 68: 1971-1984.
Eagle, H., "The Specific Amino Acid Requirements of a Mammalian Cell (Strain L) in Tissue Culture," *J. Biol. Chem.*, 1955; 214:839-852.
Eblenkamp, M. et al., "Umbilical Cord Stromal Cells (UCSC). Cells Featuring Osteogenic Differentiation Potential," *Der Orthopade*, Dec. 2004; 33:1338-1345 (English abstract on p. 1339).
Edelstein, M. L. et al., "Gene Therapy Clinical Trials Worldwide 1989-2004—An Overview," *J. Gene Med.*, 2004; 6(6):597-602.
Edlund, H., "Pancreatic Organogenesis—Developmental Mechanisms and Implications for Therapy," *Nat. Rev. Genet.*, 2002; 3:524-532.
Efrat, S. et al., "Cell Replacement Therapy for Type 1 Diabetes," *Trends in Molecular Medicine*, 2002; 8(7):334-339.
Ehtesham, M. et al., "Induction of Glioblastoma Apoptosis Using Neural Stem Cell-Mediated Delivery of Tumor Necrosis Factor-Related Apoptosis-Inducing Ligand," *Cancer Res.*, 2002; 62:7170-7174.
Ehtesham, M. et al., "The Use of Interleukin 12-Secreting Neural Stem Cells for the Treatment of Intracranial Glioma," *Cancer Res.*, 2002; 5657-5663.
Eisenhofer, G.E. et al., "Tyrosinase: A Developmentally Specific Major Determinant of Peripheral Dopamine," *FASEB J.*, 2003; 17:1248-1255.
Ende, N. et al., "Parkinson's Disease Mice and Human Umbilical Cord Blood," *J. Med.*, 2002; 33(1-4):173-180.
Engstad, C.S. et al., "The Effect of Soluble β-1,3-Glucan and Lipopolysaccharide on Cytokine Production and Coagulation Activation in Whole Blood," *Int. Immunopharmacol.*, 2002; 2:1585-1597.
Enzmann, V. et al., "Enhanced Induction of RPE Lineage Markers in Pluripotent Neural Stem Cells Engrafted Into the Adult Rat Subretinal Space," *Investig. Ophthalmol. Visual Sci.*, 2003; 44:5417-5422.
Fazleabas, A.T. et al., "Endometrial Function: Cell Specific Changes in the Uterine Environment," *Mol. & Cellular. Endo.*, 2002; 186:143-147.
Fernandes, A.M. et al., "Mouse Embryonic Stem Cell Expansion in a Microcarrier-based Stirred Culture System," *Journal of Biotechnology*, 2007; 132(2): 227-236.
Fiegel, H.C. et al., "Liver-Specific Gene Expression in Cultured Human Hematopoietic Stem Cells," *Stem Cells*, 2003;21:98-104.
Fields, G.B.,"Induction of Protein-Like Molecular Architecture by Self-Assembly Processes," *Bioorg. Med. Chem.*, 1999; 7(1):75-81.
Fischer, D. et al., "Lens-Injury-Stimulated Axonal Regeneration Throughout the Optic Pathway of Adult Rats," Exp. Neurol., 2001; 172:257-272.
Foley, A. et al., "Heart Induction: Embryology to Cardiomyocyte Regeneration," Trends Cardiovasc. Med., 2004; 14(3):121-125.
Franc, S. et al., "Microfibrillar Composition of Umbilical Cord Matrix : Characterization of Fibrillin, Collagen VI and Intact Collagen V," *Placenta*, 1988; 19:95-104.
Freed, C.R. et al., "Transplantation of Embryonic Dopamine Neurons for Severe Parkinson's Disease," *N. Engl. J. Med.*, 2001; 344(10):710-719.
Frenkel, O. et al., "Activated Macrophages for Treating Skin Ulceration: Gene Expression in Human Monocytes After Hypo-Osmotic Shock," *Clin. Exp. Immunol.*, 2002; 128:59-66.
Friedman, J.A. et al., "Biodegradable Polymer Grafts for Surgical Repair of the Injured Spinal Cord," *Neurosurgery*, 2002; 51(3):742-751.
Fukuchi, Y. et al., "Human Placenta-Derived Cells Have Mesenchymal Stem/Progenitor Cell Potential," *Stem Cells*, 2004; 22:649-658.
Fukuda, K., "Reprogramming of Bone Marrow Mesenchymal Stem Cells Into Cardiomyocytes," *C.R. Biol.*, 2002; 325:1027-1038.

(56) References Cited

OTHER PUBLICATIONS

Gellersen, B. et al., "Cyclic AMP and Progesterone Receptor Cross-Talk in Human Endometrium: A Decidualizing Affair," *J. Endocrinol.*, 2003; 178(3):357-372.
Gerdes, D. et al., "Cloning and Tissue Expression of Two Putative Steroid Membrane Receptors," *Biol. Chem.*, 1998; 379:907-911.
Gökhan, S. et al., "Basic and Clinical Neuroscience Applications of Embryonic Stem Cells," *Anat. Rec. (New Anat)*, 2001; 265:142-156.
Goodwin, H.S. et al., "Multilineage Differentiation Activity by Cells Isolated from Umbilical Cord Blood: Expression of Bone, Fat, and Neural Markers," *Biology of Blood and Marrow Transplantation*, 2001; 7: 581-588.
Gosiewska, A. et al., "Development of a Three-Dimensional Transmigration Assay for Testing Cell-Polymer Interactions for Tissue Engineering Applications," *Tissue Eng.*, 2001; 7(3):267-277.
Gottleib, D.I. "Large-Scale Sources of Neural Stem Cells," *Annu. Rev. Neurosci.*, 2002; 25:381-407.
Gröhn, P. et al., "Collagen-Coated $BA^{2+}$-Alginate Microcarriers for the Culture of Anchorage-Dependent Mammalian Cells," *BioTechniques*, 1997; 22(5): 970-975.
Gupta, S. et al., "Isolation and Characterization of Kidney-Derived Stem Cells," *J. of Am. Soci. of Nephrol.*, 2006; 17(11):3028-3040.
Halvorsen, Y.C. et al., "Extracellular Matrix Mineralization and Osteoblast Gene Expression by Human Adipose Tissue-Derived Stromal Cells," *Tissue Eng.*, 2001; 7(6):729-741.
Hanahan, D. "Heritable Formation of Pancreatic β-Cell Tumours in Transgenic Mice Expressing Recombinant Insulin/Simian Virus 40 Oncogenes," *Nature*, 1985; 315:115-122.
Hartgerink, J.D. et al., "Peptide-Amphiphile Nanofibers: A Versatile Scaffold for the Preparation of Self-Assembling Materials," *PNAS*, 2002; 99(8):5133-5138.
Haruta, M. et al., "In Vitro and In Vivo Characterization of Pigment Epithelial Cells Differentiated From Primate Embryonic Stem Cells," *Investig. Ophthalmol. & Visual Sci.*, 2004; 45(3):1020-1025.
Hayflick, L., "The Longevity of Cultured Human Cells," *J. Am. Geriatr. Soc.*, 1974; 22(1):1-12.
Hayflick, L., "The Strategy of Senescence," *Gerontologist*, 1974; 14(1):37-45.
Haynesworth et al., "Cell Surface Antigens on Human Marrow-Derived Mesenchymal Cells are Detected by Monoclonal Antibodies," Bone, 1992; 13:69-80.
Herrera, M.B. et al., "Mesenchymal Stem Cells Contribute to the Renal Repair of Acute Tubular Epithelial Injury," *Int. J. Mol. Med.*, 2004; 14(6):1035-1041.
Hill, D.P. et al., "Screening for Novel Pattern Formation Genes Using Gene Trap Approaches," *Methods in Enzymology*, 1993; 225:664-681.
Hill, M. et al., "Treatment for Swallowing Difficulties (Dysphagia) in Chronic Muscle Disease," *The Cochrane Library Cochrane Database Syst Rev.*, 2004; 2:1-12.
Hishikawa, K. et al., "Musculin/MyoR is Expressed in Kidney Side Population Cells and Can Regulate Their Function," *Journal of Cell Biology*, 2005; 169(6):921-928.
Holz, F.G. et al., "Intraocular Microablation of Choroidal Tissue by a 308 nm AIDA Excimer Laser for RPE-Transplantation in Patients With Age-Related Macular Degeneration," *Biomed. Technik*, (Berlin), 2003; 48:82-85.
Hongpaisan, J., "Inhibition of Proliferation of Contaminating Fibroblasts by D-Valine in Cultures of Smooth Muscle Cells From Human Myometrium," Cell Biol. Int., 2000; 24(1):1-7.
Hoynowski, S.M. et al., "Characterization and Differentiation of Equine Umbilical Cord-Derived Matrix Cells," *Biochemical and Biophysical Research Communications*, 2007; 362:347-353.
Hu, A. et al., "Hepatic Differentiation From Embryonic Stem Cells In Vitro," *Chin. Med. J.*, 2003; 116(12):1893-1897.
Hughes, G.C. et al., "Therapeutic Angiogenesis in Chronically Ischemic Porcine Myocardium: Comparative Effects of BFGF and VEGF," *Ann. Thorac. Surg.*, 2004; 77:812-818.
Hutmacher, D.W., "Scaffold Design and Fabrication Technologies for Engineering Tissues—State of the Art and Future Perspectives," *J. Biomater. Sci. Polymer Edn.*, 2001;12(1):107-24.
Igura et al. "Human Placental Derived Stem Cells Differentiate into Neural Cells," Blood , 2002; 100(11): 517A (Abstract 2021).
In't Anker, P., et al., "Isolation of Mesenchymal Stem Cells of Fetal or Maternal Origin from Human Placenta," *Stem Cells*, 2004; 22:1338-1345.
Isacson, O., "The Production and Use of Cells As Therapeutic Agents in Neurodegenerative Diseases," *The Lancet (Neurology)*, 2003; 2:417-424.
Isacson, O., et al., "Specific Axon Guidance Factors Persist in the Adult Brain as Demonstrated by Pig Neuroblasts Transplanted to the Rat," *Neurosci.*, 1996; 75(3):827-837.
Ishii, M. et al., "Molecular Markers Distinguish Bone Marrow Mesenchymal Stem Cells From Fibroblasts," *Biochemical and Biophysical Research Communications*, 2005; 332:297-303.
Ito, Y. et al., "A Quantitative Assay Using Basement Membrane Extracts to Study Tumor Angiogenesis In Vivo," *Int. J. Cancer*, 1996; 67:148-152.
Jackson, K.A. et al., "Regeneration of Ischemic Cardiac Muscle and Vascular Endothelium by Adult Stem Cells," *J. Clin. Invest.*, 2001; 107:1395-1402.
Jaffe, E.A. et al., "Culture of Human Endothelial Cells Derived From Umbilical Veins; Identification by Morphologic and Immunologic Criteria" *J Clin Invest*, 1973; 52:2745-2756.
Janderová, L. et al., "Human Mesenchymal Stem Cells as an In Vitro Model for Human Adipogenesis," Obes. Res., 2003; 11(1):65-74.
Jang, Y.K. et al., "Retinoic Acid-Mediated Induction of Neurons and Glial Cells From Human Umbilical Cord-Derived Hematopoietic Stem Cells," *J. Neurosci. Res.*, 2004; 75(4):573-584.
Jikuhara, T. et al., "Left Atrial Function as a Reliable Predictor of Exercise Capacity in Patients With Recent Myocardial Infarction," *Chest*, 1997; 111(4):922-928.
Johe, K.K. et al., "Single Factors Direct the Differentiation of Stem Cells From the Fetal and Adult Central Nervous System," *Genes & Devel.*, 1996; 10:3129-3140.
Johnstone, B. et al., "In Vitro Chondrogenesis of Bone-Marrow-Derived Mesenchymal Progenitor Cells," *Exp. Cell Res.*, 1998; 238:265-272.
Jomura, S. et al., "Potential Treatment of Cerebral Global Ischemia with Oct-4+ Umbilical Cord Matrix Cells," Stem Cells, Sep. 7, 2006, AlphaMed Press, Downloaded from www.StemCells.com at Ethicon, Inc. on Sep. 11, 2006 and Supplemental Data: 2.
Jones, J. et al., "Insulin-Like Growth Factors and their Binding Proteins: Biological Actions," Endocrine Review, 1995; 16(1):3-34.
Jones-Villeneuve, E.M. et al., "Retinoic Acid-Induced Neural Differentiation of Embryonal Carcinoma Cells," *Mol. & Cellu. Biol.*, 1983; 3(12):2271-2279.
Jørgensen, N.R. et al., "Intercellular Calcium Signaling Occurs Between Human Osteoblasts and Osteoclasts and Requires Activation of Osteoclast P2X7 Receptors," *The Journal of Biological Chemistry*, (2002); 277(9): 7574-7580.
Joussen, A.M. "Cell Transplantation in Age Related Macular Degeneration: Current Concepts and Future Hopes," *Graefe's Arch. Clin. Exp. Ophthalmol.*, 2004; 242:1-2.
Kadiyala, S. et al., "Culture Expanded Canine Mesenchymal Stem Cells Possess Osteochondrogenic Potential In Vivo and In Vitro," *Cell Transplant.*, 1997; 6(2):125-134.
Kawata, M. et al., "Transcriptional Control of HLA-A,B,C Antigen in Human Placental Cytotrophoblast Isolated Using Trophoblast- and HLA-Specific Monoclonal Antibodies and the Fluorescence-Activated Cell Sorter," J. Exp. Med., Sep. 1984; 160:633-651.
Kicic, A. et al., "Differentiation of Marrow Stromal Cells Into Photoreceptors in the Rat Eye," J. of Neurosci., 2003; 23(21):7742-7749.
Kim, J. et al., "Dopamine Neurons Derived From Embryonic Stem Cells Function in an Animal Model of Parkinson's Disease," *Nature*, 2002; 418:50-56.
Kim, J.Y. et al., "Ocular Surface Reconstruction: Limbal Stem Cell Transplantation," *Ophthal. Clin. N. Am.*, 2003; 16:67-77.
Kim, S.K. et al., "Intercellular Signals Regulating Pancreas Development and Function," *Genes Dev.*, 2001; 15:111-127.

(56) References Cited

OTHER PUBLICATIONS

Kirschstein, R. et al., "Can Stem Cells Repair a Damaged Heart?" *Stem Cells: Scientific Progress and Future Research Directions*, 2001; 87-92.
Kisiday, J. et al., "Self-Assembling Peptide Hydrogel Fosters Chondrocyte Extracellular Matrix Production and Cell Division: Implications for Cartilage Tissue Repair," *PNAS*, 2002; 99(15):9996-10001.
Klassen, H. et al., "Stem Cells and Retinal Repair," *Prog. Retin. Eye Res.*, 2004; 23(2):149-181.
Klein, J., Immunology: The Science of Self-Nonself Discrimination, John Wiley & Sons, New York, 1982; 453-58.
Kokufuta, E. et al., "Effects of Surfactants on the Phase Transition of Poly(N-isopropylacrylamide) Gel," *Macromolecules*, 1993; 26:1053-1059.
Kurtz, A. et al., "Activity in Fetal Bovine Serum that Stimulates Erythroid Colony Formation in Fetal Mouse Livers is Insulinlike Growth Factor I," *J. Clin. Invest.*, 1985; 76;1643-1648.
Kusama et al., "Growth and morphogenesis of mouse prostate epithelial cells in collagen gel matrix culture" *Cell Biol Int Rep*, 1989; 13:569-575.
Laface, D. et al., "Gene Transfer Into Hematopoietic Progenitor Cells Mediated by an Adeno-Associated Virus Vector," *Virology*, 1988; 162:483-486.
Lang, K.J.D. et al., "Differentiation of Embryonic Stem Cells to a Neural Fate: A Route to Re-Building the Nervous System?" *J. of Neurosci. Res.*, 2004; 76:184-92.
Langeggen, H. et al., "HUVEC Take Up Opsonized Zymosan Particles and Secrete Cytokines IL-6 and IL-8 In Vitro," *FEMS Immunol. Med. Microbiol.*, 2003; 36:55-61.
Le Belle, J.E. et al., "Stem Cells for Neurodegenerative Disorders: Where Can We Go From Here?," *Biodrugs*, 2002; 16(6):389-401.
Le Bouteiller, P. et al., "Soluble HLA-G1 at the Materno-Foetal Interface-A Review," *Placenta*, 2003; 24(Suppl. A):S10-S15.
Li, A. et al., "IL-8 Directly Enhanced Endothelial Cell Survival, Proliferation, and Matrix Metalloproteinases Production and Regulated Angiogenesis," *J. Immunol.*, 2003; 170:3369-3376.
Li, C.D. et al, "Mesenchymal Stem Cells Derived From Human Placenta Suppress Allogeneic Umbilical Cord Blood Lymphocyte Proliferation," *Cell Research*, 2005; 15(7):539-547.
Li, L.X. et al., "Inherited Retinal Dystrophy in The RCS Rat: Prevention of Photoreceptor Degeneration by Pigment Epithelial Cell Transplantation," *Exp. Eye Res.*, 1988; 47:911-917.
Li, Y. et al., "Intact, Injured, Necrotic and Apoptotic Cells after Focal Cerebral Ischemia in the Rat," *J. Neurol. Sci.*, 1998; 156:119-132.
Li, Y. et al., "Intracerebral Transplantation of Bone Marrow Stromal Cells in a 1-Methyl-4-Phenyl-1,2,3,6-Tetrahydropyridine Mouse Model of Parkinson's Disease," *Neuroscience Letts.*, 2001; 315:67-70.
Li, Y. et al., "Transplanted Olfactory Ensheathing Cells Promote Regeneration of Cut Adult at Optic Nerve Axons," *J. of Neuro.*, 2003; 23(21):7783-7788.
Li, Y. et al., "Ultrastructural and Light Microscopic Evidence of Apoptosis after Middle Cerebral Artery Occlusion in the Rat," *Am. J. Pathol.*, 1995; 146(5):1045-1051.
Lindenlaub, T. et al., "Partial Sciatic Nerve Transection as a Model of Neuropathic Pain: A Qualitative and Quantitative Study," *PAIN*, 2000; 89(1): 97-106.
Lindvall, O. et al., "Stem Cell Therapy for Human Neurodegenerative Disorders—How to Make It Work," *Nature Medicine*, 2004;10(Suppl.):S42-S50.
Liu, K. et al., "Constitutive and Regulated Expression of Telomerase Reverse Transcriptase (hTERT) in Human Lymphocytes," *Proc. Natl. Acad. Sci.*, 1999; 96:5147-5152.
Liu, Y. et al., "Molecular and Genetic Mechanisms of Obesity: Implications for Future Management," *Curr. Mol. Med.*, 2003; 3(4):325-340.
Lockhart, D.J. et al., "Expression Monitoring by Hybridization to High-Density Oligonucleotide Arrays," *Nat. Biotechnol.*, 1996;14:1675-1680.

Lodie, T.A. et al., "Systematic Analysis of Reportedly Distinct Populations of Mulitpotent Bone Marrow-Derived Stem Cells Reveals a Lack of Distinction," *Tissue Engineering*, 2002; 8(5):739-751.
Lund, R.D. et al., "Cell Transplantation as a Treatment for Retinal Disease," *Progress in Retinal and Eye Research*, 2001; 20(4):415-449.
Lund, R.D. et al., "Retinal Transplantation: Progress and Problems in Clinical Application," *J. Leukocyte Biol.*, 2003; 74:151-160.
Lund, R.D. et al., "Subretinal Transplantation of Genetically Modified Human Cell Lines Attenuates Loss of Visual Function in Dystrophic Rats," *PNAS*, 2001; 98(17):9942-9997.
Luo, D. et al., "Synthetic DNA Delivery Systems," *Nat. Biotechnol.*, 2000; 18:33-36.
Luyten, F.P. et al., "Skeletal Tissue Engineering: Opportunities and Challenges," *Best Pract. Res. Clin. Rheumatol.*, 2001; 15(5):759-769.
Ma, L. et al., "Human Umbilical Cord Wharton's Jelly-Derived Mesenchymal Stem Cells Differentiation into Nerve-Like Cells," *Chinese Med. Jour.*, 2005; 118(23):1987-1993.
Ma, P.X . et al., "Synthetic Nano-Scale Fibrous Extracellular Matrix ," *J. Biomed Mater Res.*, 1999; 46(1):60-72.
MacDonald, R.J. "Expression of the Pancreatic Elastase I Gene in Transgenic Mice," *Hepatology*, 1987; 7(1):42S-51S.
Mackay, A.M. et al., "Chondrogenic Differentiation of Cultured Human Mesenchymal Stem Cells From Marrow," *Tissue Engineering*, 1998; 4(4):415-428.
Maeshima, A. et al., "Adult Kidney Tubular Cell Population Showing Phenotypic Plasticity, Tubulogenic Capacity, and Integration Capability into Developing Kidney," *Journal of American Society of Nephrology*, 2006; 17(1):188-198.
Makino et al., "Cardiomyocytes can be generated from marrow stromal cells in vitro," *J. Clin. Invest.*, 1999; 103:697-70.
Marx, W.F. et al., "Endovascular Treatment of Experimental Aneurysms by Use of Biologically Modified Embolic Devices: Coil-Mediated Intraaneurysamal Delivery of Fibroblast Tissue Allografts," *Am. J. Neuroradiol.*, 2001; 22:323-333.
Mason, A.J. et al., "The Hypogonadal Mouse: Reproductive Functions Restored by Gene Therapy," *Science*, 1986; 234:1372-1378.
Mayer-Proschel, M. et al., "Isolation of Lineage-Restricted Neuronal Precursors From Multipotent Neuroepithelial Stem Cells," *Neuron.*, 1997; 19:773-785.
"MCDB 153 Medium," Sigma-Aldrich, Inc. Available online at <http://www.sigmaaldrich.com/etc/medialib/docs/Sigma/Product_Information_Sheet/1/m7403pis.Par.001.File.tmp/m7403pis.pdf>. Last accessed Feb. 7, 2011.
McDonald J.A. et al., "Diminished Responsiveness of Male Homosexual Chronic Hepatitis B Virus Carriers With HTLV-III Antibodies to Recombinant α-Interferon," *Hepatology*, 1987; 7(4):719-723.
Mediceetty, S. et al., "Transplantation of Human Umbilical Cord Matrix Stem Cells Alleviates Apomorphine-Induced Rotations in Parkinsonian Rats", 2003, XP-002383776, 1 page.
Melero-Martin, J. et al., "Optimal In-Vitro Expansion of Chondroprogenitor Cells in Monolayer Culture," *Biotechnology and Bioengineering*, 2006; 93(3):519-533.
Merriam Webster Medline Plus Online Medical Dictionary, definitions of "undifferentiated," and "differentiate," and "differentiation." Retrieved online Mar. 6, 2007, URL:www.nlm.hih.gov/medlineplus/mplusdictionary.html.
Merriam-Webster Medline Plus Online Medical Dictionary, definitions of "iliac", "ilium" ileal/ileac and "ileum"; accessible online at http://www.nlm.nih.gov/medlineplus/mplusdictionary.html, last accessed Feb. 12, 2008.
Merriam-Webster Online Dictionary 10$^{th}$ Edition, Definition of "Scaffold" [retrieved on Sep. 12, 2008].
Merx, M.W. et al., "Transplantation of Human Umbilical Vein Endothelial Cells Improves Left Ventricular Function in a Rat Model of Myocardial Infarction," *Basic Res. Cardiol.*, 2005; 100:208-216.
Messina, D.J., et al., "Comparison of Pure and Mixed Populations of Human Fetal-Derived Neural Progenitors Transplanted Into Intact Adult Rat Brain," *Exper. Neurol.*, 2003; 184:816-829.
Mitchell, K.E. et al., "Matrix Cells From Wharton's Jelly Form Neurons and Glia," *Stem Cells*, 2003; 21:50-60.

(56) References Cited

OTHER PUBLICATIONS

Moll, S. et al., "Monitoring Warfarin Therapy in Patients With Lupus Anticoagulants," *Ann. Intern. Med.*, 1997; 127(3):177-185.

Mombaerts, P. et al., "Creation of a Large Genomic Deletion at the T-Cell Antigen Receptor β-Subunit Locus in Mouse Embryonic Stem Cells by Gene Targeting," *Proc. Nat. Acad. Sci. USA*, 1991; 88:3084-3087.

Moore, A.E. et al., "Parkinsonian Motor Deficits are Reflected by Proportional A9/A10 Dopamine Neuron Degeneration in the Rat," *Exp. Neurol.*, 2001; 172(2):363-76.

Morgenstern, J.P. et al., "Advanced Mammalian Gene Transfer: High Titre Retroviral Vectors With Multiple Drug Selection Markers and a Complementary Helper-Free Packaging Cell Line," *Nucleic Acids Res.*, 1990; 18(12):3587-3596.

Morigi, M. et al., "Mesenchymal Stem Cells are Renotropic, Helping to Repair the Kidney and Improve Function in Acute Renal Failure," *J. Am. Soc. Nephrol.*, 2004; 15(7):1794-1804.

Morishima, Y. et al., "The Clinical Significance of Human Leukocyte Antigen (HLA) Allele Compatibility in Patients Receiving a Marrow Transplant from Serologically HLA-A, HLA-B, and HLA-DR Matched Unrelated Donors," *Blood*, 2002; 99(11):4200-4206.

Moulder, J.E., "Pharmacological Intervention to Prevent or Ameliorate Chronic Radiation Injuries," *Semin. Radiat. Oncol.*, 2003; 13(1):73-84.

Nakamura, T. et al., "Ocular Surface Reconstruction Using Cultivated Mucosal Epithelial Stem Cells," *Cornea*, 2003; 22(Supp. 1):S75-S80.

Naughton et al., "Cells isolated from Wharton's jelly of the human umbilical cord develop a cartilage phenotype when treated with TGF-b in vitro," 1997; FASEB J 11:A19 (Abstract 108).

Newman, K.D. et al., "Poly(D,L lactic-co-glycolic acid) Microspheres as Biodegradable Microcarriers for Pluripotent Stem Cells," *Biomaterials*, 2004; 25:5763-5771.

Nicosia, R.F. et al., "Modulation of Microvascular Growth and Morphogenesis by Reconstituted Basement Membrane Gel in Three-Dimensional Cultures of Rat Aorta: A Comparative Study of Angiogenesis in Matrigal, Collagen, Fibrin, and Plasma Clot," *In Vitro Cell Dev. Biol.*, 1990; 26:119-128.

Ninichuk, V. et al., "Multipotent Mesenchymal Stem Cells Reduce Interstitial Fibrosis But Do Not Delay Progression of Chronic Kidney Disease in Collagen4A3-Deficient Mice," *Kidney Int.*, 2006; 70:121-129.

Nishida, K. et al., "Functional Bioengineered Corneal Epithelial Sheet Grafts From Corneal Stem Cells Expanded Ex Vivo on a Temperature-Responsive Cell Culture Surface," *Transplantation*, 2004; 77(3):379-385.

Nishishita, T. et al., "A Potential Pro-Angiogenic Cell Therapy With Human Placenta-Derived Mesenchymal Cells," *Biochemical and Biophysical Research Communications*, 2004; 325:24-31.

Nixon, P.J. et al., "The Contribution of Cone Responses to Rat Electroretinograms," *Clin. Experiment Ophthalmol.*, 2001; 29:193-196.

Nork, T.M. et al., "Swelling and Loss of Photoreceptors in Chronic Human and Experimental Glaucomas," *Arch. Ophthalmol.*, 2000; 118:235-245.

Nowak, A.P. et al., "Rapidly Recovering Hydrogel Scaffolds From Self-Assembling Diblock Copolypeptide Amphilphiles," *Nature*, 2002; 417:424-428.

Nusinowitz, S. et al., "Rod Multifocal Electroretinograms in Mice," *Invest Ophthalmol Vis. Sci.*, 1999; 40(12): 2848-2858.

Oh, S.H. et al., "Hepatocyte Growth Factor Induces Differentiation of Adult Rat Bone Marrow Cells Into a Hepatocyte Lineage In Vitro," *Biochem. & Biophys. Res. Comm.*, 2000; 279:500-504.

Okumoto, K. et al., "Differentiation of Bone Marrow Cells Into Cells That Express Liver-Specific Genes In Vitro: Implication of the Notch Signals in Differentiation," *Biochem. & Biophys. Res. Commun.*, 2003; 304:691-695.

Oliver, J.A. et al., "The Renal Papilla is a Niche for Adult Kidney Stem Cells," *J. Clin Invest.*, 2004, 114(6):795-804.

Orlic, D. et al., "Stem Cells for Myocardial Regeneration," *Circ. Res.*, 2002; 91:1092-1102.

Ornitz, D.M. et al., "Elastase I Promoter Directs Expression of Human Growth Hormone and SV40 T Antigen Genes to Pancreatic Acinar Cells in Transgenic Mice," *Cold Spring Harbor Symp. Quant. Biol.*, 1985; 50:399-409.

Osborne, N.N. et al., "Some Current Ideas on the Pathogenesis and the Role of Neuroprotection in Glaucomatous Optic Neuropathy," *Eur. J. Ophthalmol.*, 2003; 13(Supp. 3):S19-S26.

Palù, G. et al., "In Pursuit of New Developments for Gene Therapy of Human Diseases," *J. Biotechnol.*, 1999; 68:1-13.

Panepucci, R.A. et al., "Comparison of Gene Expression of Umbilical Cord Vein and Bone Marrow-Derived Mesenchymal Stem Cells," *Stem Cells*, 2004; 22(7):1263-78.

Pera, M.F. et al., "Human Embryonic Stem Cells", *J. Cell Science*, 2000; 113:5-10.

Phipps, J.A. et al., "Paired-Flash Identification of Rod and Cone Dysfunction in the Diabetic Rat," *Investigative Ophthalmology & Visual Science*, 2004; 45:4592-4600.

Pisharodi, M. et al., "An Animal Model for Neuron-Specific Spinal Cord Lesions by the Microinjection of N-Methylaspartate, Kainic Acid, and Quisqualic Acid," *Appl. Neurophysiology*, 1985; 48:226-233.

Pittenger, M.F. et al., "Mesenchymal Stem Cells and Their Potential as Cardiac Therapeutics," *Circ. Res.*, 2004; 95:9-20.

Pittenger, M.F. et al., "Multilineage Potential of Adult Human Mesenchymal Stem Cells," *Science*, 1999; 284:143-47 and seven pages of online supplementary material.

Plaia, T., et al., "Characterization of a New NIH-Registered Variant Human Embryonic Stem Cell Line, BG01V: A Tool for Human Embryonic Stem Cell Research," *Stem Cells*, 2006: 24(3):531-546.

Pountos, I. et al., "Mesenchymal Stem Cell Tissue Engineering: Techniques for Isolation, Expansion and Application," *Injury*, 2007; 38(Supp. 4):S23-33.

Quaini, F. et al., "Chimerism of the Transplanted Heart," *NEJM*, 2002; 346:5-15.

Rabbany, S.Y. et al., "Molecular Pathways Regulating Mobilization of Marrow-Derived Stem Cells for Tissue Revascularization," *Trends in Molecular Med.*, 2003; 9(3):109-117.

Rafii, S. et al., "Therapeutic Stem and Progenitor Cell Transplantation for Organ Vascularization and Regeneration," *Nature Med.*, 2003; 9(6):702-712.

Rahman, Z. et al., "Isolation and Primary Culture Urothelial Cells from Normal Human Bladder," *Urol. Research*, 1987; 15:315-320.

Ramon-Cueto, A. et al., "Functional Recovery of Paraplegic Rats and Motor Axon Regeneration in Their Spinal Cords by Olfactory Ensheathing Glia," *Neuron*, 2000; 25:425-435.

Readhead, C. et al., "Expression of a Myelin Basic Protein Gene in Transgenic Shiverer Mice: Correction of the Dysmyelinating Phenotype," *Cell*, 1987; 48:703-712.

Refaie, A. et al., "Experimental Islet Cell Transplantation in Rats: Optimization of the Transplantation Site," *Trans. Proc.*, 1998; 30:400-403.

Rehman, J. et al., "Secretion of Angiogenic and Antiapoptotic Factors by Human Adipose Stromal Cells," *Circulation*, 2004; 109:1292-1298.

Reubinoff, B.E. et al., "Neural Progenitors From Human Embryonic Stem Cells," *Nature Biotechnology*, 2001; 19:1134-1140.

Reyes, M. et al., "Purification and Ex Vivo Expansion of Postnatal Human Marrow Mesodermal Progenitor Cells," *Blood*, 2001; 98(9):2615-2625.

Rezai, K.A. et al., "Iris Pigment Epithelium Transplantation," *Graefe's Arch. Clin. Ophthalmol.*, 1997; 235:558-562.

Rickard, D.J. et al., "Induction of Rapid Osteoblast Differentiation in Rat Bone Marrow Stromal Cell Cultures by Dexamethasone and BMP-2," *Dev. Biol.*, 1994; 161:218-228.

Rios, M. et al., "Catecholamine Synthesis is Mediated by Tyrosinase in the Absence of Tyrosine Hydroxylase," *J. Neurosci.*, 1999, 19(9):3519-3526.

Romanov, Y.A. et al., "Searching for Alternative Sources of Postnatal Human Mesenchymal Stem Cells: Candidate MSC-Like Cells from Umbilical Cord," *Stem Cells*, 2003; 21:105-110.

(56) References Cited

OTHER PUBLICATIONS

Rosen, E.M. et al., "HGF/SF in Angiogenesis," *Ciba Found. Symp.*, 1997; 212:215-229.
Roskams, A.J. et al., "Directing Stem Cells and Progenitor Cells on the Stage of Spinal Cord Injury," *Exp. Neurol.*, 2005; 193:267-272.
Russo, E., Cultivating Policy from Cell Types, *The Scientist*, 2001; 15(11):6 (printout is numbered 1-6).
Rutherford, A. et al., "Eyeing-Up Stem Cell Transplantation," *Trends in Molecular Medicine*, 2001; 7(1):11.
Sagrinati, C. et al., "Isolation and Characterization of Multipotent Progenitor Cells from the Bowman's Capsule of Adult Human Kidney," *Journal of American Society of Nephrology*, 2006; 17(9)2443-56.
Sahn, D.J. et al., "Recommendations Regarding Quantitation in M-Mode Echocardiography: Results of a Survey of Echocardiographic Measurements," *Circulation*, 1978; 58(6):1072-83.
Sakariassen, K.S. et al., "Methods and Models to Evaluate Shear-Dependent and Surface Reactivity-Dependent Antithrombotic Efficacy," *Thromb. Res.*, 2001; 104:149-174.
Salcedo, R. et al., "Human Endothelial Cells Express CCR2 and Respond to MCP-1: Direct Role of MCP-1 in Angiogenesis and Tumor Progression," *Blood*, 2000; 96(1):34-40.
Salgado, A.J. et al., "Bone Tissue Engineering: State of the Art and Future Trends," *Macromol. Biosci.*, 2004; 4:743-765.
Sauvè, Y. et al., "The Relationship Between Full Field Electroretinogram and Perimetry-Like Visual Thresholds in RCS Rats During Photoreceptor Degeneration and Rescue by Cell Transplants," *Vision Res.*, 2004; 44(1):9-18.
Schallert, T. et al., "Use-Dependent Structural Events in Recovery of Function," *Brain Plasticity, Adv. Neurol.*, 1997; 73:229-238.
Schouten, J.W. et al., "A Review and Rationale for the Use of Cellular Transplantation as a Therapeutic Strategy for Traumatic Brain Injury," *Journal of Neurotrauma*, 2004; 21(11):1501-1538.
Schraermeyer, U. et al., "Subretinally Transplanted Embryonic Stem Cells Rescue Photoreceptor Cells From Degeneration in the RCS Rats," *Cell Transplantation*, 2001; 10:673-680.
Schreuder, G.M. et al., "The HLA Dictionary 1999: A Summary of HLA-A, -B, -C,—DRB1/3/4/5, -DQB1 Alleles and Their Association with Serologically Defined HLA-A, -B, -C, -DR and —DQ Antigens," *Tissue Antigens*, 1999; 54(4):409-37.
Schwartz, R.E. et al., "Multipotent Adult Progenitor Cells From Bone Marrow Differentiate Into Functional Hepatocyte-Like Cells," *J. of Clin. Invest.*, 2002; 109:1291-1302.
Sébire, G. et al., "In Vitro Production of IL-6, IL-1β, and Tumor Necrosis Factor-α by Human Embryonic Microglial and Neural Cells," *J. Immunol.*, 1993; 150(4):1517-1523.
Seiji, T. et al., Possibility of Regenerative Medicine Using Human Amniotic Cells, Regenerative Medicine, 2002; 1(2):79-85.
Sethe, S. et al., "Aging of Mesenchymal Stem Cells," Ageing Research Reviews, 2006; 5:91-116.
Shani, M., "Tissue-Specific Expression of Rat Myosin Light-Chain 2 Gene in Transgenic Mice," *Nature*, 1985; 314:283-286.
Shimizu, T. et al., "Fabrication of Pulsatile Cardiac Tissue Grafts Using a Novel 3-Dimensional Cell Sheet Manipulation Technique and Temperature-Responsive Cell Culture Surfaces," *Circulation Research*, 2002; 90:e40-e48.
Shimizu, T. et al., "Cell Sheet Engineering for Myocardial Tissue Reconstruction," *Biomaterials*, 2003; 24:2309-2316.
Shuto, T. et al., "Dexamethasone Stimulates Osteoclast-Like Cell Formation by Inhibiting Granulocyte-Macrophage Colony-Stimulating Factor Production in Mouse Bone Marrow Cultures," *Endocrinology*, 1994; 134(3):1121-1126.
Siminoff, R. et al., "Properties of Reptilian Cutaneous Mechanoreceptors," *Exp. Neurol.*, 1968; 20:403-414.
Song, H. et al., "Astroglia Induce Neurogenesis From Adult Neural Stem Cells," *Nature*, 2002; 417(6884):39-44.
Sordillo, L.M. et al., "Culture of Bovine Mammary Epithelial Cells in D-Valine Modified Medium: Selective Removal of Contaminating Fibroblasts," *Cell Biol. Int. Rep.*, 1988; 12(5):354-365.
Storch, T.G. "Oxygen Concentration Regulates 5-Azacytidine-Induced Myogenesis in $C_3H/10T1/2$ Cultures," *Biochim. Biophys. Acta*, 1990; 1055:126-129.
Street, C.N. et al., "Stem Cells: A Promising Source of Pancreatic Islets for Transplantation in Type 1 Diabetes," *Curr. Top Dev. Biol.*, 2003; 58:111-136.
Svendsen, C.N. "The Amazing Astrocyte," *Nature*, 2002; 417:29-32.
Svendsen, C.N. et al., "Long-Term Survival of Human Central Nervous System Progenitor Cells Transplanted Into a Rat Model of Parkinson's Disease," *Experim. Neurol.*, 1997; 148:135-146.
Swift, G.H. et al., "Tissue-Specific Expression of the Rat Pancreatic Elastase I Gene in Transgenic Mice," *Cell*, 1984; 38:639-646.
Tao, W., "Application of Encapsulated Cell Technology for Retinal Degenerative Disease", *Expert. Opin. Biol. Ther.*, 2006; 6(7): 717-726.
Taylor, D.A. et al., "Cardiac Chimerism as a Mechanism for Self-Repair: Does it Happen and if so to What Degree?" *Circulation*, 2002; 106:2-4.
Taylor, D.A. et al., "Regenerating Functional Myocardium: Improved Performance After Skeletal Myoblast Transplantation," *Nature Medicine*, 1998; 4(8):929-1200).
Timmermans, F. et al., "Stem Cells for the Heart, Are We There Yet?" Cardiology, 2003; 100:176-185.
Toma, C. et al., "Human Mesenchymal Stem Cells Differentiate to a Cardiomyocyte Phenotype in the Adult Murine Heart," Circulation 2002; 105:93-98.
Tomita, M. et al., "Bone Marrow-Derived Stem Cells Can Differentiate Into Retinal Cells in Injured Rat Retina," Stem Cells, 2002; 20:279-283.
Tremain, N. et al., "MicroSAGE Analysis of 2,353 Expressed Genes in a Single Cell-Derived Colony of Undifferentiated Human Mesenchymal Stem Cells Reveals mRNAs of Multiple Cell Lineages," *Stem Cells*, 2001; 19:408-418.
Tresco, P.A. et al., "Cellular Transplants As Sources for Therapeutic Agents," *Advanced Drug Delivery Reviews*, 2000; 42:3-27.
Tsonis, P.A. et al., "Lens and Retina Regeneration: Transdifferentiation, Stem Cells and Clinical Applications," *Experim. Eye Res.*, 2004; 78:161-172.
Turner, D., "The Human Leucocyte Antigen (HLA) System," *Vox Sang.*, 2004; 87(Suppl 1):S87-S90.
Tusher, V.G. et al., "Significance Analysis of Microarrays Applied to the Ionizing Radiation Response," *PNAS*, 2001; 98(9):5116-5121.
Ujike, H. et al., "Gene Expression Related to Synaptogenesis, Neuritogenesis, and MAP Kinase in Behavioral Sensitization to Psychostimulants," *Ann. N.Y. Acad. Sci.*, 2002; 965:55-67.
Ulloa-Montoya, F. et al., "Culture Systems for Pluripotent Stem Cells," *Journal of Bioscience and Bioengineering*, 2005; 100(1):12-27.
Urbich, C. et al., "Endothelial Progenitor Cells Characterization and Role in Vascular Biology,", *Circ. Res.*, 2004; 95:343-353.
Vajsar, J. et al., "Walker-Warburg Syndrome," *Orphanet Journal of Rare Diseases*, 2006; 1:29.
Van Hoffelen, S.J. et al., "Incorporation of Murine Brain Progenitor Cells Into the Developing Mammalian Retina," *Invest. Ophthalmol. Vis. Sci.*, 2003; 44(1):426-434.
Vassliopoulos, G. et al., "Transplanted Bone Marrow Regenerates Liver by Cell Fusion," *Nature*, 2003; 422:901-904.
Verma, I. M. et al., "Gene Therapy—Promises, Problems and Prospects," *Nature*, 1997; 389:239-242.
Vermot-Desroches, C. et al., "Heterogeneity of Antigen Expression Among Human Umbilical Cord Vascular Endothelial Cells: Identification of Cell Subsets by Co-Expression of Haemopoietic Antigens," *Immunol. Lett.*, 1995; 48:1-9.
Villegas-Perez, M.P. et al., "Influences of Peripheral Nerve Grafts on the Survival and Regrowth of Axotomized Retinal Ganglion Cells in Adult Rats," *J. Neurosci.*, 1988; 8(1):265-280.
Villegas-Perez, M.P. et al., "Rapid and Protracted Phases of Retinal Ganglion Cell Loss Follow Axotomy in the Optic Nerve of Adult Rats," *J. Neurobiology*, 1993; 24(1):23-36.
von Koskull, H. et al., "Induction of Cytokeratin Expression in Human Mesenchymal Cells," *J. Cell Physiol.*, 1987; 133:321-329.
Walboomers, X .F. et al., "Cell and Tissue Behavior on Micro-Grooved Surfaces," *Odontology*, 2001; 89:2-11.

(56) References Cited

OTHER PUBLICATIONS

Walker, M.B. et al. (eds.), Dictionary of Science and Technology, Definition of graft, Larousse, 1995; 486-487, 558-559.
Wang, D. et al., "Synthesis and Characterization of a Novel Degradable Phosphate-Containing Hydrogel," *Biomaterials*, 2003; 24:3969-3980.
Wang, X. et al., "Cell Fusion Is the Principal Source of Bone-Marrow-Derived Hepatocytes," *Nature*, 2003; 422:897-900.
Wang, Y. et al., "Enhanced Recovery of Hematopoietic Progenitor and Stem Cells from Cultivated, Postpartum Human Placenta," *Blood*, 2001; 98(11): 183a (Abstract 769).
Webster, T.J. et al., "Nanoceramic Surface Roughness Enhances Osteoblast and Osteoclast Functions for Improved Orthopaedic/Dental Implant Efficacy," *Scripta Materialia*, 2001; 44(8/9):1639-1642.
Wegman, A. et al., "Nonsteroidal Anti-Inflammatory Drugs or Acetaminophen for Osteoarthritis of the Hip or Knee? A Synstematic Review of Evidence and Guidelines," *J. Rheumatol.*, 2004; 31(2):344-354.
Weiss, M.L. et al., "Human Umbilical Cord Matrix Stem Cells: Preliminary Characterization and Effect of Transplantation in a Rodent Model of Parkinson's Disease," *Stem Cells*, 2006; 24:781-792.
Weiss, M.L. et al., "Transplantation of Porcine Umbilical Cord Matrix Cells Into the Rat Brain," *Exp. Neur.*, 2003; 182:288-299.
Wenning, G.K. et al., "Neural Transplantation in Animal Models of Multiple System Atrophy: A Review," *J. Nueral Transm.*, 1999; Suppl.(55):103-113.
Wikipedia, Definition of "Iliac crest" provided by Wikipedia, the free encyclopedia; retrieved from the Internet at URL: http:///en.wikipedia.org/wiki/Iliac_crest; downloaded on Dec. 18, 2007.
Williams, J.T. et al., "Cells Isolated From Adult Human Skeletal Muscle Capable of Differentiating Into Multiple Mesodermal Phenotypes," *Am. Surg.* Jan. 1999:65(I):22-26.
Wobus, A.M. et al., "Retinoic Acid Accelerates Embryonic Stem Cell-Derived Cardiac Differentiation and Enhances Development of Ventricular Cardiomyocytes," *J. Mol. Cell Cardiol.*, 1997; 29:1525-1539.
Wolford, L.M. et al., "Considerations in Nerve Repair," *BUMC Proceedings*, 2003; 16:152-156.
Woodbury, D., et al., "Adult Rat and Human Bone Marrow Stromal Cells Differentiate Into Neurons," *J. Neurosci. Res.*, 2000; 61:364-370.
Wulf, G.G. et al., "Mesengenic Progenitor Cells Derived From Human Placenta," *Tissue Engineering*, 2004; 10(7/8):1136-1147.
Xu, A. et al.,"Soft, Porous Poly(D,L lactide-co-glycotide) Microcarriers Designed for Ex Vivo Studies and for Transplantation of Adherent Cell Types including Progenitors," *Annals of the New York Academy of Sciences*, 2001, vol. 944: 144-159.
Xu, C. et al., "Characterization and Enrichment of Cardiomyocytes Derived From Human Embryonic Stem Cells," *Circ. Res.*, 2002; 91:501-508.
Xu, Y. et al., "Dopamine, In the Presence of Tyrosinase, Covalently Modifies and Inactivates Tyrosine Hydroxylase," *J. Neurosci. Res.*, 1998; 54:691-697.
Yamashima, T., "Implication of Cysteine Proteases Calpain, Cathepsin and Caspase in Ischemic Neuronal Death of Primates," *Progress in Neurobiology*, 2000; 62:273-295.
Yang, C. et al., "Enhancement of Neovascularization With Cord Blood CD133+ Cell-Derived Endothelial Progenitor Cell Transplantation," *Thrombosis and Haemostasis*, 2004; 91:1202-1212.
Yang, H. et al., "Region-Specific Differentiation of Neural Tube-Derived Neuronal Restricted Progenitor Cells After Heterotopic Transplantation," *PNAS*, 2000; 97(24):13366-13371.
Ye Q. et al., "Recovery of Placental-Derived Adherent Cells With Mesenchymal Stem Cell Characteristics", *Blood*, 2001; 98(11 Part 2):147B (Abstract No. 4260).
Yip, H.K., et al., "Axonal Regeneration of Retinal Ganglion Cells: Effect of Trophic Factors," *Prog. Retin Eye Res.*, 2000; 19(5):559-575.
Yokoo, T. et al., "Stem Cell Gene Therapy for Chronic Renal Failure," *Curr Gene Ther.*, 2003; 3:387-394.
Yu, M. et al., "Mid-Trimester Fetal Blood-Derived Adherent Cells Share Characteristics Similar to Mesenchymal Stem Cells But Full-Term Umbilical Cord Blood Does Not," *British J. of Haematology*, 2004; 124:666-675.
Zangani, D. et al., "Multiple Differentiation Pathways of Rat Mammary Stromal Cells In Vitro: Acquisition of a Fibroblast, Adipocyte or Endothelial Phenotype Is Dependent on Hormonal and Extracellular Matrix Stimulation," *Differentiation*, 1999; 64:91-101.
Zeng, B.Y. et al., "Regenerative and Other Responses to Injury in the Retinal Stump of the Optic Nerve in Adult Albino Rats: Transection of the Intracranial Optic Nerve," *J. Anat.*, 1995; 186:495-508.
Zhang, J, et al., "Differentiation potential of bone marrow mesenchymal stem cells into retina in normal and laser-injured rat eye", *Science in China Ser. C Life Science*, 2004; 47:241-250.
Zhang, L. et al., "A Test for Detecting Long-Term Sensorimotor Dysfunction in the Mouse after Focal Cerebral Ischemia," *J. Neurosci. Methods*, 2002; 117:207-214.
Zhang, S. et al., "In Vitro Differentiation of Transplantable Neural Precursors From Human Embryonic Stem Cells," *Nature Biotechnology*, 2001; 19:1129-1133.
Zhang, X. et al., "Efficient Adeno-Associated Virus-Mediated Gene Expression in Human Placenta-Derived Mesenchymal Cells," *Microbiol. Immunol.*, 2003; 47(1):109-116.
Zhang, Y. et al., "Comparison of Mesenchymal Stem Cells from Human Placenta and Bone Marrow," *Chinese Medical Journal*, 2004; 117:882-887.
Zhang, Z.G. et al., "Correlation of VEGF and Angiopoietin Expression with Disruption of Blood-Brain Barrier and Angiogenesis after Focal Cerebral Ischemia," *J. Cereb. Blood Flow Metab.*, 2002; 22(4):379-392.
Zimmerman, S. et al., "Lack of Telomerase Activity in Human Mesenchymal Stem Cells," *Leukemia*, 2003; 17:1146-1149.
Zuloff-Shani, A. et al., "Macrophage Suspensions Prepared From a Blood Unit for Treatment of Refractory Human Ulcers," *Transfus. Apheresis Sci.*, 2004; 30:163-167.
In the U. S. Patent and Trademark Office, Non-Final Office Action in re: U.S. Appl. No. 11/322,372, dated Jan. 16, 2014, 17 pages.
In the U. S. Patent and Trademark Office, Non-Final Office Action in re: U.S. Appl. No. 11/321,864, dated Jan. 29, 2014, 9 pages.
In the U. S. Patent and Trademark Office, Non-Final Office Action in re: U.S. Appl. No. 11/321,863, dated Jan. 31, 2014, 17 pages.
In the U. S. Patent and Trademark Office, Final Office Action in re: U.S. Appl. No. 11/317,574, dated Feb. 3, 2014, 16 pages.
In the U. S. Patent and Trademark Office, Non-Final Office Action in re: U.S. Appl. No. 10/876,998, dated Feb. 11, 2014, 14 pages.
In the U.S. Patent and Trademark Office, Non-Final Office Action in re: U.S. Appl. No. 12/389,305, dated Mar. 6, 2014, 37 pages.
In the U. S. Patent and Trademark Office, Non-Final Office Action in re: U.S. Appl. No. 11/316,104 dated Mar. 14, 2014, 11 pages.
In the U.S. Patent and Trademark Office, Non-Final Office Action in re: U.S. Appl. No. 12/389,305 dated Mar. 21, 2014, 47 pages.
In the U.S. Patent and Trademark Office, Non-Final Office Action in re: U.S. Appl. No. 10/877,446 dated Mar. 21, 2014, 21 pages.
In the U.S. Patent and Trademark Office, Non-Final Office Action in re: U.S. Appl. No. 11/316,104 dated Mar. 21, 2014, 20 pages.
In the U.S. Patent and Trademark Office, Non-Final Office Action in re: U.S. Appl. No. 11/315,969 dated Mar. 21, 2014, 15 pages.
Baksh, D. et al., "Comparison of proliferative and multilineage differentiation potential of human mesenchymal stem cells derived from umbilical cord and bone marrow." *Stem Cells*, 2007; 25: 1384-1392.
Bhatia, R. et al., "A clinically suitable ex vivo expansion culture system for LTC-IC and CFC using stroma-conditioned medium," *Exp Hematol.*, 1997; 25(9): 980-91 (Abstract only).
Covas, D. T. et al., "Isolation and culture of umbilical vein mesenchymal stem cells," *Brazilian Journal of Medical and Biological Research*, 2003; 36: 1179-1183.
Deans, R.J. et al., "Mesenchymal stem cells: Biology and potential clinical uses," Experimental Hematology, 2000; 28: 875-884.
Henderson, GI, et al., "Inhibition of Placental Valine Uptake after Acute and Chronic Maternal Ethanol Consumption", *J Pharmacol Exp Therap*, 1981; 216:465-472.

(56) References Cited

OTHER PUBLICATIONS

Kestendjieva, S. et al., "Characterization of mesenchymal stem cells isolated from the human umbilical cord," *Cell Biology International*, 2008; 32: 724-732.

Kocher, A.A. et al., "Neovascularization of ischemic myocardium by human bone-marrow-derived angioblasts prevents cardiomyocyte apoptosis, reduces remodeling and improves cardiac function," *Nature Medicine*, 2001, 7: 430-6.

Lonza (Cambex), human mesenchymal stem cells, downloaded Jan. 31, 2014.

Nehlin et al., "Immunogenicity and immune-modulating properties of human stem cells," *Stem Cells in Clinical Research*, 2011.

Shake et al., "Mesenchymal stem cell implantation in a swine myocardial infarct model: engraftment and functional effects," *Ann Thorac Surg*, 2002: 73: 1919-1926.

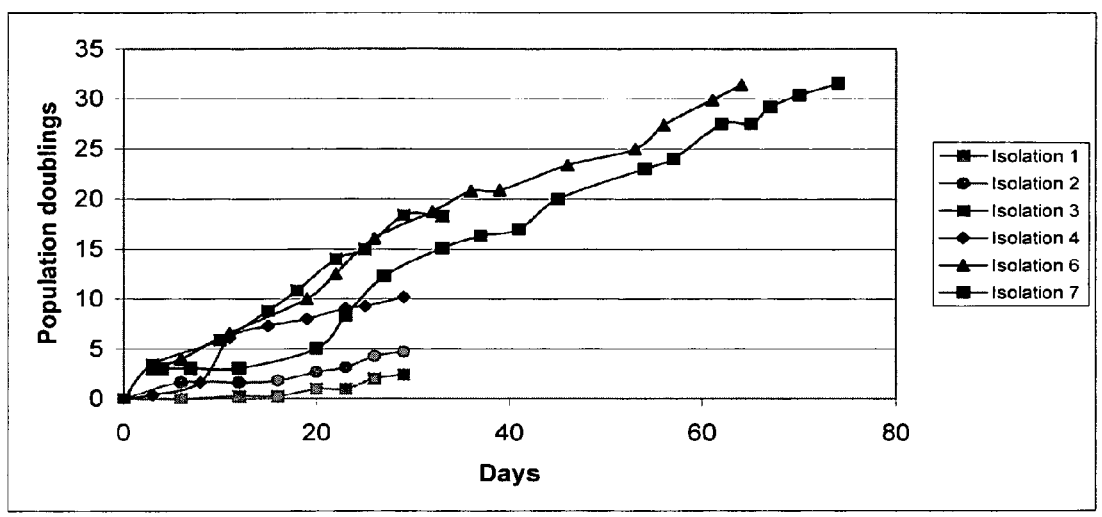

SEQUENCE LISTING

<160> NUMBER OF SEQ ID NOS: 16

<210> SEQ ID NO 1
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 1
gagaaatcca aagagcaaat gg                                              22

```
<210> SEQ ID NO 2
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 2
agaatggaaa actggaatag g                                           21

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 3
tcttcgatgc ttcggattcc                                             20

<210> SEQ ID NO 4
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 4
gaattctcgg aatctctgtt g                                           21

<210> SEQ ID NO 5
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 5
ttacaagcag tgcagaaaac c                                           21

<210> SEQ ID NO 6
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 6
agtaaacatt gaaaccacag cc                                          22

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 7
tctgcagctc tgtgtgaagg                                             20

<210> SEQ ID NO 8
<211> LENGTH: 22
<212> TYPE: DNA
<213> ORGANISM: Artificial Sequence
<220> FEATURE:
<223> OTHER INFORMATION: Oligonucleotide primer
```

```
<400> SEQUENCE: 8
cttcaaaaac ttctccacaa cc                                      22

<210> SEQ ID NO 9
<211> LENGTH: 17
<212> TYPE: DNA
<213> ORGANISM: Artificial Sequence
<220> FEATURE:
<223> OTHER INFORMATION: Oligonucleotide primer

<400> SEQUENCE: 9
cccacgccac gctctcc                                            17

<210> SEQ ID NO 10
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 10
tcctgtcagt tggtgctcc                                          19

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 11
ctggattggc gttgtttgtg                                         20

<210> SEQ ID NO 12
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 12
tcccaaggtg gagtgctgta g                                       21

<210> SEQ ID NO 13
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 13
ctgttgcgca catccctgcc c                                       21

<210> SEQ ID NO 14
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 14
ggcagtctgg ctttctcaga tt                                      22

<210> SEQ ID NO 15
<211> LENGTH: 21
```

```
<212> TYPE: DNA
<213> ORGANISM: Artificial Sequence
<220> FEATURE:
<223> OTHER INFORMATION: Oligonucleotide primer

<400> SEQUENCE: 15
ccctctccct tacccttagc a                                              21

<210> SEQ ID NO 16
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 16
ctgtgaaagg acctgtctgt cgc                                            23
```

POSTPARTUM CELLS DERIVED FROM UMBILICAL TISSUE AND METHODS OF MAKING AND USING THE SAME

CROSS-REFERENCE TO RELATED APPLICATIONS

This application is a divisional of U.S. application Ser. No. 11/315,897, filed Dec. 22, 2005 now abandoned, which in turn is a continuation-in-part of U.S. patent application Ser. No: 10/877,012, filed Jun. 25, 2004, now U.S. Pat. No. 7,510,873, issued Mar. 31, 2009, which claims benefit of U.S. Provisional Application Ser. No. 60/483,264, filed Jun. 27, 2003, the entire contents of each of which are incorporated by reference herein. Application Ser. No. 11/315,897 also claims benefit of U.S. Provisional Application No. 60/639,088, filed Dec. 23, 2004, the entirety of which is also herein incorporated by reference.

FIELD OF THE INVENTION

This invention relates to mammalian, preferably human, cell therapy, and more particularly to isolated cells derived from postpartum umbilicus, methods of deriving such cells, and methods of their use and growth on various media, including media which are serum-containing or serum-free.

BACKGROUND OF THE INVENTION

As the modern understanding of disease has advanced, the potential utility of cell therapy for improving the prognosis of those afflicted has resulted in increased interest in new sources of human cells useful for therapeutic purposes. One such source of human cells is postpartum tissues, and in particular, the umbilicus or umbilical cord.

Recently, attention has focused on the banking of umbilical cord blood (or simply "cord blood") as a potential source of, for example, hematopoietic cells for use by an individual for whom cord blood has been banked at birth. Such cells would be useful for those individuals, for example, who require therapeutic radiation which may eliminate functional portions of their immune system. Rather than requiring a bone marrow donor carefully matched to avoid rejection, the individual's own banked cord blood could be used to reconstitute the lost immune cells, and restore immune function.

Still more recently, there has been interest in obtaining stem cells from cord blood, due to the wider potential therapeutic applications of such cells. Stem cells are understood in general terms as cells that 1) have the ability to self-renew for long periods through cell division from a single cell; and 2) have the ability to differentiate into specific cell types given the proper conditions. Accordingly, stem cells are potentially useful in treating a population of individuals, and not merely the person from whose cord blood the cells were initially obtained.

In particular, cord blood has been considered as a source of hematopoietic progenitor stem cells. Banked (or cryopreserved) cord blood, or stem cells isolated therefrom have been deemed useful for hematopoietic reconstitution, for example in bone marrow and related transplantations. (Boyse et al., U.S. Pat. Nos. 5,004,681 and 5,192,553).

In addition to cord blood, other sources of therapeutic cells from the human umbilicus have been explored, including cells isolated from the Wharton's Jelly, umbilical vein or artery tissue, and the umbilical matrix itself. Such cells have been largely uncharacterized, or only minimally characterized with respect to their physiological, biochemical, immunological, and genetic properties.

For example, Purchio et al. (U.S. Pat. No. 5,919,702) have isolated chondrogenic progenitor cells (or prechondrocytes) from Wharton's Jelly. They reported the isolation of cells from human umbilical cord Wharton's Jelly by removing blood and blood vessels and incubating the tissue under conditions purported to allow the prechondrocytes to proliferate. As such, the method did not distinguish the desired cells from the different cell types present in Wharton's Jelly, but rather relied on migration from the tissue or selecting growth conditions favoring prechondrocytes. The prechondrocytes were expanded mitotically after they were established. Cells at passages 2 to 4 were reported as useful to produce cartilage, if triggered by the addition of exogenous growth factors, such as BMP-13 or TGF-beta. Uses of the cells for direct injection or implantation, or use with a hydrogel or tissue matrix, were proposed. However, it was considered important that the cells not exceed about 25% confluence. The cells were not characterized with respect to their biochemical or immunological properties, or with respect to their gene expression.

Weiss et al. (U.S. Patent Application Publication US2003/0161818) proposed procedures for isolating pluripotent or lineage-committed cells from mammalian Wharton's Jelly or non-blood umbilical cord matrix sources. The cells isolated were reported to differentiate into hematopoietic, mesenchymal or neuroectodermal lines. The cell lines were not characterized with respect to their identifying properties. Limited characterization was provided with respect to cells after differentiation towards neural lines. Reference was made to Wharton's Jelly-derived bovine and porcine cells that were $CD34^-$, $CD45^-$.

Weiss et al. also reported investigating transplantation of porcine umbilical cord matrix cells into rat brain. (*Exp. Neur.* 182: 288-299, 2003). No enzymatic treatment was used in the isolation procedure. They obtained two distinct populations—spherical and flat mesenchymal cells. The cells were genetically modified to express GFP. The cells did not appear to stimulate immune rejection when implanted cross-species.

Mitchell et al. (*Stem Cells* 21:50-60, 2003) reported obtaining Wharton's Jelly matrix cells from porcine umbilical cords. The undifferentiated cells were reported to be positive for telomerase and a subpopulation was also reported positive for c-kit expression, i.e., telomerase$^+$, $CD117^+$. The cells were also reported to produce alpha-smooth muscle actin, indicative of their myofibroblast-like nature. The cells purportedly could differentiate along neural lines in the presence of growth factors. However, both the differentiated and undifferentiated cells were found to express NSE, a marker for neural stem cells. The need for clonal lines and characterization in terms of proliferative capacity, karyotype analysis, and expression of HLA antigens was recognized.

Romanov et al. (*Stem Cells* 21(1):105-110, 2003) reported a procedure to isolate mesenchymal stem cell (MSC)-like cells from human umbilical cord vein. Their procedure involved treatment of the excised vein tissue with collagenase and required that the enzymatic digestion be short (15 minutes) to obtain the cell population of interest (a subendothelial layer of the vein). In particular, the procedure avoided inclusion of smooth muscle cells (SMCs) and fibroblasts by leaving the deeper layers of the tissue intact, purportedly removing only the outer layers. The resulting "nearly homogenous" cell population was reported to contain approximately 0.5-1% endothelial cells that they also sought to avoid. The cells were reported to be predominantly $CD34^-$ and to produce alpha-smooth muscle actin.

Because of the diversity of cell populations that are found in umbilical cord matrix, there is a need in the art for methods of isolating defined non-blood cells and populations thereof derived from mammalian umbilical cord; as well as a need for cell lines derived from mammalian umbilicus that are characterized with respect to their biochemistry (e.g. secretion of growth factors), immunology (cell surface markers and potential to stimulate immune responses) and expression of various genes. This need is particularly compelling for cells derived from human umbilicus.

With regard to media for culturing cells most contain at least some fetal bovine or calf serum. Generally, commercially available media formulations utilize serum supplements of about 10-20% (v/v). The serum component is often integral to the survival and expansion of cell populations. A myriad of proteins are found in bovine serum, including for example PDGF and FGFs, known growth factors that can have significant influence on cell growth and differentiation on cell populations, including populations of stem and progenitor cells.

In spite of the advantages of including bovine serum (or serum of other species), there are, however, a number of disadvantages to supplementing medium with animal serum instead of using chemically-defined or serum-free media when culturing therapeutic cells or producing biologics. Cell and tissue homeostasis occurs under environmental conditions that lack blood-derived serum. Thus, long-term cell exposure to serum and blood-related products simulates a tissue injury paradigm. Further, lot-to-lot variation in composition of serum, including in the stimulatory proteins and any inhibitory substances requires time consuming and expensive pre-testing to ensure each batch meets the standards for therapeutic product development or production. Finally, increased concerns about the transmission of diseases such as bovine spongiform encephalopathy (BSE) from the use of animal-related products may ultimately retard or preclude FDA approval of cell-based therapies developed with foreign serum.

BRIEF DESCRIPTION OF THE FIGURES

FIG. 1: Long-term growth potential of umbilical cells isolated under different conditions. Conditions that allowed for more than 5 population doublings were further analyzed for long-term growth potential. Cells were cultured using the indicated media formulations and culture conditions until cells reached senescence. Senescence was determined when cells failed to achieve greater than one population doubling during the study time interval.

SUMMARY OF THE INVENTION

In a first aspect, the invention provides isolated umbilicus-derived cells (UDCs) that are derived from mammalian umbilical cord tissue substantially free of blood. The cells are capable of self-renewal and expansion in culture. The umbilicus-derived cells have the potential to differentiate into cells of other phenotypes. In preferred embodiments, the cells are derived from human umbilicus.

The cells have been characterized as to several of their cellular, genetic, immunological, and biochemical properties. For example, the cells have been characterized by their growth properties in culture, by their cell surface markers, by their gene expression, by their ability to produce certain biochemical trophic factors, and by their immunological properties.

In certain embodiments, the postpartum-derived cell is an umbilicus-derived cell. In other embodiments it is a placenta-derived cell. In specific embodiments, the cell has all identifying features of either of cell types UMB 022803 (P7) (ATCC Accession No. PTA-6067); or UMB 022803 (P17) (ATCC Accession No. PTA-6068).

In another of its several aspects, cell cultures comprising the isolated umbilicus-derived cells of the invention are provided. The cultures of umbilical cells are free of maternal cells in certain preferred embodiments.

Methods of culturing and expanding umbilicus-derived cells and cell cultures and populations comprising them are provided.

In another aspect of the invention isolated umbilicus-derived cells having specific cell surface marker expression profiles are provided, wherein particular cell surface marker proteins are produced. In particular, the cells produce one or more of CD10, CD13, CD44, CD73, CD90, CD141, PDGFr-alpha, or HLA-A,B,C. In addition, the cells do not produce one or more of CD31, CD34, CD45, CD117, CD141, or HLA-DR,DP,DQ, as detected by flow cytometry.

The cells of the invention have also been characterized according to their expression of a wide variety of genes. Accordingly, another aspect of the invention provides isolated umbilicus-derived cells, which relative to a human cell that is a fibroblast, a mesenchymal stem cell, or an ileac crest bone marrow cell, have reduced expression of genes for one or more of: short stature homeobox 2; heat shock 27 kDa protein 2; chemokine (C—X—C motif) ligand 12 (stromal cell-derived factor 1); elastin (supravalvular aortic stenosis, Williams-Beuren syndrome); *Homo sapiens* mRNA; cDNA DKFZp586M2022 (from clone DKFZp586M2022); mesenchyme homeobox 2 (growth arrest-specific homeobox); sine oculis homeobox homolog 1 (*Drosophila*); crystallin, alpha B; disheveled associated activator of morphogenesis 2; DKFZP586B2420 protein; similar to neuralin 1; tetranectin (plasminogen binding protein); src homology three (SH3) and cysteine rich domain; cholesterol 25-hydroxylase; runt-related transcription factor 3; interleukin 11 receptor, alpha; procollagen C-endopeptidase enhancer; frizzled homolog 7 (*Drosophila*); hypothetical gene BC008967; collagen, type VIII, alpha 1; tenascin C (hexabrachion); iroquois homeobox protein 5; hephaestin; integrin, beta 8; synaptic vesicle glycoprotein 2; neuroblastoma, suppression of tumorigenicity 1; insulin-like growth factor binding protein 2, 36 kDa; *Homo sapiens* cDNA FLJ12280 fis, clone MAMMA1001744; cytokine receptor-like factor 1; potassium intermediate/small conductance calcium-activated channel, subfamily N, member 4; integrin, beta 7; transcriptional co-activator with PDZ-binding motif (TAZ); sine oculis homeobox homolog 2 (*Drosophila*); KIAA1034 protein; vesicle-associated membrane protein 5 (myobrevin); EGF-containing fibulin-like extracellular matrix protein 1; early growth response 3; distal-less homeobox 5; hypothetical protein FLJ20373; aldo-keto reductase family 1, member C3 (3-alpha hydroxysteroid dehydrogenase, type II); biglycan; transcriptional co-activator with PDZ-binding motif (TAZ); fibronectin 1; proenkephalin; integrin, beta-like 1 (with EGF-like repeat domains); *Homo sapiens* mRNA full length insert cDNA clone EUROIMAGE 1968422; EphA3; KIAA0367 protein; natriuretic peptide receptor C/guanylate cyclase C (atrionatriuretic peptide receptor C); hypothetical protein FLJ14054; *Homo sapiens* mRNA; cDNA DKFZp564B222 (from clone DKFZp564B222); BCL2/adenovirus E1B 19 kDa interacting protein 3-like; AE binding protein 1; and cytochrome c oxidase subunit VIIa polypeptide 1 (muscle). In addition, these isolated human umbilicus-derived cells express a gene for each of interleukin 8; reticulon 1; chemokine (C—X—C motif) ligand 1 (melanoma growth stimulating activity, alpha); chemokine (C—X—C motif) ligand 6 (granulocyte chemotactic protein 2); chemokine (C—X—C motif) ligand 3; and tumor necrosis factor, alpha-induced protein 3, wherein the expression is increased relative to that of a human cell which is a fibroblast, a mesenchymal stem cell, an ileac crest bone marrow cell, or placenta-derived cell. The cells are capable of self-renewal and expansion in culture, and have the potential to differentiate into cells of other phenotypes. Also provided are therapeutic cell cultures comprising the isolated human umbilicus-derived cells.

In another of its several aspects, the invention provides isolated human umbilicus-derived cells capable of self-renewal and expansion in culture and which have the potential to differentiate into cells of other phenotypes, wherein the cells do not stimulate allogeneic lymphocytes in a mixed lymphocyte reaction, and expresses PD-L2, but not HLA-G, CD178, HLA-DR, HLA-DP, HLA-DQ, CD80, CD86, or B7-H2. In some preferred embodiments, the cells do not stimulate allogeneic PBMCs. More preferably they do not stimulate allogeneic lymphocytes, allogeneic T-cells, or naïve T-cells, or generate other adverse immunological responses in either matched or unmatched recipients. The cells also can produce vimentin and alpha-smooth muscle actin in certain embodiments.

In another aspect, the invention provides isolated human umbilicus-derived cells that secrete one or more of the angiogenic factors MCP-1, IL-6, IL-8, GCP-2, HGF, KGF, FGF, HB-EGF, BDNF, TPO, or TIMP1. In certain embodiments, the cells secrete several or all of the aforementioned molecules. In other embodiments, the cells do not secrete one or more of the angiogenic factors SDF-1alpha, TGF-beta2, ANG2, PDGFbb or VEGF, as detected by ELISA. In particular embodiments, they secrete few or none of those molecules.

In another aspect of the invention, therapeutic cell cultures are provided, the cell cultures comprising the isolated cells as described above for use in treating patients in need of angiogenesis-stimulating trophic factors. Such therapeutic cell cultures are also provided for use in treating a patient in need of neural growth stimulating trophic factors.

Methods of deriving cells from non-blood human umbilical tissue are provided. The cells are capable of self-renewal and expansion in culture, and have the potential to differentiate into cells of other phenotypes. The method comprises (a) obtaining human umbilical tissue; (b) removing substantially all of the blood to yield a substantially blood-free umbilical tissue, (c) dissociating the tissue by mechanical or enzymatic treatment, or both, (d) resuspending the tissue in a culture medium, and (e) providing growth conditions which allow for the growth of a human umbilicus-derived cell capable of self-renewal and expansion in culture and having the potential to differentiate into cells of other phenotypes. Preferred methods involve enzymatic treatment with, for example, collagenase and dispase, or collagenase, dispase, and hyaluronidase, and such methods are provided herein.

Isolated human umbilicus-derived cells derived by the above method are also provided herein. The cells maintain a consistent normal karyotype notwithstanding repeated passaging in certain embodiments. Also provided are cultures of human umbilicus-derived cells derived by the above method, wherein the cultures are free of maternal cells. Further provided are cells and cultures of such cells wherein the cells isolated by any of a variety of methods in any of a variety of media, even when cultured under a wide range of conditions, are capable of maintaining a substantially consistent profile of expressed surface markers, or substantially consistent profile of expression of genes that characterize the cells, e.g. "signature gene profiles" including for example, expression patterns of which are specific to certain stem cells and/or to certain postpartum cells.

Co-cultures comprising the cells or cultures of the invention with other mammalian cells are also provided herein. Preferably these co-cultures comprise another human cell line whose growth or therapeutic potential, for example, is improved by the presence of the umbilicus-derived cells. Such co-cultures are useful for therapeutic application in vitro or in vivo.

Also provided herein are therapeutic compositions comprising an umbilicus-derived cell and another therapeutic agent, factor, or bioactive agent. Such factors include, but are not limited to, IGF, LIF, PDGF, EGF, FGF, as well as antithrombogenic, antiapoptotic agents, anti-inflammatory agents, immunosuppressive or immunomodulatory agents, and antioxidants. Such therapeutic compositions can further comprise one or more additional cell types in addition to the UDCs and the bioactive component.

In addition to the above, compositions derived from the cells are provided herein. Cell lysates, soluble cell fractions and membrane-enriched cell fractions are provided herein. Extracellular matrices derived from the cells, for example, comprising basement membranes are also useful and are provided herein.

Compositions of the invention also include conditioned culture media as provided herein. Such media have first been used to grow the cells or cultures of the invention, which during growth secrete one or more useful products into the medium. Conditioned medium from these novel cells are useful for many purposes, including for example, supporting the growth of other mammalian cells in need of growth factors or trophic factors secreted into the media by the cells and cultures of the invention, and promoting, for example, angiogenesis.

Methods are provided of inducing the cells to differentiate along a pathway towards progenitors of various cells, or even into terminally differentiated cells themselves. Such cells have utility for therapeutic treatment of certain conditions, disorders and disease states. Such cells also have utility for diagnostic protocols, such as for use in assays to identify therapeutic agents.

The invention also provides methods of utilizing the differentiated umbilicus-derived cells or the progenitors for therapeutic uses, including but not limited to angiogenic application, neuronal applications, soft tissue applications, occular applications, and applications wherein the cells are useful in treatment of heart, kidney, bone, cartilage, pancreas, liver, and other tissues alone or in combination with other therapeutic agents.

Kits are also provided herein. Kits useful for the growth, isolation and use of the umbilical-derived cells are provided.

In another of it several aspects, the invention provides isolated postpartum-derived cells comprising a "signature gene profile" which distinguishes the PPDCs from other cells of different origin and from other known toti-and pluripotent cells. Preferred signature gene profiles comprise those wherein mRNA from genes for reticulon, oxidized LDL receptor, and IL-8 are present independent of whether the cells are grown in medium containing serum or medium free of serum. Also provide are such cells further comprising the ability to alter the expression of its cell surface markers when grown in medium containing serum relative to that in serum free medium. Of particular interest presently are cells wherein the markers for PDGF receptor alpha and HLA-ABC can be altered.

Also provided are methods for the preparation of therapeutic cells or cultures comprising: isolating cells; initially expanding the cells to a useful number in a serum-containing medium which supports cell expansion but in which the cells produce a quantity of the cell surface marker HLA-ABC; transferring the cells to a medium in which the cells produce a decreased amount of the cell surface marker HLA-ABC; and passaging the cells in the medium in which the cells produce a decreased amount of the HLA-ABC, thereby preparing a therapeutic cell or culture. In presently preferred embodiments, the medium in which the cells produce a decreased amount of the cell surface marker HLA-ABC is a serum-free medium. The methods are particularly useful for the production of therapeutic cells or cultures for implantation or grafting.

Also provided in accordance with present invention are serum-free media for the expansion of postpartum-derived cells wherein the media has one or more growth factors added. Presently preferred growth factors to be added are bFGF, EGF, or PDGF.

Methods are also provided for isolating and culturing postpartum cells, particularly umbilicus-derived cells, in serum-containing and serum-free media, with or without beta-mercaptoethanol, with or without various growth factors, on surfaces coated with gelatin, or CELLBIND, or other treatments to allow attachment. Methods of culturing the cells also include varied conditions of oxygen, and other growth parameters.

In another aspect, the invention provides therapeutic cultures comprising postpartum-derived cells expanded in serum-free medium. Preferred cultures having a signature gene profile wherein mRNA from genes for reticulon, oxidized LDL receptor, and IL-8 are present independent of whether the cells are grown in medium containing serum or medium free of serum.

Also provided are cell culture banks and depositories and the like comprising postpartum-derived cells and cultures of the invention.

These and further aspects of the invention will be described in greater detail below.

DETAILED DESCRIPTION

Definitions

Various terms used throughout the specification and claims are defined as set forth below.

Stem cells are undifferentiated cells defined by the ability of a single cell both to self-renew, and to differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation, and to contribute substantially to most, if not all, tissues following injection into blastocysts.

Stem cells are classified according to their developmental potential as: (1) tot/potent; (2) pluripotent; (3) multipotent; (4) oligopotent; and (5) unipotent. Totipotent cells are able to give rise to all embryonic and extraembryonic cell types. Pluripotent cells are able to give rise to all embryonic cell types. Multipotent cells include those able to give rise to a subset of cell lineages, but all within a particular tissue, organ, or physiological system (for example, hematopoietic stem cells (HSC) can produce progeny that include HSC (self-renewal), blood cell-restricted oligopotent progenitors, and all cell types and elements (e.g., platelets) that are normal components of the blood). Cells that are oligopotent can give rise to a more restricted subset of cell lineages than multipotent stem cells; and cells that are unipotent are able to give rise to a single cell lineage (e.g., spermatogenic stem cells).

Stem cells are also categorized on the basis of the source from which they may be obtained. An adult stem cell is generally a multipotent undifferentiated cell found in tissue comprising multiple differentiated cell types. The adult stem cell can renew itself. Under normal circumstances, it can also differentiate to yield the specialized cell types of the tissue from which it originated, and possibly other tissue types. An embryonic stem cell is a pluripotent cell from the inner cell mass of a blastocyst-stage embryo. A fetal stem cell is one that originates from fetal tissues or membranes. A postpartum stem cell is a multipotent or pluripotent cell that originates substantially from extraembryonic tissue available after birth, namely, the placenta and the umbilical cord. These cells have been found to possess features characteristic of pluripotent stem cells, including rapid proliferation and the potential for differentiation into many cell lineages. Postpartum stem cells may be blood-derived (e.g., as are those obtained from umbilical cord blood) or non-blood-derived (e.g., as obtained from the non-blood tissues of the umbilical cord and placenta).

Embryonic tissue is typically defined as tissue originating from the embryo (which in humans refers to the period from fertilization to about six weeks of development. Fetal tissue refers to tissue originating from the fetus, which in humans refers to the period from about six weeks of development to parturition. Extraembryonic tissue is tissue associated with, but not originating from, the embryo or fetus. Extraembryonic tissues include extraembryonic membranes (chorion, amnion, yolk sac and allantois), umbilical cord and placenta (which itself forms from the chorion and the maternal decidua basalis).

Differentiation is the process by which an unspecialized ("uncommitted") or less specialized cell acquires the features of a specialized cell, such as a nerve cell or a muscle cell, for example. A differentiated cell is one that has taken on a more specialized ("committed") position within the lineage of a cell. The term committed, when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell. As used herein, the lineage of a cell defines the heredity of the cell, i.e. which cells it came from and what cells it can give rise to. The lineage of a cell places the cell within a hereditary scheme of development and differentiation.

In a broad sense, a progenitor cell is a cell that has the capacity to create progeny that are more differentiated than itself, and yet retains the capacity to replenish the pool of progenitors. By that definition, stem cells themselves are also progenitor cells, as are the more immediate precursors to terminally differentiated cells. When referring to the cells of the present invention, as described in greater detail below, this broad definition of progenitor cell may be used. In a narrower sense, a progenitor cell is often defined as a cell that is intermediate in the differentiation pathway, i.e., it arises from a stem cell and is intermediate in the production of a mature cell type or subset of cell types. This type of progenitor cell is generally not able to self-renew. Accordingly, if this type of cell is referred to herein, it will be referred to as a non-renewing progenitor cell or as an intermediate progenitor or precursor cell.

As used herein, the phrase differentiates into a mesodermal, ectodermal or endodermal lineage refers to a cell that becomes committed to a specific mesodermal, ectodermal or endodermal lineage, respectively. Examples of cells that differentiate into a mesodermal lineage or give rise to specific mesodermal cells include, but are not limited to, cells that are adipogenic, chondrogenic, cardiogenic, dermatogenic, hematopoietic, hemangiogenic, myogenic, nephrogenic, urogenitogenic, osteogenic, pericardiogenic, or stromal. Examples of cells that differentiate into ectodermal lineage include, but are not limited to epidermal cells, neurogenic cells, and neurogliagenic cells. Examples of cells that differentiate into endodermal lineage include, but are not limited to, pleurigenic cells, hepatogenic cells, cells that give rise to the lining of the intestine, and cells that give rise to pancreogenic and splanchogenic cells.

The cells of the present invention are generally referred to as umbilicus-derived cells (or UDCs). They also may sometimes be referred to more generally herein as postpartum-derived cells or postpartum cells (PPDCs). In addition, the cells may be described as being stem or progenitor cells, the latter term being used in the broad sense. The term derived is used to indicate that the cells have been obtained from their biological source and grown or otherwise manipulated in vitro (e.g., cultured in a growth medium to expand the population and/or to produce a cell line). The in vitro manipulations of umbilical stem cells and the unique features of the umbilicus-derived cells of the present invention are described in detail below.

Various terms are used to describe cells in culture. Cell culture refers generally to cells taken from a living organism and grown under controlled condition ("in culture" or "cultured"). A primary cell culture is a culture of cells, tissues, or organs taken directly from an organism(s) before the first subculture. Cells are expanded in culture when they are placed in a growth medium under conditions that facilitate cell growth and/or division, resulting in a larger population of the cells. When cells are expanded in culture, the rate of cell proliferation is sometimes measured by the amount of time needed for the cells to double in number. This is referred to as doubling time.

A cell line is a population of cells formed by one or more subcultivations of a primary cell culture. Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but not limited to the seeding density, substrate, medium, growth conditions, and time between passaging.

A conditioned medium is a medium in which a specific cell or population of cells has been cultured, and then removed. When cells are cultured in a medium, they may secrete cellular factors that can provide trophic support to other cells. Such trophic factors include, but are not limited to hormones, cytokines, extracellular matrix (ECM), proteins, vesicles, antibodies, and granules. The medium containing the cellular factors is the conditioned medium.

Generally, a trophic factor is defined as a substance that promotes or at least supports, survival, growth, proliferation and/or maturation of a cell, or stimulates increased activity of a cell.

When referring to cultured vertebrate cells, the term senescence (also replicative senescence or cellular senescence) refers to a property attributable to finite cell cultures; namely, their inability to grow beyond a finite number of population doublings (sometimes referred to as Hayflick's limit). Although cellular senescence was first described using fibroblast-like cells, most normal human cell types that can be grown successfully in culture undergo cellular senescence. The in vitro lifespan of different cell types varies, but the maximum lifespan is typically fewer than 100 population doublings (this is the number of doublings for all the cells in the culture to become senescent and thus render the culture unable to divide). Senescence does not depend on chronological time, but rather is measured by the number of cell divisions, or population doublings, the culture has undergone. Thus, cells made quiescent by removing essential growth factors are able to resume growth and division when the growth factors are re-introduced, and thereafter carry out the same number of doublings as equivalent cells grown continuously. Similarly, when cells are frozen in liquid nitrogen after various numbers of population doublings and then thawed and cultured, they undergo substantially the same number of doublings as cells maintained unfrozen in culture. Senescent cells are not dead or dying cells; they are actually resistant to programmed cell death (apoptosis), and have been maintained in their nondividing state for as long as three years. These cells are very much alive and metabolically active, but they do not divide. The nondividing state of senescent cells has not yet been found to be reversible by any biological, chemical, or viral agent.

As used herein, the term Growth Medium generally refers to a medium sufficient for the culturing of umbilicus-derived cells. In particular, one presently preferred medium for the culturing of the cells of the invention herein comprises Dulbecco's Modified Essential Media (also abbreviated DMEM herein). Particularly preferred is DMEM-low glucose (also DMEM-LG herein) (Invitrogen, Carlsbad, Calif.). The DMEM-low glucose is preferably supplemented with 15% (v/v) fetal bovine serum (e.g. defined fetal bovine serum, Hyclone, Logan Utah), antibiotics/antimycotics (preferably penicillin (100 Units/milliliter), streptomycin (100 milligrams/milliliter), and amphotericin B (0.25 micrograms/milliliter), (Invitrogen, Carlsbad, Calif.)), and 0.001% (v/v) 2-mercaptoethanol (Sigma, St. Louis Mo.). In some cases different growth media are used, or different supplementations are provided, and these are normally indicated in the text as supplementations to, or deletions from the Growth Medium.

In other embodiments, the growth medium is not supplemented with serum, and more preferably the medium is not supplemented with any animal-derived protein material. This is presently preferred for example for growing cells for clinical or preclinical uses. Such media lacking serum altogether, and in even more preferably lacking any animal protein supplementation, may be used for both isolation and growth of cells in accordance with the instant invention.

Also relating to the present invention, the term standard growth conditions, as used herein refers to culturing of cells at 37° C., in a standard atmosphere comprising 5% $CO_2$. Relative humidity is maintained at about 100%. While foregoing the conditions are useful for culturing, it is to be understood that such conditions are capable of being varied by the skilled artisan who will appreciate the options available in the art for culturing cells, for example, varying the temperature, $CO_2$, rotation or agitation, relative humidity, oxygen, growth medium, and the like.

The following abbreviations are used herein:
ANG2 (or Ang2) for angiopoietin 2;
APC for antigen-presenting cells;
BDNF for brain-derived neurotrophic factor;
bFGF for basic fibroblast growth factor;
bid (or BID) for "bis in die" (twice per day);
BME for beta mercaptoethanol (or 2-mercaptoethanol);
BSP for bone sialoprotein;
CK18 for cytokeratin 18;
CXC ligand 3 for chemokine receptor ligand 3;
DAPI for 4'-6-diamidino-2-phenylindole-2-HCl
DMEM for Dulbecco's Minimal Essential Medium; also used herein as synonymous with Dulbecco's Modified Eagle Medium. The skilled artisan will appreciate the composition is the same by either name.
DMEM:lg (or DMEM:Lg, DMEM:LG) for DMEM with low glucose;
EDTA for ethylenediaminetetraacetic acid;
EGF for epidermal growth factor;
ERG for Electroretmalgram;
FACS for fluorescent activated cell sorting;
FBS for fetal bovine serum;
FCS, fetal calf serum;
GCP-2 for granulocyte chemotactic protein 2;
GFAP for glial fibrillary acidic protein;
HB-EGF for heparin-binding epidermal growth factor;
HCAEC for human coronary artery endothelial cells;
HGF for hepatocyte growth factor;
hMSC for human mesenchymal stem cells;
HNF-1 alpha for hepatocyte-specific transcription factor;
HUVEC for human umbilical vein endothelial cells;
I309 for a chemokine and the ligand for the CCR8 receptor and is responsible for chemoattraction of TH2 type T-cells. I309 binds to endothelial cells, stimulates chemotaxis and invasion of these cells, and enhances HUVEC differentiation into capillary-like structures in an in vitro Matrigel assay. Furthermore, I309 is an inducer of angiogenesis in vivo in both the rabbit cornea and the chick chorioallantoic membrane assay (CAM).
IL-6 for interleukin-6;
IL-8 for interleukin-8;
K19 for keratin 19;
K8 for keratin 8;
KGF for keratinocyte growth factor;
MCP-1 for monocyte chemotactic protein 1;
MDC for macrophage-derived chemokine;
MIP1alpha for macrophage inflammatory protein 1 alpha;
MIP1beta for macrophage inflammatory protein 1beta;
MSC for mesenchymal stem cells;
NHDF for normal human dermal fibroblasts;
NPE for Neural Progenitor Expansion media;
PBMC for peripheral blood mononuclear cell;
PBS for phosphate buffered saline;
PDGFbb for platelet derived growth factor;
PDGFr/alpha for platelet derived growth factor receptor alpha;
PD-L2 for programmed-death ligand 2;
PE for phycoerythrin
PO for "per os" (by mouth);
PPDC for postpartum-derived cell;
Rantes (or RANTES) for regulated on activation, normal T cell expressed and secreted;
rhGDF-5 for recombinant human growth and differentiation factor 5;
SC for subcutaneously;
SDF-1alpha for stromal-derived factor 1 alpha;
SHH for sonic hedgehog;
SOP for standard operating procedure;
TARC for thymus and activation-regulated chemokine;
TCP for Tissue culture plastic;
TGFbeta2 for transforming growth factor beta2;
TGFbeta-3 for transforming growth factor beta-3;
TIMP1 for tissue inhibitor of matrix metalloproteinase 1;
TPO for thrombopoietin;
TuJ1 for BIII Tubulin;
UDC for umbilicus-derived cell;
VEGF for vascular endothelial growth factor;
vWF for von Willebrand factor;
alphaFP for alpha-fetoprotein;
Description Various patents and other publications are cited herein and throughout the specification, each of which is incorporated in its entirety by reference herein.

In a first aspect, the invention provides isolated umbilicus-derived cells comprising cells derived from human umbilical cord tissue substantially free of blood. The cells are capable of self-renewal and expansion in culture. The umbilicus-derived cells have the potential to differentiate into cells of other phenotypes. In preferred embodiments, the cells can differentiate into any cell of ectodermal, mesodermal, or endodermal origin. The invention provides, in one of its several aspects cells that are isolated from human umbilical tissues. The cells, as disclosed herein, preferably are not derived from umbilical cord blood. Nor are they endothelial cells derived from, for example, blood vessels. Rather, the cells are derived of the remaining umbilicus tissues.

The cells have been characterized as to several of their cellular, genetic, immunological, and biochemical properties. For example, the cells have been well-characterized by their cell surface markers, by their gene expression, by their ability to produce certain biochemical trophic factors, and by their immunological properties.

In another of its several aspects, cell cultures comprising the isolated umbilicus-derived cells of the invention are provided. The cultures are free of maternal cells in preferred embodiments herein. Also preferred are cells that have a normal karyotype, and those that maintain their karyotype as they are passaged. Most highly preferred are those cells that have and maintain a normal karyotype throughout passaging until at least after senescence.

Methods of culturing and expanding umbilicus-derived cells and cell cultures comprising them are provided. Presently preferred are cells that require no added growth factors, but rather, are capable of expansion in many available culture media, especially those supplemented with for example, fetal bovine serum. Preferred media for culturing and expansion of the cells include Growth Medium, defined herein as medium comprising Dulbecco's Modified Essential Media (also abbreviated DMEM herein). Preferred is DMEM-low glucose (also DMEM-LG herein) (Invitrogen, Carlsbad, Calif.).

The DMEM-low glucose is most preferably supplemented with 15% (v/v) fetal bovine serum (e.g. defined fetal bovine serum, Hyclone, Logan Utah), antibiotics/antimycotics (preferably penicillin at 100 Units/milliliter, streptomycin at 100 micrograms/milliliter, and amphotericin B at 0.25 micrograms/milliliter; (Invitrogen, Carlsbad, Calif.)), and 0.001% (v/v) 2-mercaptoethanol (Sigma, St. Louis Mo.).

The skilled artisan will appreciate that the Growth Medium can be variously supplemented and altered in any of the ways known in the art, and may be optimized for particular reasons. Also preferred for either isolation of cells from postpartum tissue or growth and culturing of the cells are those media which lack any added serum, and those media which are serum-free and animal protein-free. Such media are particularly preferred for uses in isolating or culturing cells for preclinical or clinical use. Also useful are media which are lacking beta-mercaptoethanol as an additive. In addition, the cells are able to grow in many other culture media, including chemically defined media in the absence of added serum. Several such media are exemplified below. In addition to routine culturing and maintenance of the cells, many other media are known in the art for affecting differentiation of such potent cells into specific types of cells or progenitors of specific cells. The skilled artisan will appreciate that these media are useful for many purposes, and are included within the scope of the invention, but they are not necessarily preferred for routine culturing and expansion.

In addition to the flexibility of the cells with respect to culturing medium, the cells can grow under a variety of environmental conditions. In particular, the cells can grow under a wide range of atmospheric conditions. Presently preferred are atmospheres which range from about 5% $O_2$ to about 20% or more $O_2$. The cells grow and expand well in Growth Medium under these conditions, typically in the presence of about 5% $CO_2$, and the balance of the atmosphere as nitrogen. The skilled artisan will appreciate that the cells may tolerate broader ranges of conditions in different media, and that optimization for specific purposes may be appropriate.

Although the cells have not demonstrated any requirements for specific growth factors, the cells have demonstrated a requirement for L-valine over D-valine. Thus preferred culture media should have the L-isomer of this amino acid present. In addition to the demonstrated flexibility of the cells with respect to their growth requirements, preferred are the isolated cells that can attach and expand on either a coated or an uncoated tissue culture vessel. Tissue culture vessels include plates, flasks, tubes and the like, made of any of the materials known in the art—e.g. plastic, polystyrene, glass. Such vessels, where coated, are coated with any of a variety of compounds as are known in the art. Presently preferred coated vessels comprise a coating with gelatin, laminin, collagen, polyornithine, polylysine, vitronectin, or fibronectin, for example.

The isolated cells of the invention also preferably expand in the presence of from about 2% to about 15% serum, preferably Fetal Bovine Serum, and more preferably defined Fetal Bovine Serum. The cells also expand in the presence or absence of beta-mercaptoethanol, and in the presence or absence of added growth factors including one or more of EGF, bFGF, PDGF, VEGF, IGF-I, and LIF. The skilled artisan will appreciate that these flexible growth requirements allow for many options when culturing or working with these cells. In certain embodiments, cells are grown in Advanced DMEM (Gibco) containing any one of the previously mentioned growth factors, particularly bFGF. As described above, while presently Growth Medium is preferred, there is no absolute requirement for serum; growth has been accomplished in serum-free medium.

The cells can also be grown as attachment-dependent cultures on a variety of surfaces. Presently preferred are surfaces treated with gelatin, more prefereably CELLBIND where culture completely free of animal protein are required. Other coatings are compatible with growth of attachment-dependent cultures such as those provided herein.

In a preferred embodiment, the cells have excellent doubling and expansion potential and are suitable for use in diagnostic and therapeutic applications because their numbers can be scaled up readily. The isolated cells preferably can double sufficiently to generate yields of greater than about $10^{14}$ cells in less than about 80 days in culture when seeded at about $10^3$ cells/$cm^2$ in a suitable medium. More preferred are cells that can double sufficiently to generate greater than about $10^{15}$ cells in less than about 80 days in culture when seeded at about 5,000 cells/$cm^2$. Still more preferred is the isolated cell which can double sufficiently to generate greater than about $10^{17}$ cells in less than about 65 days in culture when seeded at about 5,000 cells/$cm^2$.

The isolated cells of the invention can undergo extensive doublings. Preferably, the cells undergo at least 30 doublings before reaching senescence. More preferably, at least 40 doublings in culture are attainable. Still more preferable are those cells that can achieve more than 40 doublings before becoming senescent. The cells of the invention are preferably able to undergo division over a longer period of time, than are, for example, human mesenchymal cells, or human fibroblasts, cultured under the same conditions.

In one embodiment, umbilical cells are isolated in the presence of one or more enzyme activities. A broad range of digestive enzymes for use in cell isolation from tissue are known in the art, including enzymes ranging from those considered weakly digestive (e.g. deoxyribonucleases and the neutral protease, dispase) to strongly digestive (e.g. papain and trypsin). Presently preferred are mucolytic enzyme activities, metalloproteases, neutral proteases, serine proteases (such as trypsin, chymotrypsin, or elastase), and deoxyribonucleases. More preferred are enzyme activities selected from metalloproteases, neutral proteases and mucolytic activities. Presently preferred are cells that are isolated in the presence of one or more activities of collagenase, hyaluronidase and dispase. More preferred are those cells isolated in the presence of a collagenase from *Clostridium histolyticum*, and either of the protease activities, dispase and thermolysin. Still more preferred are cells isolated with collagenase and dispase enzyme activities. Also preferred are such cells isolated in the presence of a hyaluronidase activity, in addition to collagenase and dispase activity.

In another aspect of the invention, isolated umbilicus-derived cells having specific cell surface marker expression profiles are provided. Preferred cells are characterized in either their production or lack of production of one or more cell surface markers selected from CD10, CD13, CD31, CD44, CD45, CD73, CD90, CD117, CD141, PDGFr-alpha, HLA-A,B,C, and HL-DR, DP,DQ. More preferred are cells that are characterized with respect to their production, or lack thereof, of several (e.g., two, four, five, or eight), or even ten of, or all of, the foregoing, to provide a profile of the cell. In preferred embodiments, the cells produce one or more of CD10, CD13, CD44, CD73, CD90, PDGFr-alpha, or HLA-A,B,C. More preferred are cells that express several or all of the foregoing markers. Still more preferred are those cell which express each of CD10, CD13, CD44, CD73, CD90, PDGFr-alpha, and HLA-A,B,C.

Preferred cells may also be characterized with respect to markers they do not produce, and such information is also useful in forming a characterization or immunological profile of the cell. Preferably, the cells do not produce one or more of CD31, CD34, CD45, CD117, CD141, or HLA-DR,DP,DQ, as detected by flow cytometry. More preferred are cells that do not produce several or more of the foregoing. Still more preferred are cells for which production of none of CD31, CD34, CD45, CD117, CD141, or HLA-DR,DP,DQ can be detected by flow cytometry under the conditions described herein.

In other preferred embodiments, the cells can be shown to produce several or more of the CD 10, CD 13, CD44, CD73, CD90, PDGFr-alpha, and HLA-A,B,C and concomitantly not produce one, or several, or more of CD31, CD34, CD45, CD117, CD141, or HLA-DR,DP,DQ as detected by flow cytometry. More highly preferred are cells that produce each of CD10, CD13, CD44, CD73, CD90, PDGFr-alpha, and HLA-A,B,C and concomitantly not produce any of CD31, CD34, CD45, CD117, CD141, or HLA-DR,DP,DQ as detected by flow cytometry.

Such cells are highly characterized with respect to their production of these cell surface proteins. In preferred embodiments, the characterization of the cells with respect to such production remains substantially constant and does not change substantially with variations in isolation procedure, passage, culture conditions, or even the coating or lack thereof on a tissue culture vessel.

The cells of the invention have also been characterized according to their expression of a wide variety of genes. Accordingly, another aspect of the invention provides isolated human umbilicus-derived cells, which are characterized, relative to a human cell that is a fibroblast, a mesenchymal stem cell, or an ileac crest bone marrow cell, in their expression of genes for: short stature homeobox 2; heat shock 27 kDa protein 2; chemokine (C—X—C motif) ligand 12 (stromal cell-derived factor 1); elastin (supravalvular aortic stenosis, Williams-Beuren syndrome); *Homo sapiens* mRNA; cDNA DKFZp586M2022 (from clone DKFZp586M2022); mesenchyme homeobox 2 (growth arrest-specific homeobox); sine oculis homeobox homolog 1 (*Drosophila*); crystallin, alpha B; disheveled associated activator of morphogenesis 2; DKFZP586B2420 protein; similar to neuralin 1; tetranectin (plasminogen binding protein); src homology three (SH3) and cysteine rich domain; B-cell translocation gene 1, anti-proliferative; cholesterol 25-hydroxylase; runt-related transcription factor 3; hypothetical protein FLJ23191; interleukin 11 receptor, alpha; procollagen C-endopeptidase enhancer; frizzled homolog 7 (*Drosophila*); hypothetical gene BC008967; collagen, type VIII, alpha 1; tenascin C (hexabrachion); iroquois homeobox protein 5; hephaestin; integrin, beta 8; synaptic vesicle glycoprotein 2; *Homo sapiens* cDNA FLJ12280 fis, clone MAMMA1001744; cytokine receptor-like factor 1; potassium intermediate/small conductance calcium-activated channel, subfamily N, member 4; integrin, alpha 7; DKFZP586L151 protein; transcriptional co-activator with PDZ-binding motif (TAZ); sine oculis homeobox homolog 2 (*Drosophila*); KIAA1034 protein; early growth response 3; distal-less homeobox 5; hypothetical protein FLJ20373; aldo-keto reductase family 1, member C3 (3-alpha hydroxysteroid dehydrogenase, type II); biglycan; fibronectin 1; proenkephalin; integrin, beta-like 1 (with EGF-like repeat domains); *Homo sapiens* mRNA full length insert cDNA clone EUROIMAGE 1968422; EphA3; KIAA0367 protein; natriuretic peptide receptor C/guanylate cyclase C (atrionatriuretic peptide receptor C); hypothetical protein FLJ14054; *Homo sapiens* mRNA; cDNA DKFZp564B222 (from clone DKFZp564B222); vesicle-associated membrane protein 5 (myobrevin); EGF-containing fibulin-like extracellular matrix protein 1; BCL2/adenovirus E1B 19 kDa interacting protein 3-like; AE binding protein 1; cytochrome c oxidase subunit VIIa polypeptide 1 (muscle); neuroblastoma, suppression of tumorigenicity 1; insulin-like growth factor binding protein 2, 36 kDa; as well as interleukin 8; reticulon 1; chemokine (C—X—C motif) ligand 1 (melanoma growth stimulating activity, alpha); chemokine (C—X—C motif) ligand 6 (granulocyte chemotactic protein 2); chemokine (C—X—C motif) ligand 3; and tumor necrosis factor, alpha-induced protein 3.

In one embodiment, preferred cells have the cell surface marker characterization described above and are further characterized in their relative gene expression. For example, some preferred cells have the cell surface characterization described above and express a gene for one or more of interleukin 8; reticulon 1; chemokine (C—X—C motif) ligand 1 (melanoma growth stimulating activity, alpha); chemokine (C—X—C motif) ligand 6 (granulocyte chemotactic protein 2); chemokine (C—X—C motif) ligand 3; or tumor necrosis factor, alpha-induced protein 3. More preferred are those cells that express a gene for several, (e.g., at least two, four, five or more) of each of the foregoing. The cells are capable of self-renewal and expansion in culture, and have the potential to differentiate into cells of other phenotypes. Also provided are therapeutic cell cultures comprising the isolated human umbilicus-derived cells.

Also provided are UDCs comprising the cell surface marker characterization and which relative to a human cell that is a fibroblast, a mesenchymal stem cell, or an ileac crest bone marrow cell, have reduced expression of one or more genes selected from: short stature homeobox 2; heat shock 27 kDa protein 2; chemokine (C—X—C motif) ligand 12 (stromal cell-derived factor 1); elastin (supravalvular aortic stenosis, Williams-Beuren syndrome); *Homo sapiens* mRNA; cDNA DKFZp586M2022 (from clone DKFZp586M2022); mesenchyme homeobox 2 (growth arrest-specific homeobox); sine oculis homeobox homolog 1 (*Drosophila*); crystallin, alpha B; disheveled associated activator of morphogenesis 2; DKFZP586B2420 protein; similar to neuralin 1; tetranectin (plasminogen binding protein); src homology three (SH3) and cysteine rich domain; B-cell translocation gene 1, anti-proliferative; cholesterol 25-hydroxylase; runt-related transcription factor 3; hypothetical protein FLJ23191; interleukin 11 receptor, alpha; procollagen C-endopeptidase enhancer; frizzled homolog 7 (*Drosophila*); hypothetical gene BC008967; collagen, type VIII, alpha 1; tenascin C (hexabrachion); iroquois homeobox protein 5; hephaestin; integrin, beta 8; synaptic vesicle glycoprotein 2; *Homo sapiens* cDNA FLJ12280 fis, clone MAMMA1001744; cytokine receptor-like factor 1; potassium intermediate/small conductance calcium-activated channel, subfamily N, member 4; integrin, alpha 7; DKFZP586L151 protein; transcriptional co-activator with PDZ-binding motif (TAZ); sine oculis homeobox homolog 2 (*Drosophila*); KIAA1034 protein; early growth response 3; distal-less homeobox 5; hypothetical protein FLJ20373; aldo-keto reductase family 1, member C3 (3-alpha hydroxysteroid dehydrogenase, type II); biglycan; fibronectin 1; proenkephalin; integrin, beta-like 1 (with EGF-like repeat domains); *Homo sapiens* mRNA full length insert cDNA clone EUROIMAGE 1968422; EphA3; KIAA0367 protein; natriuretic peptide receptor C/guanylate cyclase C (atrionatriuretic peptide receptor C); hypothetical protein FLJ14054; *Homo sapiens* mRNA; cDNA DKFZp564B222 (from clone DKFZp564B222); vesicle-associated membrane protein 5 (myobrevin); EGF-containing fibulin-like extracellular matrix protein 1; BCL2/adenovirus BIB 19 kDa interacting protein 3-like; AE binding protein 1; cytochrome c oxidase subunit VIIa polypeptide 1 (muscle); neuroblastoma, suppression of tumorigenicity 1; insulin-like growth factor binding protein 2, 36 kDa. Preferred are cells that have reduced expression of a gene for several (e.g., at least 5, 10, 15, 20, 25, 30, 35, 40, 45, 50 or more, or even all) of the foregoing.

Still more highly preferred are those cells having the cell surface marker characterization as described herein above and which also express a gene for each of interleukin 8; reticulon 1; chemokine (C—X—C motif) ligand 1 (melanoma growth stimulating activity, alpha); chemokine (C—X—C motif) ligand 6 (granulocyte); chemokine (C—X—C motif) ligand 3; or tumor necrosis factor, alpha-induced protein 3, and which relative to a human cell that is a fibroblast, a mesenchymal stem cell, or an ileac crest bone marrow cell, have reduced expression of one or more genes selected from: short stature homeobox 2; heat shock 27 kDa protein 2; chemokine (C—X—C motif) ligand 12 (stromal cell-derived factor 1); elastin (supravalvular aortic stenosis, Williams-Beuren syndrome); *Homo sapiens* mRNA; cDNA DKFZp586M2022 (from clone DKFZp586M2022); mesenchyme homeobox 2 (growth arrest-specific homeobox); sine oculis homeobox homolog 1 (*Drosophila*); crystallin, alpha B; disheveled associated activator of morphogenesis 2; DKFZP586B2420 protein; similar to neuralin 1; tetranectin (plasminogen binding protein); src homology three (SH3) and cysteine rich domain; B-cell translocation gene 1, anti-proliferative; cholesterol 25-hydroxylase; runt-related transcription factor 3; hypothetical protein FLJ23191; interleukin 11 receptor, alpha; procollagen C-endopeptidase enhancer; frizzled homolog 7 (*Drosophila*); hypothetical gene BC008967; collagen, type VIII, alpha 1; tenascin C (hexabrachion); iroquois homeobox protein 5; hephaestin; integrin, beta 8; synaptic vesicle glycoprotein 2; *Homo sapiens* cDNA FLJ12280 fis, clone MAMMA1001744; cytokine receptor-like factor 1; potassium intermediate/small conductance calcium-activated channel, subfamily N, member 4; integrin, alpha 7; DKFZP586L151 protein; transcriptional co-activator with PDZ-binding motif (TAZ); sine oculis homeobox homolog 2 (*Drosophila*); KIAA1034 protein; early growth response 3; distal-less homeobox 5; hypothetical protein FLJ20373; aldo-keto reductase family 1, member C3 (3-alpha hydroxysteroid dehydrogenase, type II); biglycan; fibronectin 1; proenkephalin; integrin, beta-like 1 (with EGF-like repeat domains); *Homo sapiens* mRNA full length insert cDNA clone EUROIMAGE 1968422; EphA3; KIAA0367 protein; natriuretic peptide receptor C/guanylate cyclase C (atrionatriuretic peptide receptor C); hypothetical protein FLJ14054; *Homo sapiens* mRNA; cDNA DKFZp564B222 (from clone DKFZp564B222); vesicle-associated membrane protein 5 (myobrevin); EGF-containing fibulin-like extracellular matrix protein 1; BCL2/adenovirus BIB 19 kDa interacting protein 3-like; AE binding protein 1; cytochrome c oxidase subunit VIIa polypeptide 1 (muscle); neuroblastoma, suppression of tumorigenicity 1; insulin-like growth factor binding protein 2, 36 kDa.

In another of its aspects, the invention provides isolated human umbilicus-derived cells, which relative to a human cell that is a fibroblast, a mesenchymal stem cell, or an ileac crest bone marrow cell, have reduced expression of genes for each of: short stature homeobox 2; heat shock 27 kDa protein 2; chemokine (C—X—C motif) ligand 12 (stromal cell-derived factor 1); elastin (supravalvular aortic stenosis, Williams-Beuren syndrome); *Homo sapiens* mRNA; cDNA DKFZp586M2022 (from clone DKFZp586M2022); mesenchyme homeobox 2 (growth arrest-specific homeobox); sine oculis homeobox homolog 1 (*Drosophila*); crystallin, alpha B; disheveled associated activator of morphogenesis 2; DKFZP586B2420 protein; similar to neuralin 1; tetranectin (plasminogen binding protein); src homology three (SH3) and cysteine rich domain; B-cell translocation gene 1, anti-proliferative; cholesterol 25-hydroxylase; runt-related transcription factor 3; hypothetical protein FLJ23191; interleukin 11 receptor, alpha; procollagen C-endopeptidase enhancer; frizzled homolog 7 (*Drosophila*); hypothetical gene BC008967; collagen, type VIII, alpha 1; tenascin C (hexabrachion); iroquois homeobox protein 5; hephaestin; integrin, beta 8; synaptic vesicle glycoprotein 2; *Homo sapiens* cDNA FLJ12280 fis, clone MAMMA1001744; cytokine receptor-like factor 1; potassium intermediate/small conductance calcium-activated channel, subfamily N, member 4; integrin, alpha 7; DKFZP586L151 protein; transcriptional co-activator with PDZ-binding motif (TAZ); sine oculis homeobox homolog 2 (*Drosophila*); KIAA1034 protein; early growth response 3; distal-less homeobox 5; hypothetical protein FLJ20373; aldo-keto reductase family 1, member C3 (3-alpha hydroxysteroid dehydrogenase, type II); biglycan; fibronectin 1; proenkephalin; integrin, beta-like 1 (with EGF-like repeat domains); *Homo sapiens* mRNA full length insert cDNA clone EUROIMAGE 1968422; EphA3; KIAA0367 protein; natriuretic peptide receptor C/guanylate cyclase C (atrionatriuretic peptide receptor C); hypothetical protein FLJ14054; *Homo sapiens* mRNA; cDNA DKFZp564B222 (from clone DKFZp564B222); vesicle-associated membrane protein 5 (myobrevin); EGF-containing fibulin-like extracellular matrix protein 1; BCL2/adenovirus E1B 19 kDa interacting protein 3-like; AE binding protein 1; cytochrome c oxidase subunit VIIa polypeptide 1 (muscle); neuroblastoma, suppression of tumorigenicity 1; insulin-like growth factor binding protein 2, 36 kDa; and which express a gene for each of interleukin 8; reticulon 1; chemokine (C—X—C motif) ligand 1 (melanoma growth stimulating activity, alpha); chemokine (C—X—C motif) ligand 6 (granulocyte chemotactic protein 2); chemokine (C—X—C motif) ligand 3; and tumor necrosis factor, alpha-induced protein 3, wherein the expression is increased relative to that of a human cell which is a fibroblast, a mesenchymal stem cell, an ileac crest bone marrow cell, or placenta-derived cell. Such cells need not be characterized with respect to their cell surface markers, but such cells preferably are capable of self-renewal and expansion in culture and also have the ability to differentiate in culture. Most preferred are cells which are isolated as adherent cells as described below, however, such cells can also be grown after isolation in a spherical form under certain conditions, thus they are not obligatorily adherent.

Certain preferred embodiments include cells as described above which also produce vimentin or alpha-smooth muscle actin. More preferred are cells that produce both vimentin and alpha-smooth muscle actin. The production of these proteins appears to distinguish the cells of the instant invention from hematopoietic cells isolated form umbilical cord blood for example.

In preferred embodiments, the above gene expression profiles are substantially stable and do not vary with passaging or normal culturing conditions. Of course, it is understood that such a profile may vary when cells are grown under conditions which stimulate or induce differentiation into other phenotypes, for example, or the expression of a different set of genes.

The invention also provides therapeutic cell cultures comprising the cell having the cell surface production or gene expression profiles, or both, as described above. Cell banks comprising therapeutic cultures are similarly included with in the scope of the invention. For example, a cell bank may include cultured cells of the invention at various passages, as well as cells of the invention which have been induced to differentiate to different phenotypes. Other cells may be successfully banked either separately or in co-culture with the cells of the invention. A complete cell bank may include the banked cells of a wide variety of individuals. In preferred embodiments, banked cells are stored cryopreserved at −180° C. for example. Cells are preferably stored at −90° C. in some embodiments. The cells of the invention are readily cryopreserved under a variety of conditions such as are known in the art.

In preferred embodiments, the cells lack the cell surface molecules required to substantially stimulate allogeneic lymphocytes in a mixed lymphocyte reaction. In more preferred embodiments, the cells lack the surface molecules required to substantially stimulate CD4+ T-cells in in vitro assessments, or in vivo in allogeneic, syngeneic, or autologous recipients. Still more preferred are those cells that do cause not any substantial adverse immunological consequences for in vivo applications. The therapeutic cell cultures lack detectable amounts of at least two, or several, or all of the stimulating proteins HLA-DR, HLA-DP, HLA-DQ, CD80, CD86, and B7-H2, as determined by flow cytometry. Those lacking all of the foregoing are most preferred. Also preferred are therapeutic cell cultures which further lack detectable amounts of one or both of the immunomodulating proteins HLA-G and CD178, as determined by flow cytometry. Also preferred are therapeutic cell cultures which express detectable amounts of the immuno-modulating protein PD-L2, as determined by flow cytometry. In one embodiment, the therapeutic cell culture does not substantially stimulate a lymphocyte mediated response in vitro, as compared to allogeneic controls in a mixed lymphocyte reaction.

In another of its several aspects, the invention provides isolated human umbilicus-derived cells capable of self-renewal and expansion in culture and which have the potential to differentiate into cells of other phenotypes, wherein the cells do not substantially stimulate allogeneic lymphocytes in a mixed lymphocyte reaction. More preferred are cells which do not substantially stimulate CD4+ T cells, and which produce PD-L2, but not one or more of HLA-G, CD178, HLA-DR, HLA-DP, HLA-DQ, CD80, CD86, or B7-H2. The cells also can produce vimentin or alpha-smooth muscle actin in certain embodiments. More preferred are cells producing both vimentin and alpha-smooth muscle actin. Still more preferred are those cells not producing any of HLA-G, CD178, HLA-DR, HLA-DP, HLA-DQ, CD80, CD86, and B7-H2.

Cells of the invention which secrete useful molecules, for example, growth factors, are presently preferred. Such cells have utility not only for the their cellular properties but for their secreted molecules, for example in conditioned medium, or cell-free lysates. In another aspect, the invention provides isolated human umbilicus-derived cells that secrete one or more of the angiogenic factors MCP-1, IL-8, GCP-2, HGF, KGF, FGF, HB-EGF, TPO, or TIMP 1. In certain embodiments, the cells secrete all of the foregoing factors. The cells do not secrete one or more of the angiogenic factors SDF-1alpha, TGF-beta2, ANG2, PDGFbb or VEGF, as detected by ELISA. In certain embodiments they secrete none of SDF-1alpha, TGF-beta2, ANG2, PDGFbb or VEGF, as detected by ELISA.

In another aspect, the cells of the invention are defined according to a combination of many of the characteristics provided herein. For example, the invention provides isolated umbilicus-derived cells comprising L-valine-requiring cells derived from mammalian postpartum tissue substantially free of blood. The cells are capable of self-renewal and expansion in culture and have the potential to differentiate into cells of other phenotypes; for example cardiomyocytes, or their progenitors. Cells may be isolated from umbilicus tissue of any mammal of interest by the techniques provided herein. Human cells are presently preferred. The cells can be grown under a wide range of conditions, including a wide variety of culture media, and environmental conditions. The cells can be grown at least from about 35° C. to about 39° C., and possibly a wider range depending on other conditions. The cells can be grown in chemically-defined media, or in medium with added mammalian serum, for example fetal bovine serum. The cells also tolerate cryopreservation at various stages. Cells can be maintained frozen, or banked at temperatures preferably at or below −80° C. for long periods. Other preferred temperatures range from about −90° C. to about −180° C. or below. Specialized electric freezers can be used, or cells can be stored in the liquid or vapor phases of nitrogen. Tissues can also be banked prior to the isolation of the cells. Preferably Good Banking Procedures, such as are known in the art, are followed.

The cells are capable of growth in atmospheres containing oxygen from about 5% to at least about 20% and comprise at least one of the following characteristics: the cells have the potential for at least about 40 doublings in culture; the cells preferably are adherent, thus attachment and expansion on a coated or uncoated tissue culture vessel is preferred, wherein a coated tissue culture vessel comprises a coating of gelatin, laminin, collagen, polyornithine, polylysine, vitronectin, or fibronectin;

The cells preferably produce of at least one of tissue factor, vimentin, and alpha-smooth muscle actin; more preferred are cells which produce each of tissue factor, vimentin, and alpha-smooth muscle actin; production of at least one of CD10, CD13, CD44, CD73, CD90, PDGFr-alpha, PD-L2 and HLA-A,B,C is also preferred. The cells are also characterized in their lack of production of at least one of CD31, CD34, CD45, CD80, CD86, CD117, CD141, CD178, B7-H2, HLA-G, and HLA-DR,DP,DQ, as detected by flow cytometry; more preferable cells lack production of all of these surface markers. Also preferred are cells which express at least one of interleukin 8; reticulon 1; chemokine (C—X—C motif) ligand 1 (melanoma growth stimulating activity, alpha); chemokine (C—X—C motif) ligand 6 (granulocyte chemotactic protein 2); chemokine (C—X—C motif) ligand 3; and tumor necrosis factor, alpha-induced protein 3. Preferred cells also have expression, which relative to a human cell that is a fibroblast, a mesenchymal stem cell, or an ileac crest bone marrow cell, is reduced for at least one of: short stature homeobox 2; heat shock 27 kDa protein 2; chemokine (C—X—C motif) ligand 12 (stromal cell-derived factor 1); elastin (supravalvular aortic stenosis, Williams-Beuren syndrome); *Homo sapiens* mRNA; cDNA DKFZp586M2022 (from clone DKFZp586M2022); mesenchyme homeobox 2 (growth arrest-specific homeobox); sine oculis homeobox homolog 1 (*Drosophila*); crystallin, alpha B; dishevealed associated activator of morphogenesis 2; DKFZP586B2420 protein; similar to neuralin 1; tetranectin (plasminogen binding protein); src homology three (SH3) and cysteine rich domain; B-cell translocation gene 1, anti-proliferative; cholesterol 25-hydroxylase; runt-related transcription factor 3; hypothetical protein FLJ23191; interleukin 11 receptor, alpha; procollagen C-endopeptidase enhancer; frizzled homolog 7 (*Drosophila*); hypothetical gene BC008967; collagen, type VIII, alpha 1; tenascin C (hexabrachion); iroquois homeobox protein 5; hephaestin; integrin, beta 8; synaptic vesicle glycoprotein 2; *Homo sapiens* cDNA FLJ12280 fis, clone MAMMA1001744; cytokine receptor-like factor 1; potassium intermediate/small conductance calcium-activated channel, subfamily N, member 4; integrin, alpha 7; DKFZP586L151 protein; transcriptional co-activator with PDZ-binding motif (TAZ); sine oculis homeobox homolog 2 (*Drosophila*); KIAA1034 protein; early growth response 3; distal-less homeobox 5; hypothetical protein FLJ20373; aldo-keto reductase family 1, member C3 (3-alpha hydroxysteroid dehydrogenase, type II); biglycan; fibronectin 1; proenkephalin; integrin, beta-like 1 (with EGF-like repeat domains); *Homo sapiens* mRNA full length insert cDNA clone EUROIMAGE 1968422; EphA3; KIAA0367 protein; natriuretic peptide receptor C/guanylate cyclase C (atrionatriuretic peptide receptor C); hypothetical protein FLJ14054; *Homo sapiens* mRNA; cDNA DKFZp564B222 (from clone DKFZp564B222); vesicle-associated membrane protein 5 (myobrevin); EGF-containing fibulin-like extracellular matrix protein 1; BCL2/adenovirus E1B 19 kDa interacting protein 3-like; AE binding protein 1; cytochrome c oxidase subunit VIIa polypeptide 1 (muscle); neuroblastoma, suppression of tumorigenicity 1; insulin-like growth factor binding protein 2, 36 kDa; the skilled artisan will appreciate that the expression of a wide variety of genes is conveniently characterized on a gene array, for example on a Affymetrix GENECHIP®.

The cells secrete a variety of biochemically-active factors, such as growth factors, chemokines, cytokines and the like. Preferred cells secrete at least one of MCP-1, IL-6, IL-8, GCP-2, HGF, KGF, FGF, HB-EGF, BDNF, TPO, MIPlalpha, RANTES, and TIMP1; preferred cells may alternatively be characterized in their lack of secretion of at least one of TGF-beta2, ANG2, PDGFbb, MIP1beta, I309, MDC, and VEGF, as detected by ELISA. These and other characteristics are available to identify and characterize the cells, and distinguish the cells of the invention from others known in the art.

In preferred embodiments, the cell comprises two or more of the foregoing characteristics. More preferred are those cells comprising, three, four, or five or more of the characteristics. Still more preferred are those isolated postpartum cells comprising six, seven, or eight or more of the characteristics. Still more preferred presently are those cells comprising all nine of the claimed characteristics.

Also presently preferred are cells that produce at least two of tissue factor, vimentin, and alpha-smooth muscle actin. More preferred are those cells producing all three of the proteins tissue factor, vimentin, and alpha-smooth muscle actin.

The skilled artisan will appreciate that cell markers are subject to vary somewhat under vastly different growth conditions, and that generally herein described are characterizations in Growth Medium, or variations thereof. Postpartum-derived cells that produce of at least one, two, three, or four of CD10, CD13, CD44, CD73, CD90, PDGFr-alpha, PD-L2 and HLA-A,B,C are preferred. More preferred are those cells producing five, six, or seven of these cell surface markers. Still more preferred are postpartum cells that can produce all eight of the foregoing cell surface marker proteins.

Similarly, postpartum cells that lack production of at least one, two, three, or four of the proteins CD31, CD34, CD45, CD80, CD86, CD117, CD141, CD178, B7-H2, HLA-G, and HLA-DR,DP,DQ, as detected by flow cytometry are presently preferred. Cells lacking production of at least five, six, seven or eight or more of these markers are also preferred. More preferred are cells which lack production of at least nine or ten of the cell surface markers. Most highly preferred are those cells lacking production of all eleven of the foregoing identifying proteins.

Presently preferred cells produce each of CD10, CD13, CD44, CD73, CD90, PDGFr-alpha, and HLA-A,B,C, and do not produce any of CD31, CD34, CD45, CD117, CD141, or HLA-DR,DP,DQ, as detected by flow cytometry.

Presently, it is preferred that postpartum-derived cells express at least one, two or three of interleukin 8; reticulon 1; chemokine (C—X—C motif) ligand 1 (melanoma growth stimulating activity, alpha); chemokine (C—X—C motif) ligand 6 (granulocyte chemotactic protein 2); chemokine (C—X—C motif) ligand 3; and tumor necrosis factor, alpha-induced protein 3. More preferred are those cells which express four or five, and still more preferred are cell capable of expressing all six of the foregoing genes.

For some embodiments, preferred are cells, which relative to a human cell that is a fibroblast, a mesenchymal stem cell, or an ileac crest bone marrow cell, have reduced expression for at least one of the genes corresponding to: short stature homeobox 2; heat shock 27 kDa protein 2; chemokine (C—X—C motif) ligand 12 (stromal cell-derived factor 1); elastin (supravalvular aortic stenosis, Williams-Beuren syndrome); *Homo sapiens* mRNA; cDNA DKFZp586M2022 (from clone DKFZp586M2022); mesenchyme homeobox 2 (growth arrest-specific homeobox); sine oculis homeobox homolog 1 (*Drosophila*); crystallin, alpha B; disheveled associated activator of morphogenesis 2; DKFZP586B2420 protein; similar to neuralin 1; tetranectin (plasminogen binding protein); src homology three (SH3) and cysteine rich domain; B-cell translocation gene 1, anti-proliferative; cholesterol 25-hydroxylase; runt-related transcription factor 3; hypothetical protein FLJ23191; interleukin 11 receptor, alpha; procollagen C-endopeptidase enhancer; frizzled homolog 7 (*Drosophila*); hypothetical gene BC008967; collagen, type VIII, alpha 1; tenascin C (hexabrachion); iroquois homeobox protein 5; hephaestin; integrin, beta 8; synaptic vesicle glycoprotein 2; *Homo sapiens* cDNA FLJ12280 fis, clone MAMMA1001744; cytokine receptor-like factor 1; potassium intermediate/small conductance calcium-activated channel, subfamily N, member 4; integrin, alpha 7; DKFZP586L151 protein; transcriptional co-activator with PDZ-binding motif (TAZ); sine oculis homeobox homolog 2 (*Drosophila*); KIAA1034 protein; early growth response 3; distal-less homeobox 5; hypothetical protein FLJ20373; aldo-keto reductase family 1, member C3 (3-alpha hydroxysteroid dehydrogenase, type II); biglycan; fibronectin 1; proenkephalin; integrin, beta-like 1 (with EGF-like repeat domains); *Homo sapiens* mRNA full length insert cDNA clone EUROIMAGE 1968422; EphA3; KIAA0367 protein; natriuretic peptide receptor C/guanylate cyclase C (atrionatriuretic peptide receptor C); hypothetical protein FLJ14054; *Homo sapiens* mRNA; cDNA DKFZp564B222 (from clone DKFZp564B222); vesicle-associated membrane protein 5 (myobrevin); EGF-containing fibulin-like extracellular matrix protein 1; BCL2/adenovirus E1B 19 kDa interacting protein 3-like; AE binding protein 1; cytochrome c oxidase subunit VIIa polypeptide 1 (muscle); neuroblastoma, suppression of tumorigenicity 1; insulin-like growth factor binding protein 2, 36 kDa. More preferred are cells that have, relative to human fibroblasts, mesenchymal stem cells, or ileac crest bone marrow cells, reduced expression of at least 5, 10, 15 or 20 genes corresponding to those listed above. Presently more preferred are cell with reduced expression of at least 25, 30, or 35 of the genes corresponding to the listed sequences. Also more preferred are those postpartum-derived cells having expression that is reduced, relative to that of a human fibroblast, a mesenchymal stem cell, or an ileac crest bone marrow cell, of genes corresponding to 35 or more, 40 or more, or even all of the sequences listed.

Secretion of certain growth factors and other cellular proteins can make cells of the invention particularly useful. Preferred postpartum-derived cells secrete at least one, two, three or four of MCP-1, IL-6, IL-8, GCP-2, HGF, KGF, FGF, HB-EGF, BDNF, TPO, MIP1a, RANTES, and TIMP1. Cells which secrete more than five, six, seven or eight of the listed proteins are also useful and preferred. Cells which can secrete at least nine, ten, eleven or more of the factors are more preferred, as are cells which can secrete twelve or more, or even all thirteen of the proteins in the foregoing list.

While secretion of such factors is useful, cells can also be characterized by their lack of secretion of factors into the medium. Umbilicus-derived cells that lack secretion of at least one, two, three or four of TGF-beta2, ANG2, PDGFbb, MIP1 beta, I309, MDC, and VEGF, as detected by ELISA, are presently preferred for use. Cells that are characterized in their lack of secretion of five or six of the foregoing proteins are more preferred. Cells which lack secretion of all seven of the factors listed above are also preferred.

In another aspect of the invention, therapeutic cell cultures are provided, the cell cultures comprising the isolated cells as described above for use in treating patients in need of angiogenesis-stimulating trophic factors. Such therapeutic cell cultures are also provided for use in treating a patient in need of neural growth stimulating trophic factors.

Methods of deriving UDCs from human umbilical tissue are provided. The cells are capable of self-renewal and expansion in culture, and have the potential to differentiate into cells of other phenotypes. The method comprises (a) obtaining human umbilical tissue; (b) removing substantially all of blood to yield a substantially blood-free umbilical tissue, (c) dissociating the tissue by mechanical or enzymatic treatment, or both, (d) resuspending the tissue in a culture medium, and (e) providing growth conditions which allow for the growth of a human umbilicus-derived cell capable of self-renewal and expansion in culture and having the potential to differentiate into cells of other phenotypes.

Tissue can be obtained from any completed pregnancy, term or less than term, whether delivered vaginally, or through other routes, for example surgical Cesarean section. Obtaining tissue from tissue banks is also considered within the scope of the present invention.

The tissue is rendered substantially free of blood by any means known in the art. For example, the blood can be physically removed by washing, rinsing, and diluting and the like, before or after bulk blood removal for example by suctioning or draining. Other means of obtaining a tissue substantially free of blood cells might include enzymatic or chemical treatment.

Dissociation of the umbilical tissues can be accomplished by any of the various techniques known in the art, including by mechanical disruption, for example, tissue can be aseptically cut with scissors, or a scalpel, or such tissue can be otherwise minced, blended, ground, or homogenized in any manner that is compatible with recovering intact or viable cells from human tissue.

In a presently preferred embodiment, the isolation procedure also utilizes an enzymatic digestion process. Many enzymes are known in the art to be useful for the isolation of individual cells from complex tissue matrices to facilitate growth in culture. As discussed above, a broad range of digestive enzymes for use in cell isolation from tissue is available to the skilled artisan. Ranging from weakly digestive (e.g. deoxyribonucleases and the neutral protease, dispase) to strongly digestive (e.g. papain and trypsin), such enzymes are available commercially. A nonexhaustive list of enzymes compatible herewith includes mucolytic enzyme activities, metalloproteases, neutral proteases, serine proteases (such as trypsin, chymotrypsin, or elastase), and deoxyribonucleases. Presently preferred are enzyme activities selected from metalloproteases, neutral proteases and mucolytic activities. For example, collagenases are known to be useful for isolating various cells from tissues. Deoxyribonucleases can digest single-stranded DNA and can minimize cell-clumping during isolation. Enzymes can be used alone or in combination. Serine protease are preferably used in a sequence following the use of other enzymes as they may degrade the other enzymes being used. The temperature and time of contact with serine proteases must be monitored. Serine proteases may be inhibited with alpha 2 microglobulin in serum and therefore the medium used for digestion is preferably serum-free. EDTA and DNase are commonly used and may improve yields or efficiencies. Preferred methods involve enzymatic treatment with for example collagenase and dispase, or collagenase, dispase, and hyaluronidase, and such methods are provided wherein in certain preferred embodiments, a mixture of collagenase and the neutral protease dispase are used in the dissociating step. More preferred are those methods which employ digestion in the presence of at least one collagenase from *Clostridium histolyticum*, and either of the protease activities, dispase and thermolysin. Still more preferred are methods employing digestion with both collagenase and dispase enzyme activities. Also preferred are methods which include digestion with a hyaluronidase activity in addition to collagenase and dispase activities. The skilled artisan will appreciate that many such enzyme treatments are known in the art for isolating cells from various tissue sources. For example, the LIBERASE Blendzyme (Roche) series of enzyme combinations are very useful and may be used in the instant methods. Other sources of enzymes are known, and the skilled artisan may also obtain such enzymes directly from their natural sources. The skilled artisan is also well-equipped to assess new, or additional enzymes or enzyme combinations for their utility in isolating the cells of the invention. Preferred enzyme treatments are 0.5, 1, 1.5, or 2 hours long or longer. In other preferred embodiments, the tissue is incubated at 37° C. during the enzyme treatment of the dissociation step. Diluting the digest may also improve yields of cells as cells may be trapped within a viscous digest.

While the use of enzyme activities is presently preferred, it is not required for isolation methods as provided herein. Methods based on mechanical separation alone may be successful in isolating the instant cells from the umbilicus as discussed above.

The cells can be resuspended after the tissue is dissociated into any culture medium as discussed herein above. Cells may be resuspended following a centrifugation step to separate out the cells from tissue or other debris. Resuspension may involve mechanical methods of resuspending, or simply the addition of culture medium to the cells.

Providing the growth conditions allows for a wide range of options as to culture medium, supplements, atmospheric conditions, and relative humidity for the cells. A preferred temperature is 37° C., however the temperature may range from about 35° C. to 39° C. depending on the other culture conditions and desired use of the cells or culture.

Presently preferred are methods which provide cells which require no exogenous growth factors, except as are available in the supplemental serum provided with the Growth Medium. Also provided herein are methods of deriving umbilical cells capable of expansion in the absence of particular growth factors. The methods are similar to the method above, however they require that the particular growth factors (for which the cells have no requirement) be absent in the culture medium in which the cells are ultimately resuspended and grown in. In this sense, the method is selective for those cells capable of division in the absence of the particular growth factors. Preferred cells in some embodiments are capable of growth and expansion in chemically-defined growth media with no serum added. In such cases, the cells may require certain growth factors, which can be added to the medium to support and sustain the cells. Presently preferred factors to be added for growth on serum-free media include one or more of FGF, EGF, IGF, and PDGF. In more preferred embodiments, two, three or all four of the factors are add to serum free or chemically defined media. In other embodiments, LIF is added to serum-free medium to support or improve growth of the cells.

Also provided are methods wherein the cells can expand in the presence of from about 5% to about 20% oxygen in their atmosphere. Methods to obtain cells that require L-valine require that cells be cultured in the presence of L-valine. After a cell is obtained, its need for L-valine can be tested and confirmed by growing on D-valine containing medium that lacks the L-isomer.

Methods are provided wherein the cells can undergo at least 25, 30, 35, or 40 doublings prior to reaching a senescent state. Methods for deriving cells capable of doubling to reach $10^{14}$ cells or more are provided. Preferred are those methods which derive cells that can double sufficiently to produce at least about $10^{14}$, $10^{15}$, $10^{16}$, or $10^{17}$ or more cells when seeded at from about $10^3$ to about $10^6$ cells/cm$^2$ in culture. Preferably these cell numbers are produced within 80, 70, or 60 days or less.

Isolated human umbilicus-derived cells derived by the above method are also provided herein. The cells maintain a consistent normal karyotype notwithstanding repeated passaging in certain embodiments. Also provided are cultures of human umbilicus-derived cells derived by the above method, wherein the cultures are free of maternal cells. Therapeutic cultures are provided which are obtained by the methods of the invention.

There are many uses for the cells of the instant invention. For example, because of the trophic factors secreted by the cells, they may be useful for the growth, maintenance, support or the like, of other useful cells, either directly or indirectly. For example, the cells may be used to make conditioned media, or may be cocultured with another cells of interest, including direct or indirect ex vivo coculture of cells intended to be used therapeutically in an autologous recipient. For direct coculture, the cells may be mixed together, while for indirect coculture, the cells may be cultured in compartments separated by semi-permeable membranes which exclude cell migration. For example, polycarbonate, polyester (PET), and collagen-coated polytetrafluoroethylene (PTFE) membranes of about less 3 microns nominal pore size exclude cell migration and are useful for such purposes. Such membranes for culture systems are able to exchange, for example, soluble growth factors between the umbilical-derived cells and another cell type. Examples are known in the art and some are available commercially (e.g. TRANSWELL culture membranes (Corning Inc, Corning N.Y.)).

Also provided herein are therapeutic compositions comprising an umbilicus-derived cell and another therapeutic agent or factor. Such factors include, but are not limited to, IGF, LIF, PDGF, EGF, FGF, as well as antithrombogenic and antiapoptotic agents. Such therapeutic compositions can further comprise one or more additional cell types.

In addition to the above, compositions derived from the cells themselves are provided herein. Cell lysates, soluble cell fractions and membrane-enriched cell fractions are all provided herein. Cell lysates include lysates in which substantially all, and more preferably all of the cells have been lysed, for example by mechanical shear, enzymatic treatment, detergent or other chemical treatment, and the like, or combinations thereof. The resulting lysates include all of the components of the cell and have many utilities, for example in supporting or maintaining growth of the cells of the invention or other cells of interest. In addition the cell lysates can serve as starting material for the purification or enrichment of desirable cell products. In preferred embodiments, cell lysates are further separated into at least a soluble cell fraction and a membrane-enriched cell fraction. Each may be useful for specific purposes. For example, where in vivo uses are contemplated, for example administration by injection, soluble cell fractions may be particularly useful in minimizing stimulation of allogeneic PBMCs. More particularly, soluble cell fractions preferably lack the required antigens to stimulate adverse immunological reactions, for example stimulation of allogeneic lymphocytes, allogeneic CD4$^+$ T cells, or even naïve CD4$^+$ T cells. Extracellular matrices derived from the cells, for example comprising basement membranes are also useful and are provided herein. Such extracellular material is useful for in vitro assays, for example, angiogenesis assays. They also may be useful in vivo as part of a therapeutic regimen. For example, extracellular matrix compounds are known for use in augmentation and repair such as applications relating to healing of acute and chronic wounds, or in cosmetic and reconstructive surgery. The extracellular matrix material is often useful where collagen-like properties are desirable. Extracellular matrix material is particularly useful in application requiring elasticity or viscosity because the extracellular matrix appears to be able to provide these attributes. Another application of extracellular matrix is in combination with an implantable therapeutic device. Techniques for cellular disruption range from gentle to harsh, the skilled artisan is well-equipped to select the technique for cell disruption based on the end-use of the cell lysate so obtained.

Compositions of the invention also include conditioned culture media as provided herein. Such media have first been used to grow the cells or cultures of the invention, which during growth secrete one or more useful products into the medium. Conditioned medium from these novel cells are useful for many purposes, including for example, supporting the growth of other mammalian cells in need of growth factors or trophic factors secreted into the media by the cells and cultures of the invention, and promoting, for example, angiogenesis. Conditioned media are useful for the secreted growth factors they contain, and preferably the conditioned media of the instant invention contain one or more growth factors useful for supporting the growth of another mammalian cell in need of such growth factors. The use of conditioned media is well understood by those of skill in the art. Continuous culture systems for generating conditioned culture medium are contemplated herein, and the cells of the invention are useful for large scale or continuous production of secreted cellular products such as growth factors.

Preferably, the conditioned media of the invention comprise one or more of MCP-1, IL-6, IL-8, GCP-2, HGF, KGF, FGF, HB-EGF, BDNF, TPO, or TIMP1. More preferred are those conditioned media which comprise several, (e.g., at least two, three or four) of the foregoing. Still more preferred are those which contain many (e.g., at least five, six, seven eight or more) of the growth factors listed. Also preferred are conditioned media which comprise additional secreted molecules of interest.

Another embodiment provides a mammalian cell culture comprising the conditioned medium and a mammalian cell in need of MCP-1, IL-6, IL-8, GCP-2, HGF, KGF, FGF, HB-EGF, BDNF, TPO, or TIMP1. Culturing in conditioned media provides for indirect methods of supporting, for example, the growth or maintenance of other cells. For example, such indirect methods provide ways of expanding populations of mammalian cells, which due to their growth factor requirements, are difficult to expand in culture in the absence of the conditioned medium.

Another aspect of the invention provides co-cultures comprising the umbilicus-derived cells and another mammalian cell of any phenotype. These co-cultures can comprise cells of any phenotype and may, for example, provide a way of expanding populations of mammalian cells, which due to their growth factor requirements are difficult to expand. This is a way of using the properties of the umbilicus-derived cells directly to support the growth of other cells. Such co-cultures are also of use in vivo for various applications, particularly where the use of such cells does not generate an undesired immunological response. The presence of the umbilicus-derived cells can encourage establishment and growth of cells, for example into implanted scaffolds, or at surgical repair sites. In preferred embodiments, the co-cultures comprise a human cell line in addition to the umbilicus-derived cell. Still more preferred would be to use the cells in a family member or person closely related to the donor. More preferred yet would be the co-cultures for use in the individual from whom the cells were derived.

In other aspects of the invention, uses of the cultures are provided. For example, the cultures of umbilicus-derived cells are useful in promoting angiogenesis. They are also useful in the treatment of soft tissue disease or injury. In preferred embodiments, the therapeutic cell cultures are grown on a scaffold or matrix. The growth on the scaffold or matrix or similar substrate can be in vivo, in vitro, or a combination of these. For in vivo application, the substrate can be surgically applied, for example as a repair to damage soft tissue. The substrate can be seeded with UDCs, or pretreated with UDC-conditioned medium, or cell lysates or soluble cell extracts, or other cell fraction, including an extracellular matrix, prior to surgical use. For in vitro applications, the cells can help other cells to establish on or within the substrate or its interstices. For example, skin or other soft tissue of dermal or subdermal layers can be grown in vitro on such substrates for later use. For combination uses, a population of cells can be established in vitro on the substrate or scaffold and then surgically attached, grafted, or implanted for further growth. Preestablishing a cell population, particularly one that secretes angiogenic factors may lead to much faster healing. Presently preferred for such scaffolds are nonpermanent, bioabsorbable polymeric matrices and the like.

A variety of scaffolds or matrices are known in the arts of tissue engineering and wound healing for example, and are useful with the cells and methods herein. Examples include, but are not limited to mats, foams, or self assembling peptides. Preferred mats comprise nonwoven fibers. Nonwoven mats may, for example, be formed using fibers comprised of a synthetic absorbable copolymer of glycolic and lactic acids (PGA/PLA), sold under the trade name VICRYL (Ethicon, Inc., Somerville, N.J.). Foams preferred for use herein include porous foams such as those comprising, for example, poly(epsilon-caprolactone)/poly(glycolic acid) (PCL/PGA) copolymer, as discussed in U.S. Pat. No. 6,355,699. Self assembling peptides and hydrogels formed therefrom are known in the art, and include RAD 16 hydrogel, exemplified herein. Such materials are frequently used as supports for growth of cells or tissue.

Also provided herein are additional uses for the therapeutic cell cultures of the invention that include, but are not limited to, use in the treatment of bone disease or injury, the treatment of pancreatic disease or injury, the treatment of kidney disease or injury, the treatment of neural disease or injury, cardiac disease or injury, and the treatment of hepatic disease or injury.

In another of its aspects, the invention provides higher order structures such as implantable tissue structures comprising the cells of the invention, implantable human tissue matrix comprising the cells, human tissues comprising the cells, and human organs comprising these cells.

The invention also provides, in another of its several aspects, injectable therapeutic cells comprising isolated human umbilicus-derived cells capable of self-renewal and expansion in culture and having the potential to differentiate into cells of other phenotypes, wherein the cells do not substantially stimulate allogeneic lymphocytes in a mixed lymphocyte reaction, and produce PD-L2, but not HLA-G, CD178, HLA-DR, HLA-DP, HLA-DQ, CD80, CD86, or B7-H2. This injectable therapeutic cell composition is useful as a therapeutic treatment in any application where undifferentiated cells can be recruited to a site through the circulation. In preferred embodiments, the injectable cell is treated to inactivate tissue factor. Such treatment includes any treatment capable of inactivating tissue factor without destroying the integrity of the cell. More preferred are treatments which have no effect on viability, doubling time or expansion. The injectable cell is treated with an anti-tissue factor antibody in one presently preferred embodiment.

In conjunction with therapeutic cells, other biologically active molecules, such as antithrombogenic agents, anti-apoptotic agents, and anti-inflammatory agents may be useful and may be administered in sequence with, or coadministered with the cells, individually or in combinations or two or more such compounds or agents. For example, anti-apoptotic agents may be useful to minimize programmed cell death. Such agents include but are not limited to EPO, EPO derivatives and analogs, and their salts, TPO, IGF-I, IGF-II, hepatocyte growth factor (HGF), and caspase inhibitors. Anti-inflammatory agents include but are not limited to P38 MAP kinase inhibitors, statins, IL-6 and IL-1 inhibitors, Pemirolast, Tranilast, Remicade, Sirolimus, nonsteroidal anti-inflammatory compounds, for example, Tepoxalin, Tolmetin, and Suprofen.

Other bioactive factors or therapeutic agents which can be coadministered with the therapeutic cells of the invention include, for example, antithrombogenic factors, or immunomodulatory agents, and antioxidants. Examples of immunosuppressive and immunomodulatory agents include calcineurin inhibitors, for example cyclosporine, Tacrolimus, mTOR inhibitors such as Sirolimus or Everolimus; anti-proliferatives such as azathioprine and mycophenolate mofetil; corticosteroids for example prednisolone or hydrocortisone; antibodies such as monoclonal anti-IL-2Rα receptor antibodies, Basiliximab, Daclizumab; polyclonal anti-T-cell antibodies such as anti-thymocyte globulin (ATG), anti-lymphocyte globulin (ALG), and the monoclonal anti-T cell antibody OKT3. Antithrombogenic compounds which can be therapeutically provided in conjunction with the cells of the invention include, for example, heparin, heparin derivatives, urokinase, and PPack (dextrophenylalanine proline arginine chloromethylketone); antithrombin compounds, platelet receptor antagonists, anti-thrombin antibodies, anti-platelet receptor antibodies, aspirin, dipyridamole, protamine, hirudin, prostaglandin inhibitors, and platelet inhibitors. Antioxidants are well known in the art of course and any pharmaceutically acceptable antioxidant may be administered in conjunction with the cells of the invention including probucol; vitamins A, C, and E, coenzyme Q-10, glutathione, L cysteine, N-acetylcysteine, or antioxidant derivative, analogs or salts of the foregoing.

In another aspect of the invention, kits for the growth and maintenance, the isolation and the use of the umbilical-derived cells are provided. The cells, cell lysates, soluble cell fractions, membrane fractions and matrices can conveniently be employed as parts of kits, for example, for a kit for culture or implantation. The invention provides a kit including the UDCs and additional components, including instructions for growth or maintenance, isolation, or use of the cells or cell fractions, together with for example, matrix (e.g., a scaffold) material, hydrating agents (e.g., physiologically-compatible saline solutions, prepared cell culture media), cell culture substrates (e.g., culture dishes, plates, vials, etc.), cell culture media (whether in liquid or dehydrated form), antibiotic compounds, hormones, and the like. Kits for growth can for example include all of the components of the Growth Medium as used herein, including serum, for example fetal bovine serum. While the kit can include any such components, preferably it includes all ingredients necessary for its intended use. If desired, the kit also can include cells (typically cryopreserved), which can be seeded into the lattice as described herein. Kits for isolation will contain everything required to practice the isolation methods as provided herein, except for the umbilicus tissue which should be obtained fresh or frozen from a tissue bank at the time of isolation. The surgical equipment for dissociating the tissue, preferred enzymes, or choices of enzymes in stable form are provided, as are the buffers and medium, cell strainers and the like, as required or preferred for the method as disclosed above. Detailed instructions with optional steps and lists of suppliers of optional or alternative materials are also conveniently provided. Control cells can be included for comparison of the cells isolated to, for example the UDC cultures deposited with the ATCC. Kits for utilizing the umbilicus-derived cells preferably contain populations of the cells, or therapeutic compositions comprising the cells, components and products, or fractions or conditioned media derived from the cells as described above. In some embodiments, the kits may include one or more cell populations, including at least UDCs and a pharmaceutically acceptable carrier (liquid, semi-solid or solid). The populations in some embodiments are homogenous or even clonal cell lines of UDCs. In other embodiments, the kits include other cell lines for use in coculture. Therapeutic application kits preferably include additional bioactive agents as desired for example anithrombogenic agents, anti-inflammatory agents, antiapoptotic agents, and immunosuppressive or immunomodulatory compounds. The kits also optionally may include a means of administering the cells, for example by injection. The kits further may include instructions for use of the cells. Kits prepared for field hospital use, such as for military use, may include full-procedure supplies including tissue scaffolds, surgical sutures, and the like, where the cells are to be used in conjunction with repair of acute injuries. Kits for assays and in vitro methods as described herein may contain one or more of (1) UDCs or fractions, components or products of UDCs, (2) reagents for practicing the in vitro method, (3) other cells or cell populations, as appropriate, for example for cocultures and (4) instructions for conducting the in vitro method.

Also provided herein are isolated postpartum-derived cells comprising a "signature gene profile." Preferred are cells wherein the signature genes are reticulon, oxidized LDL receptor, and IL-8. In preferred embodiments, the cells comprise a profile which includes mRNA from genes for reticulon, oxidized LDL receptor, and IL-8. Most preferably, the profile comprises genes which are present independent of whether the cells are grown in medium containing serum or medium free of serum, and which further distinguish the postpartum-derived cell from other cell that are totipotent or pluripotent. In certain embodiments, the isolated postpartum-derived cells further comprise the ability to alter their expression of cell surface markers when grown in medium containing serum relative to that in serum free medium. In other embodiments of the isolated postpartum-derived cells, the markers for PDGFreceptor alpha and HLA-ABC are altered. This plasticity of the cells with respect to their cell surface markers allows the cells to be engineered in certain respects to provided full advantage of the cells desirous properties and to minimize any unwanted or deleterious properties relating to cell surface markers. This is particularly useful in engineering or preparing cells for implantation or for use in grafting where adverse immunological reactions and rejection are concerns.

In another of its several aspects, the invention provides a method for the preparation of therapeutic cells or cultures comprising: isolating cells; initially expanding the cells to a useful number in a serum-containing medium which supports cell expansion but in which the cells produce a quantity of the cell surface marker HLA-ABC; transferring the cells to a medium in which the cells produce a decreased amount of the cell surface marker HLA-ABC; and passaging the cells in the medium in which the cells produce a decreased amount of the HLA-ABC, thereby preparing a therapeutic cell or culture. In certain embodiments, the medium in which the cells produce a decreased amount of the cell surface marker HLA-ABC is a serum-free medium. This is useful for the manufacture and commercial application of the cells and therapeutic cultures particularly where required by regulatory agencies and the like. Such methods are beneficial and desirable for the production of therapeutic cells or cultures for implantation and grafting.

The invention provides in another aspect, serum-free media for the expansion of postpartum-derived cells. Preferred media have one or more exogenous growth factors added. Presently preferred are media wherein the one or more growth factors added are bFGF, EGF, or PDGF. Even more preferred are media wherein the one or more added growth factors includes bFGF by itself or in combination with other growth factors beneficial for the growth of the cells or for optimizing the expression of certain cell surface markers.

In preferred embodiments, the serum-free media of the invention provide support for the expansion for at least 5 passages of the cells with no reduction in the cells viability and no senescence. More preferred are media which support 10, 15, 20 or more passages of the cells, with the populations still capable of more passaging. Even more preferred are media which support 25, 28, 30, 33 and 35 or more passages. Most preferred are media capable of supporting the cells for about 40 or more passages.

Also provided in conjunction with the present invention are therapeutic cultures comprising postpartum-derived cells expanded in serum-free medium Such cells have any useful properties and are more readily suited for commercial application and regulatory approval having, for example, little risk of disease transmission related to foreign animal serum or proteins. In certain preferred embodiments, the therapeutic cultures comprise cells having a signature gene profile wherein mRNA from genes for reticulon, oxidized LDL receptor, and IL-8 are present independent of whether the cells are grown in medium containing serum or medium free of serum. Such cultures may comprise a single cell type or may consist of multiple cell types including PPDCs and other cell types as additional cells present in the co- or mixed culture.

Also provided herein are cell culture banks comprising the postpartum-derived cells and cultures of the invention.

The following examples describe several aspects of embodiments of the invention in greater detail. These examples are intended to further illustrate aspects of the invention described herein. These examples should not be construed to limit the aspect so exemplified.

EXAMPLE 1

Isolation of Cells from Postpartum Umbilicus Tissues

Postpartum umbilicus tissues were obtained upon birth of either a full term or pre-term pregnancy. Cells were harvested from five separate donors of umbilicus tissue. Different methods of cell isolation were tested for their ability to yield cells with: 1) the potential to differentiate into cells with different phenotypes, a characteristic common to stem cells, or 2) the potential to provide critical trophic factors useful for other cells and tissues.

Methods & Materials

Umbilical cell isolation. Umbilical cords were obtained from National Disease Research Interchange (NDRI, Philadelphia, Pa.). The tissues were obtained following normal deliveries. The cell isolation protocols were performed aseptically in a laminar flow hood. To remove blood and debris, the cord was washed in phosphate buffered saline (PBS; Invitrogen, Carlsbad, Calif.) in the presence of penicillin at 100 Units/milliliter and streptomycin at 100 milligrams/milliliter, and amphotericin B at 0.25 micrograms/milliliter (Invitrogen Carlsbad, Calif.). The tissues were then mechanically dissociated in 150 $cm^2$ tissue culture plates in the presence of 50 milliliters of medium (DMEM-Low glucose or DMEM-High glucose; Invitrogen), until the tissue was minced into a fine pulp. The chopped tissues were transferred to 50 milliliter conical tubes (approximately 5 grams of tissue per tube).

The tissue was then digested in either DMEM-Low glucose medium or DMEM-High glucose medium, each containing 100 Units/milliliter, streptomycin at 100 milligrams/milliliter, and amphotericin B at 0.25 micrograms/milliliter and the digestion enzymes. In some experiments an enzyme mixture of collagenase and dispase was used ("C:D") (collagenase (Sigma, St Louis, Mo.), 500 Units/milliliter; and dispase (Invitrogen), 50 Units/milliliter, in DMEM-Low glucose medium). In other experiments a mixture of collagenase, dispase and hyaluronidase ("C:D:H") was used (C:D: H=collagenase, 500 Units/milliliter; dispase, 50 Units/milliliter; and hyaluronidase (Sigma), 5 Units/milliliter, in DMEM-Low glucose). The conical tubes containing the tissue, medium and digestion enzymes were incubated at 37° C. in an orbital shaker (Environ, Brooklyn, N.Y.) at 225 rpm for 2 hrs.

After digestion, the tissues were centrifuged at 150×g for 5 minutes, the supernatant was aspirated. The pellet was resuspended in 20 milliliters of Growth Medium (DMEM:Low glucose (Invitrogen), 15 percent (v/v) fetal bovine serum (FBS; defined fetal bovine serum; Lot #AND18475; Hyclone, Logan, Utah), 0.001% (v/v) 2-mercaptoethanol (Sigma), penicillin at 100 Units per milliliter, streptomycin at 100 micrograms per milliliter, and amphotericin B at 0.25 micrograms per milliliter; (each from Invitrogen, Carlsbad, Calif.)). The cell suspension was filtered through a 70-micron nylon BD FALCON Cell Strainer (BD Biosciences, San Jose, Calif.). An additional 5 milliliters rinse comprising Growth Medium was passed through the strainer. The cell suspension was then passed through a 40-micrometer nylon cell strainer (BD Biosciences, San Jose, Calif.) and chased with a rinse of an additional 5 milliliters of Growth Medium.

The filtrate was resuspended in Growth Medium (total volume 50 milliliters) and centrifuged at 150×g for 5 minutes. The supernatant was aspirated and the cells were resuspended in 50 milliliters of fresh growth medium. This process was repeated twice more.

After the final centrifugation, supernatant was aspirated and the cell pellet was resuspended in 5 milliliters of fresh growth medium. The number of viable cells was determined using Trypan blue staining. Cells were then cultured under standard conditions.

The cells isolated from umbilical cord tissues were seeded at 5,000 cells/$cm^2$ onto gelatin-coated T-75 flasks (Corning Inc., Corning, N.Y.) in Growth Medium. After two days, spent medium and unadhered cells were aspirated from the flasks. Adherent cells were washed with PBS three times to remove debris and blood-derived cells. Cells were then replenished with Growth Medium and allowed to grow to confluence (about 10 days from passage 0) to passage 1. On subsequent passages (from passage 1 to 2 etc), cells reached sub-confluence (75-85 percent confluence) in 4-5 days. For these subsequent passages, cells were seeded at 5,000 cells/$cm^2$. Cells were grown in a humidified incubator with 5 percent carbon dioxide at 37° C.

Cell Isolation using LIBERASE Blendzymes. Cells were isolated from postpartum tissues in DMEM-Low glucose medium with LIBERASE (2.5 milligrams per milliliter, Blendzyme 3; Roche Applied Sciences, Indianapolis, Ind.) and hyaluronidase (5 Units/milliliter, Sigma). Digestion of the tissue and isolation of the cells was as described for other protease digestions above, however, the LIBERASE/hyaluronidase mixture was used instead of the C:D or C:D:H enzyme mixture. Tissue digestion with LIBERASE resulted in the isolation of cell populations from postpartum tissues that expanded readily.

Cell isolation using other enzyme combinations. Procedures were compared for isolating cells from the umbilical cord using differing enzyme combinations. Enzymes compared for digestion included: i) collagenase; ii) dispase; iii) hyaluronidase; iv) collagenase:dispase mixture (C:D); v) collagenase:hyaluronidase mixture (C:H); yl) dispase:hyaluronidase mixture (D:H); and vii) collagenase:dispase:hyaluronidase mixture (C:D:H). Differences in cell isolation utilizing these different enzyme digestion conditions were observed (Table 1-1).

Isolation of cells from residual blood in the cords. Other attempts were made to isolate pools of cells from umbilical cord by different approaches. In one instance umbilical cord was sliced and washed with growth medium to dislodge the blood clots and gelatinous material. The mixture of blood, gelatinous material and growth medium was collected and centrifuged at 150×g. The pellet was resuspended and seeded onto gelatin coated flasks in growth medium. From these experiments a cell population was isolated that readily expanded.

Isolation of cells from cord blood. Cells have also been isolated from cord blood samples attained from NDRI. The isolation protocol used was that of International patent application US0229971 by Ho et al. Samples (50 milliliter and 10.5 milliliters, respectively) of umbilical cord blood (NDRI, Philadelphia Pa.) were mixed with lysis buffer (filter-sterilized 155 millimolar ammonium chloride, 10 millimolar potassium bicarbonate, 0.1 millimolar EDTA buffered to pH 7.2 (all components from Sigma, St. Louis, Mo.)). Cells were lysed at a ratio of 1:20 cord blood to lysis buffer. The resulting cell suspension was vortexed for 5 seconds, and incubated for 2 minutes at ambient temperature. The lysate was centrifuged (10 minutes at 200×g). The cell pellet was resuspended in Complete Minimal Essential Medium (Gibco, Carlsbad Calif.) containing 10 percent fetal bovine serum (Hyclone, Logan Utah), 4 millimolar glutamine (Mediatech Herndon, Va.), penicillin at 100 Units per milliliter and streptomycin at 100 micrograms per milliliter (Gibco, Carlsbad, Calif.). The resuspended cells were centrifuged (10 minutes at 200×g), the supernatant was aspirated, and the cell pellet was washed in complete medium. Cells were seeded directly into either T75 flasks (Corning, N.Y.), T75 laminin-coated flasks, or T175 fibronectin-coated flasks (both Becton Dickinson, Bedford, Mass.).

TABLE 1-1

Isolation of cells from umbilical cord tissue using varying enzyme combinations

| Enzyme Digest | Cells Isolated | Cell Expansion |
| --- | --- | --- |
| Collagenase | X | X |
| Dispase | + (>10 h) | + |
| Hyaluronidase | X | X |
| Collagenase:Dispase | ++ (<3 h) | ++ |
| Collagenase:Hyaluronidase | ++ (<3 h) | + |
| Dispase:Hyaluronidase | + (>10 h) | + |
| Collagenase:Dispase:Hyaluronidase | +++ (<3 h) | +++ |

Key: + = good, ++ = very good, +++ = excellent, X = no success

Isolation of cells using different enzyme combinations and growth conditions. Cells attached and expanded well between passage 0 and 1 under all conditions tested for enzyme digestion and growth (Table 1-2). Cells in experimental conditions 5-8 and 13-16 proliferated well up to 4 passages after seeding, at which point they were cryopreserved. All cells were cryopreserved for further analysis.

TABLE 1-2

Isolation and culture expansion of postpartum cells under varying conditions:

| Condition | Medium | 15% FBS | BME | Gelatin | 20% O$_2$ | Growth Factors |
| --- | --- | --- | --- | --- | --- | --- |
| 1 | DMEM-Lg | Y | Y | Y | Y | N |
| 2 | DMEM-Lg | Y | Y | Y | N (5%) | N |
| 3 | DMEM-Lg | Y | Y | N | Y | N |
| 4 | DMEM-Lg | Y | Y | N | N (5%) | N |
| 5 | DMEM-Lg | N (2%) | Y | N (Laminin) | Y | EGF/FGF (20 ng/ml) |
| 6 | DMEM-Lg | N (2%) | Y | N (Laminin) | N (5%) | EGF/FGF (20 ng/ml) |
| 7 | DMEM-Lg | N (2%) | Y | N (Fibronectin) | Y | PDGF/VEGF |
| 8 | DMEM-Lg | N (2%) | Y | N (Fibronectin) | N (5%) | PDGF/VEGF |
| 9 | DMEM-Lg | Y | N | Y | Y | N |
| 10 | DMEM-Lg | Y | N | Y | N (5%) | N |
| 11 | DMEM-Lg | Y | N | N | Y | N |
| 12 | DMEM-Lg | Y | N | N | N (5%) | N |
| 13 | DMEM-Lg | N (2%) | N | N (Laminin) | Y | EGF/FGF (20 ng/ml) |
| 14 | DMEM-Lg | N (2%) | N | N (Laminin) | N (5%) | EGF/FGF (20 ng/ml) |
| 15 | DMEM-Lg | N (2%) | N | N (Fibronectin) | Y | PDGF/VEGF |
| 16 | DMEM-Lg | N (2%) | N | N (Fibronectin) | N (5%) | PDGF/VEGF |

Isolation of cells using different enzyme combinations and growth conditions. To determine whether cell populations could be isolated under different conditions and expanded under a variety of conditions immediately after isolation, cells were digested in Growth Medium with or without 0.001 percent (v/v) 2-mercaptoethanol (Sigma, St. Louis, Mo.), using the enzyme combination of C:D:H, according to the procedures provided above. All cells were grown in the presence of penicillin at 100 Units per milliliter and streptomycin at 100 micrograms per milliliter. Under all tested conditions cells attached and expanded well between passage 0 and 1 (Table 1-2). Cells in conditions 5-8 and 13-16 were demonstrated to proliferate well up to 4 passages after seeding at which point they were cryopreserved.

Results

Cell isolation using different enzyme combinations. The combination of C:D:H, provided the best cell yield following isolation, and generated cells that expanded for many more generations in culture than the other conditions (Table 1-1). An expandable cell population was not attained using collagenase or hyaluronidase alone. No attempt was made to determine if this result is specific to the collagenase that was tested.

Isolation of cells from residual blood in the cords. Nucleated cells attached and grew rapidly. These cells were analyzed by flow cytometry and were similar to cells obtained by enzyme digestion.

Isolation of cells from cord blood. The preparations contained red blood cells and platelets. No nucleated cells attached and divided during the first 3 weeks. The medium was changed 3 weeks after seeding and no cells were observed to attach and grow.

Summary. Populations of cells could be isolated from umbilical tissue efficiently using the enzyme combination collagenase (a metalloprotease), dispase (neutral protease) and hyaluronidase (mucolytic enzyme which breaks down hyaluronic acid). LIBERASE, which is a blend of collagenase and a neutral protease, may also be used. Blendzyme 3, which is collagenase (4 Wunsch units/gram) and thermolysin (1714 casein Units/gram), was also used together with hyaluronidase to isolate cells. These cells expanded readily over many passages when cultured in growth expansion medium on gelatin coated plastic.

Cells were also isolated from residual blood in the cords, but not cord blood. The presence of cells in blood clots washed from the tissue, which adhere and grow under the conditions used, may be due to cells being released during the dissection process.

Reference

1. Ho, Tony, W., et al., WO2003025149 A2 "CELL POPULATIONS WHICH CO-EXPRESS CD49C AND CD90" NEURONYX, INC. application No. US0229971 US, Filed 20020920, A2 Published 20030327, A3 Published 20031218

EXAMPLE 2

Growth Characteristics of Umbilicus-Derived Cells

The cell expansion potential of umbilicus-derived cells was compared to other populations of isolated stem cells. The process of cell expansion to senescence is referred to as Hayflick's limit (Hayflick L. The longevity of cultured human cells. *J. Am. Geriatr. Soc.* 22(1):1-12, 1974; Hayflick L. The strategy of senescence. *Gerontologist* 14(1):37-45), 1974).

Materials and Methods

Gelatin-coating flasks. Tissue culture plastic flasks were coated by adding 20 milliliters 2% (w/v) gelatin (Type B: 225 Bloom; Sigma, St Louis, Mo.) to a T75 flask (Corning Inc., Corning, N.Y.) for 20 minutes at room temperature. After removing the gelatin solution, 10 milliliters phosphate-buffered saline (PBS) (Invitrogen, Carlsbad, Calif.) were added and then aspirated.

Comparison of expansion potential of umbilicus-derived cells with other cell populations. For comparison of growth expansion potential the following cell populations were utilized: i) Mesenchymal stem cells (MSC; Cambrex, Walkersville, Md.); ii) Adipose-derived cells (U.S. Pat. No. 6,555,374 B1; U.S. Patent Application US20040058412); iii) Normal dermal skin fibroblasts (cc-2509 lot #9F0844; Cambrex, Walkersville, Md.); and iv) Umbilicus-derived cells. Cells were initially seeded at 5,000 cells/cm$^2$ on gelatin-coated T75 flasks in Growth Medium. For subsequent passages, cell cultures were treated as follows. After trypsinization, viable cells were counted after Trypan blue staining. Cell suspension (50 microliters) was combined with Trypan blue (50 microliters, Sigma, St. Louis Mo.). Viable cell numbers were estimated using a hemocytometer.

Following counting, cells were seeded at 5,000 cells/cm$^2$ onto gelatin-coated T 75 flasks in 25 milliliters of fresh Growth Medium. Cells were grown in a standard atmosphere (5 percent carbon dioxide (v/v)) at 37° C. The Growth Medium was changed twice per week. When cells reached about 85 percent confluence they were passaged; this process was repeated until the cells reached senescence.

At each passage, cells were trypsinized and counted. The viable cell yield, population doublings [ln (cells final/cells initial)/ln 2], and doubling time (time in culture/population doubling) were calculated. For the purposes of determining optimal cell expansion, the total cell yield per passage was determined by multiplying the total yield for the previous passage by the expansion factor for each passage (i.e. expansion factor=cells final/cells initial).

Expansion potential of cell banks at low density. The expansion potential of cells banked at passage 10 was also tested. A different set of conditions was used. Normal dermal skin fibroblasts (cc-2509 lot #9F0844; Cambrex, Walkersville, Md.), umbilicus-derived cells, and placenta-derived cells were tested. These cell populations had been banked at passage 10 previously, having been cultured at 5,000 cells/cm$^2$ at each passage to that point. The effect of cell density on the cell populations following cell thaw at passage 10 was determined. Cells were thawed under standard conditions, counted using Trypan blue staining. Thawed cells were then seeded at 1,000 cells/cm$^2$ in Growth Medium. Cells were grown under standard atmospheric conditions at 37° C. Growth Medium was changed twice a week. Cells were passaged as they reached about 85% confluence. Cells were subsequently passaged until senescence, i.e., until they could not be expanded any further. Cells were trypsinized and counted at each passage. The cell yield, population doubling (ln (cells final/cells initial)/ln 2) and doubling time (time in culture)/population doubling). The total cell yield per passage was determined by multiplying total yield for the previous passage by the expansion factor for each passage (i.e., expansion factor=cells final/cells initial).

Expansion of umbilicus-derived cells at low density from initial cell seeding. The expansion potential of freshly isolated umbilicus-derived cell cultures under low cell seeding conditions was tested in another experiment. Umbilicus-derived cells were isolated as described in a previous example. Cells were seeded at 1,000 cells/cm$^2$ and passaged as described above until senescence. Cells were grown under standard atmospheric conditions at 37° C. Growth Medium was changed twice per week. Cells were passaged as they reached about 85% confluence. At each passage, cells were trypsinized and counted by Trypan blue staining. The cell yield, population doubling (ln(cell final/cell initial)/ln 2) and doubling time (time in culture/population doubling) were calculated for each passage. The total cell yield per passage was determined by multiplying the total yield for the previous passage by the expansion factor for each passage (i.e. expansion factor=cell final/cell initial). Cells were grown on gelatin and non-gelatin coated flasks.

Expansion of cells in low oxygen culture conditions. It has been demonstrated that low $O_2$ cell culture conditions can improve cell expansion in certain circumstances (Csete, Marie; Doyle, John; Wold, Barbara J.; McKay, Ron; Studer, Lorenz. Low oxygen culturing of central nervous system progenitor cells. US20040005704). In order to determine if cell expansion of umbilicus-derived cells could be improved by altering cell culture conditions, cultures of umbilicus-derived cells were grown in low oxygen conditions. Cells were seeded at 5,000 cells/cm$^2$ in Growth Medium on gelatin coated flasks. Cells were initially cultured under standard atmospheric conditions through passage 5, at which point they were transferred to low oxygen (5% $O_2$) culture conditions.

Other growth conditions. In other experiments cells were expanded on non-coated, collagen-coated, fibronectin-coated, laminin-coated and Matrigel-coated plates. Cultures have been demonstrated to expand well on these different matrices.

Results

Comparison of expansion potential of umbilicus-derived cells with other cell populations. Umbilicus-derived cells expanded for more than 40 passages generating cell yields of >1E17 cells in 60 days. In contrast, MSCs and fibroblasts senesced after <25 days and <60 days, respectively. Although both adipose-derived and'omental cells expanded for almost 60 days they generated total cell yields of 4.5E12 and 4.24E13 respectively. Thus, when seeded at 5,000 cells/cm$^2$ under the experimental conditions utilized, umbilicus-derived cells expanded much better than the other cell types grown under the same conditions (Table 2-1).

TABLE 2-1

Growth characteristics for different cell populations grown to senescence

| Cell Type | Senescence | Total Population Doublings | Yield (Total Cells) |
|---|---|---|---|
| MSC | 24 d | 8 | 4.72E7 |
| Adipose-derived cell | 57 d | 24 | 4.5E12 |
| Fibroblasts | 53 d | 26 | 2.82E13 |
| Umbilical | 65 d | 42 | 6.15E17 |

Expansion of potential of cell banks at low density. Umbilicus-derived and fibroblast cells expanded for greater than 10 passages generating cell yields of >1E11 cells in 60 days (Table 2-2). Under these conditions both the fibroblasts and the umbilicus-derived cell populations senesced after 80 days, completing >50 and >40 population doublings respectively.

TABLE 2-2

Growth characteristics for different cell populations using low density growth expansion from passage 10 through senescence

| Cell Type (Passage No.) | Senescence | Total Population Doublings | Yield (Total Cells) |
|---|---|---|---|
| Fibroblast (P10) | 80 days | 43.68 | 2.59E11 |
| Umbilical (P10) | 80 days | 53.6 | 1.25E14 |

Expansion of cells in low oxygen culture conditions. Cells expanded well under the reduced oxygen conditions, however, culturing under low oxygen conditions does not appear to have a significant effect on cell expansion for postpartum-derived cells. These results are preliminary in the sense that any ultimate conclusions to be made regarding the effect of reduced oxygen would best be drawn from experiments on growing cells in low oxygen from initial isolation. Standard atmospheric conditions have already proven successful for growing sufficient numbers of cells, and low oxygen culture is not required for the growth of postpartum-derived cells.

Summary. The current cell expansion conditions of growing isolated umbilicus-derived cells at densities of about 5,000 cells/cm$^2$, in Growth Medium on gelatin-coated or uncoated flasks, under standard atmospheric oxygen, are sufficient to generate large numbers of cells at passage 11. Furthermore, the data suggests that the cells can be readily expanded using lower density culture conditions (e.g. 1,000 cells/cm$^2$). Umbilicus-derived cell expansion in low oxygen conditions also facilitates cell expansion, although no incremental improvement in cell expansion potential has yet been observed when utilizing these conditions for growth. Presently, culturing umbilicus-derived cells under standard atmospheric conditions is preferred for generating large pools of cells. However, when the culture conditions are altered, umbilicus-derived cell expansion can likewise be altered. This strategy may be used to enhance the proliferative and differentiative capacity of these cell populations.

Under the conditions utilized, while the expansion potential of MSC and adipose-derived cells is limited, umbilicus-derived cells expand readily to large numbers.

References

1) Hayflick L. The longevity of cultured human cells. *J Am Geriatr Soc.* 22:1-12, 1974.

2) Hayflick L. The strategy of senescence. *Gerontologist* 14(1):37-45, 1974.

3) U.S. Pat. Application No. 20040058412

4) U.S. Pat. Application No. 20040048372

6) Csete, Marie; Doyle, John; Wold, Barbara J.; McKay, Ron; and Studer, Lorenz. Low oxygen culturing of central nervous system progenitor cells. U.S. Pat. Application No. 20040005704.

EXAMPLE 3

Growth of Umbilicus-derived Cells in Medium Containing D-Valine

It has been reported that medium containing D-valine instead of the normal L-valine isoform can be used to selectively inhibit the growth of fibroblast-like cells in culture (Hongpaisan, 2000; Sordillo et al., 1988). Experiments were performed to determine whether umbilicus-derived cells could grow in medium containing D-valine.

Methods & Materials

Umbilicus-derived cells (P5) and fibroblasts (P9) were seeded at 5,000 cells/cm$^2$ in gelatin-coated T75 flasks (Corning, Corning, N.Y.). After 24 hours the medium was removed and the cells were washed with phosphate buffered saline (PBS) (Gibco, Carlsbad, Calif.) to remove residual medium. The medium was replaced with a modified Growth Medium (DMEM with D-valine (special order Gibco), 15% (v/v) dialyzed fetal bovine serum (Hyclone, Logan, Utah), 0.001% (v/v) betamercaptoethanol (Sigma), penicillin at 50 Units/milliliter and streptomycin at 50 milligrams/milliliter (Gibco)).

Results

Neither the umbilicus-derived cells nor the fibroblast cells seeded in the D-valine-containing medium proliferated, unlike cells seeded in Growth Medium containing dialyzed serum. Fibroblasts cells changed morphologically, increasing in size and changing shape. All of the cells died and eventually detached from the flask surface after four weeks. Thus, it may be concluded that umbilicus-derived cells require L-valine for cell growth and to maintain long-term viability.

References

Hongpaisan J. (2000) Inhibition of proliferation of contaminating fibroblasts by D-valine in cultures of smooth muscle cells from human myometrium. *Cell Biol Int.* 24:1-7.

Sordillo L M, Oliver S P, Akers R M. (1988) Culture of bovine mammary epithelial cells in D-valine modified medium: selective removal of contaminating fibroblasts. *Cell Biol Int Rep.* 12:355-64.

EXAMPLE 4

Karyotype Analysis of Umbilicus-Derived PPDCs

Cell lines used in cell therapy are preferably homogeneous and free from any contaminating cell type. Human cells used in cell therapy should have a normal number (46) of chromosomes with normal structure. To identify umbilicus-derived cell lines that are homogeneous and free from cells of non-umbilical tissue origin, karyotypes of cell samples were analyzed.

Materials and Methods

PPDCs from postpartum tissue of a male neonate were cultured in Growth Media. Postpartum tissue from a male neonate (X,Y) was selected to allow distinction between neonatal-derived cells and maternal derived cells (X,X). Cells were seeded at 5,000 cells per square centimeter in Growth Medium in a T25 flask (Corning, Corning, N.Y.) and expanded to 80% confluence. A T25 flask containing cells was filled to the neck with Growth Media. Samples were delivered to a clinical cytogenetics lab by courier (estimated lab to lab transport time is one hour). Chromosome analysis was performed by the Center for Human & Molecular Genetics at the New Jersey Medical School, Newark, N.J. Cells were analyzed during metaphase when the chromosomes are best visualized. Of twenty cells in metaphase counted, five were analyzed for normal homogeneous karyotype number (two). A cell sample was characterized as homogeneous if two karyotypes were observed. A cell sample was characterized as heterogeneous if more than two karyotypes were observed. Additional metaphase cells were counted and analyzed when a heterogeneous karyotype number (four) was identified.

Results

All cell samples sent for chromosome analysis were interpreted by as exhibiting a normal appearance. Each of the cell samples was characterized as homogeneous. (Table 4-1).

TABLE 4-1

Karyotype results of PPDCs.

| Tissue | Passage | Metaphase cells counted | Metaphase cells analyzed | Number of karyotypes | ISCN Karyotype |
|---|---|---|---|---|---|
| Umbilical | 23 | 20 | 5 | 2 | 46, XX |
| Umbilical | 6 | 20 | 5 | 2 | 46, XY |
| Umbilical | 3 | 20 | 5 | 2 | 46, XX |

Summary. Chromosome analysis identified umbilicus-derived PPDCs whose karyotypes appear normal as interpreted by a clinical cytogenetic laboratory. Karyotype analysis also identified cell lines free from maternal cells, as determined by homogeneous karyotype.

EXAMPLE 5

Flow Cytometric Evaluation of Human Umbilicus-Derived Cell Surface Markers

Characterization of cell surface proteins or "markers" by flow cytometry can be used to determine a cell line's identity. The consistency of expression can be determined from multiple donors, and in cells exposed to different processing and culturing conditions. Postpartum cell lines isolated from the umbilicus were characterized by flow cytometry, providing a profile for the identification of these cell lines.

Materials and Methods

Media and culture vessels. Cells were cultured in Growth Medium, in plasma-treated T75, T150, and T225 tissue culture flasks (Corning, Corning, N.Y.) until confluent. The growth surfaces of the flasks were coated with gelatin by incubating 2% (w/v) gelatin (Sigma, St. Louis, Mo.) for 20 minutes at room temperature.

Antibody staining. Adherent cells in flasks were washed in phosphate buffered saline (PBS); (Gibco, Carlsbad, Mo.) and detached with Trypsin/EDTA (Gibco). Cells were harvested, centrifuged, and resuspended in 3% (v/v) FBS in PBS at a cell concentration of $1 \times 10^7$ per milliliter. In accordance with the manufacture's specifications, antibody to the cell surface marker of interest (see below) was added to 100 microliters of cell suspension and the mixture was incubated in the dark for 30 minutes at 4° C. After incubation, cells were washed with PBS and centrifuged to remove unbound antibody. Cells were resuspended in 500 microliters PBS and analyzed by flow cytometry.

Flow cytometry analysis. Flow cytometry analysis was performed with a FACScalibur instrument (Becton Dickinson, San Jose, Calif.).

Antibodies to cell surface markers. The following antibodies to cell surface markers were used.

TABLE 5-1

Antibodies used in characterizing cell surface markers of UDCs.

| Antibody | Manufacture | Catalog Number |
|---|---|---|
| CD10 | BD Pharmingen (San Diego, CA) | 555375 |
| CD13 | BD Pharmingen | 555394 |
| CD31 | BD Pharmingen | 555446 |
| CD34 | BD Pharmingen | 555821 |
| CD44 | BD Pharmingen | 555478 |
| CD45RA | BD Pharmingen | 555489 |
| CD73 | BD Pharmingen | 550257 |
| CD90 | BD Pharmingen | 555596 |
| CD117 | BD Pharmingen | 340529 |
| CD141 | BD Pharmingen | 559781 |
| PDGFr-alpha | BD Pharmingen | 556002 |
| HLA-A, B, C | BD Pharmingen | 555553 |
| HLA-DR, DP, DQ | BD Pharmingen | 555558 |
| IgG-FITC | Sigma (St. Louis, MO) | F-6522 |
| IgG- PE | Sigma | P-4685 |

Passage to Passage Comparison. Umbilicus-derived cells were analyzed at passages 8, 15, and 20.

Donor to Donor Comparison. To compare differences among donors, umbilical from different donors were compared to each other.

Surface Coating Comparison. Umbilicus-derived cells cultured on gelatin-coated flasks was compared to umbilicus cultured on uncoated flasks.

Results

Umbilicus-Derived Cell Characterization. Umbilicus-derived cells analyzed by flow cytometry showed positive expression of CD10, CD13, CD44, CD73, CD90, PDGFr-alpha and HLA-A, B, C, indicated by the increased values of fluorescence relative to the IgG control (data not shown). These cells were negative for detectable expression of CD31, CD34, CD45, CD117, CD141, and HLA-DR, DP, DQ, indicated by fluorescence values comparable to the IgG control (data not shown). Variations in florescence values of positive curves were accounted for. The mean (i.e. CD13) and range (i.e. CD90) of the positive curves showed some variation, but the curves appear normal, confirming a homogenous population. Both curves individually exhibited values greater than the IgG control.

Passage to Passage Comparison. Umbilical cells at passage 8, 15, and 20 analyzed by flow cytometry all expressed CD10, CD13, CD44, CD73, CD90, PDGFr-alpha and HLA-A, B, C, indicated by increased fluorescence relative to the IgG control. These cells were negative for CD31, CD34, CD45, CD117, CD141, and HLA-DR, DP, DQ, indicated by fluorescence values consistent with the IgG control. Variations in florescence detection values of positive curves were within expected ranges. While the means (i.e. CD13) of the positive curves varied all curves individually exhibited values greater than the IgG control.

Donor to Donor Comparison. Umbilicus-derived cells isolated from separate donors analyzed by flow cytometry each showed positive expression of CD10, CD13, CD44, CD73, CD90, PDGFr-alpha and HLA-A, B, C, reflected in the increased values of fluorescence relative to the IgG control. These cells were negative for expression of CD31, CD34, CD45, CD117, CD141, and HLA-DR, DP, DQ with fluorescence values consistent with the IgG control. Variations in florescence detection values of positive curves were accounted for. While the mean (i.e. CD10) of the positive curves varied, both curves individually exhibited values greater than the IgG control.

The Effect of Surface Coating with Gelatin. Umbilical cells expanded on gelatin and uncoated flasks analyzed by flow cytometry all were positive for expression of CD10, CD13, CD44, CD73, CD90, PDGFr-alpha and HLA-A, B, C, with increased values of fluorescence relative to the IgG control. These cells were negative for expression of CD31, CD34, CD45, CD117, CD141, and HLA-DR, DP, DQ, with fluorescence values consistent with the IgG control.

Summary. Analysis of umbilicus-derived postpartum cells by flow cytometry has established a profile useful to identify these cell lines. Umbilicus-derived postpartum cells are positive for CD10, CD13, CD44, CD73, CD90, PDGFr-alpha, HLA-A,B,C and negative for CD31, CD34, CD45, CD117, CD141 and HLA-DR, DP, DQ. This identity was consistent between variations in variables including the donor, passage, culture vessel surface coating, and digestion enzymes used in isolation and preparation of the cells. Some variation in individual fluorescence value histogram curve means and ranges were observed, but all positive curves under all conditions tested were normal and expressed fluorescence values greater than the IgG control, thus confirming that the cells comprise a homogenous population, which has positive expression of the markers.

EXAMPLE 6

Analysis of Cells by Oligonucleotide Array

Oligonucleotide arrays were used to compare gene expression profiles of umbilicus- and placenta-derived cells with fibroblasts, human mesenchymal stem cells, and another cell line derived from human bone marrow. This analysis provided a characterization of the postpartum-derived cells and identified unique molecular markers for these cells.

Materials and Methods
Isolation and Culture of Cells
Postpartum tissue-derived cells. Human umbilical cords and placenta were obtained from National Disease Research Interchange (NDRI, Philadelphia, Pa.) from normal full term deliveries with patient consent. The tissues were received and cells were isolated as described in Example 1. Cells were cultured in Growth Medium on gelatin-coated tissue culture plastic flasks. The cultures were incubated at 37° C. with 5% $CO_2$.

Fibroblasts. Human dermal fibroblasts were purchased from Cambrex Incorporated (Walkersville, Md.; Lot number 9F0844) and ATCC CRL-1501 (CCD39SK). Both lines were cultured in DMEM/F12 medium (Invitrogen, Carlsbad, Calif.) with 10% (v/v) fetal bovine serum (Hyclone) and penicillin/streptomycin (Invitrogen)). The cells were grown on standard tissue-treated plastic.

Human Mesenchymal Stem Cells (hMSC). hMSCs were purchased from Cambrex Incorporated (Walkersville, Md.; Lot numbers 2F1655, 2F1656 and 2F1657) and cultured according to the manufacturer's specifications in MSCGM Media (Cambrex). The cells were grown on standard tissue cultured plastic at 37° C. with 5% $CO_2$.

Human Ileac Crest Bone Marrow Cells (ICBM). Human ileac crest bone marrow was received from NDRI with patient consent. The marrow was processed according to the method outlined by Ho, et al. (WO03/025149). The marrow was mixed with lysis buffer (155 mM $NH_4Cl$, 10 mM $KHCO_3$, and 0.1 mM EDTA, pH 7.2) at a ratio of 1 part bone marrow to 20 parts lysis buffer. The cell suspension was vortexed, incubated for 2 minutes at ambient temperature, and centrifuged for 10 minutes at 500×g. The supernatant was discarded and the cell pellet was resuspended in Minimal Essential Medium-alpha (Invitrogen) supplemented with 10% (v/v) fetal bovine serum and 4 mM glutamine. The cells were centrifuged again and the cell pellet was resuspended in fresh medium. The viable mononuclear cells were counted using Trypan-blue exclusion (Sigma, St. Louis, Mo.). The mononuclear cells were seeded in tissue-cultured plastic flasks at $5 \times 10^4$ cells/cm$^2$. The cells were incubated at 37° C. with 5% $CO_2$ at either standard atmospheric $O_2$ or at 5% $O_2$. Cells were cultured for 5 days without a media change. Media and non-adherent cells were removed after 5 days of culture. The adherent cells were maintained in culture.

Isolation of mRNA and GENECHIP Analysis. Actively growing cultures of cells were removed from the flasks with a cell scraper in cold phosphate buffered saline (PBS). The cells were centrifuged for 5 minutes at 300×g. The supernatant was removed and the cells were resuspended in fresh PBS and centrifuged again. The supernatant was removed and the cell pellet was immediately frozen and stored at −80° C. Cellular mRNA was extracted and transcribed into cDNA. cDNA was then transcribed into cRNA and biotin-labeled. The biotin-labeled cRNA was hybridized with Affymetrix GENECHIP HG-U133A oligonucleotide arrays (Affymetrix, Santa Clara, Calif.). The hybridizations and data collection were performed according to the manufacturer's specifications. The hybridization and data collection was performed according to the manufacturer's specifications. Data analyses were performed using "Significance Analysis of Microarrays" (SAM) version 1.21 computer software (Tusher, V. G. et al., 2001, Proc. Natl. Acad. Sci. USA 98: 5116-5121). Licenses for the analysis software are available through the Office of Technology Licensing, Stanford University, and more information is available on the World Wide Web at Professor Tibshirani's web site in the Dep't of Statistics, Stanford University (www-stat.stanford.edu/~tibs/SAM/).

Results

Fourteen different populations of cells were analyzed in this study. The cells along with passage information, culture substrate, and culture media are listed in Table 6-1.

TABLE 6-1

Cells analyzed by the microarray study. The cells lines are listed by their identification code along with passage at the time of analysis, cell growth substrate, and growth media.

| Cell Population | Passage | Substrate | Media |
| --- | --- | --- | --- |
| Umbilical (022803) | 2 | Gelatin | DMEM, 15% FBS, βME |
| Umbilical (042103) | 3 | Gelatin | DMEM, 15% FBS, βME |
| Umbilical (071003) | 4 | Gelatin | DMEM, 15% FBS, βME |
| Placenta (042203) | 12 | Gelatin | DMEM, 15% FBS, βME |
| Placenta (042903) | 4 | Gelatin | DMEM, 15% FBS, βME |
| Placenta (071003) | 3 | Gelatin | DMEM, 15% FBS, βME |
| ICBM (070203) (5% $O_2$) | 3 | Plastic | MEM 10% FBS |
| ICBM (062703) (std $O_2$) | 5 | Plastic | MEM 10% FBS |
| ICBM (062703)(5% $O_2$) | 5 | Plastic | MEM 10% FBS |
| hMSC (Lot 2F1655) | 3 | Plastic | MSCGM |
| hMSC (Lot 2F1656) | 3 | Plastic | MSCGM |
| hMSC (Lot 2F1657) | 3 | Plastic | MSCGM |
| hFibroblast (9F0844) | 9 | Plastic | DMEM-F12, 10% FBS |
| hFibroblast (CCD39SK) | 4 | Plastic | DMEM-F12, 10% FBS |

The data were evaluated by Principle Component Analysis with SAM software as described above. Analysis revealed 290 genes that were expressed in different relative amounts in the cells tested. This analysis provided relative comparisons between the populations.

Table 6-2 shows the Euclidean distances that were calculated for the comparison of the cell pairs. The Euclidean distances were based on the comparison of the cells based on the 290 genes that were differentially expressed among the cell types. The Euclidean distance is inversely proportional to similarity between the expression of the 290 genes.

TABLE 6-2

The Euclidean Distances for the Cell Pairs. The Euclidean distance was calculated for the cell types using the 290 genes that were expressed differentially between the cell types. Similarity between the cells is inversely proportional to the Euclidean distance.

| Cell Pair | Euclidean Distance |
|---|---|
| ICBM-hMSC | 24.71 |
| Placenta-umbilical | 25.52 |

TABLE 6-2-continued

The Euclidean Distances for the Cell Pairs. The Euclidean distance was calculated for the cell types using the 290 genes that were expressed differentially between the cell types. Similarity between the cells is inversely proportional to the Euclidean distance.

| Cell Pair | Euclidean Distance |
|---|---|
| ICBM-Fibroblast | 36.44 |
| Fibroblast-placenta | 37.09 |
| Fibroblast-MSC | 39.63 |
| ICBM-Umbilical | 40.15 |
| Fibroblast-Umbilical | 41.59 |
| MSC-Placenta | 42.84 |
| MSC-Umbilical | 46.86 |
| ICBM-placenta | 48.41 |

Tables 6-3, 6-4, and 6-5 show the expression of genes increased in placenta-derived cells (Table 6-3), increased in umbilical cord-derived cells (Table 6-4), and reduced in umbilical cord and placenta-derived cells (Table 6-5).

TABLE 6-3

Genes which are specifically increased in expression in the placenta-derived cells as compared to the other cell lines assayed.

Genes Increased in Placenta-Derived Cells

| Probe Set ID | Gene Name | NCBI Accession Number |
|---|---|---|
| 209732_at | C-type (calcium dependent, carbohydrate-recognition domain) lectin, superfamily member 2 (activation-induced) | AF070642 |
| 206067_s_at | Wilms tumor 1 | NM_024426 |
| 207016_s_at | aldehyde dehydrogenase 1 family, member A2 | AB015228 |
| 206367_at | Renin | NM_000537 |
| 210004_at | oxidized low density lipoprotein (lectin-like) receptor 1 | AF035776 |
| 214993_at | *Homo sapiens*, clone IMAGE: 4179671, mRNA, partial cds | AF070642 |
| 202178_at | protein kinase C, zeta | NM_002744 |
| 209780_at | hypothetical protein DKFZp564F013 | AL136883 |
| 204135_at | downregulated in ovarian cancer 1 | NM_014890 |
| 213542_at | *Homo sapiens* mRNA; cDNA DKFZp547K1113 (from clone DKFZp547K1113) | AI246730 |

TABLE 6-4

Genes which are specifically increased in expression in umbilical cord-derived cells as compared to the other cell lines assayed.
Genes Increased in Umbilicus-Derived Cells

| Probe Set ID | Gene Name | NCBI Accession Number |
|---|---|---|
| 202859_x_at | Interleukin 8 | NM_000584 |
| 211506_s_at | Interleukin 8 | AF043337 |
| 210222_s_at | reticulon 1 | BC000314 |
| 204470_at | chemokine (C-X-C motif) ligand 1 (melanoma growth stimulating activity | NM_001511 |
| 206336_at | chemokine (C-X-C motif) ligand 6 (granulocyte chemotactic protein 2) | NM_002993 |
| 207850_at | Chemokine (C-X-C motif) ligand 3 | NM_002090 |
| 203485_at | reticulon 1 | NM_021136 |
| 202644_s_at | tumor necrosis factor, alpha-induced protein 3 | NM_006290 |

TABLE 6-5

Genes which were decreased in expression in the umbilical
cord and placenta cells as compared to the other cell lines assayed.
Genes Decreased in Umbilicus- and Placenta-Derived Cells

| Probe Set ID | Gene name | NCBI Accession Number |
|---|---|---|
| 210135_s_at | short stature homeobox 2 | AF022654.1 |
| 205824_at | heat shock 27 kDa protein 2 | NM_001541.1 |
| 209687_at | chemokine (C-X-C motif) ligand 12 (stromal cell-derived factor 1) | U19495.1 |
| 203666_at | chemokine (C-X-C motif) ligand 12 (stromal cell-derived factor 1) | NM_000609.1 |
| 212670_at | elastin (supravalvular aortic stenosis, Williams-Beuren syndrome) | AA479278 |
| 213381_at | Homo sapiens mRNA; cDNA DKFZp586M2022 (from clone DKFZp586M2022) | N91149 |
| 206201_s_at | mesenchyme homeobox 2 (growth arrest-specific homeobox) | NM_005924.1 |
| 205817_at | Sine oculis homeobox homolog 1 (Drosophila) | NM_005982.1 |
| 209283_at | crystallin, alpha B | AF007162.1 |
| 212793_at | dishevelled associated activator of morphogenesis 2 | BF513244 |
| 213488_at | DKFZP586B2420 protein | AL050143.1 |
| 209763_at | similar to neuralin 1 | AL049176 |
| 205200_at | Tetranectin (plasminogen binding protein) | NM_003278.1 |
| 205743_at | src homology three (SH3) and cysteine rich domain | NM_003149.1 |
| 200921_s_at | B-cell translocation gene 1, anti-proliferative | NM_001731.1 |
| 206932_at | cholesterol 25-hydroxylase | NM_003956.1 |
| 204198_s_at | runt-related transcription factor 3 | AA541630 |
| 219747_at | hypothetical protein FLJ23191 | NM_024574.1 |
| 204773_at | Interleukin 11 receptor, alpha | NM_004512.1 |
| 202465_at | Procollagen C-endopeptidase enhancer | NM_002593.2 |
| 203706_s_at | Frizzled homolog 7 (Drosophila) | NM_003507.1 |
| 212736_at | hypothetical gene BC008967 | BE299456 |
| 214587_at | Collagen, type VIII, alpha 1 | BE877796 |
| 201645_at | Tenascin C (hexabrachion) | NM_002160.1 |
| 210239_at | iroquois homeobox protein 5 | U90304.1 |
| 203903_s_at | Hephaestin | NM_014799.1 |
| 205816_at | integrin, beta 8 | NM_002214.1 |
| 203069_at | synaptic vesicle glycoprotein 2 | NM_014849.1 |
| 213909_at | Homo sapiens cDNA FLJ12280 fis, clone MAMMA1001744 | AU147799 |
| 206315_at | cytokine receptor-like factor 1 | NM_004750.1 |
| 204401_at | potassium intermediate/small conductance calcium-activated channel, subfamily N, member 4 | NM_002250.1 |
| 216331_at | integrin, alpha 7 | AK022548.1 |
| 209663_s_at | integrin, alpha 7 | AF072132.1 |
| 213125_at | DKFZP586L151 protein | AW007573 |
| 202133_at | transcriptional co-activator with PDZ-binding motif (TAZ) | AA081084 |
| 206511_s_at | Sine oculis homeobox homolog 2 (Drosophila) | NM_016932.1 |
| 213435_at | KIAA1034 protein | AB028957.1 |
| 206115_at | early growth response 3 | NM_004430.1 |
| 213707_s_at | distal-less homeobox 5 | NM_005221.3 |
| 218181_s_at | hypothetical protein FLJ20373 | NM_017792.1 |
| 209160_at | aldo-keto reductase family 1, member C3 (3-alpha hydroxysteroid dehydrogenase, type II) | AB018580.1 |
| 213905_x_at | Biglycan | AA845258 |
| 201261_x_at | Biglycan | BC002416.1 |
| 202132_at | transcriptional co-activator with PDZ-binding motif (TAZ) | AA081084 |
| 214701_s_at | fibronectin 1 | AJ276395.1 |
| 213791_at | Proenkephalin | NM_006211.1 |
| 205422_s_at | Integrin, beta-like 1 (with EGF-like repeat domains) | NM_004791.1 |
| 214927_at | Homo sapiens mRNA full length insert cDNA clone EUROIMAGE 1968422 | AL359052.1 |
| 206070_s_at | EphA3 | AF213459.1 |
| 212805_at | KIAA0367 protein | AB002365.1 |
| 219789_at | natriuretic peptide receptor C/guanylate cyclase C (atrionatriuretic peptide receptor C) | AI628360 |
| 219054_at | hypothetical protein FLJ14054 | NM_024563.1 |
| 213429_at | Homo sapiens mRNA; cDNA DKFZp564B222 (from clone DKFZp564B222) | AW025579 |
| 204929_s_at | vesicle-associated membrane protein 5 (myobrevin) | NM_006634.1 |
| 201843_s_at | EGF-containing fibulin-like extracellular matrix protein 1 | NM_004105.2 |
| 221478_at | BCL2/adenovirus E1B 19 kDa interacting protein 3-like | AL132665.1 |
| 201792_at | AE binding protein 1 | NM_001129.2 |
| 204570_at | cytochrome c oxidase subunit VIIa polypeptide 1 (muscle) | NM_001864.1 |
| 201621_at | neuroblastoma, suppression of tumorigenicity 1 | NM_005380.1 |
| 202718_at | Insulin-like growth factor binding protein 2, 36 kDa | NM_000597.1 |

Tables 6-6, 6-7, and 6-8 show the expression of genes increased in human fibroblasts (Table 6-6), ICBM cells (Table 6-7), and MSCs (Table 6-8).

TABLE 6-6

Genes which were increased in expression in fibroblasts as compared to the other cell lines assayed.
Genes increased in fibroblasts dual specificity phosphatase 2
KIAA0527 protein
Homo sapiens cDNA: FLJ23224 fis, clone ADSU02206
dynein, cytoplasmic, intermediate polypeptide 1
ankyrin 3, node of Ranvier (ankyrin G)
inhibin, beta A (activin A, activin AB alpha polypeptide)
ectonucleotide pyrophosphatase/phosphodiesterase 4 (putative function)
KIAA1053 protein
microtubule-associated protein 1A
zinc finger protein 41
HSPC019 protein
Homo sapiens cDNA: FLJ23564 fis, clone LNG10773
Homo sapiens mRNA; cDNA DKFZp564A072 (from clone DKFZp564A072)
LIM protein (similar to rat protein kinase C-binding enigma)
inhibitor of kappa light polypeptide gene enhancer in B-cells, kinase complex-associated protein
hypothetical protein FLJ22004
Human (clone CTG-A4) mRNA sequence
ESTs, Moderately similar to cytokine receptor-like factor 2; cytokine receptor CRL2 precursor [Homo sapiens]
transforming growth factor, beta 2
hypothetical protein MGC29643
antigen identified by monoclonal antibody MRC OX-2
putative X-linked retinopathy protein

TABLE 6-7

Genes which were increased in expression in the ICBM-derived cells as compared to the other cell lines assayed.
Genes Increased In ICBM Cells cardiac ankyrin repeat protein
MHC class I region ORF
integrin, alpha 10
hypothetical protein FLJ22362
UDP-N-acetyl-alpha-D-galactosamine:polypeptide N-acetylgalactosaminyltransferase 3 (GalNAc-T3)
interferon-induced protein 44
SRY (sex determining region Y)-box 9 (campomelic dysplasia, autosomal sex-reversal)
keratin associated protein 1-1
hippocalcin-like 1
jagged 1 (Alagille syndrome)
proteoglycan 1, secretory granule

TABLE 6-8

Genes which were increased in expression in the MSC cells as compared to the other cell lines assayed.
Genes Increased In MSC Cells interleukin 26
maltase-glucoamylase (alpha-glucosidase)
nuclear receptor subfamily 4, group A, member 2
v-fos FBJ murine osteosarcoma viral oncogene homolog
hypothetical protein DC42
nuclear receptor subfamily 4, group A, member 2
FBJ murine osteosarcoma viral oncogene homolog B
WNT1 inducible signaling pathway protein 1
MCF.2 cell line derived transforming sequence
potassium channel, subfamily K, member 15
cartilage paired-class homeoprotein 1
Homo sapiens cDNA FLJ12232 fis, clone MAMMA1001206
Homo sapiens cDNA FLJ34668 fis, clone LIVER2000775
jun B proto-oncogene TABLE 6-8-continued Genes which were increased in expression in the MSC cells as compared to the other cell lines assayed.
Genes Increased In MSC Cells B-cell CLL/lymphoma 6 (zinc finger protein 51)
zinc finger protein 36, C3H type, homolog (mouse)

Summary. The present study was performed to provide a molecular characterization of the postpartum cells derived from umbilical cord and placenta. This analysis included cells derived from three different umbilical cords and three different placentas. The study also included two different lines of dermal fibroblasts, three lines of mesenchymal stem cells, and three lines of ileac crest bone marrow cells. The mRNA that was expressed by these cells was analyzed on a GENECHIP oligonucleotide array that contained oligonucleotide probes for 22,000 genes.

The analysis revealed that transcripts for 290 genes were present in different amounts in these five different cell types. These genes include ten genes that are specifically increased in the placenta-derived cells and seven genes specifically increased in the umbilical cord-derived cells. Fifty-four genes were found to have specifically lower expression levels in placenta and umbilical cord.

The expression of selected genes has been confirmed by PCR, as shown in Example 7. Postpartum-derived cells generally, and umbilical derived cells, in particular, have distinct gene expression profiles, for example, as compared to other human cells, such as the bone marrow-derived cells and fibroblasts tested here.

EXAMPLE 7

Cell Markers in Umbilicus-Derived Cells

Gene expression profiles of cells derived from the human umbilical cord were compared with those of cells derived from other sources using an Affymetrix GENECHIP. Six "signature" genes were identified: oxidized LDL receptor 1, interleukin-8 (IL-8), renin, reticulon, chemokine receptor ligand 3 (CXC ligand 3), and granulocyte chemotactic protein 2 (GCP-2). These "signature" genes were expressed at relatively high levels in umbilicus-derived cells.

The procedures described in this example were conducted to verify the microarray data and compare data for gene and protein expression, as well as to establish a series of reliable assays for detection of unique identifiers for umbilicus-derived cells.

Methods & Materials

Cells. Umbilicus-derived cells (four isolates), and Normal Human Dermal Fibroblasts (NHDF; neonatal and adult) were grown in Growth Medium in gelatin-coated T75 flasks. Mesenchymal Stem Cells (MSCs) were grown in Mesenchymal Stem Cell Growth Medium Bullet kit (MSCGM; Cambrex, Walkerville, Md.).

For IL-8 experiments, cells were thawed from liquid nitrogen and plated in gelatin-coated flasks at 5,000 cells/cm$^2$, grown for 48 hours in Growth Medium and then grown further for 8 hours in 10 milliliters of serum starvation medium [DMEM-low glucose (Gibco, Carlsbad, Calif.), penicillin (50 Units/milliliter), streptomycin (50 micrograms/milliliter) (Gibco) and 0.1% (w/v) Bovine Serum Albumin (BSA; Sigma, St. Louis, Mo.)]. RNA was then extracted and the supernatants were centrifuged at 150×g for 5 minutes to remove cellular debris. Supernatants were frozen at −80° C. until ELISA analysis.

Cell culture for ELISA assay. Cells derived from human umbilical cord, as well as human fibroblasts derived from human neonatal foreskin, were cultured in Growth Medium in gelatin-coated T75 flasks. Cells were frozen at passage 11 in liquid nitrogen. Cells were thawed and transferred to 15 milliliter centrifuge tubes. After centrifugation at 150×g for 5 minutes, the supernatant was discarded. Cells were resuspended in 4 milliliters culture medium and counted. Cells were grown in a 75 cm$^2$ flask containing 15 milliliters of Growth Medium at 375,000 cell/flask for 24 hours. The medium was changed to a serum starvation medium for 8 hours. Serum starvation medium was collected at the end of incubation, centrifuged at 14,000×g for 5 minutes (and stored at −20° C.).

To estimate the number of cells in each flask, 2 milliliters of trypsin/EDTA (Gibco, Carlsbad, Calif.) were added each flask. After cells detached from the flask, trypsin activity was neutralized with 8 milliliters of Growth Medium. Cells were transferred to a 15 milliliter centrifuge tube and centrifuged at 150×g for 5 minutes. Supernatant was removed and 1 milliliter Growth Medium was added to each tube to resuspend the cells. Cell number was determined with a hemocytometer.

ELISA assay. The amount of IL-8 secreted by the cells into serum starvation medium was analyzed using ELISA assays (R&D Systems, Minneapolis, Minn.). All assays were conducted according to the instructions provided by the manufacturer.

Total RNA isolation. RNA was extracted from confluent umbilicus-derived cells and fibroblasts, or for IL-8 expression, from cells treated as described above. Cells were lysed with 350 microliters buffer RLT containing beta-mercaptoethanol (Sigma, St. Louis, Mo.) according to the manufacturer's instructions (RNeasy Mini Kit; Qiagen, Valencia, Calif.). RNA was extracted according to the manufacturer's instructions (RNeasy Mini Kit; Qiagen, Valencia, Calif.) and subjected to DNase treatment (2.7 Units/sample) (Sigma St. Louis, Mo.). RNA was eluted with 50 microliters DEPC-treated water and stored at −80° C. RNA was also extracted from human umbilical cord. Tissue (30 milligrams) was suspended in 700 microliters of buffer RLT containing beta-mercaptoethanol. Samples were mechanically homogenized and the RNA extraction proceeded according to manufacturer's specification. RNA was extracted with 50 microliters of DEPC-treated water and stored at −80° C.

Reverse transcription. RNA was reverse-transcribed using random hexamers with the TaqMan reverse transcription reagents (Applied Biosystems, Foster City, Calif.) at 25° C. for 10 minutes, 37° C. for 60 minutes, and 95° C. for 10 minutes. Samples were stored at −20° C.

Genes identified by cDNA microarray as uniquely regulated in postpartum cells (signature genes—including oxidized LDL receptor, interleukin-8, renin, and reticulon), were further investigated using real-time and conventional PCR.

Real-time PCR. PCR was performed on cDNA samples using gene expression products sold under the trade name ASSAYS-ON-DEMAND (Applied Biosystems) gene expression products. Oxidized LDL receptor (Hs00234028); renin (Hs00166915); reticulon (Hs00382515); CXC ligand 3 (Hs00171061); GCP-2 (Hs00605742); IL-8 (Hs00174103); and GAPDH were mixed with cDNA and TaqMan Universal PCR master mix according to the manufacturer's instructions (Applied Biosystems) using a 7000 sequence detection system with ABI Prism 7000 SDS software (Applied Biosystems). Thermal cycle conditions were initially 50° C. for 2 minutes and 95° C. for 10 minutes, followed by 40 cycles of 95° C. for 15 seconds and 60° C. for 1 minute. PCR data were analyzed according to manufacturer's specifications (User Bulletin #2 from Applied Biosystems for ABI Prism 7700 Sequence Detection System).

Conventional PCR. Conventional PCR was performed using an ABI PRISM 7700 (Perkin Elmer Applied Biosystems, Boston, Mass.) to confirm the results from real-time PCR. PCR was performed using 2 microliters of cDNA solution (1× Taq polymerase (trade name AMPLITAQ GOLD) universal mix PCR reaction buffer (Applied Biosystems) and initial denaturation at 94° C. for 5 minutes. Amplification was optimized for each primer set. For IL-8, CXC ligand 3, and reticulon (94° C. for 15 seconds, 55° C. for 15 seconds and 72° C. for 30 seconds for 30 cycles); for renin (94° C. for 15 seconds, 53° C. for 15 seconds and 72° C. for 30 seconds for 38 cycles); for oxidized LDL receptor and GAPDH (94° C. for 15 seconds, 55° C. for 15 seconds and 72° C. for 30 seconds for 33 cycles). Primers used for amplification are listed in Table 7-1. Primer concentration in the final PCR reaction was 1 micromolar except for GAPDH which was 0.5 micromolar. GAPDH primers were the same as for real-time PCR, except that the manufacturer's TaqMan probe was not added to the final PCR reaction. Samples were separated on 2% (w/v) agarose gel and stained with ethidium bromide (Sigma, St. Louis, Mo.). Images were captured on 667 film (Universal Twinpack, VWR International, South Plainfield, N.J.) using a fixed focal-length POLAROID camera (VWR International, South Plainfield, N.J.).

TABLE 7-1

Primers used

| Primer name | Primers |
|---|---|
| Oxidized LDL receptor | S: 5'-GAGAAATCCAAAGAGCAAATGG-3 (SEQ ID NO: 1)' <br> A: 5'-AGAATGGAAAACTGGAATAGG-3' (SEQ ID NO: 2) |
| Renin | S: 5'-TCTTCGATGCTTCGGATTCC-3' (SEQ ID NO: 3) <br> A: 5'-GAATTCTCGGAATCTCTGTTG-3' (SEQ ID NO: 4) |
| Reticulon | S: 5'-TTACAAGCAGTGCAGAAAACC-3' (SEQ ID NO: 5) <br> A: 5'-AGTAAACATTGAAACCACAGCC-3' (SEQ ID NO: 6) |
| Interleukin-8 | S: 5'-TCTGCAGCTCTGTGTGAAGG-3' (SEQ ID NO: 7) <br> A: 5'-CTTCAAAAACTTCTCCACAACC-3' (SEQ ID NO: 8) |
| Chemokine (CXC) ligand 3 | S: 5'-CCCACGCCACGCTCTCC-3' (SEQ ID NO: 9) <br> A: 5'-TCCTGTCAGTTGGTGCTCC-3' (SEQ ID NO: 10) |

Immunofluorescence. Cells were fixed with cold 4% (w/v) paraformaldehyde (Sigma-Aldrich, St. Louis, Mo.) for 10 minutes at room temperature. Umbilicus-derived cells at passage 0 (P0) (one isolate, directly after isolation) and passage 11 (P11) (two isolates of umbilicus-derived cells), and fibroblasts (P11) were used. Immunocytochemistry was performed using antibodies directed against the following epitopes:vimentin (1:500, Sigma, St. Louis, Mo.), desmin ((Sigma) 1:150; raised against rabbit; or (Chemicon, Temecula, Calif.) 1:300, raised against mouse), alpha-smooth muscle actin (SMA; 1:400; Sigma), cytokeratin 18 (CK18; 1:400; Sigma), von Willebrand Factor (vWF; 1:200; Sigma), and CD34 (human CD34 Class III; 1:100; DAKOCytomation, Carpinteria, Calif.). In addition, the following markers were tested on passage 11 postpartum cells: anti-human GROalpha-PE (1:100; Becton Dickinson, Franklin Lakes, N.J.), anti-human GCP-2 (1:100; Santa Cruz Biotech, Santa Cruz, Calif.), anti-human oxidized LDL receptor 1 (ox-LDL R1; 1:100; Santa Cruz Biotech), and anti-human NOGO-A (1:100; Santa Cruz, Biotech).

Cultures were washed with phosphate-buffered saline (PBS) and exposed to a protein blocking solution containing PBS, 4% (v/v) goat serum (Chemicon, Temecula, Calif.), and 0.3% (v/v) Triton (Triton X-100; Sigma, St. Louis, Mo.) for 30 minutes to access intracellular antigens. Where the epitope of interest was located on the cell surface (CD34, ox-LDL R1), Triton X-100 was omitted in all steps of the procedure in order to prevent epitope loss. Furthermore, in instances where the primary antibody was raised against goat (GCP-2, ox-LDL R1, NOGO-A), 3% (v/v) donkey serum was used in place of goat serum throughout. Primary antibodies, diluted in blocking solution, were then applied to the cultures for a period of 1 hour at room temperature. The primary antibody solutions were removed and the cultures were washed with PBS prior to application of secondary antibody solutions (1 hour at room temperature) containing block along with goat anti-mouse IgG-Texas Red (1:250; Molecular Probes, Eugene, Oreg.) and/or goat anti-rabbit IgG-Alexa 488 (1:250; Molecular Probes) or donkey anti-goat IgG-FITC (1:150, Santa Cruz Biotech). Cultures were then washed and 10 micromolar DAPI (Molecular Probes) applied for 10 minutes to visualize cell nuclei.

Following immunostaining, fluorescence was visualized using an appropriate fluorescence filter on an Olympus inverted epi-fluorescent microscope (Olympus, Melville, N.Y.). In all cases, positive staining represented fluorescence signal above control staining where the entire procedure outlined above was followed with the exception of application of a primary antibody solution (no 1° control). Representative images were captured using a digital color videocamera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

FACS analysis. Adherent cells in flasks were washed in phosphate buffered saline (PBS) (Gibco, Carlsbad, Calif.) and detached with Trypsin/EDTA (Gibco, Carlsbad, Calif.). Cells were harvested, centrifuged, and resuspended 3% (v/v) FBS in PBS at a concentration of $1 \times 10^7$ cells/milliliter. One hundred microliter aliquots were delivered to conical tubes. Cells stained for intracellular antigens were permeabilized with Perm/Wash buffer (BD Pharmingen, San Diego, Calif.). Antibody was added to aliquots as per manufactures specifications and the cells were incubated for in the dark for 30 minutes at 4° C. After incubation, cells were washed with PBS and centrifuged to remove excess antibody. Cells requiring a secondary antibody were resuspended in 100 microliters of 3% FBS. Secondary antibody was added as per manufactures specification and the cells were incubated in the dark for 30 minutes at 4° C. After incubation, cells were washed with PBS and centrifuged to remove excess secondary antibody. Washed cells were resuspended in 0.5 milliliter PBS and analyzed by flow cytometry. The following antibodies were used: oxidized LDL receptor 1 (sc-5813; Santa Cruz, Biotech), GROalpha (555042; BD Pharmingen, Bedford, Mass.), Mouse IgG1 kappa, (P-4685 and M-5284; Sigma), Donkey against Goat IgG (sc-3743; Santa Cruz, Biotech.). Flow cytometry analysis was performed with FACSCalibur (Becton Dickinson San Jose, Calif.).

Results

Results of real-time PCR for selected "signature" genes performed on cDNA from cells derived from human umbilical cord, adult and neonatal fibroblasts, and Mesenchymal Stem Cells (MSCs) indicate that both reticulon and oxidized LDL receptor expression were higher in umbilicus-derived cells as compared to other cells. The data obtained from real-time PCR were analyzed by the ΔΔCT (delta delta CT) method and expressed on a logarithmic scale. No significant differences in the expression levels of CXC ligand 3 and GCP-2 were found between postpartum cells and controls. The results of real-time PCR were confirmed by conventional PCR. Sequencing of PCR products further validated these observations. No significant difference in the expression level of CXC ligand 3 was found between postpartum cells and controls using conventional PCR CXC ligand 3 primers listed in Table 7-1.

The expression of the cytokine, IL-8 in postpartum cells was elevated in both Growth Medium-cultured and serum-starved postpartum-derived cells. All real-time PCR data were validated with conventional PCR and by sequencing PCR products.

After growth in serum-free media, the conditioned media were examined for the presence of IL-8. The greatest amounts of IL-8 were detected in media in which umbilical cells had been grown (Table 7-2). No IL-8 was detected in medium in which human dermal fibroblasts had been grown.

TABLE 7-2

| IL-8 protein expression measured by ELISA | |
| --- | --- |
| Cell type | IL-8 secretion |
| hFibro | ND |
| UMBC Isolate 1 | 2058.42 ± 144.67 |
| UMBC Isolate 2 | 2368.86 ± 22.73 |

Results of the ELISA assay for interleukin-8 (IL-8) performed on spent media in which had been grown umbilicus-derived cells and human skin fibroblasts.
Values are presented here are pg/million cells, n = 2, sem.
ND: Not Detected Cells derived from the human umbilical cord at passage 0 were probed for the expression of selected proteins by immunocytochemical analysis. Immediately after isolation (passage 0), cells were fixed with 4% paraformaldehyde and exposed to antibodies for six proteins: von Willebrand Factor, CD34, cytokeratin 18, desmin, alpha-smooth muscle actin, and vimentin. Umbilicus-derived cells were positive for alpha-smooth muscle actin and vimentin, with the staining pattern consistent through passage 11.

The expression of GROalpha, GCP-2, oxidized LDL receptor 1 and reticulon in umbilicus-derived cells at passage 11 was investigated by immunocytochemistry.

Summary. Concordance between gene expression levels measured by microarray and PCR (both real-time and conventional) has been established for four genes: oxidized LDL receptor 1, renin, reticulon, and IL-8. The expression of these genes was regulated at the mRNA level in postpartum cells. IL-8 was also regulated at the protein level. Differences in expression of GCP-2 and CXC ligand 3 were not confirmed at the mRNA level.

Cells derived from the human umbilical cord at passage 0 were probed for the expression of alpha-smooth muscle actin and vimentin, and were positive for both. The staining pattern was preserved through passage 11, suggesting that expression of vimentin and alpha-smooth muscle actin are preserved in cells with passaging, at least in the Growth Medium used.

EXAMPLE 8

Immunohistochemical Characterization of Umbilical Cord-Derived Cell Phenotypes The phenotypes of cells found within human umbilical cord tissue was analyzed by immunohistochemistry.

Materials & Methods

Tissue Preparation. Human umbilical cord tissue was harvested and immersion fixed in 4% (w/v) paraformaldehyde overnight at 4° C. Immunohistochemistry was performed using antibodies directed against the following epitopes (see Table 8-1): vimentin (1:500; Sigma, St. Louis, Mo.), desmin (1:150, raised against rabbit; Sigma; or 1:300, raised against mouse; Chemicon, Temecula, Calif.), alpha-smooth muscle actin (SMA; 1:400; Sigma), cytokeratin 18 (CK18; 1:400; Sigma), von Willebrand Factor (vWF; 1:200; Sigma), and CD34 (human CD34 Class III; 1:100; DAKOCytomation, Carpinteria, Calif.). In addition, the following markers were tested: anti-human GROalpha-PE (1:100; Becton Dickinson, Franklin Lakes, N.J.), anti-human GCP-2 (1:100; Santa Cruz Biotech, Santa Cruz, Calif.), anti-human oxidized LDL receptor 1 (ox-LDL R1; 1:100; Santa Cruz Biotech), and anti-human NOGO-A (1:100; Santa Cruz Biotech). Fixed specimens were trimmed with a scalpel and placed within OCT embedding compound (Tissue-Tek OCT; Sakura, Torrance, Calif.) on a dry ice bath containing ethanol. Frozen blocks were then sectioned (10 microns thick) using a standard cryostat (Leica Microsystems) and mounted onto glass slides for staining.

Immunohistochemistry. Immunohistochemistry was performed similar to previous studies (e.g., Messina, et al. (2003) Exper. Neural. 184: 816-829). Tissue sections were washed with phosphate-buffered saline (PBS) and exposed to a protein blocking solution containing PBS, 4% (v/v) goat serum (Chemicon, Temecula, Calif.), and 0.3% (v/v) Triton (Triton X-100; Sigma) for 1 hour to access intracellular antigens. In instances where the epitope of interest would be located on the cell surface (CD34, ox-LDL R1), triton was omitted in all steps of the procedure in order to prevent epitope loss. Furthermore, in instances where the primary antibody was raised against goat (GCP-2, ox-LDL R1, NOGO-A), 3% (v/v) donkey serum was used in place of goat serum throughout the procedure. Primary antibodies, diluted in blocking solution, were then applied to the sections for a period of 4 hours at room temperature. Primary antibody solutions were removed, and cultures washed with PBS prior to application of secondary antibody solutions (1 hour at room temperature) containing block along with goat anti-mouse IgG-Texas Red (1:250; Molecular Probes, Eugene, Oreg.) and/or goat anti-rabbit IgG-Alexa 488 (1:250; Molecular Probes) or donkey anti-goat IgG-FITC (1:150; Santa Cruz Biotech). Cultures were washed, and 10 micromolar DAPI (Molecular Probes) was applied for 10 minutes to visualize cell nuclei.

Following immunostaining, fluorescence was visualized using the appropriate fluorescence filter on an Olympus inverted epifluorescent microscope (Olympus, Melville, N.Y.). Positive staining was represented by fluorescence signal above control staining. Representative images were captured using a digital color videocamera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

TABLE 8-1

Summary of Primary Antibodies Used

| Antibody | Concentration | Vendor |
| --- | --- | --- |
| Vimentin | 1:500 | Sigma, St. Louis, MO |
| Desmin (rb) | 1:150 | Sigma |
| Desmin (m) | 1:300 | Chemicon, Temecula, CA |
| alpha-smooth muscle actin (SMA) | 1:400 | Sigma |
| Cytokeratin 18 (CK18) | 1:400 | Sigma |
| von Willebrand factor (vWF) | 1:200 | Sigma |
| CD34 III | 1:100 | DakoCytomation, Carpinteria, CA |
| GROalpha-PE | 1:100 | BD, Franklin Lakes, NJ |
| GCP-2 | 1:100 | Santa Cruz Biotech |
| Ox-LDL R1 | 1:100 | Santa Cruz Biotech |
| NOGO-A | 1:100 | Santa Cruz Biotech |

Results

Umbilical Cord Characterization. Vimentin, desmin, SMA, CK18, vWF, and CD34 markers were expressed in a subset of the cells found within umbilical cord. In particular, vWF and CD34 expression were restricted to blood vessels contained within the cord. CD34+ cells were on the innermost layer (lumen side). Vimentin expression was found throughout the matrix and blood vessels of the cord. SMA was limited to the matrix and outer walls of the artery and vein, but not contained with the vessels themselves. CK18 and desmin were observed within the vessels only, desmin being restricted to the middle and outer layers.

Summary. Vimentin, desmin, alpha-smooth muscle actin, cytokeratin 18, von Willebrand Factor, and CD34 are produced in cells within human umbilical cord.

EXAMPLE 9

Secretion of Trophic Factors by Umbilicus-Derived Cells

The secretion of selected trophic factors from umbilicus-derived PPDCs was measured. Factors were selected that have angiogenic activity (i.e., hepatocyte growth factor (HGF) (Rosen et al. (1997) Ciba Found. Symp. 212:215-26), monocyte chemotactic protein 1 (MCP-1) (Salcedo et al. (2000) Blood 96; 34-40), interleukin-8 (IL-8) (Li et al. (2003) J. Immunol. 170:3369-76), keratinocyte growth factor (KGF), basic fibroblast growth factor (bFGF), vascular endothelial growth factor (VEGF) (Hughes et al. (2004) Ann. Thorac. Surg. 77:812-8), tissue inhibitor of matrix metalloproteinase 1 (TIMP1), angiopoietin 2 (ANG2), platelet derived growth factor (PDGFbb), thrombopoietin (TPO), heparin-binding epidermal growth factor (HB-EGF), stromal-derived factor 1alpha (SDF-1alpha)), neurotrophic/neuroprotective activity (brain-derived neurotrophic factor (BDNF) (Cheng et al. (2003) Dev. Biol. 258; 319-33), interleukin-6 (IL-6), granulocyte chemotactic protein-2 (GCP-2), transforming growth factor beta2 (TGFbeta2)), or chemokine activity (macrophage inflammatory protein 1 alpha (MIP1alpha), macrophage inflammatory protein 1 beta (MIP1beta), monocyte chemoattractant-1 (MCP-1), Rantes (regulated on activation, normal T cell expressed and secreted), 1309, thymus and activation-regulated chemokine (TARC), Eotaxin, macrophage-derived chemokine (MDC), IL-8).

Methods & Materials

Cell Culture. PPDCs derived from umbilical cord, as well as human fibroblasts derived from human neonatal foreskin, were cultured in Growth Medium on gelatin-coated T75 flasks. Cells were cryopreserved at passage 11 and stored in liquid nitrogen. After thawing, Growth Medium was added to the cells, followed by transfer to a 15 milliliter centrifuge tube and centrifugation of the cells at 150×g for 5 minutes. The cell pellet was resuspended in 4 milliliters Growth Medium, and cells were counted. Cells were seeded at 5,000 cells/cm$^2$ in T75 flasks each containing 15 milliliters of Growth Medium, and cultured for 24 hours. The medium was changed to a serum-free medium (DMEM-low glucose (Gibco), 0.1% (w/v) bovine serum albumin (Sigma), penicillin (50 Units/ milliliter) and streptomycin (50 micrograms/milliliter, Gibco)) for 8 hours. Conditioned serum-free medium was collected at the end of incubation by centrifugation at 14,000×g for 5 minutes and stored at −20° C.

To estimate the number of cells in each flask, cells were washed with phosphate-buffered saline (PBS) and detached using 2 milliliters trypsin/EDTA (Gibco). Trypsin activity was inhibited by addition of 8 milliliters Growth Medium. Cells were centrifuged at 150×g for 5 minutes. The supernatant was removed, and cells were resuspended in 1 milliliter Growth Medium. Cell number was estimated with a hemocytometer.

ELISA assay. Cells were grown at 37° C. in 5% carbon dioxide and atmospheric oxygen. The amount of MCP-1, IL-6, VEGF, SDF-1alpha, GCP-2, IL-8, and TGF-beta2 produced by each cell sample was determined by ELISA (R&D Systems, Minneapolis, Minn.). All assays were performed according to the manufacturer's instructions. Values presented are picograms per milliliter per million cells (n=2, sem).

SearchLight Multiplexed ELISA assay. Chemokines (MIP I alpha, MIP1beta, MCP-1, Rantes, I309, TARC, Eotaxin, MDC, IL8), BDNF, and angiogenic factors (HGF, KGF, bFGF, VEGF, TIMP1, ANG2, PDGFbb, TPO, HB-EGF were measured using SearchLight Proteome Arrays (Pierce Biotechnology Inc.). The Proteome Arrays are multiplexed sandwich ELISAs for the quantitative measurement of two to sixteen proteins per well. The arrays are produced by spotting a 2×2, 3×3, or 4×4 pattern of four to sixteen different capture antibodies into each well of a 96-well plate. Following a sandwich ELISA procedure, the entire plate is imaged to capture the chemiluminescent signal generated at each spot within each well of the plate. The signal generated at each spot is proportional to the amount of target protein in the original standard or sample.

Results

ELISA assay. MCP-1 and IL-6 were secreted by umbilicus-derived PPDCs and dermal fibroblasts (Table 9-1). SDF-1alpha and GCP-2 were secreted by fibroblasts. GCP-2 and IL-8 were secreted by umbilicus-derived PPDCs. TGF-beta2 was not detected from either cell type by ELISA.

TABLE 9-1

ELISA Results: Detection of Trophic Factors

| | MCP-1 | IL-6 | VEGF | SDF-1α | GCP-2 | IL-8 | TGF-beta2 |
|---|---|---|---|---|---|---|---|
| Fibroblast | 17 ± 1 | 61 ± 3 | 29 ± 2 | 19 ± 1 | 21 ± 1 | ND | ND |
| Umbilical (022803) | 1150 ± 74 | 4234 ± 289 | ND | ND | 160 ± 11 | 2058 ± 145 | ND |
| Umbilical (071003) | 2794 ± 84 | 1356 ± 43 | ND | ND | 2184 ± 98 | 2369 ± 23 | ND |

Key: ND: Not Detected., =/− sem

SearchLight Multiplexed ELISA assay. TIMP1, TPO, KGF, HGF, FGF, HBEGF, BDNF, MIP1beta, MCP1, RANTES, I309, TARC, MDC, and IL-8 were secreted from umbilicus-derived PPDCs (Tables 9-2 and 9-3). No Ang2, VEGF, or PDGFbb were detected.

TABLE 9-2

SearchLight Multiplexed ELISA assay results

| | TIMP1 | ANG2 | PDGFbb | TPO | KGF | HGF | FGF | VEGF | HBEGF | BDNF |
|---|---|---|---|---|---|---|---|---|---|---|
| hFB | 19306.3 | ND | ND | 230.5 | 5.0 | ND | ND | 27.9 | 1.3 | ND |
| U1 | 57718.4 | ND | ND | 1240.0 | 5.8 | 559.3 | 148.7 | ND | 9.3 | 165.7 |
| U3 | 21850.0 | ND | ND | 1134.5 | 9.0 | 195.6 | 30.8 | ND | 5.4 | 388.6 |

Key: hFB (human fibroblasts), U1 (umbilicus-derived PPDC (022803)), U3 (umbilicus-derived PPDC (071003)). ND: Not Detected.

TABLE 9-3

SearchLight Multiplexed ELISA assay results

| | MIP1a | MIP1b | MCP1 | RANTES | I309 | TARC | Eotaxin | MDC | IL8 |
|---|---|---|---|---|---|---|---|---|---|
| hFB | ND | ND | 39.6 | ND | ND | 0.1 | ND | ND | 204.9 |
| U1 | ND | 8.0 | 1694.2 | ND | 22.4 | 37.6 | ND | 18.9 | 51930.1 |
| U3 | ND | 5.2 | 2018.7 | 41.5 | 11.6 | 21.4 | ND | 4.8 | 10515.9 |

Key: hFB (human fibroblasts), U1 (umbilicus-derived PPDC (022803)), U3 (umbilicus-derived PPDC (071003)). ND: Not Detected.

Summary. Umbilicus-derived cells secreted a number of trophic factors. Some of these trophic factors, such as HGF, bFGF, MCP-1 and IL-8, play important roles in angiogenesis. Other trophic factors, such as BDNF and IL-6, have important roles in neural regeneration or protection.

EXAMPLE 10

In Vitro Immunology

Postpartum cell lines were evaluated in vitro for their immunological characteristics in an effort to predict the immunological response, if any, these cells would elicit upon in vivo transplantation. Postpartum cell lines were assayed by flow cytometry for the expression of HLA-DR, HLA-DP, HLA-DQ, CD80, CD86, and B7-H2. These proteins are expressed by antigen-presenting cells (APC) and are required for the direct stimulation of naïve $CD4^+$ T cells (Abbas & Lichtman, CELLULAR AND MOLECULAR IMMUNOLOGY, 5th Ed. (2003) Saunders, Philadelphia, p. 171). The cell lines were also analyzed by flow cytometry for the expression of HLA-G (Abbas & Lichtman, CELLULAR AND MOLECULAR IMMUNOLOGY, 5th Ed. (2003) Saunders, Philadelphia, p. 171), CD178 (Coumans, et. al., (1999) *Journal of Immunological Methods* 224, 185-196), and PD-L2 (Abbas & Lichtman, CELLULAR AND MOLECULAR IMMUNOLOGY, 5th Ed. (2003) Saunders, Philadelphia, p. 171; Brown, et. al. (2003) *The Journal of Immunology* 170, 1257-1266). The expression of these proteins by cells residing in placental tissues is thought to mediate the immuno-privileged status of placental tissues in utero. To predict the extent to which postpartum umbilicus-derived cell lines elicit an immune response in vivo, the cell lines were tested in a one-way mixed lymphocyte reaction (MLR).

Materials and Methods

Cell culture. Cells were cultured in Growth Media in T75 flasks (Corning, Corning, N.Y.) coated with 2% gelatin (Sigma, St. Louis, Mo.) until confluent.

Antibody Staining. Cells were washed in phosphate buffered saline (PBS) (Gibco, Carlsbad, Calif.) and detached with Trypsin/EDTA (Gibco, Carlsbad, Mo.). Cells were harvested, centrifuged, and resuspended in 3% (v/v) FBS in PBS at a cell concentration of $1 \times 10^7$ per milliliter. Antibody (Table $10^{-1}$) was added to one hundred microliters of cell suspension as per manufacturer's specifications and incubated in the dark for 30 minutes at 4° C. After incubation, cells were washed with PBS and centrifuged to remove unbound antibody. Cells were re-suspended in five hundred microliters of PBS and analyzed by flow cytometry using a FACSCalibur instrument (Becton Dickinson, San Jose, Calif.).

TABLE 10-1

Antibodies

| Antibody | Manufacture | Catalog Number |
|---|---|---|
| HLA-DR, DP, DQ | BD Pharmingen (San Diego, CA) | 555558 |
| CD80 | BD Pharmingen | 557227 |
| CD86 | BD Pharmingen | 555665 |
| B7-H2 | BD Pharmingen | 552502 |
| HLA-G | Abcam (Cambridgeshire, UK) | ab 7904-100 |
| CD178 | Santa Cruz (San Cruz, CA) | sc-19681 |
| PD-L2 | BD Pharmingen | 557846 |
| Mouse IgG2alpha | Sigma (St. Louis, MO) | F-6522 |
| Mouse IgG1kappa | Sigma | P-4685 |

Mixed Lymphocyte Reaction. Cryopreserved vials of passage 10 umbilicus-derived PPDCs labeled as cell line "A" were sent on dry ice to CTBR (Senneville, Quebec) to conduct a mixed lymphocyte reaction using CTBR SOP no. CAC-031. Peripheral blood mononuclear cells (PBMCs) were collected from multiple male and female volunteer donors. Six human volunteer blood donors were screened to identify a single allogeneic donor that exhibited a robust proliferation response in a mixed lymphocyte reaction with the other five blood donors. This donor was selected as the allogeneic positive control donor. The remaining five blood donors were selected as recipients. Stimulator (donor) allogeneic PBMC, autologous PBMC, and postpartum cell lines were treated with mitomycin C. Autologous and mitomycin C-treated stimulator cells were added to responder (recipient) PBMCs and cultured for 4 days. After incubation, [$^3$H]thymidine was added to each sample and cultured for 18 hours. Following harvest of the cells, radiolabeled DNA was extracted, and [$^3$H]-thymidine incorporation was measured using a scintillation counter. Reactions were performed in triplicate using two-cell culture plates with three receivers per plate The stimulation index for the allogeneic donor (SIAD) was calculated as the mean proliferation of the receiver plus mitomycin C-treated allogeneic donor divided by the baseline proliferation of the receiver. The stimulation index of the postpartum cells was calculated as the mean proliferation of the receiver plus mitomycin C-treated postpartum cell line divided by the baseline proliferation of the receiver.

Results

Mixed Lymphocyte Reaction-Umbilicus-Derived Cells. Results are shown below in Tables 10-2 and -3. The average stimulation index ranged from 6.5 (plate 1) to 9 (plate 2) and the allogeneic donor positive controls ranged from 42.75 (plate 1) to 70 (plate 2) (Table 10-3).

TABLE 10-2

Mixed Lymphocyte Reaction Data- Cell Line A (Umbilicus)
DPM for Proliferation Assay

| Analytical number | Culture System | Replicates | | | Mean | SD | CV |
|---|---|---|---|---|---|---|---|
| | | 1 | 2 | 3 | | | |
| Plate ID: Plate1 | | | | | | | |
| IM04-2478 | Proliferation baseline of receiver | 1074 | 406 | 391 | 623.7 | 390.07 | 62.5 |
| | Control of autostimulation (Mitomycin C treated autologous cells) | 672 | 510 | 1402 | 861.3 | 475.19 | 55.2 |
| | MLR allogenic donor IM04-2477 (Mitomycin C treated) | 43777 | 48391 | 38231 | 43466.3 | 5087.12 | 11.7 |
| | MLR with cell line (Mitomycin C treated cell type A) | 2914 | 5622 | 6109 | 4881.7 | 1721.36 | 35.3 |
| | SI (donor) | | | | 70 | | |
| | SI (cell line) | | | | 8 | | |

TABLE 10-2-continued

Mixed Lymphocyte Reaction Data- Cell Line A (Umbilicus)
DPM for Proliferation Assay

| Analytical number | Culture System | Replicates | | | Mean | SD | CV |
|---|---|---|---|---|---|---|---|
| | | 1 | 2 | 3 | | | |
| IM04-2479 | Proliferation baseline of receiver | 530 | 508 | 527 | 521.7 | 11.93 | 2.3 |
| | Control of autostimulation (Mitomycin C treated autologous cells) | 701 | 567 | 1111 | 793.0 | 283.43 | 35.7 |
| | MLR allogenic donor IM04-2477 (Mitomycin C treated) | 25593 | 24732 | 22707 | 24344.0 | 1481.61 | 6.1 |
| | MLR with cell line (Mitomycin C treated cell type A) | 5086 | 3932 | 1497 | 3505.0 | 1832.21 | 52.3 |
| | SI (donor) | | | | 47 | | |
| | SI (cell line) | | | | 7 | | |
| IM04-2480 | Proliferation baseline of receiver | 1192 | 854 | 1330 | 1125.3 | 244.90 | 21.8 |
| | Control of autostimulation (Mitomycin C treated autologous cells) | 2963 | 993 | 2197 | 2051.0 | 993.08 | 48.4 |
| | MLR allogenic donor IM04-2477 (Mitomycin C treated) | 25416 | 29721 | 23757 | 26298.0 | 3078.27 | 11.7 |
| | MLR with cell line (Mitomycin C treated cell type A) | 2596 | 5076 | 3426 | 3699.3 | 1262.39 | 34.1 |
| | SI (donor) | | | | 23 | | |
| | SI (cell line) | | | | 3 | | |
| IM04-2481 | Proliferation baseline of receiver | 695 | 451 | 555 | 567.0 | 122.44 | 21.6 |
| | Control of autostimulation (Mitomycin C treated autologous cells) | 738 | 1252 | 464 | 818.0 | 400.04 | 48.9 |
| | MLR allogenic donor IM04-2477 (Mitomycin C treated) | 13177 | 24885 | 15444 | 17835.3 | 6209.52 | 34.8 |
| | MLR with cell line (Mitomycin C treated cell type A) | 4495 | 3671 | 4674 | 4280.0 | 534.95 | 12.5 |
| | SI (donor) | | | | 31 | | |
| | SI (cell line) | | | | 8 | | |
| | Plate ID: Plate 2 | | | | | | |
| IM04-2482 | Proliferation baseline of receiver | 432 | 533 | 274 | 413.0 | 130.54 | 31.6 |
| | Control of autostimulation (Mitomycin C treated autologous cells) | 1459 | 633 | 598 | 896.7 | 487.31 | 54.3 |
| | MLR allogenic donor IM04-2477 (Mitomycin C treated) | 24286 | 30823 | 31346 | 28818.3 | 3933.82 | 13.7 |
| | MLR with cell line (Mitomycin C treated cell type A) | 2762 | 1502 | 6723 | 3662.3 | 2724.46 | 74.4 |
| | SI (donor) | | | | 70 | | |
| | SI (cell line) | | | | 9 | | |
| IM04-2477 (allogenic donor) Cell line type A | Proliferation baseline of receiver | 312 | 419 | 349 | 360.0 | 54.34 | 15.1 |
| | Control of autostimulation (Mitomycin treated autologous cells) | 567 | 604 | 374 | 515.0 | 123.50 | 24.0 |
| | Proliferation baseline of receiver | 5101 | 3735 | 2973 | 3936.3 | 1078.19 | 27.4 |
| | Control of autostimulation (Mitomycin treated autologous cells) | 1924 | 4570 | 2153 | 2882.3 | 1466.04 | 50.9 |

TABLE 10-3

Average stimulation index of umbilical cells and an allogeneic donor in a mixed lymphocyte reaction with five individual allogeneic receivers.
Average Stimulation Index

| | Recipient | Umbilicus |
|---|---|---|
| Plate 1 (receivers 1-4) | 42.75 | 6.5 |
| Plate 2 (receiver 5) | 70 | 9 |

Antigen Presenting Cell Markers Produced by Umbilicus-Derived Cells.

The histograms of the flow cytometry analysis show umbilical cells were negative for production of HLA-DR, DP, DQ, CD80, CD86, and B7-H2, because the fluorescence values were comparable to the IgG control. This indicates that umbilical cell lines lack the cell surface molecules required to directly stimulate CD4$^+$ T cells.

Immuno-modulating Markers in Umbilicus-Derived Cells. The umbilical cells analyzed by flow cytometry were positive for expression of PD-L2, as reflected in the increase in fluorescence relative to the IgG control. The cells were negative for expression of CD178 and HLA-G, as noted by fluorescence values consistent with the IgG control.

Summary. In the mixed lymphocyte reactions conducted with umbilical cell lines the average stimulation index ranged from 6.5 to 9, while that of the allogeneic positive controls ranged from 42.75 to 70. Umbilical cell lines did not express detectable amounts of the stimulating proteins HLA-DR, HLA-DP, HLA-DQ, CD80, CD86, and B7-H2, as measured by flow cytometry. Umbilical cell lines also did not express the immuno-modulating proteins HLA-G and CD178, but expression of PD-L2 was detected by flow cytometry. Allogeneic donor PBMCs contain antigen-presenting cells expressing HLA-DR, DQ, CD8, CD86, and B7-H2, thereby allowing for the stimulation of allogeneic lymphocytes. The absence on umbilicus-derived cells of antigen-presenting cell surface molecules required for the direct stimulation of naïve CD4$^+$ T cells, as well as the presence of PD-L2, an immuno-modulating protein, could account for the low stimulation index exhibited by these cells in a MLR as compared to allogeneic controls.

EXAMPLE 11

Plasma Clotting Assay

Cells useful for therapy may be injected systemically for certain applications where the cells are able to target the site of action. It is important that injected cells not cause thrombosis, as it may be fatal. Tissue factor, a membrane-bound procoagulant glycoprotein, is the initiator of the extrinsic clotting cascade, which is the predominant coagulation pathway in vivo. Tissue factor also plays an important role in embryonic vessel formation, for example, in the formation of the primitive vascular wall (Brodsky et al. (2002) *Exp. Nephrol.* 10:299-306). To determine the potential for PPDCs to initiate clotting, umbilicus-derived PPDCs were evaluated for tissue factor expression and for their ability to initiate plasma clotting.

Methods & Materials

Human Tissue Factor. Human tissue factor (SIMPLASTIN, Organon Teknika Corporation, Durham, N.C.), was reconstituted with 20 milliliters distilled water. The stock solution was serially diluted (1:2) in eight tubes. Normal human plasma (George King Bio-Medical, Overland Park, Kans.) was thawed at 37° C. in a water bath and then stored in ice before use. 100 microliters phosphate buffered saline (PBS), 10 microliters diluted SIMPLASTIN, 30 microliters 0.1 Molar calcium chloride, and 100 microliters of normal human plasma were added to each well of a 96-well plate. A negative control well did not receive any SIMPLASTIN. The plate was immediately placed in a temperature-controlled microplate reader and absorbance measured at 405 nanometer at 40 second intervals for 30 minutes.

J-82 and umbilicus-derived cells. J-82 cells (ATCC, MD) were grown in Iscove's modified Dulbecco's medium (IMDM; Gibco, Carlsbad, Calif.) containing 10% (v/v) fetal bovine serum (FBS; Hyclone, Logan Utah), 1 millimolar sodium pyruvate (Sigma Chemical, St. Louis, Mo.), 2 millimolar L-Glutamine (Mediatech Herndon, Va.), 1×non-essential amino acids (Mediatech Herndon, Va.). At about 70% confluence, cells were transferred at 100,000, 50,000 and 25,000 cells/well to wells of 96-well plate. Umbilicus-derived cells were cultured in Growth Medium in gelatin-coated T75 flasks (Corning, Corning, N.Y.). Umbilicus-derived cells at passage 18 were transferred to wells at a density of 50,000 cells/well. Culture medium was removed from each well after centrifugation at 150×g for 5 minutes. Cells were suspended in PBS without calcium and magnesium. Cells incubated with anti-tissue factor antibody cells were incubated with 20 micrograms/milliliter CNTO 859 (Centocor, Malvern, Pa.) for 30 minutes. Calcium chloride (30 microliters) was added to each well. The plate was promptly placed in a temperature-controlled microplate reader and absorbance was measured at 405 nanometers at 40 second intervals for 30 minutes.

Antibody Staining. Cells were washed in PBS and detached from the flask with Trypsin/EDTA (Gibco, Carlsbad, Calif.). Cells were harvested, centrifuged, and resuspended in 3% (v/v) FBS in PBS at a cell concentration of $1 \times 10^7$ per milliliter. Antibody was added to 100 microliters of cell suspension according to the manufacturer's specifications. The cells were incubated in the dark for 30 minutes at 4° C. After incubation, cells were washed with PBS, then centrifuged at 150×g for 5 minutes to remove unbound antibody. Cells were resuspended in 100 microliters of 3% FBS and secondary antibody added in accordance with the manufacturer's instructions. Cells were incubated in the dark for 30 minutes at 4° C. After incubation, cells were washed with PBS and centrifuged to remove unbound secondary antibody. Washed cells were resuspended in 500 microliters of PBS and analyzed via flow cytometry.

Flow Cytometry Analysis. Flow cytometry analysis was performed with a FACSCalibur instrument (Becton Dickinson, San Jose, Calif.).

Results

Flow cytometry analysis revealed that umbilicus-derived postpartum cells are less active in promoting plasma clotting than the J82 cells. Although a plasma clotting assay demonstrated that the tissue factor present in the umbilicus-derived cells was active, clotting took longer than with the J-82 cells, as evidenced by the longer time to half-maximal absorbance (T½ to max; Table 11-1). The T½ to max is inversely proportional to the number of J-82 cells. Umbilicus-derived cells decreased the clotting rate as indicated by the T½ to max. Clotting was observed with both early (P5) and late (P18) passaged cells. Preincubation of umbilical cells with CNTO 859, an antibody to tissue factor, inhibited the clotting reaction, establishing that tissue factor was responsible for the clotting.

TABLE 11-1

The effect of human tissue factor (Simplastin ®) and umbilicus-derived cells (Umb) on plasma clotting. The time to half maximal absorbance (T ½ to max) at the plateau in seconds was used as a measurement unit.

| Standard (Simplastin ® Dilution) | T ½ to max (seconds) |
|---|---|
| 1:2 | 61 |
| 1:4 | 107 |
| 1:8 | 147 |
| 1:16 | 174 |
| 1:32 | 266 |
| 1:64 | 317 |
| 1:128 | 378 |
| 0 (negative control) | 1188 |
| J-82 cells | |
| 100,000 | 122 |
| 50,000 | 172 |
| 25,000 | 275 |
| Umb P5 | |
| 50,000 | 833 |
| Umb P18 | |
| 50,000 | 443 |

Summary. Umbilicus-derived PPDCs produce some tissue factor, but the addition of an antibody against tissue factor can inhibit the clotting activity of the tissue factor. Tissue factor is normally found on cells in a conformation that is inactive, but which is activated by mechanical or chemical (e.g., LPS) stress (Sakariassen et al. (2001) *Thromb. Res.* 104:149-74; Engstad et al. (2002) *Int. Immunopharmacol.* 2:1585-97). Thus, minimization of stress during the preparation process of PPDCs may prevent activation of tissue factor. In addition to the thrombogenic activity, tissue factor has been associated with angiogenic activity. For this reason, tissue factor activity may be beneficial when umbilicus-derived PPDCs are transplanted in tissue, but should be inhibited when PPDCs are injected intravenously.

EXAMPLE 12

Transplantation of Umbilicus-derived Cells

Cells derived from the postpartum umbilical cord are useful for regenerative therapies. Tissue produced by SCID mice following transplantation of a biodegradable material with and without umbilicus-derived cells was evaluated. The materials evaluated were VNW nonwoven scaffolds, 35/65 PCL/PGA foam, and a self-assembling peptide hydrogel.

Methods & Materials

Cell Culture. Umbilicus-derived cells were grown in Growth Medium in gelatin-coated flasks.

Matrix Preparation. A nonwoven scaffold was prepared using a traditional needle punching technique as described below. Fibers, comprised of a synthetic absorbable copolymer of glycolic and lactic acids (PGA/PLA), were obtained from Ethicon, Inc. (Somerville, N.J.). The fibers were filaments of approximately 20 microns in diameter. The fibers were cut and crimped into substantially uniform 2-inch lengths to form 2-inch staple fibers. A dry lay needle-punched nonwoven matrix was prepared utilizing the PGA/PLA staple fibers, hereinafter "VNW". The staple fibers were opened and carded on standard nonwoven machinery. The resulting mat was in the form of webbed staple fibers. The webbed staple fibers were needle-punched to form the dry lay needle-punched nonwoven scaffold. The nonwoven scaffold was rinsed in water followed by another incubation in ethanol to remove any residual chemicals or processing aids used during the manufacturing process.

Foams, composed of 35/65 poly(epsilon-caprolactone)/poly(glycolic acid) (35/65 PCL/PGA) copolymer, were formed by the process of lyophilization, as described in U.S. Pat. No. 6,355,699.

A self assembling peptide hydrogel (RAD16 self-assembling peptides (3D Matrix, Cambridge, Mass.)) was obtained as a sterile 1% (w/v) solution in water.

Sample Preparation. One million viable cells were seeded in 15 microliters Growth Medium onto 5 millimeter diameter, 2.25 millimeter thick VNW scaffolds (64.33 milligrams/cc); or 5 millimeter diameter 35/65 PCL/PGA foam disks. Cells were allowed to attach for two hours before adding more Growth Medium to cover the scaffolds. Cells were grown on scaffolds overnight. Control scaffolds without cells were also incubated in medium.

The self-assembling peptide solution was mixed 1:1 with $1 \times 10^6$ cells in 10% (w/v) sucrose (Sigma, St Louis, Mo.), 10 millimolar HEPES (pH about 7), in Dulbecco's modified medium (DMEM; Gibco) immediately before use. The final concentration of cells in the self-assembling peptide hydrogel was $1 \times 10^6$ cells/100 microliters.

Test Material (N=4/condition)
1. VNW scaffold+$1 \times 10^6$ umbilicus-derived cells
2. 35/65 PCL/PGA foam+$1 \times 10^6$ umbilicus-derived cells
3. Self-assembling peptide+$1 \times 10^6$ umbilicus-derived cells
4. 35/65 PCL/PGA foam
5. VNW scaffold Animal Preparation. The animals utilized in this study were handled and maintained in accordance with the current requirements of the Animal Welfare Act. Compliance with the above Public Laws were accomplished by adhering to the Animal Welfare regulations (9 C.F.R.) and conforming to the current standards promulgated in the Guide for the Care and Use of Laboratory Animals, 7th edition.

Animals: Male mice (*Mus musculus*) (Fox Chase SCID; Harlan Sprague Dawley, Inc., Indianapolis, Ind.), were used at 5 weeks of age. All handling of the SCID mice took place under a hood. Each animal was individually weighed, and anesthetized with an intraperitoneal injection of a mixture of 60 milligram/kilogram KETASET (ketamine hydrochloride) (Aveco Co., Inc., Fort Dodge, Iowa), 10 milligram/kilogram ROMPUN (xylazine) (Mobay Corp., Shawnee, Kans.) and saline. After induction of anesthesia, the back of the animal from the dorsal cervical area to the dorsal lumbosacral area was clipped free of hair using electric animal clippers. The area was then scrubbed with chlorhexidine diacetate, rinsed with alcohol, dried, and painted with an aqueous iodophor solution of 1% available iodine. Ophthalmic ointment was applied to the eyes to prevent drying of the tissue during the anesthetic period.

Subcutaneous Implantation Technique. Four skin incisions, each approximately 1 centimeter in length, were made on the dorsa of the mice. Two cranial implantation sites, one each to the left and right of the vertebral column, were located transversely over the dorsal lateral thoracic region, about 5 millimeters caudal to the palpated inferior edge of the scapula. Two additional implants, one on each side of the midline, were placed transversely over the gluteal muscle area at the caudal sacro-lumbar level, about 5 millimeters caudal to the palpated iliac crest. Implants were randomly placed in these sites. The skin was separated from the underlying connective tissue to make a small pocket and the implant placed (or injected in the case of the self-assembling peptide) about 1 centimeter caudal to the incision. The appropriate test material was implanted into the subcutaneous space. The skin incision was closed with metal clips.

Animal Housing. Animals were individually housed in microisolator cages throughout the course of the study within a temperature range of 64° F.-79° F. and relative humidity of 30% to 70%, and maintained on a 12 hour light/12 hour dark (approximately) cycle. The diet consisted of Irradiated Pico Mouse Chow 5058 (Purina Co.) and water provided ad libitum.

Mice were euthanized by carbon dioxide inhalation at designated intervals. The subcutaneous implants with the overlying skin were excised and frozen for histology.

Histology. Excised skin with implant was fixed with 10% neutral buffered formalin (Richard-Allan Scientific, Kalamazoo, Mich.). Samples with overlying and adjacent tissue were centrally bisected, paraffin-processed, and embedded on cut surface using routine methods. Embedded tissue was sectioned (five-micron sections) on a microtome and stained with hematoxylin and eosin (Poly Scientific, Bay Shore, N.Y.) using routine methods.

Results

There was minimal ingrowth of tissue into control foams without umbilicus-derived cells implanted subcutaneously in SCID mice after 30 days. In contrast, there was extensive tissue fill into foams implanted with umbilicus-derived cells.

There was some tissue ingrowth in VNW scaffolds. Nonwoven scaffolds seeded with umbilicus-derived cells showed increased matrix deposition and mature blood vessels.

Summary. Human umbilicus-derived cells were shown to dramatically increase good quality tissue formation in biodegradable scaffolds. Synthetic absorbable nonwoven scaffolds, foam discs (5.0 millimeters diameter×1.0 millimeter thick), or self-assembling peptide hydrogels were seeded with cells derived from human umbilical cord and implanted subcutaneously bilaterally in the dorsal spine region of SCID mice. The umbilicus-derived cells enhanced tissue ingrowth and blood vessel formation on the scaffolds in immune deficient mice, compared to that on scaffolds not seeded with umbilicus-derived cells.

EXAMPLE 13

Transplantation of Umbilicus-derived Cells Under the Kidney Capsule

Transplantation of pancreatic islets to the kidney capsule is routinely performed to evaluate transplantation methodologies for the treatment of diabetes (Refaie et al., 1998). In addition to pancreatic islets, other cells may be differentiated into insulin secreting cells capable of blood glucose homeostasis. The suitability of umbilicus-derived cells for this purpose was evaluated.

Methods & Materials

Cell Culture. Umbilicus-derived cells (isolate 1, P10) were removed from liquid nitrogen storage and grown in Growth Medium on gelatin (Sigma)-coated T225 (Corning, Corning, N.Y.) flasks until confluent.

The culture medium on umbilicus-derived cells was replaced with Ham's F12 medium (Gibco) containing 10 millimolar nicotinamide (Sigma), 25 millimolar glucose (Sigma), 10 nanogram/milliliter EGF (PeproTech, Rocky Hill, N.J.), 20 nanogram/milliliter bFGF (PeproTech) and 15 millimolar GLP-1 (Sigma) and cells were further cultured for 2 weeks.

Cells from two flasks were washed with phosphate buffered saline (PBS), and a single cell suspension was obtained by using Trypsin/EDTA (Gibco). Cryopreserved GM-CSF mobilized CD34+ cells were purchased from Cambrex, Walkersville, Md. (lot 1F0174 donor 7956). CD34+ cells were thawed and washed in DMEM medium.

The cell suspension was washed twice in DMEM. Cell number and viability was estimated after Trypan blue (Sigma) staining using a hemocytometer. Aliquots of the cell suspension containing ~300,000 viable cells were centrifuged at 150×g and the cells resuspended in approximately 6 microliters of DMEM and drawn into a 20 microliter pipette tip connected to a 1 milliliter syringe. The tip of the pipette tip containing the cells was clamped using a small Ligaclip (Ethicon Endosurgery, Cincinnati Ohio).

Animal preparation. Mice (*Mus musculus*)/Fox Chase SCID/Male (Harlan Sprague Dawley, Inc., Indianapolis, Ind.) were 8 weeks of age. All handling of the SCID mice took place under a hood. The mice were individually weighed and anesthetized with an intraperitoneal injection of a mixture of 60 milligram/kilogram KETASET (ketamine hydrochloride, Aveco Co., Inc., Fort Dodge, Iowa) and 10 milligram/kilogram ROMPUN (xylazine, Mobay Corp., Shawnee, Kans.) and saline. After induction of anesthesia, the entire back of the animal from the dorsal cervical area to the dorsal lumbosacral area was clipped free of hair using electric clippers. The area was scrubbed with chlorhexidine diacetate, rinsed with alcohol, dried, and painted with an aqueous iodophor solution of 1% available iodine. Ophthalmic ointment was applied to the eyes to prevent drying of the tissue during the anesthetic period. The anesthetized and surgically prepared animal was placed in the desired recumbent position. A transverse incision was made on the left abdominal side approximately 2 centimeters caudal to the rib cage of animal. The kidney was exposed and the capsule pierced with a 26-gauge needle. A capsule lance (modified glass pipette tip) was used to create a space beneath the kidney capsule into which the cells were introduced. The cells were injected via a syringe with a micropipette tip attached. The pocket was closed by passing an ophthalmic cautery pen (Aaron Medical Industries, St. Petersburg, Fla.) over the opening (not touching the kidney). The kidney was placed back in the correct anatomical position, and the muscle layer sutured closed. The skin was closed with wound clips.

The experimental design comprised one cell transplantation in each mouse; four treatments with n-value of 4 per treatment; and three time-points (1, 14 & 30 days).

Mice were euthanized by carbon dioxide inhalation at their designated intervals. The kidney implantation sites were excised and frozen for histology.

Immunohistochemistry. Frozen kidney implantation site were embedded on edge in O.C.T. Compound (Sakura Inc., Torrance, Calif.). The kidney tissue was trimmed by cryosectioning to yield a five-micron section of the implantation site and adjacent tissue. Yielded sections were fixed in freshly prepared 4% paraformaldehyde (EM Sciences Gibbstown, N.J.) in phosphate buffered saline (Gibco) for 15 minutes. Sections were washed in PBS and incubated in 3% goat serum in PBS blocking solution for one hour. Blocking solution was removed by gentle aspiration. Sections were incubated in anti-human nuclei antibody (Chemicon International, Temecula, Calif.) diluted 1:100 in blocking solution for one hour. Sections were washed with PBS and incubated in florescent labeled goat anti-mouse IgG antibody (Molecular Probes Eugene, Oreg.), diluted 1:200 in blocking solution for 30 minutes in absence of light. Sections were washed in PBS and incubated in 10 micromolar DAPI (Molecular Probes) for five minutes. Sections were washed in PBS and examined by fluorescent microscopy.

Tri-Chrome Staining. Frozen kidney implantation sites were embedded on edge in O.C.T. Compound (Sakura Inc.). The kidney tissue was trimmed by cryosectioning to yield a five-micron section of the implantation site and adjacent tissue. Yielded sections were fixed in 10% neutral buffered formalin (Richard-Allan Scientific) for 15 minutes. Sections were stained tri-chrome (Poly Scientific) using manufactures methods.

Treatments:
1. $3 \times 10^3$ cells from umbilical cord
2. $3 \times 10^3$ cells from umbilical cord+$3 \times 10^3$ $CD34^+$ cells
Added three animals as control (No cells)
Results The viability of the umbilicus-derived cells was ~75%; that of the $CD34^+$ cells was 95%. Initial attempts to transplant $1 \times 10^6$ viable cells were unsuccessful due to the kidney capsule not being large enough to accommodate the cells. Cells were transplanted within 3 hours of trypsinization. The localization of postpartum cells under the kidney capsule was observed microscopically. There were no apparent differences in the number and distribution of umbilicus-derived cells with or without $CD34^+$ cells at each time point. There was an apparent decrease in cell numbers over time.

Staining of cells under the kidney capsule showed the retention of transplanted cells. Human cells were detected using the human nuclear antigen. All cells (human and mouse) were detected using DAPI.

Umbilicus-derived cells were microscopically observed 14 and 30 days post-transplantation. Human cells were again stained for human nuclear antigen. TriChrome staining was used to detect the presence of collagen Summary. Transplantation of cells into the renal capsule was successful. The observed reduction in cell number over time in this experiment may be due to a number of factors such as the viability of cells at the time of transplant, innate immunity and insufficient nutrient availability due to vascularization issues. While long-term survival or even growth of the cells in vivo might be useful for certain purposes, it is not required for the cells to be used in many applications, nor do these results reflect the ability of the cells to survive and grow over longer terms.

Reference

Refaie A., Gabr M. et al., (1998) Experimental islet cell transplantation in rats: Optimization of the transplantation site. Trans. Proc. 30:400-403

EXAMPLE 14

Short-Term Neural Differentiation of Umbilicus-Derived Cells

The ability umbilicus-derived postpartum cells (PPDCs) to differentiate into neural lineage cells was examined.

Materials & Methods

Isolation and Expansion of Cells. Umbilicus-derived PPDCs were isolated and expanded as described in Example 1 and 2.

Modified Woodbury-Black Protocol.

(A) This assay was adapted from an assay originally performed to test the neural induction potential of bone marrow stromal cells (1). Umbilicus PPDCs (P4) were thawed and culture expanded in Growth Media at 5,000 cells/$cm^2$ until sub-confluence (75%) was reached. Cells were then trypsinized and seeded at 6,000 cells per well of a Titretek II glass slide (VWR International, Bristol, Conn.). As controls, mesenchymal stem cells (P3; 1F2155; Cambrex, Walkersville, Md.), osteoblasts (P5; CC2538; Cambrex), omental cells (P6), adipose-derived cells (U.S. Pat. No. 6,555,374 B1) (P6) and neonatal human dermal fibroblasts (P6; CC2509; Cambrex) were also seeded under the same conditions.

All cells were initially expanded for 4 days in DMEM/F12 medium (Invitrogen, Carlsbad, Calif.) containing 15% (v/v) fetal bovine serum (FBS; Hyclone, Logan, Utah), basic fibroblast growth factor (bFGF; 20 nanogram/milliliter; Peprotech, Rocky Hill, N.J.), epidermal growth factor (EGF; 20 nanogram/milliliter; Peprotech), penicillin (50 Units/milliliter), and streptomycin (50 micrograms/milliliter (Invitrogen). After 4 days, cells were rinsed in phosphate-buffered saline (PBS; Invitrogen) and were subsequently cultured in DMEM/F12 medium+20% (v/v) FBS+penicillin (50 Units/milliliter)+streptomycin (50 micrograms/milliliter (Invitrogen) for 24 hours. After 24 hours, cells were rinsed with PBS. Cells were then cultured for 1-6 hours in an induction medium which was comprised of DMEM/F12 (serum-free) containing 200 millimolar butylated hydroxyanisole, 10 micromolar potassium chloride, 5 milligram/milliliter insulin, 10 micromolar forskolin, 4 micromolar valproic acid, and 2 micromolar hydrocortisone (all chemicals from Sigma, St. Louis, Mo.). Cells were then fixed in cold ($-20°$ C.) 100% methanol and immunocytochemistry was performed (see methods below) to assess human nestin protein expression.

(B) PPDCs (umbilicus, P11) and adult human dermal fibroblasts (1F1853, P11) were thawed and culture expanded in Growth Medium at 5,000 cells/cm$^2$ until sub-confluence (75%) was reached. Cells were then trypsinized and seeded at similar density as in (A), but onto (1) 24 well tissue culture-treated plates (TCP, Falcon brand, VWR International), (2) TCP wells+2% (w/v) gelatin adsorbed for 1 hour at room temperature, or (3) TCP wells+20 micrograms/milliliter adsorbed mouse laminin (adsorbed for a minimum of 2 hours at 37° C.; Invitrogen).

As in (A) above, cells were initially expanded and media switched at the aforementioned timeframes. One set of cultures was fixed at 5 days and six hours with cold (4° C.) 4% (w/v) paraformaldehyde (Sigma) for 10 minutes at room temperature. In the second set of cultures, the medium was removed and switched to Neural Progenitor Expansion medium (NPE) consisting of Neurobasal-A medium (Invitrogen) containing B27 (B27 supplement; Invitrogen), L-glutamine (4 millimolar), penicillin (50 Units/milliliter), and streptomycin (50 micrograms/milliliter (Invitrogen). NPE medium was further supplemented with retinoic acid (RA; 1 micromolar; Sigma). This medium was removed 4 days later and cultures were fixed with cold (4° C.) 4% (w/v) paraformaldehyde (Sigma) for 10 minutes at room temperature, and stained for nestin, GFAP, and TuJ1 protein expression (see Table 14-1).

TABLE 14-1

Summary of Primary Antibodies Used

| Antibody | Concentration | Vendor |
|---|---|---|
| Rat 401 (nestin) | 1:200 | Chemicon, Temecula, CA |
| Human Nestin | 1:100 | Chemicon |
| TuJ1 (BIII Tubulin) | 1:500 | Sigma, St. Louis, MO |
| GFAP | 1:2000 | DakoCytomation, Carpinteria, CA |
| Tyrosine hydroxylase (TH) | 1:1000 | Chemicon |
| GABA | 1:400 | Chemicon |
| Desmin (mouse) | 1:300 | Chemicon |
| Alpha smooth muscle actin | 1:400 | Sigma |
| Human nuclear protein (hNuc) | 1:150 | Chemicon |

Two Stage Differentiation Protocol. Umbilicus-derived PPDCs (P11), adult human dermal fibroblasts (P11; 1F1853; Cambrex) were thawed and culture expanded in Growth Medium at 5,000 cells/cm$^2$ until sub-confluence (75%) was reached. Cells were then trypsinized and seeded at 2,000 cells/cm$^2$, but onto 24 well plates coated with laminin (BD Biosciences, Franklin Lakes, N.J.) in the presence of NPE media supplemented with bFGF (20 nanograms/milliliter; Peprotech, Rocky Hill, N.J.) and EGF (20 nanograms/milliliter; Peprotech) (whole media composition further referred to as NPE+F+E). At the same time, adult rat neural progenitors isolated from hippocampus (P4; (062603)) were also plated onto 24 well laminin-coated plates in NPE+F+E media. All cultures were maintained in such conditions for a period of 6 days (cells were fed once during that time) at which time media were switched to the differentiation conditions listed in Table 14-2 for an additional period of 7 days. Cultures were fixed with ice-cold (4° C.) 4% (w/v) paraformaldehyde (Sigma) for 10 minutes at room temperature, and stained for human or rat nestin, GFAP, and TuJ1 protein expression.

TABLE 14-2

Summary of Conditions for Two-Stage Differentiation Protocol

| COND. # | A<br>PRE-DIFFERENTIATION | B<br>2$^{nd}$ STAGE DIFF |
|---|---|---|
| 1 | NPE + F (20 ng/ml) + E (20 ng/ml) | NPE + SHH (200 ng/ml) + F8 (100 ng/ml) |
| 2 | NPE + F (20 ng/ml) + E (20 ng/ml) | NPE + SHH (200 ng/ml) + F8 (100 ng/ml) + RA (1 micromolar) |
| 3 | NPE + F (20 ng/ml) + E (20 ng/ml) | NPE + RA (1 micromolar) |
| 4 | NPE + F (20 ng/ml) + E (20 ng/ml) | NPE + F (20 ng/ml) + E (20 ng/ml) |
| 5 | NPE + F (20 ng/ml) + E (20 ng/ml) | Growth Medium |
| 6 | NPE + F (20 ng/ml) + E (20 ng/ml) | Condition 1B + rhGDF-5 (20 ng/ml) |
| 7 | NPE + F (20 ng/ml) + E (20 ng/ml) | Condition 1B + BMP7 (20 ng/ml) |
| 8 | NPE + F (20 ng/ml) + E (20 ng/ml) | Condition 1B + GDNF (20 ng/ml) |
| 9 | NPE + F (20 ng/ml) + E (20 ng/ml) | Condition 2B + rhGDF-5 (20 ng/ml) |
| 10 | NPE + F (20 ng/ml) + E (20 ng/ml) | Condition 2B + BMP7 (20 ng/ml) |
| 11 | NPE + F (20 ng/ml) + E (20 ng/ml) | Condition 2B + GDNF (20 ng/ml) |
| 12 | NPE + F (20 ng/ml) + E (20 ng/ml) | Condition 3B + rhGDF-5 (20 ng/ml) |
| 13 | NPE + F (20 ng/ml) + E (20 ng/ml) | Condition 3B + BMP7 (20 ng/ml) |
| 14 | NPE + F (20 ng/ml) + E (20 ng/ml) | Condition 3B + GDNF (20 ng/ml) |
| 15 | NPE + F (20 ng/ml) + E (20 ng/ml) | NPE + rhGDF-5 (20 ng/ml) |
| 16 | NPE + F (20 ng/ml) + E (20 ng/ml) | NPE + BMP7 (20 ng/ml) |
| 17 | NPE + F (20 ng/ml) + E (20 ng/ml) | NPE + GDNF (20 ng/ml) |

Multiple Growth Factor Induction Protocol. Umbilicus-derived PPDCs (P11) were thawed and culture expanded in Growth Medium at 5,000 cells/cm² until sub-confluence (75%) was reached. Cells were then trypsinized and seeded at 2,000 cells/cm², onto 24 well laminin-coated plates (BD Biosciences) in the presence of NPE+F (20 nanograms/milliliter)+E (20 nanograms/milliliter). In addition, some wells contained NPE+F+E+2% FBS or 10% FBS. After four days of "pre-differentiation" conditions, all media were removed and samples were switched to NPE medium supplemented with sonic hedgehog (SHH; 200 nanograms/milliliter; Sigma, St. Louis, Mo.), FGF8 (100 nanograms/milliliter; Peprotech), BDNF (40 nanograms/milliliter; Sigma), GDNF (20 nanograms/milliliter; Sigma), and retinoic acid (1 micromolar; Sigma). Seven days post medium change, cultures were fixed with ice-cold (4° C.) 4% (w/v) paraformaldehyde (Sigma) for 10 minutes at room temperature, and stained for human nestin, GFAP, TuJ1, desmin, and alpha-smooth muscle actin expression.

Neural Progenitor Co-Culture Protocol. Adult rat hippocampal progenitors (062603) were plated as neurospheres or single cells (10,000 cells/well) onto laminin-coated 24 well dishes (BD Biosciences) in NPE+F (20 nanograms/milliliter)+E (20 nanograms/milliliter).

Umbilicus-derived PPDCs (P11) were thawed and culture expanded in NPE+F (20 nanograms/milliliter)+E (20 nanograms/milliliter) at 5,000 cells/cm² for a period of 48 hours. Cells were then trypsinized and seeded at 2,500 cells/well onto existing cultures of neural progenitors. The existing medium was exchanged for fresh medium. Four days later, cultures were fixed with ice-cold (4° C.) 4% (w/v) paraformaldehyde (Sigma) for 10 minutes at room temperature, and stained for human nuclear protein (hNuc, Chemicon) (Table 14-1 above) to identify PPDCs.

Immunocytochemistry. Immunocytochemistry was performed using the antibodies listed in Table 14-1. Cultures were washed with phosphate-buffered saline (PBS) and exposed to a protein blocking solution containing PBS, 4% (v/v) goat serum (Chemicon, Temecula, Calif.), and 0.3% (v/v) Triton (Triton X-100; Sigma) for 30 minutes to access intracellular antigens. Primary antibodies, diluted in blocking solution, were then applied to the cultures for a period of 1 hour at room temperature. Primary antibody solutions were removed and cultures washed with PBS prior to application of secondary antibody solutions (1 hour at room temperature) containing blocking solution along with goat anti-mouse IgG -Texas Red (1:250; Molecular Probes, Eugene, Oreg.) and goat anti-rabbit IgG-Alexa 488 (1:250; Molecular Probes). Cultures were then washed and 10 micromolar DAPI (Molecular Probes) was applied for 10 minutes to help visualize cell nuclei.

Following immunostaining, fluorescence was visualized using the appropriate fluorescence filter on an Olympus inverted epi-fluorescent microscope (Olympus, Melville, N.Y.). Positive staining represented fluorescence signal above control staining where the entire procedure outlined above was followed with the exception of application of a primary antibody solution. Representative images were captured using a digital color videocamera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

Results

Woodbury-Black Protocol.

(A) Upon incubation in this neural induction composition, all cell types transformed into cells with bipolar morphologies and extended processes. Other larger non-bipolar morphologies were also observed. Furthermore, the induced cell populations stained positively for nestin, a marker of multipotent neural stem and progenitor cells.

(B) When repeated on tissue culture plastic (TCP) dishes, nestin expression was not observed unless laminin was preadsorbed to the culture surface. To further assess whether nestin-expressing cells could then go on to generate mature neurons, PPDCs and fibroblasts were exposed to NPE+RA (1 micromolar), a medium composition known to induce the differentiation of neural stem and progenitor cells into such cells (2, 3, 4). Cells were stained for TuJ1, a marker for immature and mature neurons, GFAP, a marker of astrocytes, and nestin, a marker indicative of neural progenitors. TuJ1 expression was not turned on, nor were cells with neuronal morphology observed under any of the tested conditions, suggesting that neurons were not generated in the short term. Furthermore, nestin and GFAP expression, which were found in PPDCs and fibroblasts on laminin-coated substrates, were not produced under these conditions.

Two Stage Differentiation Results. Umbilicus-derived cell isolates, as well as human fibroblasts and rodent neural progenitors (as negative and positive control cell types, respectively), were plated on laminin (neural-promoting)-coated dishes and exposed to 13 different growth conditions (and two control conditions) known to promote differentiation of neural progenitors into neurons and astrocytes. In addition, two conditions were added to examine the influence of GDF5, and BMP7 on PPDC differentiation. Generally, a two-step differentiation approach was taken, where the cells were first placed in neural progenitor expansion conditions for a period of 6 days followed by full differentiation conditions for 7 days. Morphologically, umbilical cells exhibited fundamental changes in cell morphology throughout the time-course of this procedure. However, in no cases were neuronal or astrocytic-shaped cells observed except for in control, neural progenitor-plated conditions. Immunocytochemistry, negative for human nestin, TuJ1, and GFAP confirmed these morphological observations. Results are summarized in Table 14-3 below.

TABLE 14-3

Staining results for human nestin, GFAP, and TuJ1 respectively in Two Stage Differentiation Experiment. Note that + means that at least a portion (>0%) of the cells were positive for the stain indicated. Human nestin: immature neural stem and progenitor cells; GFAP: astrocytes; TuJ1: immature and mature neurons.

| CONDITION | Fibroblasts | Umbilical PPDCs | Neural Progenitors |
|---|---|---|---|
| 1 | −/−/− | −/−/− | +/+/+ |
| 2 | −/−/− | −/−/− | +/+/+ |
| 3 | −/−/− | −/−/− | +/+/+ |
| 4 | −/−/− | −/−/− | +/+/+ |
| 5 | −/−/− | −/−/− | +/+/+ |
| 6 | −/−/− | −/−/− | +/+/+ |
| 7 | −/−/− | −/−/− | +/+/+ |
| 8 | −/−/− | −/−/− | +/+/+ |
| 9 | −/−/− | −/−/− | +/+/+ |
| 10 | −/−/− | −/−/− | +/+/+ |
| 11 | −/−/− | −/−/− | +/+/+ |
| 12 | −/−/− | −/−/− | +/+/+ |
| 13 | −/−/− | −/−/− | +/+/+ |
| 14 | −/−/− | −/−/− | +/+/+ |
| 15 | −/−/− | −/−/− | +/+/+ |
| 16 | −/−/− | −/−/− | +/+/+ |
| 17 | −/−/− | −/−/− | +/+/+ |

Multiple Growth Factor Induction Results. Following a one week exposure to a variety of neural differentiation agents, cells were stained for markers indicative of neural progenitors (human nestin), neurons (TuJ1), and astrocytes (GFAP). Cells grown in the first stage in non-serum containing media had different morphologies than those cells in serum containing (2% or 10%) media, indicating potential neural differentiation. Specifically, following a two step procedure of exposing umbilical PPDCs to EGF and bFGF, followed by SHH, FGF8, GDNF, BDNF, and retinoic acid, cells showed long extended processes similar to the morphology of cultured astrocytes. When 2% FBS or 10% FBS were included in the first stage of differentiation, cell number was increased and cell morphology was unchanged from control cultures at high density. Potential neural differentiation was not evidenced by immunocytochemical analysis for human nestin, TuJ1, or GFAP.

Neural Progenitor and PPDC Co-culture Procedures. Umbilicus-derived cells were plated onto cultures of rat neural progenitors seeded two days earlier in neural expansion conditions (NPE+F+E). While visual confirmation of plated umbilicus proved that these cells were plated as single cells, human-specific nuclear staining (hNuc) 4 days post-plating (6 days total length of experiment) showed that they tended to ball up and avoid contact with the neural progenitors. Furthermore, where umbilicus cells attached, these cells spread out and appeared to be innervated by differentiated neurons that were of rat origin suggesting that the umbilical cells may have differentiated into muscle cells. This observation was based upon morphology under phase contrast microscopy. Another observation was that typically large cell bodies (larger than neural progenitors) possessed morphologies resembling neural progenitors, with thin processes spanning out in multiple directions. HNuc staining (found in one half of the cell's nucleus) suggested that in some cases these human cells may have fused with rat progenitors and assumed their phenotype. Controls wells containing neural progenitors only had fewer total progenitors and apparent differentiated cells than did co-culture wells containing umbilicus, further indicating that umbilicus-derived cells influenced the differentiation and behavior of neural progenitors either by release of chemokines and cytokines, or by contact-mediated effects.

Summary. Multiple protocols were conducted to determine the short term potential of umbilicus-derived PPDCs to differentiate into neural lineage cells. These included phase contrast imaging of morphology in combination with immunocytochemistry for nestin, TuJ1, and GFAP, proteins associated with multipotent neural stem and progenitor cells, immature and mature neurons, and astrocytes, respectively. Evidence was observed to suggest that neural differentiation occurred in certain instances in these short-term protocols.

Several notable observations were made in co-cultures of PPDCs with neural progenitors. This approach, using human PPDCs along with a xenogeneic cell type allowed for absolute determination of the origin of each cell in these cultures. First, some cells were observed in these cultures where the cell cytoplasm was enlarged, with neurite-like processes extending away from the cell body, yet only half of the body labeled with hNuc protein. Those cells may be human PPDCs that have differentiated into neural lineage cells or they may be PPDCs that have fused with neural progenitors of rat origin. Second, it appeared that neural progenitors extended neurites to PPDCs in a way that indicates the progenitors differentiated into neurons and innervated the PPDCs. Third, cultures of neural progenitors and PPDCs had more cells of rat origin and larger amounts of differentiation than control cultures of neural progenitors alone, further indicating that plated PPDCs provided soluble factors and or contact-dependent mechanisms that stimulated neural progenitor survival, proliferation, and/or differentiation.

References (1) Woodbury, D. et al. (2000). *J Neurosci. Research.* 61(4): 364-70.

(2) Jang, Y. K. et al. (2004). *J. Neurosci. Research.* 75(4): 573-84.

(3) Jones-Villeneuve, E. M. et al. (1983). *Mol Cel Biol.* 3(12): 2271-9.

(4) Mayer-Proschel, M. et al. (1997). *Neuron.* 19(4): 773-85.

EXAMPLE 15

Long-Term Neural Differentiation of Umbilicus-derived Cells

The ability of umbilicus-derived cells to undergo long-term differentiation into neural lineage cells was evaluated.

Materials & Methods

Isolation and Expansion of Postpartum Cells (PPDCs). Umbilicus-derived PPDCs were isolated and expanded as described in Examples 1 and 2.

Umbilicus-derived Cell Thaw and Plating. Frozen aliquots of umbilicus-derived cells P11 and P12, previously grown in Growth Medium were thawed and plated at 5,000 cells/cm$^2$ in T-75 flasks coated with laminin (BD, Franklin Lakes, N.J.) in Neurobasal-A medium (Invitrogen, Carlsbad, Calif.) containing B27 (B27 supplement, Invitrogen), L-glutamine (4 millimolar), penicillin (50 Units/milliliter), and streptomycin (50 micrograms/milliliters), the combination of which is herein referred to as Neural Progenitor Expansion (NPE) media. NPE medium was further supplemented with bFGF (20 nanograms/milliliter, Peprotech, Rocky Hill, N.J.) and EGF (20 nanograms/milliliter, Peprotech, Rocky Hill, N.J.), herein referred to as NPE+bFGF+EGF.

Control Cell Plating. In addition, adult human dermal fibroblasts (P11, Cambrex, Walkersville, Md.) and mesenchymal stem cells (P5, Cambrex) were thawed and plated at the same cell seeding density on laminin-coated T-75 flasks in NPE+bFGF+EGF. As a further control, fibroblasts and umbilical cells were grown in Growth Medium for the period specified for all cultures.

Cell Expansion. Media from all cultures were replaced with fresh media once a week and cells observed for expansion. In general, each culture was passaged one time over a period of one month because of limited growth in NPE+bFGF+EGF.

Immunocytochemistry. After a period of one month, all flasks were fixed with cold (4° C.) 4% (w/v) paraformaldehyde (Sigma) for 10 minutes at room temperature. Immunocytochemistry was performed using antibodies directed against TuJ1 (BIII Tubulin; 1:500; Sigma, St. Louis, Mo.) and GFAP (glial fibrillary acidic protein; 1:2000; DakoCytomation, Carpinteria, Calif.). Briefly, cultures were washed with phosphate-buffered saline (PBS) and exposed to a protein blocking solution containing PBS, 4% (v/v) goat serum (Chemicon, Temecula, Calif.), and 0.3% (v/v) Triton (Triton X-100; Sigma) for 30 minutes to access intracellular antigens. Primary antibodies, diluted in blocking solution, were then applied to the cultures for a period of 1 hour at room temperature. Primary antibody solutions were then removed and the cultures were washed with PBS prior to application of secondary antibody solutions (1 hour at room temperature) containing block along with goat anti-mouse IgG-Texas Red (1:250; Molecular Probes, Eugene, Oreg.) and goat anti-rabbit IgG-Alexa 488 (1:250; Molecular Probes). Cultures were then washed and 10 micromolar DAPI (Molecular Probes) applied for 10 minutes to visualize cell nuclei.

Following immunostaining, fluorescence was visualized using the appropriate fluorescence filter on an Olympus inverted epi-fluorescent microscope (Olympus, Melville, N.Y.). In all cases, positive staining represented fluorescence signal above control staining where the entire procedure outlined above was followed with the exception of application of a primary antibody solution. Representative images were captured using a digital color videocamera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

Results

NPE+bFGF+EGF Media Slows Proliferation of PPDCs and Alters Their Morphology. Immediately following plating, a subset of umbilical cells attached to the culture flasks coated with laminin. This may have been due to cell death as a function of the freeze/thaw process or because of the new growth conditions. Cells that did attach adopted morphologies different than those observed in Growth Media.

Upon confluence, cultures were passaged and observed for growth. Very little expansion took place of those cells that survived passage. At this point, very small cells with no spread morphology and with phase-bright characteristics began to appear in cultures of umbilical cells. These areas of the flask were followed over time. From these small cells, bifurcating processes emerged with varicosities along their lengths, features very similar to previously described PSA-NCAM+neuronal progenitors and TuJ1+ immature neurons derived from brain and spinal cord (1, 2). With time, these cells became more numerous, yet still were only found in clones.

Clones of Umbilical Cells Express Neuronal, but not Glial Proteins. Cultures were fixed at one month post-thawing/plating and stained for the neuronal protein TuJ1 and GFAP, an intermediate filament found in astrocytes. While all control cultures grown in Growth Medium and human fibroblasts and MSCs grown in NPE+bFGF+EGF medium were found to be TuJ1−/GFAP−, umbilical cells turned on expression of TuJ1. Expression was observed in cells with and without neuronal-like morphologies. No expression of GFAP was observed in either culture. The percentage of cells expressing TuJ1 with neuronal-like morphologies was less than or equal to 1% of the total population (n=3 umbilical isolates tested).

Summary. Methods for generating differentiated neurons (based on TuJ1 expression AND neuronal morphology) from umbilical cells were developed. While expression for TuJ1 was not examined earlier than one month in vitro, it is clear that at least a small population of umbilicus-derived cells can give rise to neurons either through default differentiation or through long-term induction following one month's exposure to a minimal media supplemented with 1,-glutamine, basic FGF, and EGF.

References for Example 15

(1) Mayer-Proschel, M. et al. (1997). *Neuron.* 19(4): 773-85.

(2) Yang, H. et al. (2000). *PNAS.* 97(24): 13366-71.

EXAMPLE 16

Umbilical Derived Cell Trophic Factors for Neural Progenitor Differentiation

The influence of umbilicus-derived postpartum cells (PPDCs) on adult neural stem and progenitor cell survival and differentiation through non-contact dependent (trophic) mechanisms was examined.

Materials & Methods

Adult Neural Stem and Progenitor Cell Isolation. Fisher 344 adult rats were sacrificed by $CO_2$ asphyxiation followed by cervical dislocation. Whole brains were removed intact using bone rongeurs and hippocampus tissue dissected based on coronal incisions posterior to the motor and somatosensory regions of the brain (1). Tissue was washed in Neurobasal-A medium (Invitrogen, Carlsbad, Calif.) containing B27 (B27 supplement; Invitrogen), L-glutamine (4 millimolar; Invitrogen), and penicillin (50 Units/milliliter) and streptomycin (50 micrograms/milliliter) (Invitrogen), the combination of which is herein referred to as Neural Progenitor Expansion (NPE) medium. NPE medium was further supplemented with bFGF (20 nanograms/milliliter, Peprotech, Rocky Hill, N.J.) and EGF (20 nanograms/milliliter, Peprotech, Rocky Hill, N.J.), herein referred to as NPE+bFGF+EGF.

Following wash, the overlying meninges were removed, and the tissue minced with a scalpel. Minced tissue was collected and trypsin/EDTA (Invitrogen) added as 75% of the total volume. DNAse (100 microliters per 8 milliliters total volume, Sigma, St. Louis, Mo.) was also added. Next, the tissue/medium was sequentially passed through an 18 gauge needle, 20 gauge needle, and finally a 25 gauge needle one time each (all needles from Becton Dickinson, Franklin Lakes, N.J.). The mixture was centrifuged for 3 minutes at 250×g. Supernatant was removed, fresh NPE+bFGF+EGF was added and the pellet resuspended. The resultant cell suspension was passed through a 40 micron cell strainer (Becton Dickinson), plated on laminin-coated T-75 flasks (Becton Dickinson) or low cluster 24-well plates (Becton Dickinson), and grown in NPE+bFGF+EGF media until sufficient cell numbers were obtained for the studies outlined.

PPDC Cell Plating. Postpartum-derived cells (P12) previously grown in Growth Media were plated at 5,000 cells/transwell insert (sized for 24 well plate) and grown for a period of one week in Growth Media in inserts to achieve confluence.

Adult Neural Progenitor Plating. Neural progenitors, grown as neurospheres or as single cells, were seeded onto laminin-coated 24 well plates at an approximate density of 2,000 cells/well in NPE+bFGF+EGF for a period of one day to promote cellular attachment. One day later, transwell inserts containing postpartum cells were added according to the following scheme:

(1) Transwell (umbilicus in Growth Media, 200 microliters)+neural progenitors (NPE+bFGF+EGF, 1 milliliter)

(2) Transwell (adult human dermal fibroblasts [1F1853; Cambrex, Walkersville, Md.] P12 in Growth Media, 200 microliters)+neural progenitors (NPE+bFGF+EGF, 1 milliliter)

(3) Control: neural progenitors alone (NPE+bFGF+EGF, 1 milliliter)

(4) Control: neural progenitors alone (NPE only, 1 milliliter)

Immunocytochemistry. After 7 days in co-culture, all conditions were fixed with cold 4% (w/v) paraformaldehyde (Sigma) for a period of 10 minutes at room temperature. Immunocytochemistry was performed using antibodies directed against the epitopes listed in Table 16-1. Briefly, cultures were washed with phosphate-buffered saline (PBS) and exposed to a protein blocking solution containing PBS, 4% (v/v) goat serum (Chemicon, Temecula, Calif.), and 0.3% (v/v) Triton (Triton X-100; Sigma) for 30 minutes to access intracellular antigens. Primary antibodies, diluted in blocking solution, were then applied to the cultures for a period of 1 hour at room temperature. Next, primary antibodies solutions were removed and cultures washed with PBS prior to application of secondary antibody solutions (1 hour at room temperature) containing blocking solution along with goat anti-mouse IgG-Texas Red (1:250; Molecular Probes, Eugene, Oreg.) and goat anti-rabbit IgG-Alexa 488 (1:250; Molecular Probes). Cultures were then washed and 10 micromolar DAPI (Molecular Probes) applied for 10 minutes to visualize cell nuclei.

Following immunostaining, fluorescence was visualized using the appropriate fluorescence filter on an Olympus inverted epi-fluorescent microscope (Olympus, Melville, N.Y.). In all cases, positive staining represented fluorescence signal above control staining where the entire procedure outlined above was followed with the exception of application of a primary antibody solution. Representative images were captured using a digital color videocamera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

TABLE 16-1

Summary of Primary Antibodies Used

| Antibody | Concentration | Vendor |
|---|---|---|
| Rat 401 (nestin) | 1:200 | Chemicon, Temecula, CA |
| TuJ1 (BIII Tubulin) | 1:500 | Sigma, St. Louis, MO |
| Tyrosine hydroxylase (TH) | 1:1000 | Chemicon |
| GABA | 1:400 | Chemicon |
| GFAP | 1:2000 | DakoCytomation, Carpinteria, CA |
| Myelin Basic Protein (MBP) | 1:400 | Chemicon |

Quantitative Analysis of Neural Progenitor Differentiation. Hippocampal neural progenitor differentiation was examined and quantified. A minimum of 1,000 cells were counted per condition, or if less, the total number of cells observed in that condition. The percentage of cells positive for a given stain was assessed by dividing the number of positive cells by the total number of cells as determined by DAPI (nuclear) staining.

Mass Spectrometry Analysis & 2D Gel Electrophoresis. In order to identify unique, secreted factors as a result of co-culture, conditioned media samples taken prior to culture fixation were frozen down at −80° C. overnight. Samples were then applied to ultrafiltration spin devices (nominal MW cutoff 30 kD). Retentate was subjected to immunoaffinity chromatography (anti-Human-albumin; IgY) (immunoaffinity did not remove albumin from the samples). Filtrate was analyzed by MALDI-TOFF. The eluate was applied to Cibachron Blue affinity chromatography. Samples were analyzed by SDS-PAGE and 2D gel electrophoresis.

Results

Umbilical Co-culture Stimulates Adult Neural Progenitor Differentiation. Following culture with umbilicus-derived postpartum cells, co-cultured neural progenitor cells derived from adult rat hippocampus exhibited significant differentiation along all three major lineages in the central nervous system. This effect was clearly observed after five days in co-culture, with numerous cells elaborating complex processes and losing their phase bright features characteristic of dividing progenitor cells. Conversely, neural progenitors grown alone in the absence of bFGF and EGF appeared unhealthy and survival was limited.

After completion of the procedure, cultures were stained for markers indicative of undifferentiated stem and progenitor cells (nestin), immature and mature neurons (TuJ1), astrocytes (GFAP), and mature oligodendrocytes (MBP). Differentiation along all three lineages was confirmed while control conditions did not exhibit significant differentiation as evidenced by retention of nestin-positive staining amongst the majority of cells.

The percentage of differentiated neural progenitors following co-culture with umbilicus-derived PPDCs was quantified (Table 16-2). Umbilicus-derived cells significantly enhanced the number of mature oligodendrocytes (MBP) (24.0% vs 0% in both control conditions). Furthermore, co-culture enhanced the number of GFAP+astrocytes and TuJ1+ neurons in culture (47.2% and 8.7% respectively). These results were confirmed by nestin staining indicating that progenitor status was lost following co-culture (13.4% vs 71.4% in control condition 3).

Though differentiation also appeared to be influenced by adult human fibroblasts, such cells were not able to promote the differentiation of mature oligodendrocytes nor were they able to generate an appreciable quantity of neurons. Though not quantified, fibroblasts did, however, appear to enhance the survival of neural progenitors and their progeny similar to findings for umbilicus-derived postpartum cells.

TABLE 16-2

Quantification of progenitor differentiation in control vs transwell co-culture with umbilicus-derived postpartum cells (E = EGF, F = bFGF).

| Antibody | F + E/Umb [Cond. 1] | F + E/F + E [Cond. 3] | F + E/removed [Cond. 4] |
|---|---|---|---|
| TuJ1 | 8.7% | 2.3% | 3.6% |
| GFAP | 47.2% | 30.2% | 10.9% |
| MBP | 23.0% | 0% | 0% |
| Nestin | 13.4% | 71.4% | 39.4% |

Identification of Unique Compounds. Conditioned media from umbilical test conditions along with the appropriate controls (NPE media±1.7% serum, media from co-culture with fibroblasts) were examined for differences. Potentially unique compounds were identified and excised from their respective 2D gels.

Summary. Results presented in this example indicate that the differentiation of adult neural progenitor cells following co-culture with umbilicus-derived postpartum cells is particularly profound. Specifically, a significant percentage of mature oligodendrocytes were generated in co-cultures of umbilical cells. In view of the lack of contact between umbilical cells and the neural progenitors, this result appears to be a function of soluble factors released from the umbilical cells (trophic effect).

Several other observations were made. First, there were very few cells in the control condition where EGF and bFGF were removed. Most cells died and on average, there were about 100 cells or fewer per well. Second, it is to be expected that there would be very little differentiation in the control condition where EGF and bFGF was retained in the medium throughout, since this is normally an expansion medium. While approximately 70% of the cells were observed to retain their progenitor status (nestin+), about 30% were GFAP+ (indicative of astrocytes). This may be due to the fact that such significant expansion occurred throughout the course of the procedure that contact between progenitors induced this differentiation. Similar findings have been reported in the literature (2).

References for Example 16

(1) Paxinos, G. & Watson, C. (1997). The Rat Brain in Stereotaxic Coordinates.

(2) Song, H. et al. (2002). *Nature*. 417(6884): 29-32.

EXAMPLE 17

The Effect of Trophic Factors on Angiogenesis

Angiogenesis, or the formation of new vasculature, is necessary for the growth of new tissue. Induction of angiogenesis is an important therapeutic goal in many pathological conditions. The angiogenic activity of umbilicus-derived cells in in vitro assays was examined. A well-established method of assessing angiogenic activity involving seeding endothelial cells onto a culture plate coated with a basement membrane extract (Nicosia and Toilette (1990) *In Vitro Cell Dev. Biol.* 26(2):119-28), was utilized. Treating endothelial cells on such basement membranes or extracellular matrix material with angiogenic factors will stimulate the cells to form a network that is similar to capillaries. These types of assays are common in vitro assays for testing stimulators and inhibitors of blood vessel formation (Ito et al. (1996) *Int. J. Cancer* 67(1):148-52). The protocols utilized in this example made use of a co-culture system with the umbilicus-derived cells seeded onto culture well inserts. These permeable inserts allow for the passive exchange of media components between the endothelial and the umbilicus-derived cell culture media.

Material & Methods

Cell Culture.

Umbilicus-derived cells. Human umbilical cords were received and cells were isolated as previously described (Example 1). Cells were cultured in Growth Medium on gelatin-coated tissue culture plastic flasks. The cultures were incubated at 37° C. with 5% $CO_2$. Cells used for experiments were between passages 4 and 12.

Actively growing UDCs were trypsinized, counted, and seeded onto 6.5 millimeter diameter tissue culture inserts (COSTAR TRANSWELL, Corning Inc., Corning, N.Y.) at 15,000 cells per insert. Cells were cultured on the inserts for 48-72 hours in Growth Medium with 5% $CO_2$ at 37° C.

Human mesenchymal stem cells (hMSC). hMSCs were purchased from Cambrex (Walkersville, Md.) and cultured in MSCGM (Cambrex). The cultures were incubated with 5% $CO_2$ at 37° C.

Actively growing MSCs were trypsinized and counted and seeded onto 6.5 millimeter diameter tissue culture inserts (Corning, Corning, N.Y.) at 15,000 cells per insert. Cells were cultured on the inserts for 48-72 hours in Growth Medium with 5% $CO_2$ at 37° C.

Human umbilical vein endothelial cells (HUVEC). HUVEC were obtained from Cambrex (Walkersville, Md.). Cells were grown in separate cultures in either EBM or EGM endothelial cell media (Cambrex). Cells were grown on standard tissue cultured plastic with 5% $CO_2$ at 37° C. Cells used in the assay ranged from passages 4 to 10.

Human coronary artery endothelial cells (HCAEC). HCAEC were purchased from Cambrex Incorporated (Walkersville, Md.). These cells were also maintained in separate cultures in either the EBM or EGM media formulations. Cells were grown on standard tissue cultured plastic with 5% $CO_2$ at 37° C. Cells used for experiments ranged from passages 4 to 8.

Angiogenesis Assays on Extracellular Matrix. Culture plates were coated with extracellular matrix material according to manufacturer's specifications. Briefly, extracellular matrix material (MATRIGEL, BD Discovery Lab ware, Bedford, Mass.) was thawed at 4° C. and approximately 250 microliters were distributed onto each well of a chilled 24-well culture plate (Corning). The plate was then incubated at 37° C. for 30 minutes to allow the material to solidify. Actively-growing endothelial cell cultures were trypsinized and counted. Cells were washed twice in Growth Medium supplemented with only 2% FBS by centrifugation, resuspension, and aspiration of the supernatant. Cells were seeded onto the coated wells 20,000 cells per well in approximately 0.5 milliliter Growth Medium supplemented with only 2% (v/v) FBS. Cells were then incubated for approximately 30 minutes to allow the cells to settle.

Endothelial cell cultures were then treated with either 10 nanomolar human bFGF (Peprotech, Rocky Hill, N.J.) or 10 nanomolar human VEGF (Peprotech, Rocky Hill, N.J.) to serve as positive controls for endothelial cell response. Transwell inserts seeded with postpartum cells were added to appropriate wells with Growth Medium supplemented with only 2% FBS in the insert chamber. Cultures were incubated in 5% $CO_2$ at 37° C. for approximately 24 hours. The well plate was removed from the incubator, and images of the endothelial cell cultures were collected with an Olympus inverted microscope (Olympus, Melville, N.Y.).

Results

In a co-culture system with umbilicus-derived cells, HUVEC form structured cell networks. HUVEC cells form limited cell networks in co-culture experiments with hMSC and with 10 nanomolar bFGF. HUVEC cells without any treatment showed very little or no network formation. These results suggest that the umbilicus-derived cells release angiogenic factors that stimulate the HUVEC. Similarly, HCAECs formed cell networks only in co-culture with umbilicus-derived cells.

Table 17-1 shows quantities of known angiogenic factors released by UDCs in Growth Medium at atmospheric oxygen conditions. UDCs were seeded onto inserts as described above. The cells were cultured at 37° C. in atmospheric oxygen for 48 hours on the inserts and then switched to a 2% FBS media and returned at 37° C. for 24 hours. Medium was removed, immediately frozen, and stored at −80° C., and analyzed by the SearchLight multiplex ELISA assay (Pierce Chemical Company, Rockford, Ill.). Results shown are the averages of duplicate measurements. The results show that UDCs do not release detectable levels of platelet-derived growth factor-bb (PDGFbb), heparin-binding epidermal growth factor (HB-EGF), or vascular endothelial growth factor (VEGF). The amounts of angiopoietin 2 (ANG2) detected were less than that of the culture medium control with no cells. The umbilicus-derived cells released measurable quantities of tissue inhibitor of metallinoprotease-1 (TIMP-1), thrombopoietin (TPO), and hepatocyte growth factor (HGF). The amounts of keratinocyte growth factor (KGF) and fibroblast growth factor (FGF) were very low and only slightly above those for the control medium.

TABLE 17-1

Potential angiogenic factors released from UDCs. Umbilicus-derived cells were cultured in 24 hours in media with 2% FBS in atmospheric oxygen. Medium was removed and assayed by the SearchLight multiplex ELISA assay (Pierce). Results are the means of a duplicate analysis. Values are concentrations in the media reported in picograms per milliliter of culture media.

| | TIMP1 (pg/mL) | ANG2 (pg/mL) | PDGFBB (pg/mL) | TPO (pg/mL) | KGF (pg/mL) | HGF (pg/mL) | FGF (pg/mL) | VEGF (pg/mL) | HBEGF (pg/mL) |
|---|---|---|---|---|---|---|---|---|---|
| UDCs (P4) | 81831.7 | <9.8 | <2.0 | 365.9 | 14.1 | 200.2 | 5.8 | <4.0 | <1.2 |
| Media alone | <9.8 | 25.1 | <2.0 | <6.4 | <2.0 | <3.2 | <5.4 | <4.0 | <1.2 |

Table 17-2 shows levels of known angiogenic factors released by UDCs at 5% $O_2$. UDCs were seeded onto inserts as described above. The cells were cultured in Growth Medium at 5% oxygen for 48 hours on the inserts and then switched to a 2% FBS medium and returned to 5% $O_2$ incubation for 24 hours. Medium was removed, immediately frozen, and stored at −80° C., and analyzed by the SearchLight multiplex ELISA assay (Pierce Chemical Company, Rockford, Ill.). Results shown are the averages of duplicate measurements. The results show for UDCs are comparable to those under atmospheric oxygen conditions. While there are essentially no changes in the production of ANG2, PDGFBB, FGF, VEGF, and HB-EGF by UDCs, there was a slight increase apparent in production of TIMP1, KGF, and HGF, and a slight decrease apparent in production of TPO. These apparent differences in raw data were not tested for statistical significance.

TABLE 17-2

Potential angiogenic factors released from UDCs. Cells were cultured in 24 hours in media with 2% FBS in 5% oxygen. Medium was removed and assayed by the SearchLight multiplex ELISA assay (Pierce). Results are the means of a duplicate analysis. Values are concentrations in the media reported in picograms per milliliter of culture media.

| | TIMP1 (pg/mL) | ANG2 (pg/mL) | PDGFBB (pg/mL) | TPO (pg/mL) | KGF (pg/mL) | HGF (pg/mL) | FGF (pg/mL) | VEGF (pg/mL) | HBEGF (pg/mL) |
|---|---|---|---|---|---|---|---|---|---|
| UDCs (P4) | 50244.7 | <9.8 | <2.0 | 403.3 | 10.7 | 156.8 | 5.7 | <4.0 | <1.2 |
| Media alone | <9.8 | 25.1 | <2.0 | <6.4 | <2.0 | <3.2 | <5.4 | <4.0 | <1.2 |

Summary. The results of the study show that umbilicus-derived cells can stimulate both human umbilical vein and coronary artery endothelial cells to form networks in an in vitro assay of angiogenesis. This effect is similar to that seen with known angiogenic factors in such assay systems. These results suggest that UDCs are useful for stimulating angiogenesis in vivo.

EXAMPLE 18

Differentiation of Umbilicus-derived Cells into Hepatocytes

A variety of conditions were examined to determine a suitable combination of basic media and growth factors for the differentiation of umbilicus-derived cells into hepatocytes. HNF-1alpha, a hepatocyte-specific transcription factor, cytoplasmic intermediate filament proteins, such as keratin 19 (K19), keratin 8 (K8), and cytokeratin 18 (CK18), which are markers of epithelial cells and two liver-specific secreted proteins, albumin and cytochrome p450 2B6, were selected as markers for hepatocyte differentiation (Schwartz et al. (2002) *J. Clin. Invest.* 109(10):1291-1302; Okumoto et al. (2003) *Biochem. Biophys. Res. Commun.* 304(4):691-695; Chargracui et al. (2003) *Blood* 101(8): 2973-2982).

Methods & Materials

Umbilicus-derived cells obtained according to method of Example 1, as well as neonatal or adult Normal Human Dermal Fibroblasts (NHDF), were grown in Growth Medium in gelatin-coated T75 flasks. Basic Fibroblast Growth Factor (bFGF), Oncostatin M, Hepatocyte Growth Factor (HGF), Stem Cell Factor (SCF), and Fibroblast Growth Factor 4 (FGF 4) were from PeproTech Inc. (Rocky Hill, N.J.). Platelet Derived Growth Factor BB (PDGFbb) was from R&D Systems (Minneapolis, Minn.).

The following conditions were tested:

Method 1

Umbilicus-derived cells (P5), neonatal and adult Normal Human Dermal Fibroblasts (NHDF). Cells were plated at $22.5\times10^3$ cells/cm$^2$ on 1% Matrigel (Becton-Dickinson and Co., Franklin Lakes, N.J.) in serum-free medium (60% (v/v) low glucose DMEM) (DMEM-LG; Gibco, Carlsbad, Calif.), 40% (v/v) MCDB-201 (Sigma, St. Louis, Mo.), supplemented with 1× insulin/transferrin/selenium, 4.7 micrograms/milliliter linoleic acid, 1 milligram/milliliter bovine serum albumin, 10 nanomolar Dexamethasone, 100 micromolar ascorbic acid phosphate (all from Sigma), 50 Units/milliliter penicillin, 50 micrograms/milliliter streptomycin (Gibco), 2% (v/v) FCS (Hyclone Laboratories, Logan, Utah), and 10 nanograms/milliliter each EGF and PDGFbb). After 8-12 hours, medium was removed, cells were washed twice with PBS (Gibco) and cultured in the above-described medium without EGF and PDGFbb but supplemented with 20 nanograms/milliliter HGF and/or 10 nanograms/milliliter FGF-4 (Schwartz et al. (2002) *J. Clin. Invest.* 109(10):1291-1302).

Method 2

Umbilicus-derived cells (P5), Neonatal and adult NHDF. Cells were seeded at lower density (22,500 cells/cm$^2$) in 24-well plates coated with gelatin and grown as described above.

Method 3

Umbilicus-derived cells (P17), Umbilicus-derived cells (P15), Umbilicus derived cells (P10), adult NHDF. Cells were seeded at higher density (50,000 cells/cm$^2$) in 24-well TCP plates and grown in DMEM (Gibco), B27 Supplement (Gibco), penicillin (50 Units/milliliter), streptomycin (50 micrograms/milliliter), 20 nanograms/milliliter HGF and/or 10 nanograms/milliliter FGF-4. Cells were grown in these conditions for 4 weeks.

Method 4

Umbilicus-derived cells (P4), Umbilicus-derived cells (P9), neonatal and adult NHDF. Cells were seeded at a density of 5,000 cells/cm$^2$ in T25 flasks in Chang C medium (Irvine Scientific, Santa Ana, Calif.) on either fibronectin (Pepro-Tech, Rocky Hill, N.J.) or gelatin (Sigma) and grown for two passages until confluence. Cells were then seeded at 1,000 cells/cm$^2$ in 24-well TCP plates and grown as described above until they reached about 40-60% confluence.

Method 5

Umbilicus-derived cells (P5) and adult NHDF. Cells were plated in 24-well plates on gelatin in Growth Medium supplemented with either 1 nanogram/milliliter or 10 nanograms/milliliter oncostatin M (Chargracui (2003) *Blood* 101(8): 2973-2982). Cells were grown in these conditions for 4 weeks.

Method 6

Umbilicus-derived cells (P5) and adult NHDF. Cells were plated in 24-well plates on gelatin in Growth Medium supplemented with 10 nanograms/milliliter bFGF, 10 nanograms/milliliter HGF, 10 nanograms/milliliter SCF. Cells were grown in these conditions for 4 weeks (Okumoto et al. (2003) *Biochem. Biophys. Res. Commun.* 304(4):691-695.).

Total RNA isolation and quantitative RT-PCR. RNA was extracted from umbilicus-derived cells and fibroblasts grown as described in each protocol. Cells were lysed with 350 microliters buffer RLT containing beta-mercaptoethanol (Sigma St. Louis, Mo.) according to the manufacturer's instructions (RNeasy Mini Kit, Qiagen, Valencia, Calif.) and RNA extracted according to the manufacturer's instructions (RNeasy Mini Kit, Qiagen, Valencia, Calif.) with a 2.7 Units/sample DNase treatment (Sigma). RNA was eluted with 50 microliters DEPC-treated water and stored at −80° C. RNA was reverse transcribed using random hexamers with the TaqMan reverse transcription reagents (Applied Biosystems, Foster City, Calif.) at 25° C. for 10 minutes, 37° C. for 60 minutes, and 95° C. for 10 minutes. Samples were stored at −20° C.

Real-time PCR. PCR was performed on cDNA samples using ASSAYS-ON-DEMAND gene expression products for albumin (Hs00609411), cytochrome p450 2B6 (Hs00167937), GAPDH (Applied Biosystems, Foster City, Calif.) and TaqMan Universal PCR master mix according to the manufacturer's instructions (Applied Biosystems, Foster City, Calif.) using a 7000 sequence detection system with ABI prism 7000 SDS software (Applied Biosystems, Foster City, Calif.). Thermal cycle conditions were initially 50° C. for 2 minutes and 95° C. for 10 minutes followed by 40 cycles of 95° C. for 15 seconds and 60° C. for 1 minute. PCR data were analyzed according to manufacturer's specifications (User Bulletin #2 from Applied Biosystems for ABI Prism 7700 Sequence Detection System).

Immunofluorescence. Cell cultures were fixed with cold (4° C.) 4% (w/v) paraformaldehyde for a period of 10 minutes at room temperature. Immunocytochemistry was performed using antibodies directed against the following epitopes: keratin 9 (K9; 1:400; Chemicon, Temecula, Calif.), keratin 19 (K19; 1:400; Chemicon), cytokeratin 18 (CK18; 1:400; Sigma, St. Louis, Mo.), vimentin (1:500; Sigma), desmin (1:150; Sigma), albumin (1:200; Sigma), c-met (1:400; Santa Cruz Biotech, Santa Cruz, Calif.), and HNF-1alpha (1:400; Santa Cruz Biotech). In general, cultures were washed with phosphate-buffered saline (PBS) and exposed to a protein blocking solution containing PBS, 4% (v/v) goat serum (Chemicon, Temecula, Calif.), and 0.3% (v/v) Triton (Triton X-100, Sigma) for 30 minutes to access intracellular antigens. In instances where the epitope of interest would be located on the cell surface (e.g. c-met), Triton was omitted in all steps of the procedure in order to prevent epitope loss. Primary antibodies, diluted in blocking solution, were then applied to the cultures for a period of 1 hour at room temperature. Primary antibody solutions were then removed and cultures washed with PBS prior to application of secondary antibody solutions (1 hour at room temperature) containing blocking solution along with goat anti-mouse IgG-Texas Red (1:250; Molecular Probes, Eugene, Oreg.) for K8, K19, CK18, vimentin, and albumin, goat anti-rabbit IgG-Alexa 488 (1:250; Molecular Probes) for desmin and c-met, or donkey anti-goat IgG-FITC (1:150; Santa Cruz Biotech) for HNF-1alpha staining. Cultures were washed and 10 micromolar DAPI (Molecular Probes) applied for 10 minutes to visualize cell nuclei.

Following immunostaining, fluorescence was visualized using the appropriate fluorescence filter on an Olympus inverted epi-fluorescent microscope (Olympus, Melville, N.Y.). Representative images were captured using a digital color videocamera and ImagePro software (Media Cybernetics, Carlsbad, Calif.). For triple-stained samples, each image was taken using only one emission filter. Layered montages were then prepared using Adobe Photoshop software (Adobe, San Jose, Calif.).

Results

In order to determine whether umbilicus-derived cells could express epithelial markers, cells were cultured in Chang C medium. Umbilicus-derived cells (P2) were grown in Chang C medium for 11 days. Umbilicus-derived cells stained negative for cytokeratin 18 and keratin 8 by immunocytochemistry analysis. Samples grown in Growth Medium were negative for both markers.

The effect of passage, as well as gelatin and fibronectin substrata was investigated. Cells were grown in Chang C medium for 11 days. RNA and protein expression of epithelial/hepatocyte-specific proteins were analyzed. Immunocytochemistry staining for cytokeratin18, keratin 8, keratin 19, c-met, albumin, desmin, and HNF-1alpha were negative in all conditions. Cells stained positive for vimentin. Expression of both albumin and cytochrome p450 2B6 at levels lower than that of human HepG2 cells was detected with ASSAYS-ON-DEMAND primers. Albumin and cytochrome p450 2B6 expression were also detected in cells grown in Growth Medium.

Umbilicus-derived cells were treated as described in method 1 according to a protocol developed by Schwartz et al. (2002) *J. Clin. Invest.* 109(10):1291-1302.). Both albumin and cytochrome p450 2B6 were detected with ASSAYS-ON-DEMAND primers at levels lower than HepG2 positive control. No clear pattern emerged between conditions applied and gene expression levels, i.e., albumin and cytochrome p450 2B6 expression were each also detected in control samples. Some expression of albumin and cytochrome p450 2B6 was detected with ASSAYS-ON-DEMAND primers, however, the levels were significantly lower than those observed in HepG2 cells.

Oncostatin M at low concentration of 1 nanogram/milliliter increased expression levels of cytochrome p450 2B6 in umbilicus-derived cells grown in Growth Medium on gelatin-coated flasks (data not shown). FGF-4 and HGF treatment had little effect and may have reduced the expression of albumin and cytochrome p450 2B6.

Summary. Six protocols were tested for their ability to induce differentiation of umbilicus-derived cells to hepatocyte phenotype. Expression of hepatocyte-specific markers, such as albumin and cytochrome p450 2B6 was detected, thereby indicating that the cells underwent some differentiation into hepatocytes.

EXAMPLE 19

Adipogenic Differentiation of Umbilicus-Derived Cells

Populations of stem cells have been demonstrated to differentiate into an adipogenic phenotype (Janderova et al. (2003) Obes. Res. 11(1):65-74; Zangani et al. (1999) Differentiation 64(2):91-101; Liu et al., (2003) Curr. Mol. Med. 3(4):325-40). The potential of umbilicus-derived cells to differentiate into an adipogenic phenotype was evaluated.

Methods & Materials

Adipose Differentiation. Umbilicus-derived cells (P4) were seeded at 200,000 cells per well on 6-well tissue culture-treated plates in Growth Medium. Mesenchymal stem cells (P3, IF2155), osteoblasts (P5, CC2538; Cambrex, Walkerville, Md.), omental cells (P6) (isolated from omental tissue from NDRI, following protocol used for postpartum-derived cell isolation in Example 1), adipose-derived cells (U.S. Pat. No. 6,555,374 B1) (P6), and fibroblasts (P6, CC2509) (Cambrex, Walkerville, Md.) were also seeded under the same conditions. Prior to initiation of adipogenesis, Mesenchymal Stem Cells were grown in a Mesenchymal Stem Cell Growth Medium Bullet kit (Cambrex, Walkerville, Md.). After 2 days, spent medium was aspirated off and cells were washed with phosphate buffered saline (PBS). Culture medium was then switched to Dulbecco's Minimal Essential Medium-high glucose (DMEM-Hg; Invitrogen, Carlsbad, Calif.) containing 10 percent FBS (v/v, Hyclone, Logan Utah), 0.02 milligrams insulin per milliliter (Sigma, St. Louis, Mo.), and 100 Units penicillin per milliliter, 100 milligrams streptomycin per milliliter, 0.25 micrograms amphotericin B per milliliter; (Invitrogen, Carlsbad, Calif.). Once the cells had reached confluence, spent medium was aspirated. Cells were then cultured in an adipose differentiation medium (DMEM-Hg (Invitrogen, Carlsbad, Calif.), containing 10 percent defined fetal bovine serum ((v/v), Hyclone, Logan, Utah), 0.02 milligrams per milliliter insulin (Sigma, St. Louis, Mo.) and 100 units penicillin per milliliter, 100 micrograms streptomycin per milliliter, 0.25 micrograms amphotericin B per milliliter, 5 micromolar isobutylmethylxanthine (Sigma, St. Louis, Mo.), 100 micromolar dexamethasone (Sigma, St. Louis, Mo.), and 2.5 micromolar indomethacin (Sigma, St. Louis, Mo.) for up to 4 weeks. Cells were stained with Oil-Red-0 to determine the presence of lipid droplet formation.

Oil Red O Staining. Cells were fixed with 10 percent (v/v) neutral buffered formalin (Richard-Allan Kalamazoo, Mich.). After fixation, the cells were washed in deionized water and incubated for two minutes in propylene glycol (absolute; Poly Scientific, Bay Shore, N.Y.). Propylene glycol was removed by aspiration, and samples were incubated in Oil Red O (Poly Scientific) for one hour. Staining solution was removed by aspiration and stained samples were then incubated in 85 percent (v/v) propylene glycol solution (Poly Scientific) for one minute. Stained samples were washed with two changes of de-ionized water. Stained samples were counter-stained with Mayer's Hematoxylin (Poly Scientific) and examined with light microscopy. Images were taken at magnification of 20×.

Leptin Assay. Adipose-derived cells and umbilicus-derived cells were seeded at 200,000 cells/well in 6-well tissue culture-treated plates. Cells were initially seeded in Growth Medium, which was changed to an adipogenic differentiation medium (DMEM-Hg medium; Invitrogen, Carlsbad, Calif.) containing 1 micromolar dexamethasone (Sigma, St. Louis, Mo.), 0.2 millimolar indomethasone (Sigma), 0.01 milligrams per microliter insulin (Sigma), 0.5 millimolar isobutylmethylxanthine (Sigma), 10 percent (v/v) fetal bovine serum (Cat. #SH30070.03; Hyclone, Logan, Utah), 100 Units penicillin per milliliter and 100 micrograms streptomycin per milliliters (Gibco)). At the end of the assay, the conditioned medium was collected and leptin levels were measured using an ELISA kit (Quantikine, R&D Systems, Minneapolis, Minn.).

Results

Adipose differentiation. Morphologically MSCs and adipose-derived cells demonstrated lipid formation as early as 5 days in this assay. Large amounts of lipid droplet formation were observed in these cultures by 15 days of culture. Cultures of osteoblasts also deposited large amounts of lipid under these conditions after 10 days in culture and extensively at 15 days. Lipid droplet formation was observed in umbilicus-derived and omental cell cultures after 15 days of culture. Low level lipid droplet formation was observed in the fibroblast cultures after 20 days in adipogenic-inducing conditions.

Leptin. Leptin was not detected by ELISA in umbilicus-derived cell conditioned medium.

Summary. While leptin was not detected in umbilicus-derived cells by ELISA following the adipogenic differentiation protocols used, the data clearly demonstrate that umbilicus-derived cells undergo a low level of differentiation to an adipocyte phenotype when compared to cultures of mesenchymal stem cells, adipose-derived cells, or osteoblasts.

EXAMPLE 20

Differentiation into Beta Cell Phenotype

The pancreas contains endocrine cells, organized in islets of Langerhans, that produce insulin, glucagon, somatostatin, and pancreatic polypeptide (PP). The ability of umbilicus-derived cells to differentiate towards cells with an insulin-producing phenotype was tested under eight different induction protocols.

Methods & Materials

Umbilicus-derived cells (various isolates—see below) as well as neonatal or adult Normal Human Dermal Fibroblasts (NHDF) grown in Growth Medium, in gelatin-coated T75 flasks, as well as in different beta-cell promoting differentiation conditions. Flasks were coated with 2% (w/v) gelatin solution (Sigma, St. Louis, Mo.) for 20 minutes at room temperature. Gelatin solution was aspirated off and flasks were washed with PBS. Basic Fibroblast Growth Factor (bFGF), Epidermal Growth Factor (EGF), Transforming Growth Factor alpha (TGFalpha) and Fibroblast Growth Factor 10 (FGF-10) were purchased from PeproTech Inc. (Rocky Hill, N.J.). GLP-1 was purchased from Sigma (St. Louis, Mo.)

The following protocols were tested:

Protocol 1:

Cells: Adipose-derived cells (U.S. Pat. No. 6,555,374) and omentum-derived cells, umbilicus-derived cells, (P15), (P17), (P3), and adult Normal Human Dermal Fibroblasts (NHDF) (P10) were utilized. Cells were maintained under either normal or 5% $O_2$ conditions. Cells were seeded at low density (5,000 cells/$cm^2$) in gelatin-coated T75 flasks on gelatin and grown in Ham's F12 medium (Clonetics, Santa Rosa, CA), 2% (v/v) FBS, penicillin (50 Units/milliliter), streptomycin (50 micrograms/milliliter), 10 nanograms/milliliter EGF, 20 nanograms/milliliter bFGF until confluence. Confluent cells were trypsinized and plated at 50,000 cells/cm² in 24-well Tissue Culture Polystyrene (TCPS; BD Biosciences, Bedford, Mass.) plates with or without gelatin or collagen coating. Cells were grown in Ham's F12 medium, 2% FBS, penicillin (50 Units/milliliter), streptomycin (50 micrograms/milliliter), 10 nanograms/milliliter EGF, 20 nanograms/milliliter bFGF and 15 nanomolar GLP-1 (7-37 isoform) for up to 3 weeks.

Protocol 2:

Cells: Umbilicus-derived cells, isolate 2 (P17), isolate 1 (P15), isolate 4 (P10) and adult NHDF P10 were utilized. Cells were seeded at 50,000 cells/cm² in 24-well TCP plates and grown in DMEM:Ham's F12 (1:1) medium, B-27 supplement (Gibco, Carlsbad, Calif.), 50 units of penicillin per milliliter, 50 milligrams streptomycin per milliliter, 20 nanograms/milliliter EGF, 40 nanograms/milliliter bFGF spherical clusters were generated—usually 4-6 days. Following that period, the spherical clusters were collected, centrifuged, and replated onto laminin-coated, 24-well plates (BD Biosciences, Bedford, Mass.), and cultured up to 3 weeks in B-27-supplemented medium containing 10 nanomolar GLP-1 (7-37) but no other growth factors (i.e. no bFGF and no EGF).

Protocol 3:

Cells: Umbilicus-derived cells, isolate 2 (P17) isolate 1 (P15), isolate 4 (P10), and adult NHDF (P10) were utilized. Cells were seeded at high density (50,000 cells/cm²) in 24-well TCPS plates and grown in DMEM:Ham's F12 (1:1) medium, B-27 supplement, P/S, 20 nanograms/milliliter EGF, 40 nanograms/milliliter bFGF spherical clusters were generated—usually 4-6 days. Following that period, the spherical clusters were collected, centrifuged, and replated onto laminin-coated, 24-well plates and cultured up to 3 weeks in B-27-supplemented medium containing 10 nanomolar GLP-1 (1-37 isoform) but no other growth factors (i.e. no bFGF and no EGF).

Protocol 4:

Cells: Adult NHDF (P15), umbilicus-derived, isolate 1 (P18), isolate 2 (P21), isolate 3 (P5), isolate 3 (P4), were isolated according to the method by Mitchell et al. (2). Cells were seeded at 50,000 cells/cm² in 24-well TCPS gelatin-coated plates and grown in DMEM:Ham's F12 (1:1) medium, B-27 supplement, penicillin (50 Units/milliliter), streptomycin (50 micrograms/milliliter), 10 nanograms/milliliter FGF-10, and/or 40 nanograms/milliliter TGF alpha for more than two weeks.

Protocol 5:

Cells: Adult NHDF, umbilicus-derived, isolate 1 (P18), isolate 2 (P21) isolate 3 (P5), isolate 3 (P4), were isolated according to the method by Mitchell et al. (2). Cells were seeded at 50,000 cells/cm² in 24-well TCPS gelatin-coated plates and grown in EBM-2 medium, 10 nanograms/milliliter FGF-10, and/or 40 nanograms/milliliter TGF alpha for greater than two weeks.

Protocol 6.

Cells: Umbilicus-derived, isolate 3 (P2) were utilized. Cells were seeded at 5,000 cells/cm² in T75 flasks on gelatin and grown either in Growth Medium or in Ham's F12 medium, 2% FBS, penicillin (50 Units/milliliter), streptomycin (50 micrograms/milliliter), 10 nanograms/milliliter EGF, 20 nanograms/milliliter bFGF until confluence. Confluent cells were trypsinized and plated at 50,000 cells/cm² in 24-well TCPS plates, with or without gelatin coating. Three types of basic media were used for up to 3 weeks:

Beta I medium: Ham's F12 medium, 2% FBS, 10 millimolar nicotinamide, penicillin (50 Units/milliliter), streptomycin (50 micrograms/milliliter), 25 millimolar glucose;

Beta II medium: Equal parts of DMEM/Ham's F12 media, 2% FBS, 10 millimolar nicotinamide, 25 millimolar glucose; and Endothelial Cell Basal Medium (EBM), (Clonetics, Santa Rosa, CA).

The following growth factors were added to each of the media: 10 nanograms/milliliter EGF, 20 nanograms/milliliter bFGF, 10 nanomolar GLP-1 (7-37 isoform).

Total RNA isolation and quantitative RT-PCR. RNA was extracted from umbilicus-derived cells and fibroblasts grown as described in each protocol. Cells were lysed with 350 microliters buffer RLT containing beta-mercaptoethanol (Sigma St. Louis, Mo.) according to the manufacturer's instructions (RNeasy Mini kit, Qiagen, Valencia, Calif.) and RNA extracted according to the manufacturer's instructions (RNeasy Mini kit, Qiagen, Valencia, Calif.) with a 2.7 U/sample DNase treatment (Sigma St. Louis, Mo.). RNA was eluted with 50 microliters DEPC-treated water and stored at −80° C. RNA was reversed transcribed using random hexamers with the TaqMan reverse transcription reagents (Applied Biosystems, Foster City, Calif.) at 25° C. for 10 minutes, 37° C. for 60 minutes and 95° C. for 10 minutes. Samples were stored at −20° C.

Real-time PCR. PCR was performed on cDNA samples using ASSAYS-ON-DEMAND gene expression products. PDX-1 (Hs00426216), pro-insulin (Hs00355773), Ngn-3 (Hs00360700) and Glut-2 (Hs00165775) GAPDH (Applied Biosystems, Foster City, Calif.) and TaqMan Universal PCR master mix according to the manufacturer's instructions (Applied Biosystems, Foster City, Calif.) using a 7000 sequence detection system with ABI Prism 7000 SDS software (Applied Biosystems, Foster City, Calif.). Thermal cycle conditions were initially 50° C. for 2 minutes and 95° C. for 10 minutes followed by 40 cycles of 95° C. for 15 seconds and 60° C. for 1 minutes. In addition, another set of primers designed in-house for PDX-1 and Ngn-3 were tested. Table 20-1 contains primer sequences. PCR using these primers was performed as described above. Pancreas total RNA (Ambion, Austin, Tex.) was used as control. PCR data were analyzed according to the AACT method recommended by Applied Biosystems (1).

TABLE 20-1

| Primer name | Sequence |
| --- | --- |
| PDX-1 Forward primer | 5'-CTGGATTGGCGTTGTTTGTG-3' (SEQ ID NO: 11) |
| PDX-1 Reverse primer | 5'-TCCCAAGGTGGAGTGCTGTAG-3' (SEQ ID NO: 12) |
| PDX-1-TaqMan Probe | 5'-CTGTTGCGCACATCCCTGCCC-3' (SEQ ID NO: 13) |
| Ngn-3 Forward primer | 5'-GGCAGTCTGGCTTTCTCAGATT-3' (SEQ ID NO: 14) |
| Ngn-3 Reverse primer | 5'-CCCTCTCCCTTACCCTTAGCA-3' (SEQ ID NO: 15) |
| Ngn-3 TaqMan probe | 5'-CTGTGAAAGGACCTGTCTGTCGC-3' (SEQ ID NO: 16) |

Immunofluorescence. Adult human pancreatic tissue was harvested and immersion fixed in 4% (w/v) paraformaldehyde (Sigma, St. Louis, Mo.) overnight at 4° C. Immunohistochemistry was performed using antibodies directed against the following epitopes: insulin (insulin serum; 1:50; LINCOResearch, St. Charles, Mo.), PDX-1 (1:50; Santa Cruz Biotech, Santa Cruz, Calif.), glucagon (1:100; Santa Cruz Biotech), somatostatin (1:100; DAKOCytomation, Carpinteria, Calif.), and cytokeratin 18 (CK18; 1:400; Sigma, St. Louis, Mo.). Briefly, fixed specimens were blocked off with a scalpel and placed within OCT embedding compound (Tissue-Tek OCT; Sakura, Torrance, Calif.) on a dry ice bath containing ethanol. Frozen blocks were then sectioned (10 microns thick) using a standard cryostat (Leica Microsystems), and mounted onto glass slides for staining.

Tissue sections were washed with phosphate-buffered saline (PBS) and exposed to a protein blocking solution containing PBS, 4% (v/v) goat serum (Chemicon, Temecula, Calif.), and 0.3% (v/v) Triton (Triton X-100, Sigma) for 1 hour. Primary antibodies, diluted in blocking solution, were then applied to the samples for a period of 4 hours at room temperature. Primary antibodies solutions were removed and samples washed with PBS prior to application of secondary antibody solutions for 1 hour at room temperature containing blocking solution along with goat anti-mouse IgG-Texas Red (1:250; Molecular Probes, Eugene, Oreg.) for CK18, goat anti-rabbit IgG-Alexa 488 (1:250; Molecular Probes) for glucagon and somatostatin, goat anti-guinea pig IgG-FITC (1:150; Santa Cruz Biotech) for insulin, or donkey anti-goat IgG-FITC (1:150; Santa Cruz Biotech) for PDX-1 staining. Samples were then washed and 10 micromolar DAPI (Molecular Probes) applied for 10 minutes to visualize cell nuclei.

Following immunostaining, fluorescence was visualized using the appropriate fluorescence filter on an Olympus inverted epi-fluorescent microscope (Olympus, Melville, N.Y.). Representative images were captured using a digital color videocamera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

Results

For umbilicus-derived cells treated according to protocols 1-6, expression of pancreas-specific marker was not detected using real-time PCR and the ASSAYS-ON-DEMAND primers, with the exception that low levels of Ngn-3 were detected in cells from protocol 6. The same primers produced positive results with cDNA derived from pancreatic tissue RNA.

Real-time PCR for ngn-3 was performed on cDNA samples derived from human umbilical cord grown according to protocol 6. PCR was also performed using ASSAYS-ON-DEMAND Ngn-3 primers (Hs00360700). Human pancreas-derived cDNA was used as control. No other pancreas-specific markers (PDX-1, pro-insulin or Glut-2) were detected with the ASSAYS-ON-DEMAND primers.

Experimental conditions in Protocols 2 and 6 applied to umbilicus-derived tissues, but not fibroblasts, produced structures resembling the cellular assembly of pancreatic epithelial cells into islets. These structures emerged 3-5 days after the implementation of the protocol. However unlike islets, these structures were negative for pancreatic markers (PDX-1, Ngn3, Glut-2 and pro-insulin) expression (tested by real-time PCR).

Pancreas-specific markers were detected in tissue derived from a human pancreas using immunofluorescence technique and an array of antibodies (see materials and methods). The expression of pancreas-specific markers (e.g. insulin, PDX-1, glucagon, somatostatin, and cytokeratin 18) in human pancreatic tissue was readily detectable.

Summary. Limited expression of PDX-1 and Ngn-3 has been observed in umbilicus-derived cells treated with a variety of experimental protocols. There were differences in results between in-house designed and commercially available primers. For example, while protocol number 1 gave positive data for PDX-1 and Ngn-3 using in-house designed primers, ASSAYS-ON-DEMAND primers for the same genes produced negative data. The results were not directly verified by immunological techniques. Notwithstanding such differences, expression of several pancreatic markers has been accomplished suggesting the potential of umbilicus-derived cells to differentiate towards the pancreatic phenotypes.

References for Example 20

1. User Bulletin #2 from Applied Biosystems for ABI Prism 7700 Sequence Detection System 2. Mitchell K E, Weiss M L, Mitchell B M, Martin P, Davis D, Morales L, Helwig B, Beerenstrauch M, Abou-Easa K, Hildreth T, Troyer D, Medicetty S. (2003) Matrix cells from Wharton's jelly form neurons and glia. Stem Cells 21(1):50-60.

3. H. Edlund. (2002) Pancreatic organogenesis—developmental mechanisms and implications for therapy. Nat. Rev. Genet. 3:524-532.

4. S. K. Kim and M. Hebrok. (2001) Intercellular signals regulating pancreas development and function. Genes Dev. 15:111-127.

5. Street C N, Rajotte R V, Korbutt G S. (2003) Stem cells: a promising source of pancreatic islets for transplantation in type 1 diabetes. Curr Top Dev Biol. 58:111-36.

EXAMPLE 21

Chondrogenic Differentiation of Umbilicus-Derived Cells

Cartilage damage and defects lead to approximately 600,000 surgical procedures each year in the United States alone (1). A number of strategies have been developed to treat these conditions but these have had limited success. One approach, Cartecel (Genzyme), uses autologous chondrocytes that are collected from a patient, expanded in vitro and then implanted into the patient (1). This approach has the disadvantage of collecting healthy cartilage and requiring a second procedure to implant the cultured cells. An alternative possibility is a stem cell-based therapy in which cells are placed at or near the defect site to directly replace the damaged tissue. Cells may be differentiated into chondrocytes prior to the application or progenitor cells that can differentiate in situ may be used. Such transplanted cells would replace the chondrocytes lost in the defect.

Candidate cells for this indication should be evaluated for their ability to differentiate into chondrocytes in vitro. A number of protocols have been developed for testing the ability of cells to differentiate and express chondrocyte marker genes. Umbilicus-derived cells were tested for their ability to differentiate into chondrocytes in vitro in two different assay systems: the pellet assay culture system and collagen gel cultures. The pellet culture system has been used successfully with selected lots of human mesenchymal stem cells (MSC). MSC grown in this assay and treated with transforming growth factor-beta3 have been shown to differentiate into chondrocytes (2). The collagen gel system has been used to culture chondrocytes in vitro (3). Chondrocytes grown under these conditions form a cartilage-like structure.

Materials and Methods

Cell Culture. Human umbilical cords were received and umbilicus-derived cells were prepared as described in Example 1 above. Cells were cultured in Growth Medium on gelatin-coated TCP flasks. The cultures were incubated with 5% $CO_2$ at 37° C. Cells used in experiments ranged from passages 4 through 12.

Human articular chondrocytes were purchased from Cambrex (Walkersville, Md.) and cultured in the same medium as the postpartum cells. Twenty-four hours before the experiment, the culture medium was changed to a media containing 1% FBS.

Human mesenchymal stem cells (hMSCs) were purchased from Cambrex (Walkersville, Md.) and cultured in MSCGM (Cambrex). Cells used for experiments were between passages 2 and 4.

Collagen gel assays. Cultured cells were trypsinized to remove from culture plate. Cells were washed with centrifugation twice at 300×g for 5 minutes in DMEM without serum and counted. Cells were mixed with the following components at the final concentrations listed. Rat tail collagen (1 milligram/milliliter, BD DiscoveryLabware, Bedford, Mass.), 0.01 Normal NaOH and Chondrocyte cell media DMEM, penicillin (100 Units/milliliter), streptomycin (100 micrograms/milliliter), 2 millimolar L-Glutamine, 1 millimolar Sodium Pyruvate, 0.35 millimolar L-Proline, 100 nanomolar dexamethasone, 0.17 millimolar L-Ascorbic Acid, 1% (v/v) ITS (insulin, transferring, selenium) (All components from Sigma Chemical Company). The cells were gently mixed with the medium the samples were aliquoted into individual wells of a 24 well ultra-low cluster plate (Corning, Corning, N.Y.) at a concentration of either $2\times10^5$ per well or $5\times10^5$ per well. Cultures were placed in an incubator and left undisturbed for 24 to 48 hours. Medium was replaced with fresh chondrocyte media supplemented with appropriate growth factor every 24 to 48 hours. Samples were allowed to culture for up to 28 days at which time they were removed and fixed in 10% (v/v) formalin (VWR Scientific, West Chester, Pa.) and processed for histological examination. Samples were stained with Safranin 0 or hematoxylin/eosin for evaluation.

Pellet culture assays. Cultured cells were trypsinized to remove from culture plate. Cells were washed with centrifugation twice at 300×g for 5 minutes in DMEM without serum and counted. Cells were resuspended in fresh chondrocyte medium (described above) at a concentration of $5\times10^5$ cells per milliliter. Cells were aliquoted into new polypropylene tubes at $2.5\times10^5$ cells per tube. The appropriate samples were then treated with TGF-beta3 (10 nanograms/milliliter, Sigma) or GDF-5 (100 nanograms/milliliter; R&D Systems, Minneapolis, Minn.). Cells were then centrifuged at 150×g for 3 minutes. Tubes were then transferred to the incubator at and left undisturbed for 24-48 hours in 5% $CO_2$ at 37° C. Medium was replaced with fresh chondrocyte cell media and growth factor, where appropriate, every 2-3 days. Samples were allowed to culture for up to 28 days at which time they were removed and fixed and stained as described above.

Results

Pellets were prepared and cultured and described in Methods. Pellets were grown in medium (Control), or medium supplemented with TGF beta3 (10 nanograms/milliliter) or GDF-5 (100 nanograms/milliliter), that was replaced every 2 to 3 days. Pellets were collected after 21 days of culture and stained by Safranin 0 to test for the presence of glycosoaminoglycans. The pellets treated with TGFbeta3 and GDF-5 showed some positive Safranin 0 staining as compared to control cells. The morphology of the umbilical cord cells showed some limited chondrocyte-like morphology.

Summary. Umbilicus-derived cells partially differentiated into chondrocytes in vitro in the pellet culture and the collagen gel assay systems. The umbilicus-derived cells did show some indications of glycosaminoglycan expression by the cells. Morphology showed limited similarity to cartilage tissue. These results suggest that conditions can be optimized to stimulate more complete chondrocyte differentiation of the umbilicus-derived cells.

References for Example 21

1. U.S. Markets for Current and Emerging Orthopedic Biomaterials Products and Technologies. Medtech Insight L.L.C. 2002

2. Johnstone, B, T. M. Hering, A. I. Caplan, V. M. Goldberg and J. U. Yoo. In Vitro Chondrogenesis of Bone-Marrow-Derived Mesenchymal Stem Cells. 1998. *Exp Cell Res* 238: 265-272.

3. Gosiewska, A., A. Rezania, S. Dhanaraj, M. Vyakarnam, J. Zhou, D. Burtis, L. Brown, W. Kong, M. Zimmerman and J. Geesin. Development of a Three-Dimensional Transmigration Assay for Testing Cell-Polymer Interactions for Tissue Engineering Applications. 2001 *Tissue Eng.* 7:267-277.

EXAMPLE 22

Further Evaluation of Chondrogenic Potential of Cells Derived from Umbilical Cord Tissue in an In Vitro Pellet Culture Based Assay Evaluation of the chondrogenic potential of cells derived from umbilical tissue was performed using in vitro pellet culture based assays. Cells from umbilical cord at early passage (P3) and late passage (P12) were used. The chondrogenic potential of the cells was assessed in pellet culture assays, under chondrogenic induction conditions in medium supplemented with transforming growth factor beta-3 (TGF-beta-3), recombinant human growth and differentiation factor 5 (rhGDF-5), or a combination of both.

Materials & Methods

Reagents. Dulbecco's Modified Essential Media (DMEM), Penicillin and Streptomycin, were obtained from Invitrogen, Carlsbad, Calif. Fetal calf serum (FCS) was obtained from HyClone (Logan, Utah). Mesenchymal stem cell growth medium (MSCGM) and hMSC chondrogenic differentiation bullet kit were obtained from Biowhittaker, Walkersville, Md. TGFbeta-3 was obtained from Oncogene research products, San Diego, Calif. rhGDF-5 was obtained from Biopharm, Heidelberg, Germany (WO9601316 A1, U.S. Pat. No. 5,994,094 A).

Cells. Human mesenchymal stem cells (Lot#2F1656) were obtained from Biowhittaker, Walkersville, Md. and were cultured in MSCGM according to manufacturers instructions. This lot has been tested previously, and was shown to be positive in the chondrogenesis assays. Human adult and neonatal fibroblasts were obtained from American Type Culture Collection (ATCC), Manassas, Va. and cultured in Growth Medium on gelatin-coated tissue culture plastic flasks. Postpartum tissue-derived cells, isolated from human umbilical cords as described in previous examples, were utilized. Cells were cultured in Growth Medium in a manner similar to the culture of the fibroblasts. The cell cultures were incubated at 37° C. with 5% $CO_2$. Cells used for experiments were at passages 3 and 12.

Pellet culture assay. For pellet cultures, $0.25\times10^6$ cells were placed in a 15 milliliter conical tube and centrifuged at 150×g for 5 minutes at room temperature to form a spherical pellet according to protocol for chondrogenic assay from Biowhittaker. Pellets were cultured in chondrogenic induction medium containing TGFbeta-3 (10 nanograms/milliliter), rhGDF-5 (500 nanograms/milliliter), or a combination of TGFbeta-3 (10 nanograms/milliliter), and rhGDF-5 (500 nanograms/milliliter) for three weeks. Untreated controls were cultured in growth medium. During culture, pellets were re-fed with fresh medium every other day. Treatment groups included the following:

Treatment Group
  A. Umbilicus-derived cells early passage (U EP)+rhGDF-5
  B. Umbilicus-derived cells late passage (U LP)+rhGDF-5, n=2
  C. Human Mesenchymal Stem cells (HMSC)+rhGDF-5
  D. Human adult fibroblast cells (HAF)+rhGDF-5
  E. Umbilicus-derived cells early passage (U EP)+TGF-beta-3
  F. Umbilicus-derived cells late passage (U LP)+TGFbeta-3, n=2
  G. Human Mesenchymal Stem cells (HMSC)+TGFbeta-3
  H. Human adult fibroblast cells (HAF)+TGFbeta-3
  I. Umbilicus-derived cells early passage (U EP)+rhGDF-5+TGFbeta-3
  J. Umbilicus-derived cells late passage (U LP)+rhGDF-5+TGFbeta-3, n=2
  K. Human Mesenchymal Stem cells (HMSC)+rhGDF-5+TGFbeta-3
  L. Human adult fibroblast cells (HAF)+rhGDF-5+TGFbeta-3
  M. Human neonatal fibroblast cells (HNF)+rhGDF-5+TGFbeta-3
  N. Umbilicus-derived cells early passage (U EP)
  O. Umbilicus-derived cells late passage (U LP)
  P. Human Mesenchymal Stem cells (HMSC)
  Q. Human adult fibroblast cells (HAF)

Histology of in vitro samples. At the end of the culture period pellets were fixed in 10% buffered formalin and sent to MPI Research (Mattawan, Mich.) for paraffin embedding, sectioning, and staining with Hematoxylin & Eosin (H&E) and Safranin O (SO) staining.

Results

Umbilicus-derived cells, MSCs and fibroblasts formed cell pellets in chondrogenic induction medium with the different growth factors. The size of the pellets at the end of culture period varied among the different cell types. Pellets formed with the umbilical cells tended to be larger and looser than those formed by MSCs and fibroblasts. Pellets formed with all cell types and cultured in control medium were smaller than pellets cultured in chondrogenic induction medium.

Examination of cross sections of pellets stained with H&E and Safranin 0 showed that umbilicus-derived cells at early passage had the potential to undergo chondrogenic differentiation. Chondrogenesis as assessed by cell condensation, cell morphology and Safranin O positive staining of matrix was observed in the umbilical cell pellets cultured in chondrogenic induction medium supplemented with TGFbeta-3, rhGDF-5 or both. Chondrogenesis in pellets was similar for TGFbeta-3, rhGDF-5 and the combined treatments. Control pellets cultured in growth medium showed no evidence of chondrogenesis. Chondrogenic potential of the umbilicus-derived cells was marginally lower than that observed with the MSCs obtained from Biowhittaker.

Umbilicus-derived cells at late passage did not demonstrate as distinct a chondrogenic potential as did early passage umbilical derived cells. However, this may be due to the fact that chondrogenic induction conditions were optimized for MSCs, not for postpartum derived cells. Some cell condensation was observed with fibroblast, but it was not associated with Safranin 0 staining.

EXAMPLE 23

Differentiation to the Cardiomyocyte Phenotype

There is a tremendous need for therapy that will slow the progression of and/or cure heart disease, such as ischemic heart disease and congestive heart failure. Cells that can differentiate into cardiomyocytes that can fully integrate into the patient's cardiac muscle without arrhythmias are highly desirable. Rodent mesenchymal stem cells treated with 5-azacytidine have been shown to express markers of cardiomyocytes (Fukuda et al. (2002) *C. R. Biol.* 325:1027-38). This has not been shown for adult human stem cells. Additional factors have been used to improve stem cell differentiation including low oxygen (Storch (1990) *Biochim. Biophys. Acta* 1055:126-9), retinoic acid (Wobus et al. (1997) *J. Mol. Cell. Cardiol.* 29:1525-39), DMSO (Xu et al. (2002) *Circ. Res.* 91:501-8), and chelerythrine chloride (International PCT Publication No. WO03/025149), which effects the translocation of PKC from the cytosol to plasma membrane and is an inhibitor of PKC activity.

In this example, umbilicus-derived cells were treated with 5-azacytidine either alone or in combination with DMSO or chelerythrine chloride and markers of cardiomyocytes measured by real-time PCR.

Methods & Materials

Cells. Cryopreserved umbilicus-derived cells (P10) were grown in Growth Medium in gelatin-coated flasks. Cells were seeded at $5 \times 10^4$ cells/well in 96-well plates in Growth Medium for 24 hours. The medium was changed to 0, 3, 10 and 30 micromolar 5-azacytidine (Sigma, St. Louis, Mo.) alone or with 5 microM chelerythrine chloride (Sigma), 1% (v/v) dimethylsulfoxide (DMSO) (Sigma), or 1 micromolar retinoic acid (Sigma) in MEM-alpha (Sigma), insulin, transferrin, and selenium (ITS; Sigma), 10% (v/v) fetal bovine serum, penicillin and streptomycin. The cells were incubated at 37° C., 5% (v/v) $O_2$ for 48-72 hours. The medium was changed to MEM-alpha, insulin, transferrin, and selenium, 10% (v/v) fetal bovine serum, penicillin (50 Units/milliliter) and streptomycin (50 micrograms/milliliter), and cells incubated at 37° C., 5% (v/v) $O_2$ for 14 days.

RNA extraction and reverse transcription. Cells were lysed with 150 microliters buffer RLT containing beta-mercaptoethanol (Sigma St. Louis, Mo.) according to the manufacturer's instructions (RNeasy 96 kit, Qiagen, Valencia, Calif.) and stored at −80° C. Cell lysates were thawed and RNA extracted according to the manufacturer's instructions (RNeasy 96 kit, Qiagen, Valencia, Calif.) with a 2.7 Units/sample DNase treatment (Sigma St. Louis, Mo.). RNA was eluted with 50 microliters DEPC-treated water and stored at −80° C. RNA was reverse-transcribed using random hexamers with the TaqMan reverse transcription reagents (Applied Biosystems, Foster City, Calif.) at 25° C. for 10 minutes, 37° C. for 60 minutes and 95° C. for 10 minutes. Samples were stored at −20° C.

PCR. PCR was performed on cDNA samples using ASSAYS-ON-DEMAND gene expression products cardiac myosin (Hs00165276 ml), skeletal myosin (Hs00428600), GATA 4 (Hs00171403 ml), GAPDH (Applied Biosystems, Foster City, Calif.), and TaqMan Universal PCR master mix according to the manufacturer's instructions (Applied Biosystems, Foster City, Calif.) using a 7000 sequence detection system with ABI Prism 7000 SDS software (Applied Biosystems). Thermal cycle conditions were initially 50° C. for 2 minutes and 95° C. for 10 minutes followed by 40 cycles of 95° C. for 15 seconds and 60° C. for 1 minute. cDNA from heart and skeletal muscle (Ambion, Austin Tex.) were used as controls.

Results

Control RNA from cardiac muscle showed expression of cardiac myosin and GATA 4, skeletal muscle RNA showed skeletal myosin and cardiac myosin, but no GATA 4 expression. Umbilicus-derived cells (P12) treated for 48 h with factors and cultured for a further 14 days expressed low levels of GATA 4, but no skeletal myosin or cardiac myosin. Additional samples from umbilicus-derived cells also showed expression of GATA 4.

Summary. Untreated umbilicus-derived cells constitutively express GATA 4, a nuclear transcription factor in cardiomyocytes, sertoli cells, and hepatocytes.

EXAMPLE 24

Assessment of Umbilicus-Derived Cells for Cardiovascular

Therapy in a Rodent Coronary Ligation Model

Animal models of heart failure have facilitated the understanding of the pathophysiology of the disease and have assisted in the development of new treatments for congestive heart failure (CHF). Coronary artery ligation, or the blocking of the vessels that supply the heart tissue, in the rat closely mimics the pathophysiology of acute myocardial infarction in humans and has been used successfully to study pharmacological interventions for CHF. Cell transplantation of human cells into cardiac lesions is a potential viable therapeutic treatment for CHF.

The efficacy of intracardiac human umbilicus-derived cell treatment when administered 15 minutes post-coronary artery occlusion was evaluated in a rodent model of myocardial ischemia/infarction.

Methods & Materials

The Charles River Worcester, Mass. test facility is accredited by the Association for the Assessment and Accreditation of Laboratory Animal Care, International (AAALAC) and registered with the United States Department of Agriculture to conduct research in laboratory animals. All the conditions of testing conformed to the Animal Welfare Act (9 CFR) and its amendments. The protocol was reviewed and approved by the Institutional Animal Care and Use Committee (IACUC) at the Test Facility for compliance with regulations prior to study initiation.

The animals having characteristics identified in Table 24-1 were individually housed in micro-isolator cages on autoclaved bedding. The cages conformed to standards set forth in The Guide for the Care and Use of Laboratory Animals.

TABLE 24-1

Animal characteristics

| | |
|---|---|
| Species: | *Rattus norvegicus* |
| Strain: | Rnu |
| Source: | Charles River Laboratories |
| Age at Dosing: | 6-8 weeks |
| Weight at Dosing: | ~200-250 grams |
| Number of Males (including spares): | 40 + 10 |

PURINA Certified Diet (irradiated) was provided to the animals ad libitum. This diet was routinely analyzed by the manufacturer for nutritional components and environmental contaminants. Results of the manufacturer's analyses are on file at the Test Facility.

Autoclaved filtered tap water was provided ad libitum. Samples of the filtered water were analyzed for total dissolved solids, hardness, specified microbiological content, and selected environmental contaminants. Results of these analyses are on file at the Test Facility.

Environmental controls were set to maintain temperatures of 18 to 26° C. (64 to 79° F.) with relative humidity at 30% to 70%. A 12:12 hour light:dark cycle was maintained. Ten or greater air changes per hour were maintained in the animal rooms. Upon receipt and prior to use on the study, the animals were held for a minimum of four days for conditioning according to the Test Facility Vendor Management Program as described in the Test Facility Standard Operating Procedure, Receipt, Conditioning, and Quarantine of Laboratory Animals.

Each animal was identified by a unique number indicated by an ear punch. Animals were randomly assigned to groups by a weight-ordered distribution such that individual body weights did not exceed ±20% of mean weight.

The animals were anesthetized with sodium pentobarbital (40 milligrams/kilogram) and buprenorphine (0.05 milligrams/kilogram) as a single cocktail given intramuscularly (IM). Following the establishment of anesthesia, animals were intubated using 18 to 16 gauge, 2-inch length angiocaths, or appropriate sized angiocath, and maintained on room air respiration (supplemented with oxygen) and a positive pressure ventilator throughout the surgical procedure. Additional anesthesia was given incrementally as needed. Preoperative antibiotic therapy was also administered, Benzathine/Procaine penicillin G, 40,000 Units/kilogram, IM. Additional antibiotic therapy was administered every 48 hours.

Electrode pads were placed around the appropriate paws of the animals to receive a useable ECG signal. Animals were positioned on a heating pad to help maintain body temperature throughout the procedure. A rectal temperature probe was inserted into the animal to monitor body temperature. Ophthalmic ointment was administered to each eye. The surgical sites (thoracic area) were prepared for aseptic surgery by removing any excess fur, and gently wiping the area with sponges soaked in 70% isopropyl alcohol, which was allowed to dry. Iodone (MEDISEPPS, or similar solution) was then applied to the area and allowed to dry. The area was appropriately draped for strict aseptic surgery.

A surgical incision was made on the skin over the fourth intercostal space. Blunt dissection through the muscle layers was used to access the thoracic cavity. A retractor was carefully inserted into the fourth intercostal space and opened to allow access to the interior cavity. The pericardium was carefully opened via gentle teasing with cotton swabs dampened in sterile saline solution. A damp cotton swab was used to gently push the apex of the heart into the opening where a length of 6-0 silk suture was attached into the myocardium for manipulation of the heart. After a pause to allow the heart to recover, the suture placed in the apex was used to ease the heart out of the chest cavity and to place sufficient tension on the heart to allow access to the upper heart and the left anterior descending coronary artery (LAD). Another length of 6-0 silk suture was placed into the myocardium so as to surround the LAD. The pressure on the apical suture was released and the heart allowed to return to the interior of the chest cavity.

Once the heart rate and ECG returned to baseline values, the ligatures around the LAD were tied off to occlude the LAD. This was a permanent occlusion with the suture tied off and the ends trimmed. After the ligature was tied, the surgeon looked for the following indications of successful occlusion: change in color of the area of the heart directly below the ligature to a white/grayish white as a result of the termination of blood flow to the area and a significant change in the ECG corresponding to occlusion of the LAD. Arrhythmias may have developed within the first 10 minutes of the occlusion. The rat was monitored closely during this time period in the event that resuscitation was necessary. In the event of severe arrhythmia and failure of the rat to convert to normal sinus rhythm without assistance, aid was rendered via cardiac massage. Approximately 15 minutes following the initiation of the LAD occlusion, the area of left ventricle made ischemic was treated with either vehicle or test article by direct injection into the ischemic myocardium. Treatment consisted of three to ten intramyocardial injections (100 uL/injection) into the ischemic zone of myocardium.

Human cells were grown in Growth Medium in gelatin-coated T300 flasks. Cells were washed with phosphate buffered saline (PBS, Gibco, Carlsbad Calif.) and trypsinized using Trypsin/EDTA (Gibco, Carlsbad Calif.). The trypsinization was stopped by adding Growth Medium. The cells were centrifuged at 150×g, supernatant removed, and the cell pellet was resuspended in approximately 1 milliliter Growth Medium per million cells. An aliquot of cells was removed and added to Trypan blue (Sigma, St. Louis, Mo.). The viable cell number was estimated using a hemocytometer. The cell suspension was centrifuged and resuspended in 1 milliliter Growth Medium containing 10% (v/v) DMSO (Hybrimax, Sigma, St. Louis, Mo.) per 5 million cells and transferred into Cryovials (Nalgene). The cells were cooled at approximately 1° C./minute overnight in a −80° C. freezer using a "Mr. Frosty" freezing container (Nalgene, Rochester, N.Y.). Vials of cells were transferred into liquid nitrogen. Vials were shipped from CBAT, Somerville, N.J. to Charles River, Worcester, Mass. on dry ice and stored at −80° C. Approximately 1-2 hours before injection of cells into the animal, a vial of cells was thawed rapidly in a 37° C. water bath. Under aseptic conditions in a BSL2 biosafety cabinet, cells were added to 40 milliliters PBS with magnesium and calcium (Sigma St. Louis, Mo.) and centrifuged at 150×g for 5 minutes before resuspending the cell pellet in 10 milliliters PBS. The cell number and viability was estimated as described above. The cells were centrifuged at 150×g for 5 minutes and resuspended in PBS at a final concentration of $10^6$ viable cells/100 microliters. The cell suspension was loaded into 1 milliliter syringes with a 30G needle and kept on ice. Viability was assessed again up to 5 hours on ice.

Following the administration of treatment (Table 24-2) and stabilization of the heart, the surgeon began closing the surgical incision. The retractor was removed. The lungs were over-inflated for 3 to 4 breaths and visually inspected as much as possible to ensure that they were fully re-inflated. This created a negative pressure necessary to prevent pneumothorax post-recovery. To evacuate fluid and excess air from the thoracic cavity after closing the cavity, an intravenous catheter (i.e., 20 gauge, 2 millimeters in length) was placed through the skin and muscle layers so that the tip remains in the thoracic cavity. Care was taken so that the tip did not pierce the lung or heart. The separated ribs and associated muscle was sutured together with appropriate suture. The upper layers of muscle was sutured using a simple continuous pattern. The skin was closed with 4-0 silk using a horizontal mattress pattern. A 10 milliliter syringe was attached to the intravenous catheter that had been previously placed in the thoracic cavity and the plunger slowly pulled back to withdraw fluids and air from the cavity. At the same time, the catheter was slowly withdrawn from the entry site, thereby allowing the surrounding muscle mass and skin to seal the puncture. The surgical drape was removed and fluids (i.e., lactated Ringers solution, 25 milliliters/kilogram subcutaneously [SC] or intraperitoneally [IP]) were given.

TABLE 24-2

Treatment regimens

| Gr. No. | No. of Males | Test Article | Dosage Level (cells/animal) | Dose Conc. (cells/mL) | Route/Dose Regimen | Time of Treatment Administration | Necropsy Day |
|---|---|---|---|---|---|---|---|
| 1 | 8 | Vehicle | 0 | 0 | Direct injection(s) into the ischemic region of the left ventricle of the heart, consisting of 3 to 10 intramyocardial injections of 100 μL total. | 15 minutes after coronary artery ligation | Day 28 (±1 Day) |
| 2 | 8 | Umbilical (P10) (B) | 1 million | 10 million | | | |
| 2 | 8 | Human fibroblasts 1F1853 (P10) (D) | | | | | |

Gr. = Group; No. = Number; Conc. = Concentration

Immediately after each rat had undergone treatment with test article and the incision was sutured, the animal underwent an echocardiography (ECG) examination. Anesthesia was maintained throughout the completion of the echo examination. Upon the completion of the echo examination, ventilation was discontinued, and the rat was returned to the recovery area to recover in a heated, oxygenated recovery cage.

A second echo examination of each surviving animal was completed at the end of the study (approximately 28 days post-treatment), prior to termination. During the second examination, the animals were anesthetized as described previously.

For each echo examination, the left thoracic area was shaved, and warmed, ultrasonic gel was applied to the skin to enhance contact with the transducer. Electrode pads were placed around the appropriate extremities to receive an ECG signal. Echocardiographic images included short axis and long axis views to allow for the determination of ventricular cavity dimensions, contractility, blood flow through vasculature, and wall thickness. These images were saved on optical disk for further analysis. After examination, the gel medium was removed from the skin with gauze or paper towel. The rat was removed from the ventilator and placed in a warmed recovery cage until mobile.

At the conclusion of the surgical procedures, respiratory ventilation was turned off. The animals were observed for pedal reflex. The rectal probe and ECG electrodes subsequently were removed, and the animal was extubated and placed in a warmed oxygenated recovery cage. After complete recovery from anesthesia, the animals were given buprenorphine (0.05 milligram/kilogram, SC). Observations were made regularly until the animals showed full mobility and an interest in food and water. The animals then were placed in a clean housing cage and returned to the animal housing room. Animals were monitored for surgical incision integrity twice daily post-surgery.

Analgesics (i.e., Buprenorphine, 0.05 milligram/kilogram SC.) were given twice daily for 4 days post-operatively and thereafter as needed. Visual indications of post-operative pain include lack of normal body postures and movement (e.g., animal remains in hunched position), antipathy, lack of eating/drinking, lack of grooming, and the like.

Body weight was recorded for each animal prior to initial treatment, weekly thereafter, and on the day of necropsy. Animals found dead were weighed and necropsied.

In order for the heart to be harvested, each rat was anesthetized as was done for surgery. The jugular vein was cannulated. The heart was arrested in diastole with KCl infused via the jugular cannula. The heart was then removed from the thoracic cavity. A limited necropsy was then performed on the heart after which the heart was placed in 10% neutral buffered formalin. The remainder of each carcass was then discarded with no further evaluation.

Hearts of all animals that were found dead or euthanized moribund were placed in 4% paraformaldehyde until evaluated. The remainder of each carcass was then discarded with no further evaluation.

Histology and Image Analysis. Fixed tissues sectioned with a stainless steel coronal heart matrix (Harvard Apparatus, Holliston, Mass.) yielded four two-millimeter thick serial tissue sections. Sections were processed and serially embedded in paraffin using routine methods. Five-micron sections were obtained by microtome and stained with Masson's Tri-Chrome for Connective Tissue (Poly Scientific, Bay Shore, N.Y.) using the manufacturer's procedures. Electronic photomicrographs were captured and analyzed using image analysis methods developed by Phase 3 Imaging System (Glen Mills, Pa.). Photomicrographs of the tri-chrome stained sections were colorimetrically analyzed electronically to determine the overall area of the ventricle and free wall and the area of the differential staining.

Results

There was no loss in the viability of cells over 5 hours in the vehicle when kept on ice. Cells were injected into the infarct with one to three needle entry points and multiple changes in direction of needle orientation.

Fractional shortening values were calculated as described by Sahn et al. (1978) *Circulation* 58:1072-1083. The fractional shortening of the vehicle-treated animals had a significant decrease from 47.7%±8.3% at Day 0 to 23.5%±30.2% at Day 28 (p<0.05). The animals that were treated with umbilicus-derived cells showed small, non-significant differences between the fractional shortening between Day 0 and 28. There were no significant differences between the fractional shortening between the treatment groups at Day 0.

Upon termination of the study, hearts were collected and subjected to histological analysis. The hearts were arrested in diastole and fixed. The results were calculated from an algorithm to estimate the percentage of total heart area that comprises the infarct. The infarct size in the vehicle-treated animals was 22.9%±6.7% of heart area, while the infarct size in hearts treated with umbilical cord cells was 12.5%+2.5%, with placenta-derived cells (isolate 2) was 12.9%±3.4%, and with fibroblasts was 19.3%±8.0%. The difference of infarct size of cell-treated animals relative to vehicle-treated animals was not statistically significant based on Student's t-test.

Summary. The results of the present study suggest that the umbilicus-derived cells have some benefit in reducing the damage of a surgically induced myocardial infarction in rats. The vehicle-treated animals showed a significant reduction in cardiac function from day 0 to day 28, as measured by fractional shortening, while the umbilicus-derived cell-treated animals showed minimal change over the 28-day study. The fibroblast-treated animals showed minimal change but only two animals survived the study. Evaluation of infarct size suggested that there is some modest, but not statistically significant, reduction in the infarct size in the postpartum-derived cell-treated animals as compared to the vehicle controls at Day 28. Taken together, these data support efficacy of the umbilicus-derived cells in reducing damage from a myocardial infarction.

EXAMPLE 25

Use of Umbilicus-derived Cells in the Treatment of Retinitis Pigmentosa

Currently no real treatment exists for blinding disorders that stem from the degeneration of cells in the retina. Loss of photoreceptors as a result of apoptosis or secondary degeneration lead to progressive deterioration of vision, and ultimately to blindness. Diseases in which this occurs include age-related macular degeneration (AMD) and retinitis pigmentosa (RP). RP is most commonly associated with a single gene mutation, which contributes to photoreceptor cell death.

The retinal photoreceptors and adjacent retinal pigment epithelium form a functional unit. The Royal College of Surgeons (RCS) rat presents with a tyrosine receptor kinase (Mertk) defect affecting outer segment phagocytosis, leading to photoreceptor cell death (1). Transplantation of retinal pigment epithelial (RPE) cells into the subretinal space of RCS rats was found to limit the progress of photoreceptor loss and preserve visual function (2). In this example, it is demonstrated that umbilicus-derived cells can be used to promote photoreceptor rescue in an RCS model.

Methods & Materials

Cell Transplants. Cultures of human adult umbilical and fibroblast cells (passage 10) were expanded for 1 passage. All cells were initially seeded at 5,000 cells/cm$^2$ on gelatin-coated T75 flasks in Growth Medium. For subsequent passages, all cells were treated as follows: After trypsinization, viable cells were counted after trypan blue staining. Briefly, 50 microliters of cell suspension was combined with 50 microliters of 0.04% w/v trypan blue (Sigma, St. Louis Mo.) and the viable cell number, was estimated using a hemocytometer. Cells were trypsinized and washed three times in supplement-free DMEM:Low glucose medium (Invitrogen, Carlsbad, Calif.). Cultures of human umbilical and fibroblast cells at passage 11 were trypsinized and washed twice in. Leibovitz's L-15 medium (Invitrogen, Carlsbad, Calif.).

For the transplantation procedure, dystrophic RCS rats were anesthetized with xylazine-ketamine (1 milligram/kilogram i.p. of the following mixture: 2.5 milliliters xylazine at 20 milligrams/milliliter, 5 milliliters ketamine at 100 milligrams/milliliter, and 0.5 milliliter distilled water) and their heads secured by a nose bar. Cells devoid of serum were resuspended (2×10$^5$ cells per injection) in 2 microliters of Leibovitz, L-15 medium (Invitrogen, Carlsbad, Calif.) and transplanted using a fine glass pipette (internal diameter 75-150 microns) trans-sclerally.

Cells were delivered into the dorso-temporal subretinal space of anesthetized 3 week old dystrophic-pigmented RCS rats (total N=10/cell type). Cells were injected unilaterally into the right eye, while the left eye was injected with carrier medium alone (Sham control; Leibovitz's L-15 medium). Viability of residual transplant cells remained at greater than 95% as assessed by trypan blue exclusion at the end of the transplant session. After cell injections were performed, animals were injected with dexamethasone (2 milligram/kilogram) for 10 days post transplantation. For the duration of the study, animals were maintained on oral cyclosporine A (210 milligrams/liter of drinking water; resulting blood concentration: 250-300 micrograms/liter) (Bedford Labs, Bedford, Ohio) from 2 days pre-transplantation until end of the study. Food and water were available ad libitum. Animals were sacrificed at 60 or 90 days postoperatively, with some animals being euthanitized at earlier timepoints for histological assessment of short-term changes associated with cell transplantation.

ERG recordings. Following overnight dark adaptation, animals were prepared for ERG recording under dim red light, as previously described (3). In brief, under anesthesia (with a mixture of 150 milligram/kilogram i.p ketamine, and 10 milligram/kilogram i.p. xylazine) the animal's head was secured with a stereotaxic head holder and the body temperature monitored through a rectal thermometer and maintained at 38° C. using a homeothermic blanket. Pupils were dilated using equal parts of topical 2.5% phenylephrine and 1% tropicamide. Topical anesthesia with 0.75% bupivacaine was used to prevent any corneal reflexes and a drop of 0.9% saline was frequently applied on the cornea to prevent its dehydration and allow electrical contact with the recording electrode (gold wire loop). A 25-gauge needle inserted under the scalp, between the two eyes, served as the reference electrode. Amplification (at 1-1,000 Hz bandpass, without notch filtering), stimulus presentation, and data acquisition were provided by the UTAS-3000 system from LKC Technologies (Gaithersburg, Md.). ERGs were recorded at 60 and 90 days of age in the umbilical cell groups and at 60 days only in the fibroblast groups.

Mixed a- and b-wave recording. For the quantification of dark-adapted b-waves, recordings consisted of single flash presentations (10 microseconds duration), repeated 3 to 5 times to verify the response reliability and improve the signal-to-noise ratio, if required. Stimuli were presented at six increasing intensities in one log unit steps varying from −3.6 to 1.4 log candila/m$^2$ in luminance. To minimize the potential bleaching of rods, inter-stimulus intervals were increased as the stimulus luminance was elevated from 10 seconds at lowest stimulus intensity to 2 minutes at highest stimulus intensity. The maximum b-wave amplitude was defined as that obtained from the flash intensity series, regardless of the stimulus intensity. The true $V_{max}$ from fitting the data with a Naka-Rushton curve was not used because ERG responses were often erratic at higher luminance levels in dystrophic animals and showed tendencies for depressed responses around 0.4 and 1.4 log candila/m$^2$. In order to determine the age at which ERG components were obtained or lost, criterion amplitudes were used: 20 microVolts for a- and b-waves, and 10 microVolts for STR-like responses. The amplitude of the b-wave was measured from the a-wave negative peak up to the b-wave positive apex, and not up to the peak of oscillations, which can exceed the b-wave apex (4).

Isolation of rod and cone responses. The double flash protocol was used to determine the isolation of rod and cone responses (5). A probe flash was presented 1 second after a conditioning flash, using a specific feature of the UTAS-3000 system (LKC Technologies) with calibrated ganzfeld; assuring complete recharge of the stimulator under the conditions used. The role of the conditioning flash in the procedure was to transiently saturate rods so that they were rendered unresponsive to the probe flash. Response to the probe flash was taken as reflecting cone-driven activity. A rod-driven b-wave was obtained by subtracting the cone-driven response from the mixed response (obtained following presentation of a probe flash alone, i.e. not preceded by any conditioning flash).

Functional assessment. Physiological retinal sensitivity testing was performed to demonstrate retinal response to dim light. Animals were anesthetized with a recovery dose of urethane at 1.25 grams/kilogram i.p. Physiological assessment in the animals was tested post graft in animals at 90 days by recording multiunit extracellular activity in the superior colliculus to illumination of respective visual receptive fields (6). This procedure was repeated for 20 independent points (spaced 200 millimeters apart, with each step corresponding to approximately 10-150 displacements in the visual field), covering the visual field. Visual thresholds were measured as the increase in intensity over background and maintained at 0.02 candila/m$^2$ (luminescence unit) [at least 2.6 logarithm units below rod saturation (7)], required for activating units in the superficial 200 microns of the superior colliculus with a spot of light 3° in diameter. Response parameters were compared between transplanted and sham control eyes that received vehicle alone.

Histology. Animals were sacrificed with an overdose of urethane (12.5 grams/kilogram). The orientation of the eye was maintained by placing a 6.0 suture through the superior rectus muscle prior to enucleation. After making a corneal incision, the eyes were fixed with 2.5% parafomaldehyde, 2.5% glutaraldehyde, 0.01% picric acid in 0.1 M cacodylate buffer (pH 7.4). After fixation, the cornea and lens were removed by cutting around the cilliary body. A small nick was made in the periphery of the dorsal retina prior to removal of the superior rectus to assist in maintaining orientation. The retinas were then post-fixed in 1% osmium tetroxide for 1 hour. After dehydration through a series of alcohols to epoxypropane, the retinas were embedded in TAAB embedding resin (TAAB Laboratories, Aldemarston, UK). Semi-thin sections were stained with 1% Toluidine Blue in 1% borate buffer and the ultra thin sections were contrasted with uranyl acetate and lead citrate.

For Nissl staining, sections were stained with 0.75% cresyl violet (Sigma, St. Louis, Mo.) after which they were dehydrated through graded alcohols at 70, 95 and 100% twice, placed in xylene (Sigma, St. Louis, Mo.), rinsed with PBS (pH 7.4) (Invitrogen, Carlsbad, Calif.), coverslipped and mounted with DPX mountant (Sigma, St. Louis, Mo.).

Results

ERG Recordings. Animals that received umbilicus-derived cell injections exhibited relative preservation of visual response properties 60 and 90 days post-operatively (Table 25-1). The response observed in these animals was greater than that seen with fibroblast or sham treated animals.

Umbilicus-derived cell-transplanted animals (n=6) demonstrated good improvement in all outcome measures tested at 60 days (Table 25-1), a-wave (27±11) versus sham controls (0), mixed b-wave (117±67) versus sham controls (18±13), cone-b-wave (55±25) versus sham controls (28±11), and in rod contribution (49±16%) versus sham controls (6±7%). Furthermore, at 90 days, improved responses were measured in two animals tested, with measures including: a-wave (15±7) versus sham controls (O), mixed b-wave (37±15) versus sham controls (O), cone-b-wave (16±11) versus sham controls (7±5), and in rod contribution (58±39%) versus sham controls (0%). These results indicate that visual responsiveness was improved in umbilicus-derived cell transplanted animals with evidence for photoreceptor rescue. Although a diminution in responsiveness to ERG was observed in the 90-day animals tested, their preservation of visual function in comparison to sham-treated controls was good.

In contrast to umbilicus-derived cells, fibroblast transplantations showed no improvement in any of the parameters tested.

TABLE 25-1

ERG data

| Group | a-wave | | mixed b-wave | | cone b-wave | | % rod contribution | |
|---|---|---|---|---|---|---|---|---|
| | Untreated | Treated | Untreated | Treated | Untreated | Treated | Untreated | Treated |
| Sham 60 d | 0 | 0 | 7 ± 9 | 0 | 23 ± 5 | 12 ± 16 | N/A | N/A |
| U (n = 6) 60 d | 0 | 27 ± 11 | 18 ± 13 | 117 ± 67 | 28 ± 11 | 55 ± 25 | 6 ± 7 | 49 ± 16 |
| U (n = 6) 90 d | 0 | 15 ± 7 | 0 | 37 ± 15 | 7 ± 5 | 16 ± 11 | 0 | 58 ± 39 |

N.B. Sham = control (medium only), U = Umbilicus-derived cell transplant

Histology. Following transplantation, there was no histological evidence of an inflammatory reaction and infiltrating immune cells were not observed in Nissl-stained sections in the postpartum cell groups. However, fibroblast implantations resulted in animal death (n=7) and indications of early stage inflammatory responses. Histologically at the 90 day time point in the umbilicus-derived cell transplanted animals anatomical rescue of photoreceptors was clearly demonstrated. The photoreceptors formed a thick layer separated by a gap from the inner nuclear layer, made up of other retinal cells. By comparison, the width of the outer layer in the sham control was, at best, a discontinuous single layer as opposed to around 5 cells thick in the grafted eye. In comparison to a normal animal this is marginally more than half the thickness of photoreceptor cell layers normally observed.

Functional Assessment. Efficacy of transplants in preventing visual loss was monitored by assessment of electrophysiological responsiveness in two animals. The threshold sensitivity response to light was used to define the area of visual field rescue in sham-injected control eyes versus eyes transplanted with umbilicus-derived cells. In nondystrophic rats, visual thresholds never exceeded 0.5 log candila/m$^2$ above background. In non-operated dystrophic rats, the thresholds are usually in the magnitude of 4 log candila/m$^2$ units (8). By contrast, in non-operated sham injected dystrophic rats, the thresholds were in the order of 2.9-4.9 log candila/m$^2$ units with an average threshold of 4.0 log candila/m$^2$ units, in some instances no recording could be attained. Thus, the sham-injected rats showed some highly localized functional rescue in the temporal retina. However, the human umbilicus-derived cell transplanted rats exhibited substantially greater levels of visual preservation with thresholds ranging from 0.8 to 2.1 log candila/m$^2$ units, with an average threshold of 1.3 log candila/m$^2$ units.

Summary. Transplantation of umbilicus-derived cells into dystrophic RCS rats can preserve photoreceptors. In this degenerative model, one would expect the a-wave to disappear within 30 to 60 days and the b-wave to disappear within 3 months. Thus, the basically retained a-wave indicates that real and normal rod function is preserved. Rod contribution to b-wave suggests abnormal rod function is still possible. The sustained non-rod b-wave is the measure of how much cone function is maintained, which is a real measure of vision.

Thus, the level of improvement assessed both physiologically and anatomically following umbilicus-derived cell transplantation is well defined here. ERG measurements provide an assessment of visual function after photoreceptor loss, indicating changes in electrical activity in the retina. However, ERG does not provide direct information as to image forming capability. The measurement of collicular threshold sensitivity used in this study provides an indication of relative preservation of visual fields. The importance of this measure is based on a correlation between the amounts of functional rescue and anatomical preservation and that the data collected compares with visual field perimetry testing in humans (9). The transplantation has demonstrated a retardation of the disease process in the test animals. Thus, the results presented herein demonstrate clear evidence of functional efficacy of grafting human umbilicus-derived cells into the subretinal space, and that preservation of photoreceptors occurs in the general region in which the grafted cells are located.

References for Example 25

1. D'Cruz P M, Yasumura D, Weir J, Matthes M T, Abderrahim H, LaVail M M, Vollrath D. Mutation of the receptor tyrosine kinase gene Mertk in the retinal dystrophic RCS rat. *Hum Mol Genet.* 2000 Mar. 1; 9(4):645-51.

2. Li L X, Turner J E. Inherited retinal dystrophy in the RCS rat: prevention of photoreceptor degeneration by pigment epithelial cell transplantation. *Exp Eye Res.* 1988 December; 47(6):911-7.

3. Sauve, Y, Lu, B and Lund R D. The relationship between full field electroretinogram and perimetry-like visual thresholds in RCS rats during photoreceptor degeneration and rescue by cell transplants. *Vision Res.* 2004 January; 44(1):9-18.

4. Nusinowitz, S., Ridder, W H 3rd, and Heckonlively, H R. Rod multifocal electroretinograms in mice. *Invest Ophthalmol Vis Sci.* 1999 November; 40(12):2848-58.

5. Nixon, P J, Bui, P V, Armitage, J A, and Vingrys A J. The contribution of cone responses to rat electroretinograms. *Clin Experiment Ophthalmol.* 2001 June; 29(3):193-6.

6. Lund R D, Adamson P, Sauve Y, Keegan D J, Girman S V, Wang S, Winton H, Kanuga N, Kwan A S, Beauchene L, Zerbib A, Hetherington L, Couraud P O, Coffey P, Greenwood J. Subretinal transplantation of genetically modified human cell lines attenuates loss of visual function in dystrophic rats. *Proc Natl Acad Sci USA.* 2001 Aug. 14; 98(17):9942-7.

7. Siminoff R, Kruger L. Properties of reptilian cutaneous mechanoreceptors. *Exp Neurol.* 1968 March; 20(3):403-14.

8. Blakema, G. W. and Drager, U. C. 1991. *Visual Neuroscience.* 6:577-585.

9. Beck R W, Bergstrom T J, Lichter P R. A clinical comparison of visual field testing with a new automated perimeter, the Humphrey Field Analyzer, and the Goldmann perimeter. *Ophthalmology.* 1985 January; 92(1):77-82.

EXAMPLE 26

Chondrogenic Potential of Postpartum-Derived Cells on Implantation in SCID Mice The chondrogenic potential of cells derived from umbilicus or placenta tissue was evaluated following seeding on bioresorbable growth factor-loaded scaffolds and implantation into SCID mice.

Materials & Methods

Reagents. Dulbecco's Modified Essential Media (DMEM), Penicillin and Streptomycin, were obtained from Invitrogen, Carlsbad, Calif. Fetal calf serum (FCS) was obtained from HyClone (Logan, Utah). Mesenchymal stem cell growth medium (MSCGM) was obtained from Biowhittaker, Walkersville, Md. TGFbeta-3 was obtained from Oncogene research products, San Diego, Calif. rhGDF-5 was obtained from Biopharm, Heidelberg, Germany (International PCT Publication No. WO96/01316 A1, U.S. Pat. No. 5,994,094A). Chondrocyte growth medium comprised DMEM-High glucose supplemented with 10% fetal calf serum (FCS), 10 millimolar HEPES, 0.1 millimolar nonessential amino acids, 20 micrograms/milliliter L-proline, 50 micrograms/milliliter ascorbic acid, 100 Units/milliliter penicillin, 100 micrograms/milliliter streptomycin, and 0.25 micrograms/milliliter amphotericin B. Bovine fibrinogen was obtained from Calbiochem.

Cells. Human mesenchymal stem cells (hMSC, Lot#2F1656) were obtained from Biowhittaker, Walkersville, Md. and were cultured in MSCGM according to the manufacturer's instructions. This lot was tested in the laboratory previously in in vitro experiments and was shown to be positive in the chondrogenesis assays. Human adult fibroblasts were obtained from American Type Culture Collection (ATCC, Manassas, Va.) and cultured in Growth Medium on gelatin-coated tissue culture plastic flasks. Postpartum-derived cells isolated from human umbilical cords (Lot#022703Umb) and placenta (Lot#071003Plac) were prepared as previously described (Example 1). Cells were cultured in Growth Media on gelatin-coated tissue culture plastic flasks. The cell cultures were incubated at 37° C. with 5% $CO_2$. Cells used for experiments were at passages 5 ("Low passage") and 14 ("High passage").

Scaffolds. Foams composed of 35/65 Poly(epsilon-caprolactone)(PCL)/Poly(glycolic acid) (PGA) (35/65 PCL/PGA) copolymer, reinforced with Polydioxanone (PDS) mesh (PGA/PCL foam-PDS mesh) were formed by the process of lyophilization, as described in U.S. Pat. No. 6,355,699. The foams were 4 cm×5 cm, and 1 mm thick. Foams were sterilized by treatment with ethylene oxide (ETO). Punches (3.5 millimeters) made from scaffolds were loaded with either rhGDF-5 (3.4 micrograms/scaffold), TGFbeta-3 (10 nanograms/scaffold), a combination of rhGDF-5 and TGFbeta-3, or control medium, and lyophilized.

Cell seeding on scaffolds. Placenta- and umbilicus-derived cells were treated with trypsin, and cell number and viability was determined. $7.5 \times 10^5$ cells were resuspended in 15 microliters of Growth Medium and seeded onto 3.5 millimeter scaffold punches in a cell culture dish. The cell-seeded scaffold was incubated in a cell culture incubator (37° C., 5% $CO_2$) for 2 hours after which they were placed within cartilage explant rings.

Bovine Cartilage Explants. Cartilage explants 5 millimeters in diameter were made from cartilage obtained from young bovine shoulder. Punches (3 millimeters) were excised from the center of the explant and replaced with cells seeded on 3.5 millimeters resorbable scaffold. Scaffolds with cells were retained within the explants using fibrin glue (60 microliters of bovine fibrinogen, 3 milligrams/milliliter). Samples were maintained in chondrocyte growth medium overnight, rinsed in Phosphate Buffered Saline the following day, and implanted into SCID mice.

Animals. SCID mice ((*Mus musculus*)/Fox Chase SCID/Male), 5 weeks of age, were obtained from Harlan Sprague Dawley, Inc. (Indianapolis, Ind.) and Charles River Laboratories (Portage, Mich.). Animals used in the study were selected without any apparent systematic bias. A tag was placed on each individual animal cage listing the accession number, implantation technique, animal number, species/strain, surgery date, in vivo period, and date of euthanasia. The animals were identified by sequential numbers marked on the ear with an indelible ink marker.

Experimental Design. A total of 42 mice were tested. Two scaffolds were implanted subcutaneously in each mouse as described below; 42 mice for subcutaneous implantation; 28 treatments with n-value of 3 per treatment. The study corresponds to IACUC Approval Number: Skillman IACUC 01-037. The study lasted six weeks.

SCID Implantation.

A. Body Weights

Each animal was weighed prior to being anesthetized and at necropsy.

B. Anesthesia and Surgical Preparation:

All handling of the SCID mice occurred under a hood. The mice were individually weighed and anesthetized with an intraperitoneal injection of a mixture of KETASET® (ketamine hydrochloride [60 milligram/kilogram]), ROMPUN® (xylazine [10 milligram/kilogram]), and saline.

After induction of anesthesia, the entire back of the animal from the dorsal cervical area to the dorsal lumbosacral area was clipped free of hair using electric animal clippers. The area was scrubbed with chlorhexidine diacetate, rinsed with alcohol, dried, and painted with an aqueous iodophor solution of 1% available iodine. Ophthalmic ointment was applied to the eyes to prevent drying of the tissue during the anesthetic period. The anesthetized and surgically prepared animal was placed in the desired recumbent position.

C. Subcutaneous Implantation Technique:

An approximate 2-centimeters skin incision was made just lateral to the thoracic spine parallel to the vertebral column. The skin was separated from the underlying connective tissue via blunt dissection. Each SCID mouse received 2 treatments that were placed in subcutaneous pockets created by blunt dissection in each hemithorax through one skin incision (Table 26-1) Tacking sutures of 5-0 ETHIBOND EXCEL (polyester) (Ethicon Inc, Somerville, N.J.) were used to tack the skin to musculature around each scaffold to prevent subcutaneous migration. Scaffolds were implanted for 6 weeks and then harvested. The experimental design is outlined in Table 26-1.

TABLE 26-1

Experimental Design: Treatment (N = 3 per treatment)

| | |
|---|---|
| A. | 65/35 PGA/PCL Foam + PDS mesh cultured with Placental derived cells, EP, TGFb3 |
| B. | 65/35 PGA/PCL Foam + PDS mesh cultured with Placental derived cells, EP, rhGDF-5 |
| C. | 65/35 PGA/PCL Foam + PDS mesh cultured with Placental derived cells, EP, rhGDF-5 + TGFb3 |
| D. | 65/35 PGA/PCL Foam + PDS mesh cultured with Placental derived cells, EP, control |
| E. | 65/35 PGA/PCL Foam + PDS mesh cultured with Placental derived cells, LP, TGFb3 |
| F. | 65/35 PGA/PCL Foam + PDS mesh cultured with Placental derived cells, LP, rhGDF-5 |
| G. | 65/35 PGA/PCL Foam + PDS mesh cultured with Placental derived cells, LP, rhGDF-5 + TGFb3 |
| H. | 65/35 PGA/PCL Foam + PDS mesh cultured with Placental derived cells, LP, control |
| I. | 65/35 PGA/PCL Foam + PDS mesh cultured with Umbilical derived cells, EP, TGFb3 |
| J. | 65/35 PGA/PCL Foam + PDS mesh cultured with Umbilical derived cells, EP, rhGDF-5 |
| K. | 65/35 PGA/PCL Foam + PDS mesh cultured with Umbilical derived cells, EP, rhGDF-5 + TGFb3 |
| L. | 65/35 PGA/PCL Foam + PDS mesh cultured with Umbilical derived cells, EP, control |
| M. | 65/35 PGA/PCL Foam + PDS mesh cultured with Umbilical derived cells, LP, TGFb3 |
| N. | 65/35 PGA/PCL Foam + PDS mesh cultured with Umbilical derived cells, LP, rhGDF-5 |
| O. | 65/35 PGA/PCL Foam + PDS mesh cultured with Umbilical derived cells, LP, rhGDF-5 + TGFb3 |
| P. | 65/35 PGA/PCL Foam + PDS mesh cultured with Umbilical derived cells, LP, control |
| Q. | 65/35 PGA/PCL Foam + PDS mesh cultured with hMSC, TGFb3 |
| R. | 65/35 PGA/PCL Foam + PDS mesh cultured with hMSC, rhGDF-5 |
| S. | 65/35 PGA/PCL Foam + PDS mesh cultured with hMSC, rhGDF-5 + TGFb3 |
| T. | 65/35 PGA/PCL Foam + PDS mesh cultured with hMSC, control |
| U. | 65/35 PGA/PCL Foam + PDS mesh cultured with fibroblasts, Adult TGFb3 |
| V. | 65/35 PGA/PCL Foam + PDS mesh cultured with fibroblasts, Adult rhGDF-5 |
| W. | 65/35 PGA/PCL Foam + PDS mesh cultured with fibroblasts, Adult rhGDF-5 + TGFb3 |
| X. | 65/35 PGA/PCL Foam + PDS mesh cultured with fibroblasts, Adult control |
| Y. | 65/35 PGA/PCL Foam + PDS mesh, TGFb3 |
| Z. | 65/35 PGA/PCL Foam + PDS mesh, rhGDF-5 |
| AA. | 65/35 PGA/PCL Foam + PDS mesh, rhGDF-5 + TGFb3 |
| BB. | 65/35 PGA/PCL Foam + PDS mesh, control |

D. Necropsy and Histologic Preparation

Gross examination was performed on any animals that died during the course of the study or were euthanized in moribund condition. Selected tissues were saved at the discretion of the study director and/or pathologist.

Mice were euthanized by $CO_2$ inhalation at their designated intervals. Gross observations of the implanted sites were recorded. Samples of the subcutaneous implantation sites with their overlying skin were excised and fixed in 10% buffered formalin. Each implant was bisected into halves, and one half was sent to MPI Research (Mattawan, Mich.) for paraffin embedding, sectioning, and staining with Hematoxylin & Eosin (H&E) and Safranin O (SO).

Results

New cartilage and bone formation was observed in the majority of the samples including growth factor-loaded, cell-seeded scaffolds, cell-seeded control scaffolds, and scaffolds loaded with growth factor alone. The extent of new cartilage and bone formation varied within the treatment and control groups.

Early and Late passage placenta-derived cell seeded scaffolds showed new cartilage and bone formation within the scaffolds. No obvious differences in new cartilage and bone formation was observed between the different growth factor-loaded, cell-seeded scaffolds and scaffolds seeded with cells alone. Compared to control scaffolds (without growth factors and without cells), it appeared that there was greater extent of new cartilage formation in cell-seeded scaffolds both with and without growth factors and in growth factor-loaded scaffolds alone. New cartilage formation with placenta-derived cell-seeded scaffolds was similar to MSC- and fibroblast-seeded scaffolds.

In growth factor-treated and control scaffolds seeded with umbilicus-derived cells at early and late passage, new cartilage and bone formation were observed. The extent of cartilage formation appeared to be less than that seen with placenta-derived cells. No one sample showed extensive cartilage formation as seen with the placenta-derived cells.

Bone formation appeared to be higher in scaffolds seeded with umbilicus-derived cells on scaffolds containing both TGFbeta-3 and rhGDF-5.

hMSC-loaded scaffolds also showed new cartilage and bone formation. The extent of new cartilage and bone formation was similar for all the hMSC treatment groups. Human adult fibroblast seeded scaffolds also demonstrated new cartilage and bone formation. Results were similar to those obtained with placenta-derived cells and hMSCs In the control group, in which growth factor-loaded scaffolds or scaffold alone were placed in cartilage rings and implanted, new cartilage and bone formation were also observed. Not surprisingly, the extent of new cartilage formation was greater in scaffolds with growth factor than in scaffolds without growth factor. Increased bone formation was present in the control with the combination of the two tested growth factors.

New cartilage formation was observed adjacent to the cartilage explant rings as well as within the scaffolds. New cartilage formation within the scaffolds adjacent to the cartilage rings could be a result of chondrocyte migration. Cartilage formation seen as islands within the scaffolds may be a result of either migration of chondrocytes within the scaffolds, differentiation of seeded cells or differentiation of endogenous mouse progenitor cells. This observation stems from the fact that in control growth factor-loaded scaffolds with no seeded cells, islands of chondrogenic differentiation were observed. New bone formation was observed within the scaffolds independently and also associated with chondrocytes. Bone formation may have arisen from osteoblast differentiation as well as endochondral ossification.

It is difficult to separate new cartilage and bone formation associated with chondrocytes that migrated versus that from any chondrogenic and osteogenic differentiation of seeded cells that may have occurred. Staining of sections with specific human antibodies may distinguish the contribution of the seeded cells to the observed chondrogenesis and osteogenesis. It is also possible that placenta-derived cells and umbilicus-derived cells stimulated chondrocyte migration.

Abundant new blood vessels were observed with the scaffolds loaded with placenta-derived cells and umbilicus-derived cells. Blood vessels were abundant in areas of bone formation. New blood vessels were also observed within the hMSC- and fibroblast-seeded scaffolds associated with new bone formation.

Systemic effects of the adjacent scaffold (with growth factor (GF)) on the control scaffolds (no GF, no cells) on promoting new cartilage and bone formation cannot be ruled out. Analysis of new cartilage and bone formation in scaffolds, taking into consideration the scaffolds implanted adjacent to it in SCID mice, showed no clear pattern of systemic effect of growth factor from the adjacent scaffold.

Summary. Results showed that new cartilage and bone formation were observed in growth factor and control scaffolds seeded with placenta- and umbilicus-derived cells. Results with placenta-derived cells were similar to that seen with human mesenchymal stem cells, while the extent of new cartilage like tissue formation was slightly less pronounced in umbilicus-derived cells. Growth factor-loaded scaffolds implanted without cells also demonstrated new cartilage and bone formation. These data indicate that new cartilage formation within the scaffolds may arise from chondrocytes that migrated from the bovine explants, from chondrogenic differentiation of endogenous progenitor cells, and from chondrogenic differentiation of seeded cells.

These results suggest that placenta- and umbilicus-derived cells undergo chondrogenic and osteogenic differentiation. These results also suggest that placenta- and umbilicus-derived cells may promote migration of chondrocytes from the cartilage explant into the scaffolds. Abundant new blood vessels were also observed in the scaffolds especially associated with new bone formation.

EXAMPLE 27

Identification and Development of Serum-Free Media for the Isolation and Expansion of Postpartum-Derived Cells Summary: Currently, the most common approaches to growing primary human cells for long-term culture utilize fetal bovine serum (FBS). FBS significantly stimulates cell growth because of the proteins it contains, making it a preferred substrate or supplement for in vitro cell growth. There are, however, a number of disadvantages to using media containing animal products instead of chemically-defined or at least serum-free media. As with all biological products variation in the protein composition of serum from lot to lot and increasing concerns about transmission of diseases such as bovine spongiform encephalopathy provide significant roadblocks to the commercialization or regulatory approval of cell-related products which contain or are produced with serum components.

The development of cell culture media formulations free of serum, yet retaining the ability to support cell population expansion sufficient for commercial applications was investigated. A number of media formulations were tested, using short-term or long-term cell proliferation of postpartum-derived umbilical cells as indices of usefulness.

Advanced-DMEM (Invitrogen) has been used as a basal medium to optimize serum-free growth of postpartum-derived cells. While serum-free, Advanced-DMEM is not devoid of all animal proteins. Animal protein components contained within Advanced DMEM, such as albumin and insulin, may be replaced with recombinantly-produced alternatives prior to use for making commercialized therapeutic cells or biologics. Postpartum-derived cells (PPDCs) grown from isolation in Advanced-DMEM have been characterized and shown to have reduced expression of PDGFr-alpha and HLA-ABC, relative to that seen in serum-containing media.

Introduction: Cell-based therapies have been or are being developed to treat patients with diseases as broad-ranging as myocardial infarction, stroke, ocular diseases like retinitis pigmentosa and macular degeneration, and diabetes. Bankable quantities of cells are required thus stimulating efforts to rapidly and efficiently isolate and expand such cells.

Most media for growing primary cultures of human cells incorporate some fetal bovine or calf serum. Generally, commercially available media formulations require serum supplements of about 10-20% (v/v) as this component aids in the survival and expansion of numerous cell populations. A myriad of proteins are found in the serum of cows including PDGF and FGFs, known growth factors that can have important influences on cell growth and differentiation of stem and progenitor cell populations. The disadvantages of using foreign serum products for human therapeutics is discussed above.

To overcome the disadvantages of fetal bovine serum, numerous media formulations with and without a variety of human recombinant growth factors known to aid cell expansion were evaluated. Both the short and long-term expansion profiles of postpartum-derived cells were examined and the results are reported herein. While numerous media formulations provided significant short-term benefit, several formulations were useful in expanding these cells over multiple passages.

Materials & Methods

PPDC Isolation

PPDCs were Isolated as in the previous examples.

PPC Cell Plating

Postpartum-derived cells (umbilicus 022803 (P12)) previously grown in Growth Media were plated at 5,000 cells per cm-squared and weaned of serum over the course of one week by reducing the serum content from 15% to 2%. Cells were then transferred to Growth Medium without serum prior to passage and plating for the short-term MTS assay.

MTS Assay to Assess Short-Term Expansion

In order to assess a broad range of growth conditions, a MTS assay was used to colorimetrically quantitate DNA content, an indirect measure of cell number and thus cell proliferation. Umbilicus-derived cells (022803 (P11)) were plated at a density of 1,000 cells/well (96-well plate format; equivalent of 5,000 cells/cm-squared, in 100 microliters of medium) in quadruplicate for each condition tested. Both basal media compositions with additives and complete media formulations not requiring supplementation with amino acids were tested. Refer to Table 27-1 for a list of all conditions (note that all media included penicillin/streptomycin in an effective amount, Invitrogen). After four days, samples were treated according to the manufacturer's instructions (Promega MTS Assay Kit).

Briefly, 20 microliters of CellTiter Aqueous One Solution Reagent (Promega) were pipetted into each well. Plates were incubated for 1-2 hours at 37 degrees in a humidified incubator (containing 5% carbon dioxide). Following incubation, 25 microliters of 10% SDS were added to each well to stop the formation of the soluble formazin product produced by cellular reduction of MTS. Absorbance was then recorded using a colorimetric absorbance photometer (Spectramax190, Molecular Devices) at both 490 and 700 nanometers.

Standard concentration curves were generated, and linear equations were fitted to the curves and utilized to extrapolate cell number based on the averaged values from the samples run in quadruplicate. Graphs were then generated to pictorially represent the sample values and their respective standard errors.

TABLE 27-1

| BASAL MEDIUM | SUPPLEMENT | GROWTH FACTOR(S) |
|---|---|---|
| Growth Medium (containing 15% FBS) | ITS | BFGF (F) |
| F10 | ITS + 1 | PDGF (P) |
| DMEM/low glucose | ITS + 3 | EGF (E) |
| DMEM/LG + MCDB201 (40%) | SITE | IGF-1 (I) |
| Advanced DMEM (high glucose) + L-glutamine (4 mM) | SPITE | F + P |
| UltraCulture (Cambrex) | SPIT | F + E |
| | | F + I |
| | | P + E |
| | | P + I |

*each basal medium was matched with every possible supplement and growth factor
Abbreviations: ITS = bovine pancreas-derived insulin, human transferrin, and sodium selenite; ITS + 1 = ITS components plus bovine serum albumin and linoleic acid; ITS + 3 = ITS + 1 components plus oleic acid; SITE = ITS components plus ethanolamine; SPITE = SITE components plus pyruvate; SPIT = ITS components plus pyruvate.

Long-Term Expansion Analysis

Of the approximate 150 different growth conditions tested in the MTS assay, the 9 best growth conditions plus the control (Growth Medium) were tested for their ability to support the expansion of cell populations over multiple passages. For this analysis, umbilical-derived cells (022803 (P10)) were thawed from cryopreservation (cells were previously grown in Growth Medium) and plated directly into the experimental conditions (see Table 27-2). Media used under all conditions contained penicillin/streptomycin as in the Growth Medium formulation (see above Examples). Cells were passaged every 3-4 days and passaged/trypsinized equivalently in a base medium used for that growth condition (e.g. Advanced DMEM plus bFGF). Growth curves were generated for conditions that supported the growth of umbilical-derived PPCs over greater than 10 passages. Conditions that did not support growth were not considered for further analysis at this time.

TABLE 27-2

| Medium Composition | Supplement | Growth Factor(s) |
|---|---|---|
| Growth medium | 15% fetal bovine serum (Hyclone, Logan, UT) | none |
| DMEM/LG (Gibco) + MCDB 201 (40%) | ITS + 3 | F |
| DMEM/LG (Gibco) + MCDB 201 (40%) | ITS + 3 | P |
| DMEM/LG (Gibco) + MCDB 201 (40%) | ITS + 3 | E |
| DMEM/LG (Gibco) + MCDB 201 (40%) | SITE | F |
| DMEM/LG (Gibco) + MCDB 201 (40%) | SITE | P |
| DMEM/LG (Gibco) + MCDB 201 (40%) | SITE | E |
| Advanced DMEM (high glucose) (Gibco) + L-glutamine (4 mM) | None | F |
| Advanced DMEM (high glucose) (Gibco) + L-glutamine (4 mM) | None | P |
| Advanced DMEM (high glucose) (Gibco) + L-glutamine (4 mM) | None | E |

Abbreviations: refer to table 1.

Flow Cytometry

Flow cytometric analysis of the markers used in the characterization of umbilical-derived PPCs (see Examples above) was performed to establish whether growth in Advanced DMEM+L-glutamine+bFGF (10 ng/ml) altered surface marker expression as compared to equivalent cells grown in Growth Medium (containing 15% fetal bovine serum). Results of stained samples were compared to controls with no primary antibody to establish differences between positive staining and background fluorescence levels. For these experiments, umbilical-derived cells from several donors 090304A (P4 and P10), 091504A (P4), 063004B (P4), and 042303 (P33) were used.

Cryopreservation Analysis

Umbilical cord-derived cells (042803 P21) and placenta-derived cells (071503 P10) grown in either Growth Medium or in Advanced DMEM and 10 ng/mL bFGF (Peprotech, Rocky Hill, N.J.)], in a gelatin-coated T225 flask were washed with phosphate buffered saline (PBS; Invitrogen) and trypsinized using 1 mL Trypsin/EDTA (Invitrogen). The trypsinization reaction was diluted by adding 20 mL of Advanced DMEM. Cells were centrifuged at 150×g and the supernatant was aspirated off. The cells were washed in advanced DMEM. Aliquots of cells, 60 µL, were removed and each was added to 60 trypan blue (Sigma). The number of viable cells was estimated using a hemocytometer. Cells were then centrifuged at 150×g, supernatant was removed, and the cell pellet was resuspended in the freezing formulation: advanced DMEM, penicillin/streptomycin (Invitrogen) glutamine (4 mM), 10% DMSO (v/v) (Sigma, St Louis, Mo.), 2% (w/v) bovine serum albumin (fraction V, Sigma, St. Louis, Mo.) and 10 ng/mL bFGF (Peprotech) at $1.0 \times 10^6$ cell/mL. 1 mL aliquots were distributed into cryovials (Nalgene). Cells were frozen within 15 minutes of exposure to the freezing medium in a control-rate freezer (CryoMed Freezer 7452, ThermoForma, Marietta, Ohio) using the following protocol:

| Step 1 | Wait | at 4.0° C. |
| Step 2 | 1.0° C./min | to −4.0° C. |
| Step 3 | 25.0° C./min | to −40° C. |
| Step 4 | 10.0° C./min | to −12.0° C. |
| Step 5 | 1.0° C./min | to −40° C. |
| Step 6 | 10.0° C./min | to −90° C. |
| Step 7 | END | |

Vials of cells were transferred to a nitrogen vapor storage unit (CryoMed 7400, ThermoForma, Marietta, Ohio) for 2 days before thawing rapidly in a 37° C. water bath with gentle swirling until no visible ice crystals could be detected. The cells were added to 10 mL Growth Medium and centrifuged before the cell number and viability was estimated as before. Cells were seeded onto gelatin-coated flasks at 5,000 cells/$cm^2$ to determine whether the cells were able to attach and proliferate.

Cells were also assayed for senescence using the Senescence Cells Histochemical Staining Kit (Sigma, St Louis, Mo.) according to manufacturer's specification. Briefly, cells were seeded in gelatin-coated 6-well plates at $1.5 \times 10^5$ cells per well in the Growth Medium. After three days cells were washed once with PBS (Invitrogen, Carlsbad, Calif.) and incubated in the fixative solution for 6-7 minutes at room temperature (RT). Cells were then rinsed 3 times with PBS and 1.5 mL of staining solution was added to each well. Plates were incubated at 37 C in a shaker with gentle rocking until cells stained blue. The percentage of blue (senescent) cells was determined.

An MTS assay was performed as described above. Similarly, cells were seeded in 8 replicates in 96-well plates at an initial concentration of 1,000 cells per well in the Growth medium (they were not re-seeded in Advanced DMEM).

Results

Short Term Expansion of Umbilical PPCs

Over 150 different media formulations were compared by MTS assay to examine the short-term (1, 3, and 4 day) cell proliferation of passage 11 umbilical-derived PPCs. Cells were plated at 1,000 cells per well.

With respect to the basal media (no additives), DMEM/MCDB, F10 medium, Advanced DMEM (containing L-glutamine) and Growth Medium supported umbilical-derived PPC growth over four days in culture. There was a reduction in overall cell number from day 3 to day 4 in UltraCulture medium, and the cells appeared unhealthy.

Analysis of the supplements tested indicated that, ITS+3 was superior in the expansion of umbilical-derived PPCs over 4 days, relative to the basal medium alone.

Analysis of the growth factors added to the basal media indicated that bFGF, EGF, and PDGF were all individually useful in expanding umbilical PPCs, with bFGF being the growth factor that stimulated the most expansion based on cell number at 4 days. This effect surpassed those results observed with Growth Medium. Interestingly, adding multiple growth factors did not further stimulate expansion under the conditions tested. Converting the data to population doublings between days 1 and 4, PDGF, EGF and IGF surpassed bFGF. This result may be explained by enhanced cell attachment and growth between time zero and day 1 for cells in bFGF.

Long Term Expansion Analysis

Given the results of the short-term expansion experiments aimed at narrowing the search for a serum-free alternative, 10 media combinations were selected and umbilical-derived PPCs were expanded from passage 10 (previously grown in Growth Medium) at a seeding density of 5,000 cells per centimeter squared. Aside from the control condition (Growth Medium), the only medium combinations that supported the expansion of umbilical-derived PPCs beyond 10 passages was Advanced DMEM supplemented with L-glutamine (4 mM) and bFGF (10 ng/ml). Advanced DMEM continued to support expansion of umbilical-derived PPCs, albeit at a lower rate than Growth Medium, for at least about 23 passages, with these cells eventually senescing at passage 33.

Flow Cytometry Results

Both early and late passage umbilical cells grown in supplemented Advanced DMEM (containing L-glutamine and bFGF, 10 ng/ml) were stained for a variety of cell surface markers previously used to characterize PPDCs grown in Growth Medium. Umbilical-derived PPCs grown in Growth Medium were used for comparison to evaluate differences attributable to the medium composition. While the expression of most markers was similar, two markers differed in their expression between media compositions. Both HLA-ABC and PDGFr-alpha were expressed in Growth Medium, but neither was expressed in Advanced DMEM. (Tables 27-3 & 4). This was observed with both early (P4) and late passage (P33) umbilical-derived cells.

TABLE 27-3

Medium Growth Medium
Tissue Umbilical
Sample ID 090304A
Passage 4

|  | Present/Absent | Mean | Geo Mean |
|---|---|---|---|
| CD10-PE | + | 147.44 | 91.89 |
| CD13-PE | + | 479.09 | 375.84 |

TABLE 27-3-continued

Medium Growth Medium
Tissue Umbilical
Sample ID 090304A
Passage 4

| CD31-PE | − | 1.66 | 1.46 |
|---|---|---|---|
| CD34-FITC | − | 1.65 | 1.50 |
| CD44-FITC | + | 285.41 | 253.22 |
| CD45-PE | − | 1.70 | 1.50 |
| CD73-PE | + | 296 | 250.27 |
| CD90-FITC | na | na | Na |
| CD117-PE | − | 1.84 | 1.58 |
| CD141-PE | − | 2.64 | 2.12 |
| SSEA-4-PE | +/− | 32.44 | 11.84 |
| PD-L2-FITC | +/− | 10.44 | 8.30 |
| PDGFRalpha-PE | +/− | 10.81 | 8.76 |
| HLA-ABC-PE | + | 152.15 | 124.92 |
| HLA-DRDPDQ-FITC | − | 1.86 | 1.63 |

| Controls | Mean | Geo Mean |
|---|---|---|
| IgG-PE | 2.40 | 2.03 |
| IgG-FITC | 1.86 | 1.66 |

* na = not available

TABLE 27-4

Medium AdvDMEM + bFGF
Tissue Umbilical
Sample ID 91504
Passage 4

|  | Present/Absent | Mean | Geo Mean |
|---|---|---|---|
| CD10-PE | + | 27.50 | 24.49 |
| CD13-PE | + | 20.98 | 16.87 |
| CD31-PE | − | 3.23 | 2.73 |
| CD34-FITC | − | 2.77 | 2.43 |
| CD44-FITC | + | 10.37 | 8.11 |
| CD45-PE | − | 3.12 | 2.67 |
| CD73-PE | + | 11.66 | 9.46 |
| CD90-FITC | + | 160.33 | 136.83 |
| CD117-PE | − | 3.22 | 2.69 |
| CD141-PE | − | 3.29 | 2.79 |
| SSEA-4-PE | − | 3.39 | 2.93 |
| PD-L2-FITC | Na | na | Na |
| PDGFRalpha-PE | − | 2.91 | 2.50 |
| HLA-ABC-PE | − | 5.00 | 4.62 |
| HLA-DRDPDQ-FITC | − | 2.66 | 2.34 |

| Controls | Mean | Geo Mean |
|---|---|---|
| IgG-PE | 3.19 | 2.73 |
| IgG-FITC | 2.8 | 2.46 |

* na = not available

Cryopreservation Results

The initial viability of the cells as assessed by trypan blue staining prior to cryopreservation was close to 100%. Viability of cells post thawing and % senescent cells is summarized in Table 27-5.

TABLE 27-5

| Cell type | Medium before freezing | Recovery rate | Senescence |
|---|---|---|---|
| Placenta-derived | Growth medium | 94% | ~3% |
|  | Adv DMEM + bFGF | 98% | <1% |
| Umbilical-derived | Growth medium | 77% | ~7% |
|  | Adv DMEM + bFGF | 86% | ~7% |

There was a slight reduction in cell viability in both placenta-derived and umbilical cord-derived cells grown in the Growth Medium prior to cryopreservation. The viable cells cryopreserved in the Advanced DMEM-based medium divided and produced a confluent monolayer within 3 days. There were no discernable differences in growth rates (as determined from the MTS measurements). The senescence assay revealed <1% and 3% senescent cell population of placenta-derived cells grown in Advanced DMEM and Growth Medium respectively. For umbilical cord-derived cells the percentages of senescent cells were slightly higher, approximately 7%.

Discussion and Conclusions

The data indicate that in addition to the currently used Growth Medium (containing 15% fetal bovine serum) there are media formulations that support the growth of postpartum-derived cells. Of those studied, the best defined medium formulation was Advanced DMEM (Invitrogen) containing high glucose supplemented with 10 ng/ml bFGF. This medium could support both the short and long term expansion of passage 10 umbilical-derived PPDCs previously grown in Growth Medium. Although the cells grew and the populations expanded well, growth was not as substantial as that obtained in Growth Medium with the serum supplementation.

Another unexpected finding was that Advanced DMEM grown cells lacked expression of HLA-ABC, whereas equivalent cells grown in Growth Medium did express this marker. Whether this has implications for influencing (e.g. reducing) graft rejection is unclear and will require animal studies with cells grown in serum-free media. The change in HLA-ABC and PDGFr markers may influence pre-clinical efficacy. Preliminarily, however, it would be beneficial to examine changes in gene expression as a result of cell growth in these two media formulations.

Finally, an analysis of the ability of such cells to be cryopreserved suggests that Advanced DMEM media may be of benefit in reducing the number of non-viable cells (compared with Growth Medium). For both umbilicus-derived and placental-derived PPCs, recovery rate was increased, albeit modestly. The seemingly lower recovery rate for umbilical cord-derived cells versus placenta-derived cells could be due to higher passage (21) of the cells which was also reflected in the senescence assay results. Thus, umbilicus-derived cells grown in Growth Medium can be cryopreserved in Advanced DMEM with certain advantages.

EXAMPLE 28

Further Identification and Development of Serum-Free Media for the Isolation and Expansion of Postpartum-Derived Cells Summary: The prior example described Advanced-DMEM (Invitrogen) as a useful basal medium to optimize for the serum-free growth of postpartum-derived cells. Umbilical-derived cells grown from isolation in Advanced-DMEM were characterized and shown to have reduced expression of PDGFr-alpha and HLA-ABC. Postpartum-derived cells grown in both Advanced DMEM and Growth Medium were further characterized using flow cytometry to determine the effect of growth medium on cell surface marker expression. Gene expression profiles were compared with those of other cells including dermal and foreskin fibroblasts, and mesenchymal stem cells (MSCs). Switching media can alter both HLA-ABC and PDGFr expression as determined by flow cytometry. The expression patterns for particular "signature genes" (described in Examples herein) was similar in both media. This confirms that umbilical cord-derived postpartum cells are unique cells from isolation that can be propagated in a defined medium without any apparent change in the expression of these "signature" genes. Alteration of cell surface marker expression of HLA-ABC may impact graft or implantation incorporation or rejection.

Introduction: FILA-ABC and PDGFr alpha expression was shown to be altered when postpartum cells were grown in two different media (Growth Medium versus Advanced DMEM supplemented with basic fibroblast growth factor (bFGF)). This finding was interesting and triggered further investigations into whether this phenomenon was due, for example, to the promotion of a different subpopulation of postpartum-derived cells, or whether a specific population of postpartum cells had the ability to modulate the expression of these cell surface markers in different growth media.

To investigate this question, two sets of experiments were performed. In the first, umbilicus-derived postpartum cells were grown in Growth Medium, Advanced DMEM plus bFGF, or switched between the two, and then analyzed for HLA-ABC and PDGFr expression by flow cytometry. RNA was isolated from cultures of these cells grown under identical conditions, and PCR was performed to determine the expression patterns of genes previously found to be exclusively expressed (versus other cell populations). Differences between media conditions were analyzed, as were differences between other control cell types.

The results of these experiments indicate that while the postpartum-derived cells grown in both Growth Medium and the Advanced DMEM Medium express similar patterns of genes, their cell surface marker expression may be altered between the two media. This is important for many reasons including distinguishing various postpartum-derived cells from each other as well from other stem type cells of adult, fetal or neonatal origin. The method described herein for reducing expression of HLA-ABC also opens significant opportunities for producing cells with improved properties for grafts or implantation. Such a method could reduce the chance of graft rejection in the absence of an immunosuppressant like cyclosporin A.

Materials & Methods

PPC Isolation

Cells were isolated as described herein throughout the above Examples.

PPC Cell Plating

Postpartum-derived cells (umbilicus 063004B) grown in Advanced DMEM supplemented with bFGF (as described in Example 27) from isolation were passaged at either P3 or P4, and at that point switched to Growth Medium. Cells were plated at 5,000 cells per cm-squared on standard gelatin coated tissue culture flasks. Flow cytometry was performed on P3 cells for PDGFr alpha, HLA-ABC, and HLA-DRD-PDQ, and the respective controls lacking primary antibody (IgG-PE, and IgG-FITC). P4 passaged/media switched cells were grown until passage 8 by passaging every 3 or 4 days, at which time flow cytometry was performed for the cell surface markers.

The reciprocal experiment was also performed in which cells grown in Growth Medium were switched to Advanced DMEM supplemented with bFGF (10 ng/ml). Umbilicus-derived (063004B) postpartum cells were grown in Growth Medium from isolation until passage 12. At passage 13, cells were switched to Advanced DMEM+bFGF and grown until passage 14, at which time flow cytometry was performed. Similarly, umbilicus-derived (090304A) postpartum cells were grown in Growth Medium from isolation until passage 8, and then switched at passage 9 to Advanced DMEM+bFGF. Cultures were maintained until passage 10 at which time flow cytometry was performed. Finally, umbilicus-derived (042303) postpartum cells were grown in Growth Medium from isolation until passage 10, at which time they were cryopreserved in Growth Medium supplemented with 10% DMSO (Sigma, St. Louis, Mo.) and placed in a liquid nitrogen container (protocol as described in Example 27). Cells were later thawed and directly plated at 5,000 cells per cm-squared on gelatin coated flasks in Advanced DMEM supplemented with bFGF (10 ng/ml). The cultures were maintained until passage 33, at which time flow cytometry was performed for the cell surface markers of interest.

Flow Cytometry

Flow cytometric analysis of the markers of interest was performed to determine whether growth in Advanced DMEM+bFGF (10 ng/ml) altered surface marker expression as compared to equivalent cells grown in Growth Medium (with its 15% fetal bovine serum). Results of stained samples were compared to the appropriate IgG controls to establish differences between positive staining and background fluorescence levels.

Control Cell Growth Conditions

Normal Human Dermal Fibroblasts (NHDF; neonatal and adult) were grown in Growth Medium in gelatin-coated T75 flasks. Mesenchymal Stem Cells (MSCs, Cambrex, Walkersville, Md.) were grown in Mesenchymal Stem Cell Growth Medium Bullet kit (MSCGM; Cambrex).

Total RNA isolation

RNA was extracted from confluent umbilical cord-derived cells grown in different conditions. RNA was also extracted from fibroblasts and MSCs. Cells were lysed with 350 µL buffer RLT containing beta-mercaptoethanol (Sigma, St. Louis, Mo.) according to the manufacturer's instructions (RNeasy Mini Kit; Qiagen, Valencia, Calif.) and RNA extracted according to the manufacturer's instructions (RNeasy Mini Kit; Qiagen, Valencia, Calif.) with a 2.7 U/sample DNase treatment (Sigma St. Louis, Mo.). RNA was eluted with 50 µL DEPC-treated water and stored at −80° C.

Reverse Transcription

RNA was reversed transcribed using random hexamers with the TaqMan reverse transcription reagents (Applied Biosystems, Foster City, Calif.) using a temperature/time cycle of 25° C. for 10 minutes, 37° C. for 60 minutes, and 95° C. for 10 minutes. Samples were stored at −20° C. Genes, termed "signature genes" (oxidized LDL receptor, interleukin-8, renin and reticulon), were further investigated using real-time and conventional PCR.

Real-time PCR

PCR was performed on cDNA samples using Assays-on-Demand™ gene expression products: oxidized LDL receptor (Hs00234028), renin (Hs00166915), reticulon (Hs00382515), IL-8 (Hs00174103) and GAPDH (Applied Biosystems, Foster City, Calif.) were mixed with cDNA and TaqMan Universal PCR master mix according to the manufacturer's instructions (Applied Biosystems, Foster City, Calif.) using a 7000 sequence detection system with ABI prism 7000 SDS software (Applied Biosystems, Foster City, Calif.). Thermal cycle conditions were initially 50° C. for 2 min and 95° C. for 10 min followed by 40 cycles of 95° C. for 15 sec and 60° C. for 1 min.

Conventional PCR

Conventional PCR was performed using an ABI PRISM 7700 (Perkin Elmer Applied Biosystems, Boston, Mass., USA) to confirm the results from real-time PCR. PCR was performed using 2 µL of cDNA solution, 1× AmpliTaq Gold universal mix PCR reaction buffer (Applied Biosystems, Foster City, Calif.) and initial denaturation at 94° C. for 5 minutes. Amplification was optimized for each primer set. For IL-8, and reticulon (94° C. for 15 seconds, 55° C. for 15 seconds and 72° C. for 30 seconds for 30 cycles), for renin (94° C. for 15 seconds, 53° C. for 15 seconds and 72° C. for 30 seconds for 38 cycles) for oxidized LDL receptor and GAPDH (94° C. for 15 seconds, 55° C. for 15 seconds and 72° C. for 30 seconds for 33 cycles). Primers used for amplification are listed in Table 28-1. Primer concentration in the final PCR reaction was 1 µM except for GAPDH which was 0.5 GAPDH primers were the same as real-time PCR, except that the manufacturer's TaqMan probe was not added to the final PCR reaction. Samples were run on 2% (w/v) agarose gel and stained with ethidium bromide (Sigma, St. Louis, Mo.). Images were captured using a 667 Universal Twinpack film (VWR International, South Plainfield, N.J.) using a focal-length Polaroid™ camera (VWR International, South Plainfield, N.J.).

TABLE 28-1

Primers used

| Primer name | Primers |
|---|---|
| Oxidized LDL receptor | S: 5'-GAGAAATCCAAAGAGCAAATGG-3' (SEQ ID NO: 1) <br> A: 5'-AGAATGGAAAACTGGAATAGG-3' (SEQ ID NO: 2) |
| Renin | S: TCTTCGATGCTTCGGATTCC-3' (SEQ ID NO: 3) <br> A: 5'-GAATTCTCGGAATCTCTGTTG-3' (SEQ ID NO: 4) |
| Reticulon | S: 5'-TTACAAGCAGTGCAGAAAACC-3' (SEQ ID NO: 5) <br> A: 5'-AGTAAACATTGAAACCACAGCC-3' (SEQ ID NO: 6) |
| Interleukin-8 | S: 5'-TCTGCAGCTCTGTGTGAAGG-3' (SEQ ID NO: 7) <br> A: 5'-CTTCAAAAACTTCTCCACAACC-3' (SEQ ID NO: 8) |

Results

Differences in Cell Surface Marker Expression Between Cell Populations Grown in Advanced DMEM and Growth Medium from Isolation In Example 27, umbilicus-derived postpartum cells grown in Growth Medium and Advanced DMEM+bFGF from isolation were tested utilizing flow cytometry for a full battery of antibodies to cell surface markers. While the expression of most markers was similar, two markers substantially differed in their expression between the media formulations. Both HLA-ABC and PDGFr-alpha were expressed in Growth Medium, whereas neither was expressed in Advanced DMEM (Tables 27-3 & 27-4 in Example 27).

Impact of Media Switching on Cell Surface Marker Expression

To ascertain whether the media compositions were responsible for altering cell surface marker expression, umbilicus-derived postpartum cultures were first grown in one of the two aforementioned media compositions and then switched to the other. When cells were grown initially in Advanced DMEM+bFGF and then switched to Growth Medium, cell cultures immediately turned on expression of HLA-ABC in a graded fashion with increasing passage. PDGF receptor alpha, however, did not appear to turn on, even with extended passage.

When cells were first grown in Growth Medium and then later switched to Advanced DMEM+bFGF, HLA-ABC expression was retained in the short term (063004B+P14, 090304A+P 10), but after several passages, HLA-ABC expression was lost (042303+P33). In comparison to cells grown exclusively in Growth Medium from isolation, PDGF receptor alpha expression was lost as early as the second passage in Advanced DMEM+bFGF.

In addition to HLA-ABC and PDGFr alpha, each of these isolates (except 042303+P33) was tested for HLA-DRDPDQ expression. All isolates were negative regardless of medium they were maintained in.

PCR Results

Results of real-time PCR for selected "signature" genes performed on cDNA from cells derived from human umbilical cord-derived cells grown in two different media, adult fibroblasts, and MSCs indicate that the levels of reticulon and oxidized LDL receptor RNA were higher in umbilical cord-derived cells compared to other cell types. The results also confirmed that the expression pattern of signature genes did not change with medium regardless of whether cells were cultured in Advanced DMEM+10 ng/mL bFGF, or in Growth Medium from isolation, or were subsequently switched from one medium to the other. The results of real-time PCR were confirmed by conventional PCR. Of note, was that bands, while existent, were less intense for oxLDL receptor (063004B P14, 090304A P10). Since conventional PCR is not quantitative, however, potential differences in level of expression could not be discerned here. Umbilicus-derived cells did not express renin, a marker present in placental-derived cells.

The expression of the cytokine, IL-8, in postpartum-derived cells was elevated in both Growth Medium-cultured and Advanced DMEM+10 ng/mL bFGF-cultured umbilical cord-derived cells. This observation was confirmed by conventional PCR.

Discussion and Conclusions

Switching cells between Growth Medium and Advanced DMEM supplemented with bFGF (10 ng/ml) impacts cell surface marker expression of HLA-ABC, and PDGF-r alpha in PPDCs. Under the conditions tested, HLA-DRDPDQ was not detected. HLA-ABC and PDGFr alpha expression can be modulated based on changes in the growth medium of the cells. This observation could have significant implications for the rejections of grafts or implantation of therapeutic cells. The HLA-DRDPDQ marker was never expressed regardless of media composition.

The expression of signature genes such as oxidized LDL receptor and reticulon were unchanged despite the composition of medium used to grow these umbilicus-derived postpartum cells. Because the levels of these genes were detectably higher than in other cell types such as MSCs, these genes in fact constitute a useful signature to determine and distinguish umbilicus-derived postpartum cells. Whether separate subpopulations may exist with in the umbilicus-derived population remains a question, but the consistency of the signature gene expression profile is powerful evidence that any such subpopulations are closely related to each other and more distantly related if at all to other cell types tested.

The finding that HLA-ABC expression varied suggests that, in fact, HLA-ABC expression can be modulated. Whether this could impact graft rejection is a point of further interest in that a cell population lacking the expression of this marker may be able to engraft better, potentially in the absence of immunosuppressants.

The finding that PDGFr alpha can be shut off easily and cannot be immediately turned on may indicate the delicate nature and rapid turnover of growth factor receptors and their requirement for very particular growth conditions for their expression. Given a lack of such receptors (or any other growth factor receptor because of, for example, media changes), cell potency may be altered in particular animal model paradigms.

EXAMPLE 29

Growth Characteristics of Umbilicus-Derived Cells in Standard Growth Medium and Growth Medium without BME, and on Gelatin Coated and CELLBIND Coated Flasks As described herein and above, umbilicus-derived cells can be cultured in Growth Medium in flasks with gelatin-coated surfaces. This example explored whether two of the components in a preferred cell culture protocol were required. Tested, in particular, were whether (1) beta-mercaptoethanol (BME), as an additive in the standard Growth Medium, was required for growth, and (2) whether gelatin (an animal derived protein) was required as a coating for the cell culture flasks. Additionally, the effectiveness of a synthetic coating to promote attachment, CELLBIND® (Corning, Corning, N.Y.), was tested as an alternative to gelatin or other animal-derived products. CellBIND® is a patented, commercially available flask coating that uses highly reactive plasma to reduce the aromatic groups of the polystyrene surface.

Materials & Methods

Reagents: Dulbecco's Modified Essential Media (DMEM), Penicillin and Streptomycin, were obtained from Invitrogen (Carlsbad, Calif.). Fetal bovine serum (FBS) (defined bovine serum) was obtained from Hyclone (Logan, Utah). Beta-mercaptoethanol was obtained from Sigma (St. Louis, Mo.).

Experimental Design: Umbilicus-derived cells were isolated in two mediums (Growth Medium, and Growth Medium without BME) and in vessels coated with either gelatin or CELLBIND®). Thus, four sets of conditions were tested: (1) Gelatin-Coating/Growth Medium (normal conditions), (2) CELLBIND®-Coating/Growth Medium, (3) Gelatin-Coating/Growth Medium without BME and (4) CellBIND®-Coating/Growth Medium without BME. The cells were serially passaged from isolation until senescence in their designated set of conditions. Population growth kinetics were calculated under each set of conditions to determine the effects of media and surface coating of the vessels, and to assess changes in growth. The expression of a set of cell surface markers was assessed as an initial screen for phenotypic changes.

Cells. A single umbilical cord was obtained through National Disease Research Interchange (Philadelphia, Pa.) with full consent and divided into two pieces of approximately equal size.

Isolation Procedures and Media: Postpartum cells were generally isolated as described previously herein. The tissue was minced and divided into approximately equal portions. One portion was isolated in standard Growth Medium (DMEM:LG, 15% FBS; beta-mercaptoethanol (1 piper 100 mL); 50 microliter/ml penicillin/50 microgram/ml streptomycin (1 mL per 100 mL (10,000 Units per mL)). The other portion was isolated in Growth Medium as described without beta-mercaptoethanol (BME) (Growth Medium w/o BME).

Growth of Cells: Cells isolated from each portion of the cord tissue were seeded at 3000 cells/cm$^2$ onto gelatin-coated T225 flasks and CELLBIND-coated T225 flasks (Corning) in the same medium in which they were isolated. Cells were grown at 37° C. in a humidified, 5% $CO_2$ atmosphere. As cells reached about 85% confluence they were trypsinized and counted. Viable cells were seeded at 5000 cell/cm$^2$ into new flasks with appropriate medium and surface coating. Cell Yield, population doublings (ln (cell final/cell initial)/ln 2) and doubling time (time in culture (h)/population doubling) were determined at each passage. The process was repeated until cells appeared to reach senescence, i.e. the cells appeared or lose their proliferative capabilities, or failed to proliferate further.

Cell surface markers were analyzed by flow cytometry at passages 3, 7 and 15 for cells grown on gelatin-coated vessels in media with or without BME, and at passage 7 for cells grown on CELLBIND-coated in either media. The results showed no evidence of any phenotypic changes as reflected in the expression pattern of the cell surface markers analyzed. The results are shown below in Table 29-1.

TABLE 29-1

Cell surface marker expression for cell populations grown in different conditions at passage 7. Results at passages 3 and 15 are similar.

| Passage | | P7 | | | |
|---|---|---|---|---|---|
| Medium Growth Surface | | No BME Gelatin | PHayflick Gelatin | No BME CellBIND ® | Hayflick CellBIND ® |
| Markers | CD10-PE | + | + | + | + |
| | CD13-PE | + | + | + | + |
| | CD31-PE | − | − | − | − |
| | CD34-FITC | − | − | − | − |
| | CD44-FITC | + | + | + | + |
| | CD45RA-PE | − | − | − | − |
| | CD73-PE | + | + | + | + |
| | CD90-FITC | + | + | + | + |
| | CD117-PE | − | − | − | − |
| | CD141-PE | − | − | − | − |
| | SSEA-4-PE | + | + | NA | +/− |
| | PD-L2-FITC | +/− | +/− | − | +/− |
| | PDGFRalpha-PE | +/− | − (slight + shift) | − | +/− |
| | HLA-ABC-PE | + | + | + | + |
| | HLA-DP DQ DR-FITC | − | − | − | − |

Analysis of Cell Surface Markers: Cell surface markers were analyzed by flow cytometery essentially as described herein above. Analyses were performed at passages 3, 7 and 15 for cells grown on gelatin in either standard Growth Medium or in Growth Medium without BME, and at passage 7 for cells grown on CellBIND-coatings in either Growth Medium or Growth Medium without BME. In particular, after trypsinization and counting, 500,000 cells were suspended in 100 μl of Phosphate Buffered Saline with 3% Fetal Bovine Serum per sample. To each sample 20 μl of the antibody corresponding to the marker being analyzed was added. The cells were incubated at 4° C. for 1 hour. After incubation the cells were washed once with 3 ml PBS and resuspended in 0.5 ml PBS. The samples were analyzed using a FACSCalibur (Becton Dickinson), and the results were compiled using the accompanying software (Cell Quest, BD Applications).
Results Cells isolated from umbilical cords can be cultured in media with or without BME, and on either gelatin-coated or CELLBIND-coated vessels. The greatest rate of proliferation (0.51 doublings/day) in these experiments was observed with cells cultured in Growth Medium without BME on gelatin coated flasks. Umbilicus-derived cells proliferated at higher rates in Growth Medium without BME as reflected by a greater number of doublings per day; 0.51 doublings per day (Growth Medium without BME/Gelatin) compared to 0.33 doublings per day (Standard Growth Medium/Gelatin). Cells grew on the CellBIND-coated surfaces in medium with or without BME.

Umbilicus-derived cells cultured in gelatin-coated vessels in either Growth Medium or in Growth Medium without BME were able to expand for up to about 120 days. Umbilicus-derived cells also grew in either Growth Medium or Growth Medium without BME, on the CELLBIND-coated surface for up to about 103 days.

Summary. The results provide evidence that umbilicus-derived cells can be grown in culture without BME.

EXAMPLE 30

Alternate Conditions for the Isolation of Cells from Umbilical Cord Tissue

Initial efforts to isolate a population of cells from human umbilical cord tissue were conducted using a method of tissue processing with a basic cell culture media formulation containing serum as described herein above. Here, alternative methods for isolating cells from minced umbilical cord tissue in the presence of several different media formulations and culture conditions are described. Another objective was to determine if alternate isolation conditions allowed for the outgrowth of a new cell type not previously characterized. Umbilicus-derived cells, grown from isolation under these different conditions were characterized as to their: (1) long-term growth potential, (2) cell surface marker phenotype, (3) stem cell-specific gene expression, and (4) trophic factor production. The data demonstrate that umbilicus-derived cells can be isolated using a variety of media formulations and growth conditions.
Materials & Methods Reagents. Dulbecco's Modified Essential Media (DMEM), Phosphate buffered saline, Penicillin and Streptomycin, and dispase were obtained from Invitrogen (Carlsbad, Calif.). Fetal bovine serum (FBS) (defined bovine serum) was obtained from Hyclone (Logan, Utah). Collagenase, hyaluronidase, and beta-mercaptoethanol were obtained from Sigma (St. Louis, Mo.).

Isolation of cells from human umbilical cords: Human umbilical cords were obtained from the National Disease Research Interchange (NDRI, Philadelphia, Pa.) following normal deliveries. To remove blood and debris, the cord was washed in Dulbeco's Modified Eagles Medium (DMEM-low glucose) or phosphate buffered saline (PBS). The tissues were then mechanically dissociated in tissue culture plates until the tissue was minced to a fine pulp. The minced tissue was transferred to a 50-milliliter conical tube and digested in an enzyme mixture containing 500 Units/milliliter collagenase, 500 Units/milliliter dispase, and 50 Units/milliliter hyaluronidase. The enzyme mixture was combined with a specific media formulation ("test culture medium") as outlined in Table 30-1 below. The conical tubes containing the tissue, medium, and digestion enzymes were incubated at 37° C. in an orbital shaker at 225 rpm for 2 hrs.

After digestion, the tissues were centrifuged at 150×g for 5 minutes, and the supernatant was aspirated. The pellet was resuspended in 20 milliliters of test culture media (Table 30-1). The cell suspension was filtered through a 40-micron nylon BD FALCON Cell strainer (BD Biosciences, San Jose, Calif.). The filtrate was resuspended in medium (total volume=50 milliliters) and centrifuged at 150×g for 5 minutes. The supernatant was again aspirated, and the cells were resuspended in 50 milliliters of fresh test culture medium. The process was repeated twice.

After the final centrifugation, the supernatant was aspirated and the cell pellet was resuspended in 5 milliliters of fresh test culture medium. The number of viable cells was determined using a Guava instrument (Guava Technologies, Hayward, Calif.). Cells were then plated at seeding densities of 300 cells/cm$^2$, 2000 cells/cm$^2$, or 5000 cells/cm$^2$ on gelatin-coated tissue culture flasks. Cells were cultured in medium and under conditions described in Table 30-1. Growth Media controls were used to determine viability of the isolates for each media type.

TABLE 30-1

Media formulations and culture conditions used to isolate umbilical cells from umbilical cord tissue.

| Isolation | Isolate | Media type | Culture condition | Doublings |
|---|---|---|---|---|
| 1 | Umb042105 | EGM2 (endothelial growth medium-2 (Cambrex BioScience, MD)) | Normoxia (low density) | >5 |
| 2 | Umb042105 | EGM2 | Normoxia (high density) | >5 |
| 3 | Umb052405 | REGM (Renal epithelial growth medium (Cambrex)) | Hypoxia | >5 |
| 4 | Umb052405 | REGM | Normoxia | >5 |
| 5 | Umb032905 | SmGM2 (smooth muscle growth medium-2 (Cambrex) | Normoxia (low density) | 5 |
| 6 | Umb051705 | SMGM2 | Hypoxia (high density) | >5 |
| 7 | Umb051705 | SMGM2 | Hypoxia (low density) | >5 |
| 8 | Umb032905 | SMGM2 | Normoxia (high density) | 5 |
| 9 | Umb060805 | Sonic hedgehog medium (DMEM-Low glucose (Invitrogen), 2 percent (v/v) fetal bovine serum (FBS; defined fetal bovine serum; Lot #AND18475; (Hyclone), penicillin at 100 Units/mL, streptomycin at 100 ug/mL (both from Invitrogen), 10 ng/mL recombinant sonic hedgehog growth factor (R&D Systems Inc., Minneapolis, MN)). | Hypoxia | 5 |
| 10 | Umb080305 | Keratinocyte growth medium (Gibco) | Normoxia | 5 |

"Hypoxia", indicates cultures grown under an atmosphere containing 5% oxygen.

"Normoxia", indicates cultures were grown in normal atmospheric oxygen conditions.

"Low density", indicates that cultures were initially seeded at 300 cells/cm$^2$.

"High density", indicates that cultures were initially seeded at 2000 cells/cm$^2$.

"Doublings" = approximate number of population doublings at passage 4.

FACs Analysis: Flow cytometry analysis was performed on umbilicus-derived cells grown according the media formulations and culture conditions described in Table 30-1. Cells were expanded to passage four or five in test culture medium on gelatin-coated T225 flasks at 37° C. and 5% carbon dioxide. Adherent cells were washed in PBS and detached with Trypsin/EDTA (Gibco). Cells were harvested, centrifuged and resuspended in 3% (v/v) FBS in PBS at a concentration of $1\times10^7$ cells/mL. The specific antibody was added to 100 microliters of cell suspension and the mixture was incubated in the dark for 30-45 minutes at 4° C. After incubation, cells were washed with PBS and then centrifuged to remove excess antibody. Cells were resuspended in PBS (500 microliters) and analyzed by flow, cytometry. Flow cytometry analysis was performed with a FACSCalibur instrument (Becton Dickinson, San Jose, Calif.). Antibodies used are shown in Table 30-2.

TABLE 30-2

Antibodies used for cell surface marker analysis of umbilical derived cells.

| Antibody | Manufacture | Catalog No. |
|---|---|---|
| CD10 | BD Pharmingen (San Diego, CA) | 555375 |
| CD13 | BD Pharmingen | 555394 |
| CD31 | BD Pharmingen | 555446 |
| CD34 | BD Pharmingen | 555821 |
| CD44 | BD Pharmingen | 555478 |
| CD45R | BD Pharmingen | 555489 |
| CD49c | BD Pharmingen | 556025 |
| CD73 | BD Pharmingen | 550257 |
| CD90 | BD Pharmingen | 555596 |
| CD117 | BD Pharmingen | 340529 |
| CD141 | BD Pharmingen | 559781 |
| CD 184 | BD Pharmingen | 555974 |
| HLA-A, B, C | BD Pharmingen | 555553 |
| HLA-DR, DP, DG | BD Pharmingen | 555558 |
| IgG-FITC | BD Pharmingen | 555748 |
| IgG-PE | BD Pharmingen | 555749 |

Total RNA isolation: RNA was extracted from confluent umbilical cord derived cells grown in different conditions (RNeasy Mini Kit; Qiagen, Valencia, Calif.). RNA was eluted with 50 µL DEPC-treated water and stored at −80° C.

Reverse transcription: RNA was reverse transcribed using random hexamers with the TaqMan reverse transcription reagents (Applied Biosystems, Foster City, Calif.) at 25° C. for 10 minutes, 37° C. for 60 minutes and 95° C. for 10 minutes. Samples were stored at −20° C. The expression of oxidized LDL receptor, interleukin-8 and reticulon were investigated using real-time and conventional PCR.

Real-time PCR: PCR was performed on cDNA samples using Assays-on-Demand™ gene expression products: renin (Hs00166915), oxidized LDL receptor (Hs00234028), reticulon (Hs00382515), IL-8 (Hs00174103), and GAPDH (Applied Biosystems, Foster City, Calif.) were mixed with cDNA and TaqMan Universal PCR master mix according to the manufacturer's instructions (Applied Biosystems, Foster City, Calif.) using a 7000 sequence detection system with ABI prism 7000 SDS software (Applied Biosystems, Foster City, Calif.). Thermal cycle conditions were initially 50° C. for 2 min and 95° C. for 10 min followed by 40 cycles of 95° C. for 15 sec and 60° C. for 1 min.

Conventional PCR: Conventional PCR was performed using an ABI PRISM 7700 (Perkin Elmer Applied Biosystems, Boston, Mass., USA) to confirm the results from real-time PCR. PCR was performed using 2 µl of cDNA solution, 1× AmpliTaq Gold universal mix PCR reaction buffer (Applied Biosystems, Foster City, Calif.) and initial denaturation at 94° C. for 5 minutes. Amplification was optimized for each primer set. For IL-8 and reticulon (94° C. for 15 seconds, 55° C. for 15 seconds and 72° C. for 30 seconds for 30 cycles), for renin (94° C. for 15 seconds, 53° C. for 15 seconds and 72° C. for 30 seconds for 38 cycles) for oxidized LDL receptor and GAPDH (94° C. for 15 seconds, 55° C. for 15 seconds and 72° C. for 30 seconds for 33 cycles). Primers used for amplification are listed in Table 28-3. Primer concentration in the final PCR reaction was 1 µM except for GAPDH which was 0.5 µM. GAPDH primers were the same as real-time PCR, except that the manufacturer's TaqMan probe was not added to the final PCR reaction. Samples were run on 2% (w/v) agarose gel and stained with ethidium bromide (Sigma, St. Louis, Mo.). Images were captured using 667 Universal Twinpack film (VWR International, South Plainfield, N.J.) using a focal-length camera (VWR International, South Plainfield, N.J.).

TABLE 30-3

Primers used for PCR

| Primer name | Primer sequence (F = forward, R = reverse) |
|---|---|
| Renin | F: 5'-TCTTCGATGCTTCGGATTCC-3' (SEQ ID NO: 3) |
| | R: 5'-GAATTCTCGGAATCTCTGTTG-3' (SEQ ID NO: 4) |
| Oxidized LDL receptor | F: 5'-GAGAAATCCAAAGAGCAAATGG-3' (SEQ ID NO: 1) |
| | R: 5'-AGAATGGAAAACTGGAATAGG-3' (SEQ ID NO: 2) |
| Reticulon | F: 5'-TTACAAGCAGTGCAGAAAACC-3' (SEQ ID NO: 5) |
| | R: 5'-AGTAAACATTGAAACCACAGCC-3' (SEQ ID NO: 6) |
| Interleukin-8 | F: 5'-TCTGCAGCTCTGTGTGAAGG-3' (SEQ ID NO: 7) |
| | R: 5'-CTTCAAAACTTCTCCACAACC-3' (SEQ ID NO: 8) |

ELISA: Frozen umbilicus-derived cells from different isolation conditions were thawed at passage 4 and seeded onto gelatin coated T75 flasks at 5000 cells/cm$^2$ each containing 15 milliliters of their respective growth medium (Table 30-1). Cells were cultured for 24 hours at 37° C. in 5% carbon dioxide and atmospheric oxygen. The medium was then changed to a serum-free medium (DMEM-low glucose (Gibco), 0.1% (w/v) bovine serum albumin (Sigma), penicillin (50 Units/milliliter) and streptomycin (50 ug/mL, Gibco)) and further cultured for 8 hours. Conditioned serum-free medium was collected at the end of incubation by centrifugation at 14,000×g for 5 min and stored at −20° C.

To estimate the number of cells in each flask, cells were washed with PBS and detached using 2 milliliters trypsin/EDTA (Gibco). Cell number was estimated using the Guava instrument (Guava Technologies Hayward, Calif.)). Samples were then assayed for the following factors: tissue inhibitor of metalloprotease-1 (TIMP1), platelet-derived epithelial growth factor bb (PDGFbb), Keratinocyte growth factor (KGF), hepatocyte growth factor (HGF), fibroblast growth factor (FGF), vascular endothelial growth factor (VEGF), Heparin-binding epidermal growth factor (HB-EGF), tissue inhibitor of metalloprotease-2 (TIMP2), monocyte chemotactic protein-1 (MCP1), interleukin-6 (IL6), interleukin-8 (IL8), transforming growth factor alpha (TGFa), brain-derived neurotrophic factor (BDNF), stromal-derived factor 1B (SDF1B), cilliary neurotrophic factor (CNTF), basic nerve growth factor (bNGF), neurotrophin-3 (NT3) with the Searchlight Proteome Arrays (Pierce Biotechnology Inc.).
Results
  Isolation of Umbilicus-Derived Cells
  Umbilicus-derived cells were isolated using different media compositions and culture conditions identified in Table 30-1. Some isolated cell populations were cultured under both normoxic and hypoxic (5% $O_2$) atmospheric conditions. Cells were also isolated using low (300 cells/cm$^2$) or high (2000 cells/cm$^2$) initial seeding density. Ten combinations of growth medium and growth conditions supported the growth of umbilicus-derived cells. These include EGM2, REGM and SMGM2, all under both normoxic and hypoxic atmospheric conditions. Sonic hedgehog medium and KGM, under hypoxia and normoxia respectively, also supported cell growth.
  Long-Term Expansion Analysis
  Media formulations that supported the growth of umbilicus-derived cells were selected, and cells were expanded from passage 4 or 5, at a seeding density of 5,000 cells/cm$^2$ on gelatin-coated plates. Cell populations were continually passaged for several weeks until senescence was reached. Senescence was determined when cells failed to achieve greater than one population doubling during the study time interval.
  Several isolates were tested for long term expansion potential and demonstrated growth beyond passage 4 (Table 30-4). Umb032905, isolated in SMGM2 medium under hypoxic conditions, demonstrated the most robust cell expansion potential of greater than 32 population doublings. The population reached senescence at day 74 for cells isolated at low seeding density, and at 64 days for cells isolated at high seeding density. Modest expansion potential was observed in umb052405 isolated in REGM and cultured in normoxic or hypoxic conditions (isolation 3,4). These conditions yielded 18 and 10 population doublings, respectively.

TABLE 30-4

Maximal number of cell population doublings achieved.

| Isolation | Days in culture | PD | Viability (%) |
|---|---|---|---|
| 3 | 33 | 18.3 | 86.5 |
| 4 | 29 | 10.2 | 97 |
| 6 | 64 | 31.4 | 98 |
| 7 | 74 | 31.6 | 96 |

"PD", number of population doublings achieved when cells were cultured from passage 4 to senescence. "Viability (%)", percent of cells that were alive at the time of senescence.

Surface Marker Phenotype Analysis by Flow Cytometry
  Cell populations generated from different isolation conditions were characterized by flow cytometry. Ten cell lines out of the twenty-two isolation conditions were expanded to passage 4 and cell surface marker profile was determined. Most of the cell isolations showed positive staining for CD10, CD13, CD44, CD49c, CD73, CD90, and HLA-ABC. The cells were negative under the conditions tested for surface expression of CD31, CD34, CD45, CD 117, CD141, CD184, and HLA-DR, DP, DQ. Most markers showed a similar expression pattern to cells isolated using the preferred conditions described above in prior examples, as well as to other cell isolations.
  RT-PCR Analysis
  Umbilicus-derived cell isolates were analyzed for the expression of umbilicus-derived cell-specific genes and stem cell-specific genes. The data provided in Tables 30-5 show that cells derived from all isolation conditions expressed reticulon, LDL-R, and IL-8. Table 30-5 shows the results of real-time PCR performed on cDNA from cells derived from human umbilical cords grown in different media formulations. Results are expressed as a ratio of cycle thresholds (CT) between gene of interest and the internal transcript control, GAPDH. The data indicate that expression levels of reticulon, oxidized LDL receptor, and IL-8 were all similar.

TABLE 30-5

Results of real time RT-PCR analysis of signature gene and stem cell-specific genes. Results are expressed as a CT ratio between gene of interest and an internal transcript control (GAPDH). mRNA transcripts not expressed by cells (–). nTERA-2 cells serves as a positive control for stem cell-specific gene expression.

| Isolation | Media type | Condition | renin | reticulon | LDL-R | IL-8 |
|---|---|---|---|---|---|---|
| 1 | EGM2 | Normoxia (low density) | — | 0.85 | 0.73 | 0.86 |
| 2 | EGM2 | Normoxia (high density) | — | 0.88 | 0.78 | 0.90 |
| 3 | REGM | Hypoxia | — | 1.12 | 1.05 | 0.92 |
| 5 | SMGM2 | Hypoxia (low density) | — | 0.79 | 0.73 | 0.89 |
| 6 | SMGM2 | Hypoxia (high density) | — | 0.94 | 0.90 | 1.04 |
| 7 | SMGM2 | Normoxia (low density) | — | 0.78 | 0.84 | 0.96 |
| 8 | SMGM2 | Normoxia (high density) | — | 0.74 | 0.74 | 0.91 |
| 9 | Sonic hedgehog medium | Hypoxia | — | 1.00 | 1.05 | 0.90 |
| 10 | KGM | Normoxia | — | 0.99 | 1.08 | 0.89 |
|  | nTERA-2 |  | — | — | — | 0.63 |

Analysis of trophic factor production
  The production of different growth factors and cytokines was analyzed for eight isolates (Table 30-6). All umbilicus-derived cell isolation conditions resulted in cell populations that secreted relatively high amounts (>30 pg/mL/1×10$^6$ cells) of tissue inhibitor of metalloprotease-1 (TIMP1), basic fibroblast growth factor (FGF), hepatocyte growth factor (HGF), heparin-binding epidermal growth factor (HB-EGF), tissue inhibitor of metalallinoprotease-2 (TIMP2), interleukin 8 (IL8), and stromal derived factor-1b (SDF1b). Undetectable to low amounts (<30 pg/mL/1×10$^6$ cells) of platelet-derived epithelial growth factor-bb (PDGFbb), basic nerve growth factor (NGF), and neurotrophin-3 (NT3) were detected from the same samples.
  Cells isolated with EGM2 medium yielded populations of cells that produced low amounts of many trophic factors including, keratinocyte growth factor (KGF), transforming growth factor-alpha (TGF-alpha), brain-derived neurotrophic factor (BDNF), and cilliary neurotrophic factor (CNTF). However, these cell lines produced higher amounts of interleukin-6 (IL6) compared to other cell lines tested. Cells isolated in SMGM2 under normal atmosphere with low initial seeding density produced very high (4737 pg/mL/1×10$^6$ cells) amounts of HGF. These cells also secreted very high amounts of TIMP2 (26,002 pg/mL/1×10$^6$ cells) as compared to other isolation conditions. Slightly higher amounts (39.6 pg/mL/1×10$^6$ cells) of TGF-alpha were produced by these cells than other cell lines tested.
  Alternate isolation conditions also provided populations of cells secreting variable amounts of VEGF. Umbilicus-derived cells isolated in REGM under normoxic and hypoxic conditions produced relatively high amounts of VEGF (64.8 pg/mL/1×10$^6$ cells and 131.6 pg/mL/1×10$^6$ cells, respectively). Other isolation and growth conditions showed comparatively low VEGF secretion.

TABLE 30-6

SearchLight Multiplexed ELISA assay analysis of trophic factor production in umbilical cells derived from different isolation and growth conditions. High (>30 pg/mL/1 × 10⁶ cells) amounts of trophic factor are indicated in light gray boxes and low amounts are indicated in white boxes.

| Isolation | TIMP1 | PDGFBB | KGF | HGF | FGF | VEGF | HB-EGF | TIMP2 | MCP1 |
|---|---|---|---|---|---|---|---|---|---|
| C | <9.8 | <2.0 | <2.0 | <3.2 | <5.4 | <4.0 | <3.6 | 23.7 | 15.1 |
| 1 | 42421.0 | 4.0 | 23.0 | 664.0 | 52.0 | 33.0 | 103.0 | 2257.0 | 299.0 |
| 2 | 51515.0 | 3.0 | 18.0 | 350.0 | 66.0 | 5.0 | 93.0 | 1268.0 | 752.0 |
| 3 | 371200.0 | 8.4 | 10.0 | 69.7 | 101.9 | 131.5 | 290.4 | 5700.0 | 154.7 |
| 4 | 260100.0 | <2.0 | 41.4 | 102.6 | 624.6 | 64.8 | 648.0 | 6192.0 | 122.4 |
| 5 | 225321.0 | 31.0 | 41.0 | 4737.0 | 408.0 | 29.0 | 507.0 | 26002.0 | 165.0 |
| 6 | 81300.0 | <2.0 | 31.2 | 36.5 | 259.9 | 20.5 | 257.6 | 1336.8 | 55.5 |
| 7 | 73656.0 | <2.0 | 25.3 | 45.4 | 172.6 | 18.6 | 262.6 | 1210.4 | 33.5 |
| 8 | 137349.0 | 8.0 | 24.0 | 376.0 | 383.0 | 37.0 | 366.0 | 15997.0 | 710.0 |

| Isolation | IL6 | IL8 | TGFA | BDNF | SDF1B | CNTF | B-NGF | NT3 |
|---|---|---|---|---|---|---|---|---|
| C | <.8 | <.8 | 3.7 | 8.0 | 23.4 | 104.5 | 3.2 | 2.8 |
| 1 | 34.0 | 213.0 | 4.0 | 26.0 | 61.0 | 81.0 | 4.0 | 4.0 |
| 2 | 42.0 | 2690.0 | 4.0 | 29.0 | 77.0 | 100.0 | 4.0 | 5.0 |
| 3 | 9.5 | 163.2 | 12.7 | 51.7 | 256.1 | <7.8 | 6.9 | <1.6 |
| 4 | 18.0 | 2678.4 | 39.6 | 100.8 | 507.6 | 459.0 | 28.8 | 30.6 |
| 5 | 17.0 | 770.0 | 20.0 | 99.0 | 260.0 | 394.0 | 16.0 | 13.0 |
| 6 | 27.4 | 608.0 | <2.4 | 41.8 | 200.6 | 146.7 | 11.4 | 13.7 |
| 7 | 19.3 | 923.3 | 12.6 | 33.5 | 239.6 | 237.3 | 9.7 | 14.9 |
| 8 | 30.0 | 931.0 | 13.0 | 69.0 | 157.0 | 373.0 | 13.0 | 15.0 |

"C", control sample is serum free media alone without conditioning. Results shown are the average of duplicate measurements.

Discussion

Different media formulations and culture conditions can be used to isolate cells from human umbilical cord tissue. However, these alternate isolation conditions derived cells that appear to be similar to cells isolated using the conditions initially used to isolate and characterize these cells.

Based on the surface marker profile, and gene expression analysis, cells isolated using alternate conditions yield the same cell type as those isolated in Growth Medium under the original conditions. In addition, cells obtained from all isolation conditions tested showed similar trophic factor secretion profiles. Alternate isolation conditions may stimulate some cells to produce more or less of one or more particular factors, and this may applications for therapeutic use.

Long-term growth potential is an important measurement for assessing the ability of the alternate isolation condition to produce a cell for allogeneic-based cell therapy. Conditions described in Table 30-1 generally yielded cell populations that could be expanded to approximately 5 population doublings.

After comparing long-term growth potential, surface marker phenotype, signature and stem cell specific gene expression and trophic factor production, these cell populations appear to be similar to cells isolated using standard conditions.

Biological Deposit of Umbilicus-Derived Cells and Cultures

Consistent with the detailed description and the written examples provided herein, examples of umbilicus-derived cells of the invention were deposited with the American Type Culture Collection (ATCC, Manassas, Va.) on Jun. 10, 2004, and assigned ATCC Accession Numbers as follows: (1) strain designation UMB 022803 (P7) was assigned Accession No. PTA-6067; and (2) strain designation UMB 022803 (P17) was assigned Accession No. PTA-6068.

While the present invention has been particularly shown and described with reference to the presently preferred embodiments, it is understood that the invention is not limited to the embodiments specifically disclosed and exemplified herein. Numerous changes and modifications may be made to the preferred embodiment of the invention, and such changes and modifications may be made without departing from the scope and spirit of the invention as set forth in the appended claims.

What is claimed:

1. A method for the preparation of therapeutic cells or cultures comprising:
   a) isolating cells from human umbilical cord tissue substantially free of blood, wherein the isolated cells lack production of CD117;
   b) initially expanding the cells to a useful number in a serum-containing medium which supports cell expansion, wherein the cells produce a quantity of the cell surface marker HLA-ABC;
   c) transferring the cells to a serum-free advanced Dulbecco's minimal essential medium containing L-glutamine and basic fibroblast growth factor (bFGF) in which the cells produce a decreased amount of the cell surface marker HLA-ABC; and
   d) passaging the cells in the serum-free medium in which the cells produce a decreased amount of the HLA-ABC, thereby preparing a therapeutic cell or culture.

2. The method of claim 1 wherein the cells isolated from human umbilical cord tissue substantially free of blood further have the following characteristics:
   (a) express each of CD10, CD13, CD44, CD73, CD90, PDGFr-alpha, PD-L2;
   (b) do not express CD31, CD34, CD45, CD80, CD86, CD141, CD178, B7-H2, HLA-G, or HLA-DR,DP,DQ; and
   (c) have increased expression of interleukin-8 and reticulon 1 relative to that of a human cell which is a fibroblast, a mesenchymal stem cell, or an iliac crest bone marrow cell.

3. The method of claim 1 or 2 for the production of therapeutic cells or cultures for implantation.

4. The method of claim 1 or 2 for the production of therapeutic cells or cultures for grafting.

5. The method of claim 1, wherein the isolated cells from human umbilical cord tissue substantially free of blood are cells deposited with ATCC under Accession No. PTA-6067.

6. The method of claim 1, wherein the isolated cells from human umbilical cord tissue substantially free of blood are cells deposited with ATCC under Accession No. PTA-6068.

* * * * *